US007892760B2

(12) United States Patent
Birse et al.

(10) Patent No.: US 7,892,760 B2
(45) Date of Patent: Feb. 22, 2011

(54) LUNG CANCER MARKERS, AND USES THEREOF

(75) Inventors: Charles Birse, North Potomac, MD (US); Marcia Lewis, Cohasset, MD (US); Steve Ruben, Brookville, MD (US); Mehdi Mesri, North Potomac, MD (US)

(73) Assignee: Celera Corporation, Alameda, CA (US)

( * ) Notice: Subject to any disclaimer, the term of this patent is extended or adjusted under 35 U.S.C. 154(b) by 49 days.

(21) Appl. No.: 12/273,994

(22) Filed: Nov. 19, 2008

(65) Prior Publication Data
US 2009/0176228 A1 Jul. 9, 2009

Related U.S. Application Data

(60) Provisional application No. 61/003,767, filed on Nov. 19, 2007.

(51) Int. Cl.
G01N 33/53 (2006.01)
(52) U.S. Cl. ....................................... 435/7.1
(58) Field of Classification Search .................. None
See application file for complete search history.

(56) References Cited

U.S. PATENT DOCUMENTS

| 5,324,634 | A | 6/1994 | Zucker |
| 5,869,277 | A | 2/1999 | Stetler-Stevenson et al. |
| 5,902,582 | A | 5/1999 | Hung |
| 6,534,276 | B1 | 3/2003 | Wun et al. |
| 6,811,995 | B1 | 11/2004 | Moses et al. |
| 6,946,439 | B2 | 9/2005 | Hembrough et al. |
| 7,056,660 | B1 | 6/2006 | Giesing et al. |
| 7,090,983 | B1 | 8/2006 | Muramatsu et al. |
| 2003/0087863 | A1 | 5/2003 | Martignetti et al. |
| 2004/0121343 | A1 | 6/2004 | Buechler et al. |
| 2005/0032063 | A1 | 2/2005 | Kopreski |
| 2006/0019256 | A1 | 1/2006 | Clarke et al. |
| 2006/0024692 | A1 | 2/2006 | Nakamura et al. |
| 2006/0134661 | A1 | 6/2006 | Essner |
| 2006/0160762 | A1 | 7/2006 | Zetter et al. |
| 2006/0235034 | A1 | 10/2006 | Neamati |
| 2007/0178504 | A1 | 8/2007 | Colpitts et al. |
| 2007/0264193 | A1 | 11/2007 | Shojaei et al. |
| 2008/0133141 | A1 | 6/2008 | Frost |
| 2008/0160546 | A1 | 7/2008 | Colpitts et al. |
| 2008/0213258 | A1 | 9/2008 | Massague et al. |
| 2008/0279780 | A1 | 11/2008 | Zhang et al. |
| 2008/0292546 | A1 | 11/2008 | Clarke et al. |
| 2009/0004105 | A1 | 1/2009 | Cheng et al. |
| 2009/0017030 | A1 | 1/2009 | St.Croix et al. |
| 2009/0123439 | A1 | 5/2009 | Yun et al. |

FOREIGN PATENT DOCUMENTS

| EP | 1498424 A2 | 1/2005 |
| WO | 2004023973 A2 | 3/2004 |
| WO | 2007140352 A2 | 12/2007 |
| WO | 2008022806 A2 | 2/2008 |
| WO | 2009013075 A2 | 1/2009 |
| WO | 2009079581 A1 | 6/2009 |

OTHER PUBLICATIONS

Tockman et al (Cancer Res., 1992, 52:2711s-2718s).*
Lombardi et al (Chest, 1990, 97:639-644).*
Pastor et al (Eur Respir J, 1997, 10:603-609).*
Garbisa et al (Cancer Research, 1992, 52:4548-4549).*
Ylisirnio et al (Clinical Cancer Research, 2001, 7:1633-1637).*
Albrethsen, J., et al., "Upregulated Expression of Human Neutrophil Peptides 1, 2 and 3 (HNP 1-3) in Colon Cancer Serum and Tumours: a Biomarker Study," BMC Cancer, Jan. 19, 2005, vol. 5, No. 8, 10 pages; relevant to DEFA1.
Ameshima, S., et al., "Increased Secretory Leukoprotease Inhibitor in Patients with Nonsmall Cell Lung Carcinoma," Cancer, Nov. 13, 2000, vol. 89, No. 7, pp. 1448-1456; relevant to SLPI.
Amirkhosravi, A., et al., "The Role of Tissue Factor Pathway Inhibitor in Tumor Growth Metastasis," Seminars in Thrombosis and Hemostasis, 2007, vol. 33, No. 7, pp. 643-652; relevant to TFPI.
Bajaj, M. S., et al., "Tissue Factor Pathway Inhibitor Expression by Human Pleural Mesothelial and Mesothelioma Cells," European Respiratory Journal, 2000, vol. 15, pp. 1069-1078; relevant to TFPI.
Bateman, A., et al., "The Levels and Biologic Action of the Human Neutrophil Granule Peptide HP-1 in Lung Tumors," Peptides, 1992, vol. 13, pp. 133-139; relevant to DEFA1.
Chambers, A., et al., "Osteopontin Expression in Lung Cancer," Lung Cancer, 1996, vol. 15, pp. 311-323; relevant to OPN.
Dworakowska, D., et al., "Concentration of TF and TFPI in Non-Small Cell Lung Cancer," Journal of Thrombosis and Haemostasis, 2005, vol. 3, Supp. 1, Abstract No. P1352; 2 pgs., relevant to TFPI.
Fedarko, N., et al., "Elevated Serum Bone Sialoprotein and Osteopontin in Colon, Breast, Prostate, and Lung Cancer," Clinical Cancer Research, Dec. 2001, vol. 7, pp. 4060-4066; relevant to OPN.
Garbisa, S., et al., "Correlation of Serum Metalloproteinase Levels with Lung Cancer Metastasis and Response to Therapy," Cancer Research, Aug. 15, 1992, vol. 52, pp. 4548-4549; relevant to MMP2.
Hembrough, T. A., et al., "Identification and Characterization of a Very Low Denisty Lipoprotein Recptor-Binding Peptide from Tissue Factor Pathway Inhibitor that has Antitumor and Antiangiogenic Activity," Blood, May 1, 2004, vol. 103, No. 9, pp. 3374-3380; relevant to TFPI.
Ikematsu, S., et al., "Serum Midkine Levels are Increased in Patients with Various Types of Carcinomas," British Journal of Cancer, 2000, vol. 83, No. 6, pp. 701-706; relevant to MDK.

(Continued)

Primary Examiner—Sean E Aeder

(57) ABSTRACT

Methods and compositions are provided for assessing (e.g., diagnosing), treating, and preventing diseases, especially cancer, and particular lung cancer, using lung cancer markers (LCM). Individual LCM and panels comprising multiple LCM are provided for these and other uses. Methods and compositions are also provided for determining or predicting the effectiveness of a treatment or for selecting a treatment using LCM. Methods and compositions are further provided for modulating cell function using LCM. Also provided are compositions that modulate LCM (e.g., antagonists or agonists), such as antibodies, proteins, small molecule compounds, and nucleic acid agents (e.g., RNAi and antisense agents), as well as pharmaceutical compositions thereof. Further provided are methods of screening for agents that modulate LCM, and agents identified by these screening methods.

39 Claims, 24 Drawing Sheets

OTHER PUBLICATIONS

Iversen, N., et al., "Elevated Plasma Levels of the Factor Xa-TFPI Complex in Cancer Patients," Thrombosis Research, 2002, vol. 105, pp. 33-36; relevant to TFPI.

Iversen, N., et al., "Elevated TFPI in Malignant Disease: Relation to Cancer Type and Hypercoagulation," British Journal of Haemotology, 1998, vol. 102, pp. 889-895; relevant to TFPI.

Karameris, A., et al., "Association of Expression of Metalloproteinases and Their Inhibitors with the Metastatic Potential of Squamos-Cell Lung Cancer," American Journal of Respiratory Critical Care Medicine, 1997, vol. 156, pp. 1930-1936; relevant to TIMP-1.

Koldas, M., et al., "Thrombin-Activatable Fibrinolysis Inhibitor Levels in Patients with Non-Small-Cell Lung Cancer," Clinical Lung Cancer, Mar. 2008, vol. 9, No. 2 pp. 112-115; relevant to TFPI.

Lindahl, A. K., et al., "The Present Status of Tissue Factor Pathway Inhibitor," Blood Coagulation and Fibrinolysis, 1992, vol. 3, pp. 439-449; relevant to TFPI.

Pastor, A., et al., "Diagnostic Value of SCC, CEA and CYFRA 21.1 in Lung Cancer: a Bayesian Analysis," European Respiratory Journal, 1997, vol. 10, pp. 603-609; relevant to CEA, CYFRA and SCC.

Rollin, J., et al., "Influence of MMP-2 and MMP-9 Promoter Polymorphisms on Gene Expression and Clinical Outcome of Non-Small Cell Lung Cancer," Lung Cancer, 2007, vol. 56, pp. 273-280; relevant to MMP2.

Sasaki, H., et al., "Elevated Serum Pro-MMP2 Levels in Patients with Advanced Lung Cancer are not Suitable as a Prognostic Marker," Surgery Today, 2002, vol. 32, pp. 93-95; relevant to MMP2.

Schneider, J., et al., "Tumor Markers in Detection of Lung Cancer," Advances in Clinical Chemistry, 2006, vol. 22, pp. 1-30; relevant to CEA, CYFRA, SCC and CA125.

Stieber, P., et al., "A New Marker in Lung Cancer," Cancer, 1993, vol. 72, pp. 707-713; relevant to CEA, CYFRA, SCC and CA125.

Werling, R. W., et al., "Distribution of Tissue Factor Pathway Inhibitor in Normal and Malignant Human Tissues," Thrombosis and Haemostasis, 1993, vol. 69, No. 4, pp. 366-369; relevant to TFPI.

Ylisirnio, S., et al., "Elevated Serum Levels of Type I Collagen Degradation Marker ICTP and Tissue Inhibitor of Metalloproteinase (TIMP) 1 are Associated with Poor Prognosis in Lung Cancer," Clinical Cancer Research, Jun. 2001, vol. 7, pp. 1633-1637; relevant to TIMP-1.

Zucker, S., et al., "Type IV Collagenase/Gelatinase (MMP-2) is not Increased in Plasma of Patients with Cancer," Cancer, Epidemiology, Biomarkers and Prevention, Sep. 1992, vol. 1, pp. 475-479; relevant to MMP2.

Aljada, I. S., et al., "Upregulation of the Tissue Inhibitor of Metalloproteinase-1 Protein is Associated with Progression of Human Non-Small-Cell Lung Cancer," Journal of Clinical Oncology, Aug. 15, 2004, vol. 22, No. 16, pp. 3218-3229; relevant to TIMP-1.

International Preliminary Report on Patentability for PCT Application No. US2008/084077, dated May 25, 2010.

Ohta, Y., et al., "Homologs of CD83 from Elasmobranch and Teleost Fish", The Journal of Immunology, 2004, vol. 173, pp. 4553-4560.

Pastor, A., et al., "Diagnostic Value of SCC, CEA and CYFRA 21.1 in Lung Cancer: a Bayesian Analysis", European Respiratory Journal, 1997, vol. 10, pp. 603-609.

Rollin, J., et al., "Influence of MMP-2 and MMP-9 Promoter Polymorphisms on Gene Expression and Clinical Outcome of Non-Small Cell Lung Cancer", Lung Cancer, 2007, vol. 56, pp. 273-280.

Invitation to Pay Additional Fees, dated Aug. 11, 2009.

International Preliminary Report on Patentability, dated Oct. 23, 2009.

* cited by examiner

FIGURE 1
Lung Cancer Markers

FIGURE 2
Exemplary 8-Marker Panel

Exemplary 8-Marker Panel
(TFPI, SCC, CEA, CA242, MNCAIX, OPN, Cyfra 21-1, and MIF)

Tumor (2 or more markers)
Normal (1 or 0 markers)

FP 0
TP 11
FN 1
TN 12

Sensitivity 92%
Specificity 100%

FIGURE 4
Examples of Alternative Lung Cancer Biomarkers and Panels Thereof

| | Hist | AS | AS | AS | AS | SC | A | A | A | AS | AS | AS | BA | N | N | N | N | N | N | N | N | N | N | N | N |
|---|---|---|---|---|---|---|---|---|---|---|---|---|---|---|---|---|---|---|---|---|---|---|---|---|---|
| | Stage | III | IV | III | IV | III | III | IV | IV | IIIB | IV | III | IV | | | | | | | | | | | | |
| SLPI | | 5.3 | 0.0 | 3.9 | 5.3 | 5.3 | 0.0 | 0.0 | 0.0 | 0.0 | 0.0 | 0.0 | 0.0 | 0.0 | 0.0 | 0.0 | 0.0 | 3.2 | 0.0 | 0.0 | 0.0 | 0.0 | 0.0 | 0.0 | 0.0 |
| TFPI | | 10.1 | 0.0 | 2.1 | 0.0 | 2.1 | 1.7 | 0.0 | 0.0 | 0.0 | 0.0 | 0.0 | 0.0 | 0.0 | 0.0 | 0.0 | 0.0 | 0.0 | 0.0 | 0.0 | 0.0 | 1.7 | 0.0 | 0.0 | 0.0 |
| OPN | | 33.6 | 0.0 | 0.0 | 3.4 | 2.8 | 0.0 | 3.5 | 3.4 | 4.8 | 0.0 | 0.0 | 0.0 | 0.0 | 0.0 | 0.0 | 0.0 | 0.0 | 2.7 | 0.0 | 0.0 | 0.0 | 0.0 | 0.0 | 0.0 |
| MIF | | 3.9 | 2.2 | 2.2 | 3.4 | 0.0 | 0.0 | 0.0 | 6.5 | 0.0 | 0.0 | 0.0 | 0.0 | 0.0 | 0.0 | 0.0 | 0.0 | 0.0 | 0.0 | 2.1 | 0.0 | 0.0 | 0.0 | 0.0 | 0.0 |
| TIMP1 | | 1.7 | 1.5 | 1.3 | 0.0 | 0.0 | 0.0 | 1.4 | 1.9 | 0.0 | 1.4 | 0.0 | 0.0 | 0.0 | 0.0 | 0.0 | 0.0 | 0.0 | 0.0 | 0.0 | 0.0 | 0.0 | 0.0 | 0.0 | 0.0 |
| MMP2 | | 2.8 | 0.0 | 0.0 | 0.0 | 0.0 | 0.0 | 0.0 | 0.0 | 5.2 | 0.0 | | | | | | | | | | | | | | |
| | | | | | | | | | | | | | | | | | | | | | | | | | |
| CA242 | | 4.4 | 0.0 | 0.0 | 6.8 | 3.7 | 0.0 | 1.8 | 10.3 | 2.6 | 3.3 | 0.0 | 0.0 | 0.0 | 0.0 | 0.0 | 0.0 | 0.0 | 0.0 | 0.0 | 0.0 | 2.9 | 0.0 | 0.0 | 0.0 |
| SCC | | 5.6 | 7.7 | 7.5 | 5.5 | 10.6 | 10.7 | 9.4 | 0.0 | 0.0 | 0.0 | 7.4 | 0.0 | 0.0 | 0.0 | 0.0 | 0.0 | 0.0 | 0.0 | 0.0 | 0.0 | 0.0 | 10.2 | 0.0 | 0.0 |
| CEA | | 16.9 | 16.9 | 0.0 | 16.9 | 2.2 | 0.0 | 16.9 | 15.1 | 0.0 | 3.4 | 0.0 | 0.0 | 0.0 | 0.0 | 0.0 | 0.0 | 0.0 | 0.0 | 0.0 | 0.0 | 0.0 | 0.0 | 0.0 | 0.0 |
| | | | | | | | | | | | | | | | | | | | | | | | | | |
| NSE | | 3.3 | 7.5 | 3.3 | 4.3 | 0.0 | 0.0 | 0.0 | 0.0 | 0.0 | 4.6 | 0.0 | 0.0 | 0.0 | 0.0 | 0.0 | 0.0 | 0.0 | 0.0 | 0.0 | 0.0 | 0.0 | 0.0 | 0.0 | 0.0 |
| CA724 | | 30.7 | 0.0 | 0.0 | 0.0 | 22.1 | 0.0 | 0.0 | 152.3 | 0.0 | 0.0 | 0.0 | 0.0 | 0.0 | 0.0 | 0.0 | 0.0 | 10.2 | 0.0 | 0.0 | 0.0 | 0.0 | 0.0 | 0.0 | 0.0 |
| CA199 | | 10.6 | 0.0 | 0.0 | 5.4 | 0.0 | 0.0 | 0.0 | 10.5 | 0.0 | 0.0 | 5.5 | 0.0 | 0.0 | 0.0 | 0.0 | 0.0 | 0.0 | 0.0 | 0.0 | 0.0 | 0.0 | 0.0 | 4.2 | 0.0 |
| Cyfra 21-1 | | 7.2 | 0.0 | 12.5 | 2.6 | 8.1 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| MNCAIX | | 12.7 | 4.6 | 0.0 | 0.0 | 0.0 | 0.0 | 0.0 | 0.0 | 31.7 | 0.0 | 0.0 | 0.0 | 0.0 | 0.0 | 0.0 | 0.0 | 0.0 | 0.0 | 0.0 | 0.0 | 0.0 | 0.0 | 0.0 | 3.9 |

6 Markers Assayed in Early Stage Lung Cancer Sera
Scatter Plots of ELISA data

FIGURE 6
Exemplary 11-Marker Panel
*Evaluating Panel Performance Applying Manually Defined Cut-offs for Each ELISA*

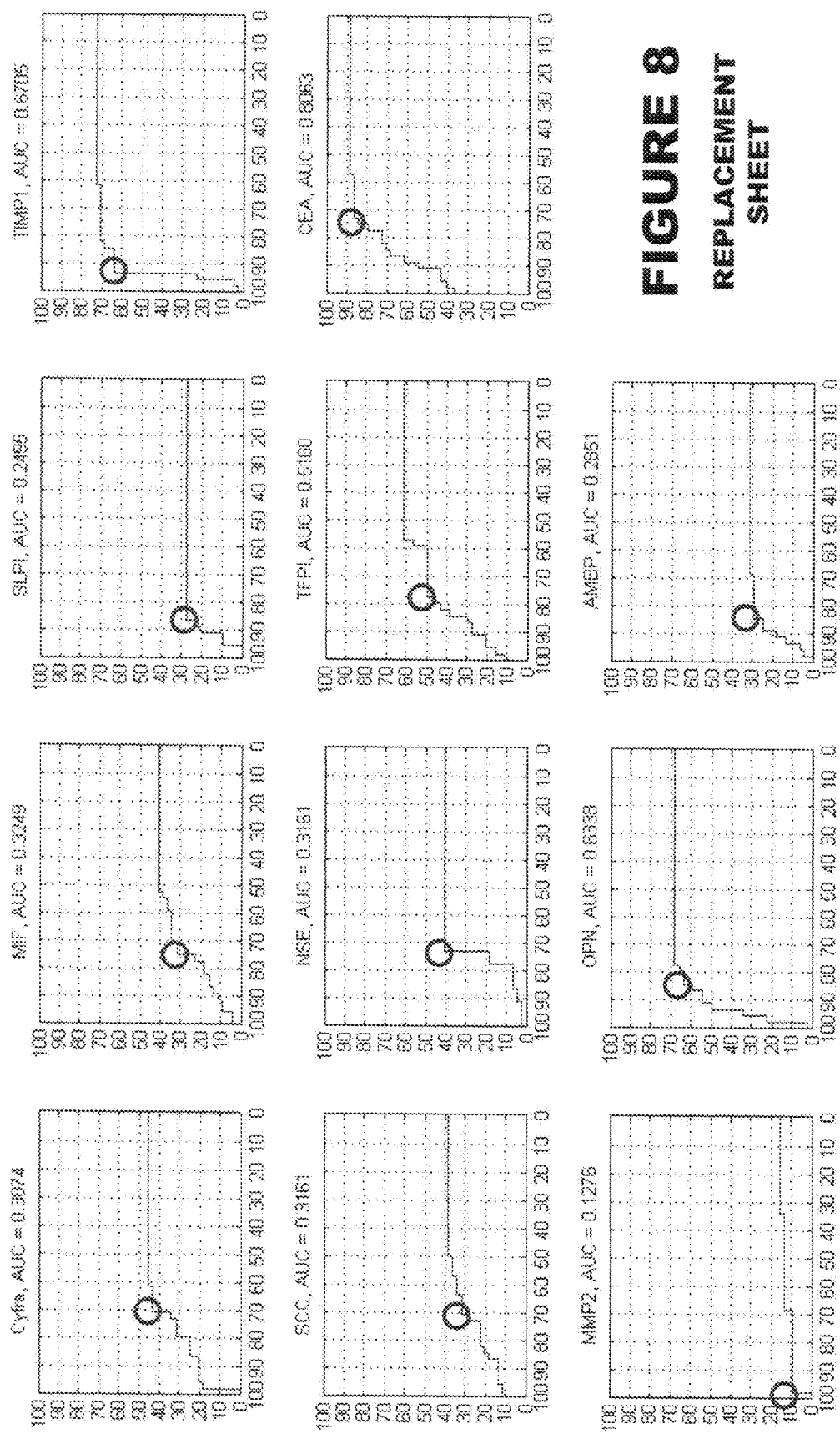
FIGURE 8
REPLACEMENT SHEET

FIGURE 11
Autoantibody Analysis

*Autoantibody Markers Can Complement Other Lung Cancer Markers*

FIGURE 12
Examples of Autoantibody Lung Cancer Markers

| Target Name | Symbol |
|---|---|
| kallikrein B, plasma (Fletcher factor) 1 | KLKB1 |
| cofilin 1 (non-muscle) | CFL1 |
| lectin, galactoside-binding, soluble, 1 (galectin 1) | LGALS1 |
| eukaryotic translation elongation factor 1 gamma | EEF1G |
| Reticulon 4 | RTN4 |
| aldolase A, fructose-bisphosphate | ALDOA |
| Heat shock protein HSP 90-alpha | HSPCA |
| poly(A) binding protein, cytoplasmic 4 (inducible form) | PABPC4 |
| N-acetylglucosamine kinase | NAGK |
| complement factor H-related 1 | CFHL1 |
| colony stimulating factor 1 receptor, | CSF1R |
| RAN binding protein 2 | RANBP2 |

\* p53 autoantibody levels were evaluated as a control

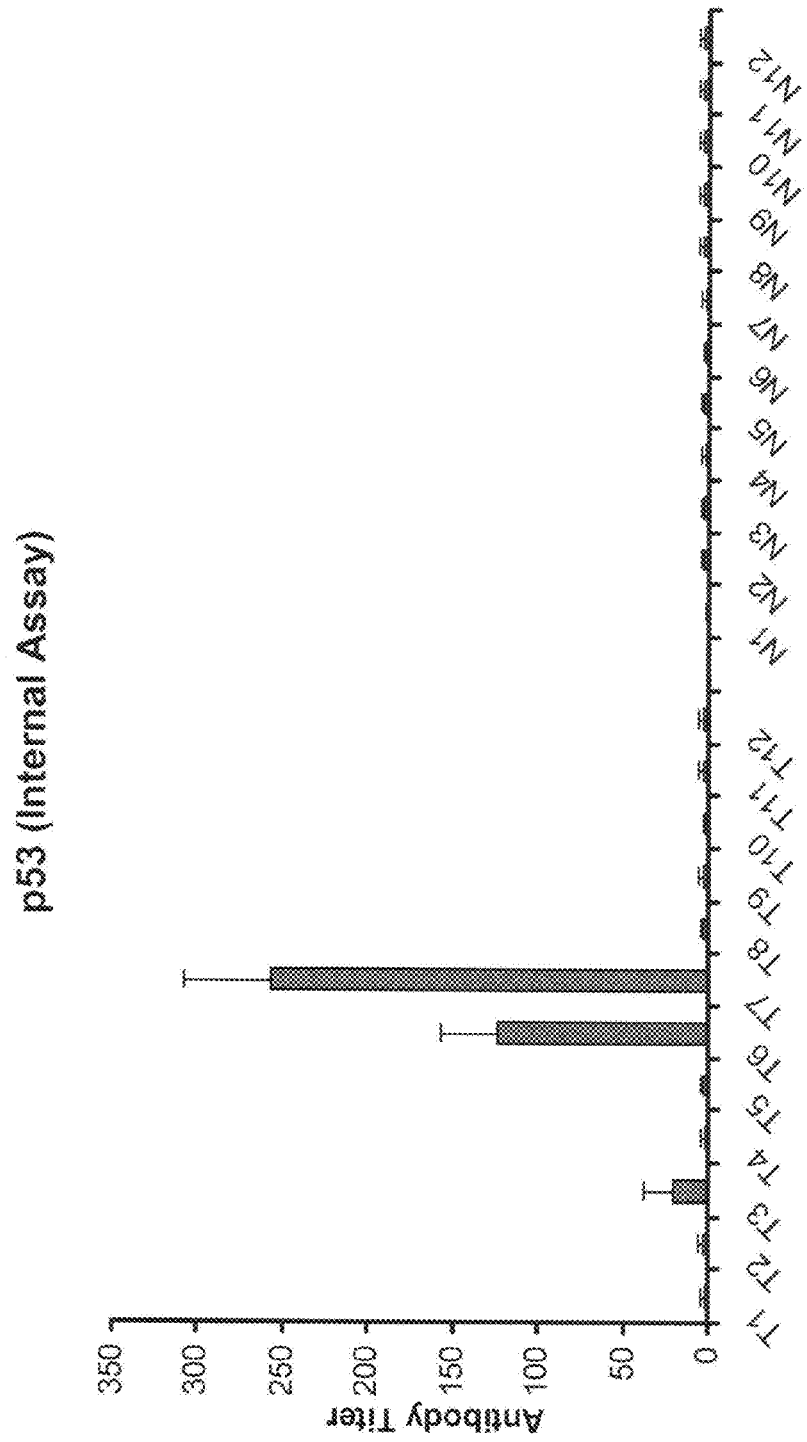

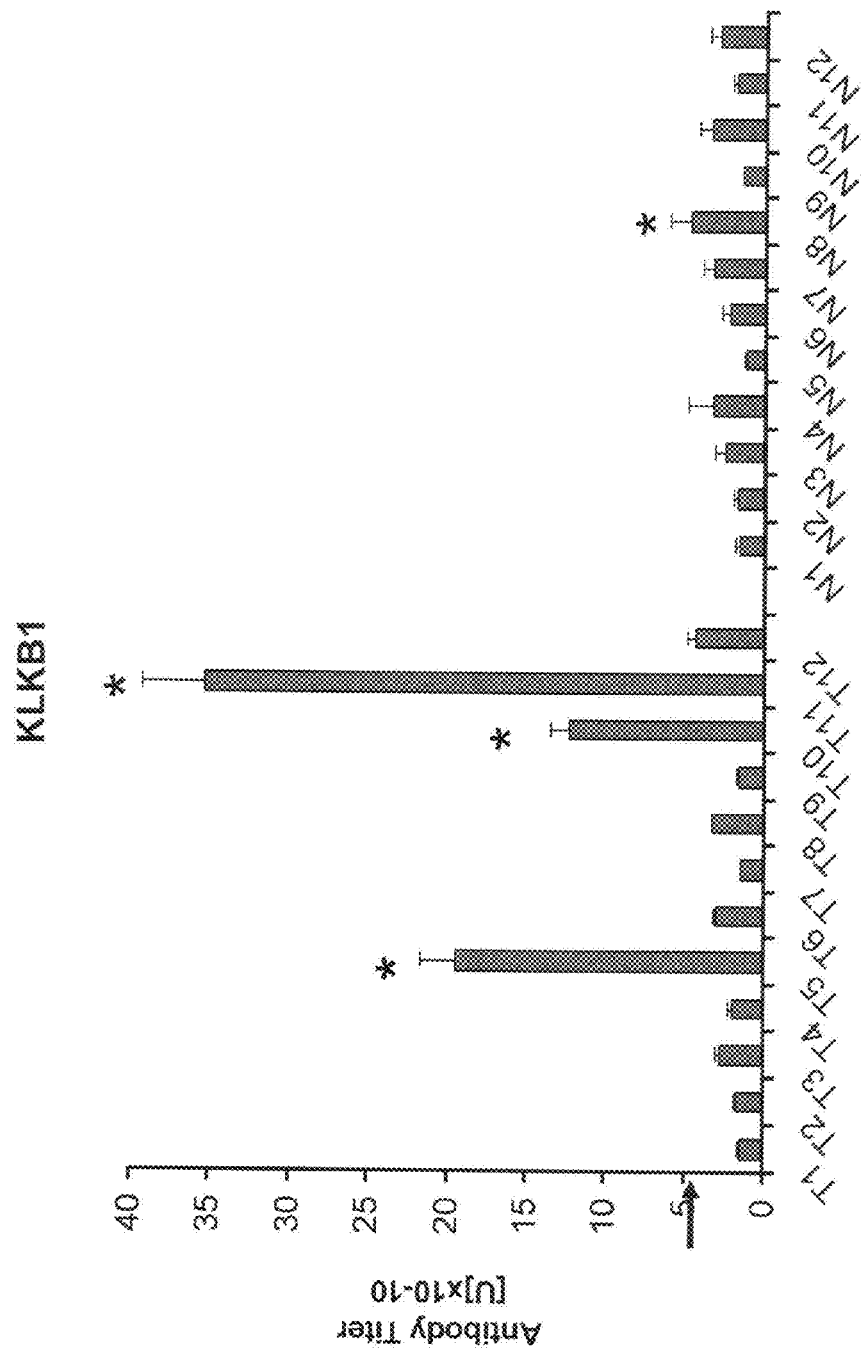

Autoantibody Responses Observed in Lung Cancer Serum Samples

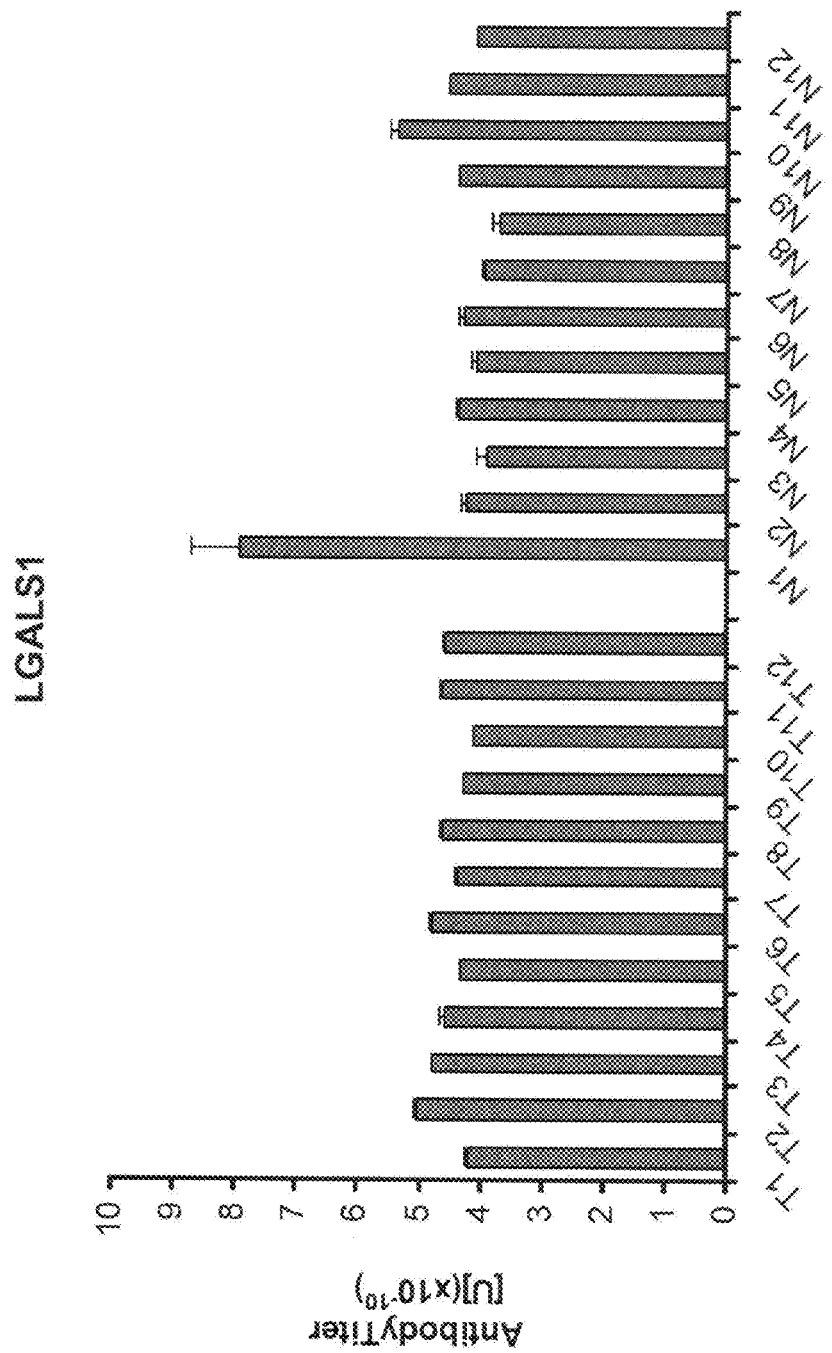

FIGURE 14
Autoantibody Detection in Lung Cancer Sera

| Autoantibody Target | | Histology | Squamous cell carcinoma | Adeno/Squamous cell carcinoma | Squamous cell carcinoma | Adeno/Squa mous cell carcinoma | Adeno/Squa mous cell carcinoma | Small-cell Carcinoma | Adeno/Squa mous cell carcinoma | Adenocarcino ma | Squamous cell carcinoma | Adeno/Squa mous cell carcinoma | Adeno/Squa mous cell carcinoma | Adenocarcino ma |
|---|---|---|---|---|---|---|---|---|---|---|---|---|---|---|
| | | Stage | STAGE III | STAGE III | STAGE III | STAGE III | STAGE IIIB | STAGE III | STAGE III | STAGE III | STAGE III | STAGE IIIB | STAGE III | STAGE III |
| Commercial Assay | p53 | Tumor | 0.0 | 0.0 | 21 | 0.0 | 0.0 | 46 | 204 | 44 | 0.0 | 0.0 | 0.0 | 52 |
| | | Normal | 0.0 | 0.0 | 0.0 | 0.0 | 0.0 | 0.0 | 0.0 | 0.0 | 0.0 | 0.0 | 0.0 | 0.0 |
| Internal Assay | p53 | Tumor | 0.0 | 0.0 | 25 | 0.0 | 0.0 | 124 | 314 | 0.0 | 0.0 | 0.0 | 0.0 | 0.0 |
| | | Normal | 0.0 | 0.0 | 0.0 | 0.0 | 0.0 | 0.0 | 0.0 | 0.0 | 0.0 | 0.0 | 0.0 | 0.0 |
| | CA12 | Tumor | 0.0 | 0.0 | 0.0 | 1.3 | 0.0 | 0.0 | 0.0 | 2.1 | 0.0 | 3.53 | 2.1 | 0.0 |
| | | Normal | 0.0 | 0.0 | 0.0 | 0.0 | 0.0 | 0.0 | 0.0 | 0.0 | 0.0 | 1.4 | 0.0 | 0.0 |
| | KLKB1 | Tumor | 0.0 | 0.0 | 0.0 | 0.0 | 4.3 | 0.0 | 0.0 | 0.0 | 0.0 | 2.7 | 7.8 | 0.0 |
| | | Normal | 0.0 | 0.0 | 0.0 | 0.0 | 0.0 | 0.0 | 0.0 | 1.0 | 0.0 | 0.0 | 0.0 | 0.0 |
| | LGALS1 | Tumor | 0.0 | 0.0 | 0.0 | 0.0 | 2.2 | 0.0 | 0.0 | 0.0 | 0.0 | 0.0 | 0.0 | 0.0 |
| | | Normal | 1.2 | 0.0 | 0.0 | 0.0 | 0.0 | 0.0 | 0.0 | 0.0 | 0.0 | 0.0 | 0.0 | 0.0 |
| | CFLN | Tumor | 0.0 | 0.0 | 0.0 | 0.0 | 0.0 | 0.0 | 0.0 | 0.0 | 0.0 | 1.1 | 2.1 | 0.0 |
| | | Normal | 0.0 | 0.0 | 0.0 | 0.0 | 0.0 | 0.0 | 0.0 | 0.0 | 0.0 | 1.1 | 0.0 | 0.0 |
| | EEF1G | Tumor | 0.0 | 1.2 | 0.0 | 1.2 | 0.0 | 0.0 | 0.0 | 0.0 | 0.0 | 0.0 | 0.0 | 0.0 |
| | | Normal | 1.2 | 0.0 | 0.0 | 0.0 | 0.0 | 0.0 | 0.0 | 0.0 | 0.0 | 0.0 | 0.0 | 0.0 |

Additional Lung Cancer Markers
*May be Added to Biomarker Panel to Enhance Performance*

FIGURE 16
Clinicopathological Characteristics of Lung Cancer Serum Samples

| | Screen | | Validation ("44x39" excl. small cell; "44x44" incl. 5 small cell cases) | | Training ("54x53") | | Testing ("50x50") | |
|---|---|---|---|---|---|---|---|---|
| | Controls | Cases | Controls | Cases | Controls | Cases | Controls | Cases |
| Gender | 12 | 12 | 44 | 39 [44, incl. 5 small cell cases] | 54 | 53 | 50 | 50 |
| Male | 8 | 8 | 26 | 23 | 38 | 36 | 31 | 26 |
| Female | 4 | 4 | 18 | 16 | 17 | 16 | 19 | 24 |
| Age | | | | | | | | |
| Mean (SD) | 54.3 (8.1) | 56.9 (9.1) | 65.6 (9.7) | 66.1 (10.2) | 67.2 (12.5) | 70.2 (9.6) | 71.6 | 73.9 |
| Smoking Status | | | | | | | | |
| N | NA | NA | 26 | 2 | | | 5 | |
| Y | NA | NA | 18 | 37 | 54 | 53 | 45 | 50 |
| Pack Years | NA | NA | 22 | 37 | 21.4 | 27.1 | 20.1 | 26.7 |
| Tumor Stage | | | | | | | | |
| I | | | | 32 | | 18 | | 14 |
| II | | | | 7 | | 13 | | 13 |
| III | | 6 | | | | 13 | | 12 |
| IV | | 6 | | | | 9 | | 11 |
| Tumor Histology | | | | | | | | |
| Adenocarcinoma | | 2 | | 19 | | 33 | | 21 |
| Squamous Cell Carcinoma | | | | 12 | | 13 | | 11 |
| Large Cell Carcinoma | | | | 3 | | 7 | | 4 |
| Other NSC | | | | 5 | | | | 7 |
| Bronchioloalveolar Carcinoma | | 1 | | | | | | 5 |
| Neuroendocrine | | | | | | | | 2 |
| Adeno-Squamous | | 7 | | | | | | |
| Oat Cell Carcinoma | | 1 | | | | | | |
| Small Cell Carcinoma | | 1 | | [5] | | | | |

FIGURE 17
Performance of Panel of Nine Biomarkers
*Split-Point Analysis Applying Manually Defined Cut-offs*

49/50 = 98% Specificity

48/50 = 96% Sensitivity

FIGURE 19
Analysis of Markers to Monitor Lung Tumor Regression/Recurrence

Reduced Levels of Markers Following Tumor Resection

| CEA | Cyfra | NSE | TIMP-1 | OPN | TFPI | MDK | SLPI | DEFA1 | SCC | GRP | # of Markers with >50% Drop |
|---|---|---|---|---|---|---|---|---|---|---|---|
| -50.8 | -10.7 | -49.3 | 37.6 | -3.5 | | -78.4 | -1.2 | -2 | -38.5 | 13.7 | 2 |
| | -93.9 | 10.2 | 9.4 | 4.7 | -10.0 | -70.4 | -8.4 | -31 | -68.1 | 56.6 | 3 |
| | | 11.3 | 1.9 | | -6.1 | | -6.3 | 17.7 | | -81.6 | 1 |
| -33.7 | -81.2 | -14.3 | 31.6 | 8.1 | 18.9 | -84.3 | 6.4 | -36.3 | | -22.1 | 2 |
| -75.9 | -19.2 | 26.3 | 49.9 | | 23.4 | | -2.4 | -21.6 | 29.9 | 149.0 | 0 |
| -15.4 | -56.5 | -32.8 | 71.5 | 61.7 | 3.0 | | 7.1 | 47.9 | | -76.3 | 3 |
| -40.2 | -11.8 | -3.2 | 85.6 | 0.6 | 1.2 | | 21.7 | 6.9 | -19.7 | -43.0 | 0 |
| 14.8 | | -2.0 | 15.4 | -22.6 | -0.8 | | 6.1 | 29.6 | -25.2 | -28.9 | 0 |
| -35.3 | 17.9 | -34.4 | 95.7 | | 30.6 | | 9.0 | -22.4 | | -13.6 | 0 |
| -39.2 | -62.8 | 3.7 | 62.2 | 32.6 | 42.9 | | -13.0 | 71 | -63.1 | -75.0 | 1 |
| -50.0 | -32.8 | -30.6 | 24.7 | 127.9 | 10.1 | | -24.9 | -9.8 | | 85.5 | 2 |
| -19.4 | | -30.0 | 11.2 | 42.2 | -12.1 | -94.0 | 12.2 | 6.4 | -63.4 | 8.4 | 0 |
| -20.7 | -98.2 | -6.0 | 32.5 | -12.2 | -60.0 | -1.0 | -3.6 | -33.5 | -36.1 | 26.9 | 4 |
| | -76.6 | -17.9 | 26.1 | | -59.7 | | 6.4 | -46 | | -49.2 | 3 |
| -11.6 | -5.4 | 32.8 | 84.9 | 382.5 | 10.7 | 232.1 | 48.0 | 2.8 | -68.1 | -75.1 | 1 |
| -5.2 | | -46.1 | 37.6 | 275.6 | -62.8 | 15.4 | 20.9 | | -71.4 | 127.1 | 3 |
| -95.9 | 73.3 | 44.1 | 77.5 | 37.6 | 16.0 | 2.9 | 30.0 | | -69.6 | | 1 |
| -66.4 | -29.2 | -27.9 | 52.3 | -46.5 | 18.4 | -40.0 | 0.1 | -27.9 | -54.2 | -74.8 | 2 |
| -90.0 | | -20.6 | -0.2 | | -0.8 | 2.3 | -12.9 | 85.3 | -81.7 | | 3 |
| -85.1 | -89.1 | -8.5 | 10.0 | 204.4 | 6.6 | -71.1 | 13.2 | -29.7 | -66.2 | | 2 |
| 27.3 | 59.2 | 1.0 | 234.1 | 41.9 | 30.2 | 63.1 | 36.3 | 619.4 | -67.4 | 79.4 | 3 |
| -42.0 | -20.6 | -23.5 | 32.0 | 103.6 | -19.5 | 97.2 | -1.0 | 46.3 | 1.6 | | 1 |
| | 7.9 | | 12.7 | 457.5 | -57.8 | -43.7 | 3.0 | -66.7 | -19.0 | -5.5 | 2 |
| | 9.8 | | 32.1 | 65.7 | 8.8 | 55.6 | 44.1 | 106.6 | -66.6 | -34.8 | 0 |
| -48.7 | -26.9 | -15.8 | 132.5 | | 5.2 | 142.5 | 6.7 | 71.4 | -11.2 | -39.9 | 1 |
| | | | 121.7 | | 85.3 | 85.9 | -2.3 | 462.9 | | | 0 |
| | | | | | | | | | | Sensitivity | 73.1% |

FIGURE 20

Expression of Biomarker Panel in Co-morbid Lung Diseases

| | Cyfra | CEA | SLPI | OPN | MDK | TFPI | TIMP1 | MMP2 | SCC | # > cut-off |
|---|---|---|---|---|---|---|---|---|---|---|
| Cut-off | 3.50 | 5.60 | 55 | 70 | 0.7 | 70 | 440 | 315 | 2.2 | |
| ASTHMA | 0.938 | 3.169 | 44.38 | 23.179 | 0 | 29.127 | 331.8 | 199.59 | 3.859 | 1 |
| | 0.278 | 2.782 | 61.02 | 12.422 | 0.071 | 38.477 | 307.8 | 194.43 | 0.607 | 1 |
| | 0.935 | 3.123 | 23.87 | 2.008 | 0 | 31.089 | 295.7 | 174.05 | 0.449 | 0 |
| | 0.129 | 3.326 | 39.99 | 11.425 | 0.079 | 47.766 | 310.8 | 185.5 | 0.274 | 0 |
| | 0.161 | 8.99 | 53.02 | 8.707 | 0.414 | 42.97 | 308.2 | 222.22 | 0.434 | 0 |
| | 0.37 | 3.662 | 30.26 | 10.858 | 0.09 | 33.236 | 325.8 | 180.14 | 0.159 | 0 |
| | 2.964 | 1.103 | 50.05 | 2.4 | 0.014 | 23.047 | 426.9 | 164.1 | 0.044 | 0 |
| | 0.555 | 0.958 | 41.67 | 7.907 | 0.058 | 31.811 | 332.1 | 154.18 | 0.625 | 0 |
| | 1.278 | 2.398 | 29.95 | 27.196 | 0.026 | 39.674 | 331 | 277.1 | 0.319 | 0 |
| | 0.65 | 2.194 | 40.93 | 11.909 | 0.224 | 36.893 | 406.8 | 186.64 | 0.141 | 0 |
| | 0.323 | 0.738 | 26.66 | 12.189 | 0.098 | 28.654 | 351.9 | 241.51 | 0.151 | 0 |
| | 0.163 | 2.454 | 32.56 | 3.517 | 0.053 | 35.709 | 286.9 | 186.38 | 0.123 | 0 |
| | 0.136 | 2.692 | 34.83 | 12.055 | 0.089 | 32.403 | 336.6 | 180.59 | 0 | 0 |
| | 1.264 | 2.914 | 24.46 | 3.523 | 0 | 40.545 | 322.1 | 157.47 | 0.28 | 0 |
| Benign Lung | 2.305 | 2.595 | 38.48 | 21.287 | 0.128 | 25.496 | 288.2 | 176.85 | 1.286 | 0 |
| | 0.621 | 31.52 | 27.13 | 2.88 | 0.052 | 23.182 | 308.8 | 190.62 | 0.431 | 0 |
| | 1.147 | 3.375 | 16.22 | 0.405 | 0 | 31.681 | 155.5 | 221.54 | 0.854 | 0 |
| | 0.425 | 4.906 | 21.52 | 2.297 | 0 | 39.045 | 248.1 | 155.7 | 1.32 | 1 |
| | 2.727 | 4.111 | 46.13 | 11.541 | 0.116 | 53.486 | 531.8 | 240.04 | 0.608 | 0 |
| | 1.085 | 2.268 | 32.74 | 3.622 | 0.067 | 42.254 | 246 | 215.56 | 0.697 | 1 |
| | 1.906 | 6.759 | 35.6 | 12.123 | 0 | 53.038 | 249.5 | 203.74 | 0.756 | 0 |
| | 1.32 | 3.421 | 24.02 | 1.658 | 0 | 27.517 | 330.4 | 175.26 | 0.701 | 1 |
| | 0.495 | 30.817 | 24.66 | 2.777 | 0.124 | 24.823 | 347.7 | 209.6 | 0.373 | 1 |
| | 0.767 | 2.49 | 38.03 | 31.37 | 0.007 | 20.45 | 321.1 | 199.98 | 1.865 | 0 |
| | 0.657 | 3.609 | 36.7 | 24.856 | | 27.759 | 387.4 | 205.74 | 0.112 | 0 |
| | 0.939 | 2.605 | 26.77 | 27.448 | 0.007 | 26.267 | 262.1 | 217.1 | 0.561 | 0 |
| Bronchitis | 0.812 | 1.44 | 51.8 | 37.672 | 0.302 | 58.738 | 322.7 | 119.71 | 1.06 | 0 |
| | 0.628 | 2.116 | 45.78 | 45.564 | 0.07 | 14.863 | 272.4 | 268.72 | 0 | 0 |
| | 1.949 | 5.379 | 37.67 | 18.749 | 0.23 | 53.203 | 317.1 | 195.39 | 2.091 | 0 |
| | 1.686 | 1.654 | 54.79 | 29.518 | 0.447 | 90.038 | 337.9 | 194.08 | 0.164 | 1 |

Integration of clinical data enhances performance of LCM panel

LUNG CANCER MARKERS, AND USES THEREOF

FIELD OF THE INVENTION

This invention relates to the field of disease assessment and therapy. The invention provides compositions and methods for assessing and treating diseases, especially cancer, and particularly lung cancer.

BACKGROUND OF THE INVENTION

Cancer is one of the leading causes of death worldwide, and cancer, especially lung cancer, is difficult to diagnose and treat effectively. Accordingly, there is a need in the art for new compositions and methods for assessing and treating various cancers, particularly lung cancer.

Lung Cancer

Lung cancer is the second most prevalent type of cancer for both men and women in the United States and is the most common cause of cancer death in both men and women. The five-year survival rate for lung cancer continues to be poor at only about 8-15%. This low survival is because lung cancer is commonly not detected until it has spread beyond the lungs. Only 16% of new lung cancer cases in the United States are detected at the earliest stage, when the cancer is still localized to the lungs. At this early stage, survival is considerably higher, with estimates as high as 70-80%. Therefore, procedures for detecting lung cancer are of critical importance to the outcome of a patient since these procedures have the potential to reduce mortality. Thus, there is a need for new diagnostic compositions and methods that are more sensitive and specific for detecting early lung cancer.

Furthermore, there is also a need for new diagnostic compositions and methods for determining the stage of a patient's disease. Stage determination has potential prognostic value and provides criteria for designing optimal therapy. Biomarkers that are indicative of different stages of lung cancer would be useful to facilitate the staging of lung cancer.

Lung cancer patients are typically monitored following initial therapy and during adjuvant therapy to determine their response to therapy and to detect persistent or recurrent disease or metastasis. Thus, there is clearly a need for lung cancer markers that are more sensitive and specific in detecting lung cancer, its recurrence, and progression.

Although imaging modalities, such as computed tomography (CT) screening, are being studied to aid in the early detection of lung cancer, controversy remains as to the ability of these methods to impact mortality (1-ELCAP Investigators, *NEJM* 2006 (355):1763-71 and Bach et al. 2007. *JAMA* 297:953-961). In addition, the most advanced imaging technologies under study are expensive and not widely available. These CT imaging tests may lead to over-diagnosis of lung cancer, resulting in significant expenses to the health care system to manage patients with pulmonary nodules observed through these CT imaging tests. Furthermore, there is significant morbidity associated with the management of the pulmonary nodules in an effort to ascertain whether the nodules are malignant or benign. It is estimated that 10-50% of smokers in a high risk group have pulmonary nodules upon imaging studies (*CHEST* 2007 *Supplement—Evidence for the Treatment of Patients With Pulmonary Nodules: When Is It Lung cancer?: AACP Evidence-Based Clinical Practice Guidelines*). Thus, there is a significant need for novel diagnostics that can be used either independently or with imaging modalities for early diagnosis and improved management of patients with lung cancer. For example, a blood test for biomarkers that has high performance (e.g., high sensitivity and specificity) for detecting lung cancer could provide a low cost complement to CT testing for early detection of cancer. If the performance of a biomarker test were sufficiently high, such a test could serve as a lower cost alternative to CT or X-ray testing. For example, only those patients that tested positive in a biomarker test may then need to undergo more expensive imaging tests. Furthermore, a biomarker test could be used, for example, in a yearly screening regimen for lung cancer.

Although there have been reports of circulating tumor markers and antigens with potential use in lung cancer (see Schneider, J. 2006. *Advances in Clin Chem*, 42: 1-41 for a review), markers currently used generally suffer from low sensitivity and less than desirable specificity, especially among smokers (Schneider, 2006), and are typically only used to monitor for recurrence of lung cancer. Thus, there is a need in the art for a panel of markers with high sensitivity (and varying specificities, depending on the clinical indication), such as for detecting lung cancer. Furthermore, there is also a need for novel markers that are useful individually or as part of a panel for detecting lung cancer. Such markers, and panels of markers, would facilitate management of patients with lung cancer, for example.

For a further review of lung cancer diagnostics, including the use of tumor biomarkers as well as CT screening, see the following citations: Schneider, "Tumor markers in detection of lung cancer", *Adv Clin Chem.* 2006; 42:1-41; Bach et al., "Computed tomography screening and lung cancer outcomes", *JAMA*. 2007 Mar. 7; 297(9):953-61; and International Early Lung Cancer Action Program Investigators et al., "Survival of patients with stage I lung cancer detected on CT screening", *N Engl J. Med.* 2006 Oct. 26; 355(17):1763-71. Also see Pepe et al., "Phases of biomarker development for early detection of cancer", *J Nat'l Cancer Inst.* 2001. 93(14): 1054-1061

Description of Tables 1-2

Tables 1 and 2 provide further information for lung cancer markers ("LCM"), including their names, symbols (alternative symbols are indicated in parentheses), Genbank protein accession numbers, and an exemplary protein sequence for each marker (except for the carbohydrate antigens CA 242, CA 19-9, and CA 72-4, for which representative journal citations are provided for each). Exemplary LCM protein sequences are provided as SEQ ID NOS:1-65 (additionally, the carbohydrate antigens CA 242, CA 19-9, and CA 72-4 are also provided). Nucleic acid sequences (e.g., mRNA transcript sequences and genomic DNA) and alternative protein sequences for each marker are well known in the art and can readily be derived using the information provided in Tables 1-2, for example.

The LCM provided in Table 1 are as follows (alternative names/symbols are indicated in parentheses): SLPI, MIF, TIMP1, TFPI, ENO2 (NSE), CEA (CEACAM5), MMP2, AMBP, Cyfra 21-1 (Cyfra, KRT19), SCC (SERPINB3), OPN, defensin (DEFA1, HNP-1, HNP1-3), CA 242, CA 19-9, CA 72-4, MN/CAIX (CA9), ProGRP (GRP), KRT18 (TPS), ECAD (CDH1), TIMP2, CD44, LGALS3BP, ERBB2 (HER-2), UPA (PLAU), DKK (DKK1), CHGA, VEGF, KITLG, PBEF (visfatin), SORT1 (sortilin), MDK (midkine), IGFBP3, IGFBP4, CTSC, ICAM3, CTGF, LCN2, EGFR, BGN, TIMP3, HGF, MUC16 (CA125), NCAM, CRP, SERPINA1 (ATT), PKM2, RBP, KLK11, KLK13, SAA, and APOC3.

The LCM provided in Table 2 (which are particularly useful as autoantibody markers) are as follows (alternative names/symbols are indicated in parentheses): TP53 (p53), KLKB1, CFL1 (CFLN), EEF1G, HSP90α (HSP90AA1), RTN4, ALDOA, GLG1, PTK7, EFEMP1, SLC3A2 (CD98), CHGB, CEACAM1, ALCAM, HSPB1 (HSP27), LGALS1, and B7H3.

Elevated levels of each of these LCM are indicative of lung cancer, except for sortilin (SORT1), for which low levels are indicative of lung cancer.

Description of Tables 3-12

Table 3 provides 35 different panels of 11 markers (each row of 11 markers represents a panel) that have at least 98% specificity and 82% sensitivity for detecting lung cancer. The total number of occurrences of each marker in these 35 11-marker panels is indicated at the bottom of Table 3. Seven markers (SLPI, TIMP1, TFPI, SCC, OPN, CEA and CA242) appear in all 35 of these panels, GRP appears in 33 of these 35 panels, MIF appears in 29 of these 35 panels, and NSE and HNP-1 each appear in 15 of these 35 panels. AMBP, Cyfra, MMP2, Ca72-4, Ca19-9, and CAIX each appear in 7-9 of these panels, as indicated in Table 3.

Table 4 provides markers the can be included in any of the panels disclosed herein. For example, the markers in Table 4 can be added to any of the panels disclosed herein and/or can replace one or more members of any of the panels disclosed herein. As a specific example, the markers in Table 4 can be added to any of the panels disclosed in Table 5 and/or can replace one or more members of any of the panels disclosed in Table 5. The markers disclosed in Table 4 are also disclosed in Table 2.

Tables 5-12 provide data for the analysis of various panels in various lung cancer uses, such as distinguishing lung cancer samples versus normal samples such as for diagnosing/detecting lung cancer (Tables 5-6 and 11-12, for example), as well as certain specific uses (these specific uses, which may be referred to herein as "indications" or as determining or assessing lung cancer "characteristics", are provided in Tables 7-10, for example). In Tables 5-12, each row represents a panel (a panel may comprise an individual marker). For each panel in Tables 5-12, data are presented based on logistic regression and/or split point analysis (as indicated in each table). Area under the curve (AUC), sensitivity at 95% specificity, and specificity at 95% sensitivity are indicated. "Size" (second column) indicates the number of markers in the given panel. Further information regarding characteristics of the sample sets (the "54×53", "50×50", and "44×44" sample sets) used in each of the analyses is provided in FIG. 16 (the "104×103" sample set used in Table 8 is the "54×53" and "50×50" sample sets combined). In Tables 5-12, and elsewhere herein, "trained" refers to the sample set (which may be referred to as the "training set") which was used to formulate cutoff levels, and "tested" refers to the sample set (which may be referred to as the "testing set") to which these cutoff levels were applied (such as to classify a sample as a lung tumor or normal sample, or other specific use, based on whether marker levels were above or below the cutoff levels established from the training set).

Table 5 provides data for logistic regression and split-point analysis of the 9-marker panel of Cyfra, SLPI, TIMP1, SCC, TFPI, CEACAM5, MMP2, OPN, and MDK, and all subcombinations thereof (including individual markers), in distinguishing lung tumor samples versus normal (i.e., control/healthy) samples, such as for diagnosing/detecting lung cancer. For each panel in Table 5, data are presented based on logistic regression and split point analysis and based on analysis of either training and testing on the same 54×53 (54 controls and 53 cases) sample set, or training on the 54×53 sample set and testing on the 50×50 (50 controls×50 cases) sample set (see FIG. 16 for characteristics of these sample sets). Area under the curve (AUC), sensitivity at 95% specificity, and specificity at 95% sensitivity are indicated. The panels are sorted based on the AUC indicated in the third column. "Size" (second column) indicates the number of markers in the given panel. Thus, Table 5 provides the 9-marker panel of Cyfra, SLPI, TIMP1, SCC, TFPI, CEACAM5, MMP2, OPN, and MDK, and all panel subcombinations thereof, including each of these nine markers individually (each row represents a panel).

Table 6 provides data for split-point analysis of panels (including individual markers) that include any of the nine markers in the panels provided in Table 5 and/or various other markers (which are not in the panels provided in Table 5) in distinguishing lung tumor samples versus normal (i.e., control/healthy) samples, such as for diagnosing/detecting lung cancer.

Table 7 provides data for logistic regression analysis of the 9-marker panel of Cyfra, SLPI, TIMP1, SCC, TFPI, CEACAM5, MMP2, OPN, and MDK, and subcombinations thereof (including individual markers), in distinguishing adenocarcinoma versus squamous cell carcinoma types of lung cancer.

Table 8 provides data for split-point analysis of the 9-marker panel of Cyfra, SLPI, TIMP1, SCC, TFPI, CEACAM5, MMP2, OPN, and MDK, and subcombinations thereof (including individual markers), in distinguishing stage I versus stage III lung cancer. In addition to their utility in distinguishing between early and late stage lung cancer (e.g., stage I or II versus stage III or IV), the panels provided in Table 8 are also useful for distinguishing between any other stages of lung cancer (e.g., any of stages I, II, III, and IV).

Table 9 provides data for split-point analysis of various panels in distinguishing small cell lung cancer (SCLC) versus other types of lung cancer (e.g., non-small cell lung cancer, NSCLC). In the left-side of Table 9, marker levels are higher in NSCLC (as compared to SCLC). In the right-side of Table 9, marker levels are higher in SCLC (as compared to NSCLC).

Table 10 provides data for split-point analysis of the 9-marker panel of Cyfra, SLPI, TIMP1, SCC, TFPI, CEACAM5, MMP2, OPN, and MDK, and subcombinations thereof (including individual markers), in distinguishing malignant lung tumors versus benign lung lesions.

Table 11 provides data for split-point analysis of various panels in distinguishing small cell lung cancer (SCLC) versus normal (i.e., control/healthy) samples.

Table 12 provides data for split-point analysis of various panels in distinguishing lung cancer (including both small cell lung cancer (SCLC) and non-small cell lung cancer (NSCLC)) versus normal (i.e., control/healthy) samples.

BRIEF DESCRIPTION OF THE FIGURES

FIG. 1. Shows relative expression levels for exemplary lung cancer markers (LCM) screened by ELISA in a sample set of 12 lung tumor and 12 normal serum samples. The left portion of the table shown in FIG. 1 provides tumor samples identified by histology and tumor state (histology abbreviations for tumor samples are "AS"=adenosquamous, "A"=adenocarcinoma, "SC"=squamous cell carcinoma, and "BAC"=bronchioalveolar carcinoma), and the right portion of the table shows normal samples (identified as "N" for histology). The table is based on mean concentration values of each sample and uses 2 standard deviations (2SD) above normal mean as the cutoff; the value is expressed as fold change from normal mean (thus, any fold change with 2SD above normal mean is above the cutoff). The column labeled "CRA MS" is a summary of mass spectrometry data that indicates the number of differentially expressed lung tumor samples and the median mass spec ratio of these samples (numerical representation of over-expression is indicated by 2.0 or more, whereas numerical representation of under-expression is indicated by 0.5 or less) (lung tumor sample abbreviations for mass spectrometry are "CL LU"=lung cancer cell lines, "TS LU"=lung cancer tissues, and "CM LU"=lung cancer conditioned medium).

FIG. 2. Shows relative expression levels based on ELISA screening of a sample set of 12 lung tumor (upper section) and 12 normal (lower section) serum samples for the eight markers TFPI, SCC (interchangeably referred to as SSC), CEA, CA242, MNCAIX, OPN, Cyfra 21-1, and MIF (as also shown in FIG. 1). The table is based on mean concentration values of each sample and uses 2 standard deviations (2SD) above normal mean as the cutoff; the value is expressed as fold change from normal mean (thus, any fold change with 2SD above normal mean is above the cutoff). Any value below the cut-off is recoded as 0. Any or all of these eight markers may be used in combination as a panel for lung cancer assessment, and the panel may optionally include additional markers.

FIG. 4. Shows relative expression levels based on ELISA screening of a sample set of 12 lung tumor (left portion; histology ("Hist") abbreviations are "AS"=adenosquamous, "A"=adenocarcinoma, "SC"=squamous cell carcinoma, "OC"=oat cell carcinoma, and "BAC"=bronchioalveolar carcinoma) and 12 normal (right portion; identified as "N" for histology) serum samples for alternate panels of LCM, including a panel of the markers SLPI, TFPI, OPN, MIF, TIMP1, and MMP2. Any or all of these markers can also be used in any combination with any or all of the following markers: CA242, SCC, CEA, NSE, CA72-4, CA19-9, Cyfra 21-1, and MN/CAIX, as shown in FIG. 4. The table is based on mean concentration values of each sample and uses two standard deviations (2SD) above normal mean as the cut-off; the value is expressed as fold change from normal mean (thus, any fold change with 2SD above normal mean is above the cutoff). Any value below the cut-off is recoded as 0.

FIG. 6. Shows results of ELISA analysis for the 11 markers Cyfra 21-1, MIF, TIMP1, TFPI, CEA, OPN, SCC, SLPI, HNP-1, GRP, and CA242 in 39 control (normal) samples (left portion, labeled "Control") and 39 lung tumor samples (right portion, labeled "Tumor"). Values shown are concentration (ng/mL). Manually defined cut-offs are indicated immediately below each marker name. The columns labeled "#>cut-off" indicate the total number of markers with elevated expression (i.e., a concentration greater than the manually defined cut-offs) in a given serum sample. "Stage" indicates lung cancer stage, and "Hist Type" indicates histology type. Any or all of these 11 markers may be used in combination as a panel for lung cancer assessment, and the panel may optionally include additional markers.

FIG. 8. Shows examples of applying a cut-off for various markers (Cyfra 21-1, MIF, SLPI, TIMP1, SCC, NSE, TFPI, CEA, MMP2, OPN, and AMBP are shown) that provides desirable performance for that marker. The circles show the approximate location of an exemplary cut-off for each marker which is the point on the curve that is closest to the upper-left corner. Different criteria can also be used, for instance false negatives could be weighted more heavily than false positives.

FIG. 11. Shows results of analysis for certain autoantibody markers (bottom table), as well as certain other lung cancer markers (top table). In the bottom table (autoantibody markers), the column labeled "Lung MS data" indicates a summary of where differential expression has been observed by mass spectrometry (CL=cell lines, TS=tissues, CM=conditioned medium, and IP=immunoprecipitation), the column labeled "SEREX data" indicates autoantibody markers that overlap with the Serological Expression (SEREX) database which identifies markers that elicit a high-titer IgG antibodies, and the column labeled "Rec Protein" indicates the source of recombinant protein used for autoantibody analysis ("vendor" indicates an external commercial source and "CRA" indicates an internal source). Histology abbreviations for tumor samples in the top table are "AS"=adenosquamous, "A"=adenocarcinoma, "SC"=squamous cell carcinoma, and "SM"=small cell carcinoma.

FIG. 12. Shows exemplary autoantibody LCM, which can be used alone or in combination with other LCM. Certain of these autoantibody LCM are also provided in Table 2 along with other autoantibody LCM.

FIG. 14. Shows autoantibody detection in lung cancer and normal serum samples for the autoantibody markers CA12, KLKB1, CFLN, LGALS1, and EEF1G, as well as p53. Autoantibody markers CA12KLKB1, and CFLN (cofilin). The table is based on mean concentration values of each sample and uses 2SD above normal mean as the cut-off. Any value below the cutoff is recoded as 0. p53 showed 0 response in normal sera, therefore absolute titers are listed for p53 (positive antibody-dependent values).

FIG. 15 shows abundance levels (in ng/mL) of these three markers in 12 normal lung and 12 lung tumor samples based on ELISA analysis. For sortilin (SORT-1), abundance levels (by relative copy number) of this marker based on mRNA expression analysis of 22 normal lung and 23 lung tumor samples is also provided. For sortilin, lung tumor samples have a decreased abundance level of this marker compared with normal lung samples.

FIG. 16. Shows clinicopathological characteristics of lung cancer serum samples used in various analyses disclosed herein.

FIG. 17. Shows results of ELISA analysis for the 9-marker panel of Cyfra, SLPI, TIMP1, SCC, TFPI, CEACAM5, MMP2, OPN, and MDK in 50 control (normal) samples (left portion, labeled "Normal") and 50 lung tumor samples (right portion, labeled "Tumor"), using split-point analysis applying manually defined cut-offs. The manually defined cut-offs are indicated immediately below each marker name. Values shown are concentration (ng/mL). The columns labeled "≧cut off" indicate the total number of markers with elevated expression (i.e., a concentration greater than or equal to the manually defined cut-offs) in a given serum sample. "Histology" indicates histology type ("adeno"=adenocarcinoma, "squ"=squamous cell carcinoma, "nsm" or "n-sm"=non-small cell carcinoma, "bro"=bronchioloalveolar carcinoma, "LG"=large cell carcinoma, and "neuro"=neuroendocrine). Any or all of these nine markers may be used in combination as a panel for lung cancer assessment, and the panel may optionally include additional markers.

FIG. 19. Shows an analysis of markers to monitor for lung tumor regression/recurrence. Percentage change in levels of biomarkers in patient serum 2-4 weeks post-surgery as compared to pre-surgical levels is indicated.

FIG. 20. Shows an analysis of the expression levels of the 9-marker panel of Cyfra, SLPI, TIMP1, SCC, TFPI, CEACAM5, MMP2, OPN, and MDK in the following co-morbid lung diseases: asthma, bronchitis, and benign lung diseases. Values shown are concentration (ng/mL). The column labeled "#>cut off" indicates the total number of markers with elevated expression (i.e., a concentration greater than the manually defined cut-offs) in a given serum sample. The manually defined cut-offs are indicated immediately below each marker name (in the row labeled "Cut-off").

DETAILED DESCRIPTION OF EXEMPLARY EMBODIMENTS OF THE INVENTION

Figure 3:
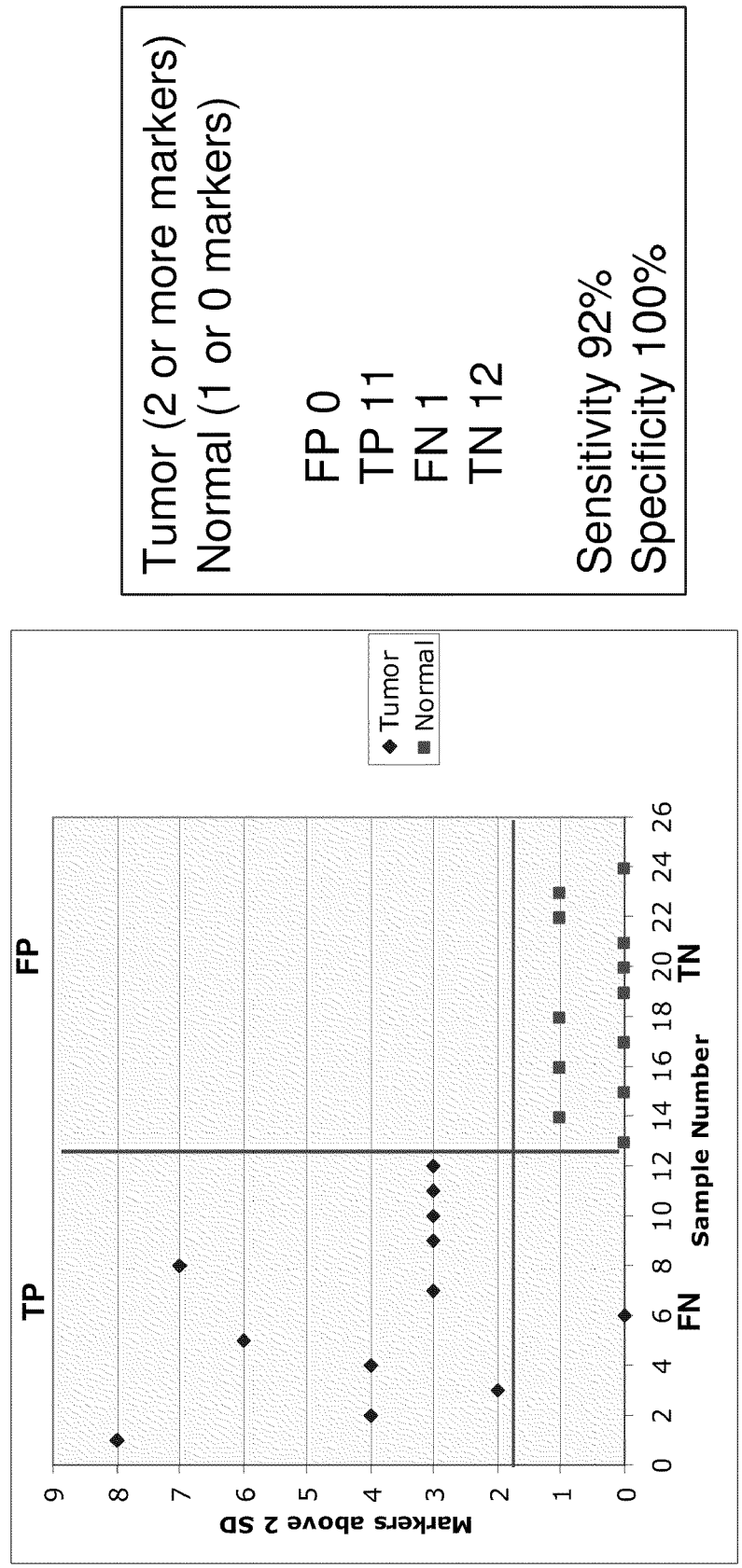
FIG. 3. Shows the performance of the eight marker panel of TFPI, SCC, CEA, CA242, MNCAIX, OPN, Cyfra 21-1, and MIF. Using an algorithm in which markers greater than or equal to two standard deviations were scored "positive", this panel of eight markers had a sensitivity of 92% and specificity of 100% among the 12 sera from lung cancer patients and 12 sera from healthy controls ("FP"=false positives, "TP"=true positives, "FN"=false negatives, and "TN"=true negatives)

The invention will best be understood by reference to the following detailed description of the exemplary embodiments, taken in conjunction with the accompanying table(s) and/or figure(s). The discussion below is exemplary and is not to be taken as limiting the scope defined by the claims.

Exemplary embodiments of the invention provide the following markers (see Tables 1-2), combinations of these markers, and methods of using these markers, particularly for lung cancer-related uses, and especially for lung cancer diagnostics (alternative names/symbols are indicated in parentheses): SLPI, MIF, TIMP1, TFPI, ENO2 (NSE), CEA (CEACAM5), MMP2, AMBP, Cyfra 21-1 (Cyfra, KRT19), SCC (SERPINB3), OPN, defensin (DEFA1, HNP-1, HNP1-3), CA 242, CA 19-9, CA 72-4, MN/CAIX (CA9), ProGRP (GRP), KRT18 (TPS), ECAD (CDH1), TIMP2, CD44, LGALS3BP, ERBB2 (HER-2), UPA (PLAU), DKK (DKK1), CHGA, VEGF, KITLG, PBEF (visfatin), SORT1 (sortilin), MDK (midkine), IGFBP3, IGFBP4, CTSC, ICAM3, CTGF, LCN2, EGFR, BGN, TIMP3, HGF, MUC16 (CA125), NCAM, CRP, SERPINA1 (ATT), PKM2, RBP, KLK11, KLK13, SAA, APOC3, TP53 (p53), KLKB1, CFL1 (CFLN), EEF1G, HSP90α (HSP90AA1), RTN4, ALDOA, GLG1, PTK7, EFEMP1, SLC3A2 (CD98), CHGB, CEACAM1, ALCAM, HSPB1 (HSP27), LGALS1, and B7H3, which are collectively referred to herein as "LCM" ("lung cancer markers"). Elevated levels of each of these LCM are indicative of lung cancer, except for sortilin (SORT1), for which low levels are indicative of lung cancer. Tables 1 and 2 provide further information for each of these LCM, including their names, symbols, Genbank protein accession numbers, and an exemplary protein sequence for each marker (except for the carbohydrate antigens CA 242, CA 19-9, and CA 72-4, for which representative journal citations are provided for each). Exemplary LCM protein sequences are provided as SEQ ID NOS: 1-65 (additionally, the carbohydrate antigens CA 242, CA 19-9, and CA 72-4 are also provided). Nucleic acid sequences (e.g., mRNA transcript sequences and genomic DNA) and alternative protein sequences for each marker are well known in the art and can readily be derived using the information provided in Tables 1-2, for example. The markers provided in Table 2 are particularly useful as autoantibody markers.

Certain embodiments of the invention provide combinations comprising, consisting of, and consisting essentially of the following nine LCM, and subcombinations thereof (these nine LCM may be referred to herein as the "9-marker panel", which is shown in FIG. 17 and Table 5, for example): Cyfra, SLPI, TIMP1, SCC, TFPI, CEACAM5, MMP2, OPN, and MDK. Certain embodiments of the invention provide compositions based on this 9-marker panel and subcombination thereof, and methods of using this 9-marker panel, particularly for uses related to lung cancer (such as detecting lung cancer). In certain embodiments, one or more members of this 9-marker panel is replaced by one or more markers shown in Table 4 and/or one or more markers shown in Table 4 is added to this 9-marker panel. With respect to the nine markers Cyfra, SLPI, TIMP1, SCC, TFPI, CEACAM5, MMP2, OPN, and MDK, elevated levels are indicative of lung cancer (for all of the LCM disclosed herein, elevated levels are indicative of lung cancer, except for sortilin (SORT1), for which low levels are indicative of lung cancer). In certain embodiments, if the levels of two or more markers (i.e., a "plurality") of the 9-marker panel are elevated in a sample (e.g., a serum sample) from an individual, this indicates that the individual has lung cancer. In various other embodiments, if the levels of one or more, three or more, four or more, five or more, six or more, seven or more, eight or more, or all nine markers of the 9-marker panel are elevated in a sample from an individual, this indicates that the individual has lung cancer. In certain embodiments, a marker is classified as being elevated if its level is greater than (or greater than or equal to) a predetermined cutoff level.

Furthermore, certain embodiments of the invention provide combinations comprising, consisting of, and consisting essentially of the following six LCM (each of which is also contained in the above 9-marker panel), and subcombinations thereof (these six LCM may be referred to herein as the "6-marker subset of the 9-marker panel", which is shown in Table 5): Cyfra, SLPI, TIMP1, TFPI, CEACAM5, and MDK. Certain embodiments of the invention provide compositions based on this 6-marker subset of the 9-marker panel and subcombination thereof, and methods of using this 6-marker subset of the 9-marker panel, particularly for uses related to lung cancer (such as detecting lung cancer). In certain embodiments, one or more members of this 6-marker subset of the 9-marker panel is replaced by one or more markers shown in Table 4 and/or one or more markers shown in Table 4 is added to this 6-marker subset of the 9-marker panel. With respect to the six markers Cyfra, SLPI, TIMP1, TFPI, CEACAM5, and MDK, elevated levels are indicative of lung cancer (for all of the LCM disclosed herein, elevated levels are indicative of lung cancer, except for sortilin (SORT1), for which low levels are indicative of lung cancer). In certain embodiments, if the levels of two or more markers (i.e., a "plurality") of the 6-marker subset of the 9-marker panel are elevated in a sample (e.g., a serum sample) from an individual, this indicates that the individual has lung cancer. In various other embodiments, if the levels of one or more, three or more, four or more, five or more, or all six markers of the 6-marker subset of the 9-marker panel are elevated in a sample from an individual, this indicates that the individual has lung cancer. In certain embodiments, a marker is classified as being elevated if its level is greater than (or greater than or equal to) a predetermined cutoff level.

Exemplary embodiments of the invention provide LCM and combinations of LCM (combinations of LCM may be interchangeably referred to herein as panels), and uses thereof, particularly uses related to lung cancer. For example, exemplary embodiments of the invention provide methods and compositions for assessing (e.g., diagnosing/detecting, prognosing, or predicting drug response), treating, and preventing diseases, especially cancer, and particularly lung cancer, using LCM. Furthermore, the compositions and methods of the invention may be suitable for other types of cancer, particularly other epithelial cell-related cancers and solid tumors, as well as other lung diseases.

LCM proteins and fragments thereof (LCM peptides), LCM carbohydrate antigens and fragments thereof, and LCM nucleic acid molecules and fragments thereof encoding LCM proteins and peptides, are collectively referred to as "LCM" or "markers" (which may be interchangeably referred to as "biomarkers", "antigens", or "targets").

The terms "protein" and "polypeptide" are used herein interchangeably. Furthermore, references herein to proteins/polypeptides may also typically encompass carbohydrate antigens ("CA"); for example, references to LCM proteins/polypeptides may also typically encompass the carbohydrate antigens CA 242, CA 19-9, and CA 72-4. Exemplary LCM protein/polypeptide sequences are provided as SEQ ID NOS: 1-65 (additionally, carbohydrate antigens CA 242, CA 19-9, and CA 72-4 are also provided). A "peptide" typically refers to a fragment of a protein/polypeptide. Thus, peptides are interchangeably referred to as fragments. References herein to proteins, peptides, carbohydrate antigens, nucleic acid molecules, and antibodies typically are not limited to the full-size or full-length molecule, but also can encompass fragments of these molecules (unless a particular sequence or structure is explicitly stated).

As used herein, a "lesion" (e.g., a lung lesion) may be interchangeably referred to as a "nodule" (e.g., a lung nodule), and "lung" may be interchangeably referred to as "pulmonary".

As used herein, "subcombinations" (of LCM) may be interchangeably referred to as "subsets" (of LCM).

"Abundance level" may be interchangeably referred to herein as "expression level", or just "level" or "abundance". Determination of LCM levels may be referred to herein as "quantifying" LCM, or "quantification" of LCM.

A "differential" abundance level is a level of a marker (e.g., LCM protein or nucleic acid) in a test sample (e.g., a disease sample) either above or below the normal abundance level of the same marker in a corresponding control or normal sample or group of control/normal samples (e.g., a sample set or population). Thus, for example, a "differential" abundance level can encompass either a "high" (or "increased") or "low" (or "decreased") abundance level. An example of a normal abundance level for a LCM is the mean abundance level of the marker in individuals who do not have lung cancer, which may be the mean abundance of the marker in, for example, a particular control sample set or population of individuals who do not have lung cancer. The normal abundance may also be the typical abundance level of a marker in a normal cell (e.g., a normal lung cell) compared with the typical abundance level of the marker in a corresponding disease cell (e.g., a lung cancer cell).

An example of a "high", "increased", or "elevated" (these terms are used herein interchangeably) abundance level for a LCM is an abundance level that is at least two standard deviations above the normal abundance level of the marker (e.g., the mean abundance level of the marker in individuals who do not have lung cancer). An example of a "low" or "decreased" abundance level for a LCM is an abundance level that is at least two standard deviations below the normal abundance level of the marker (e.g., the mean abundance level of the marker in individuals who do not have lung cancer). Thus, in this particular example, an abundance level that is between 2 standard deviations above and 2 standard deviations below the mean abundance level of the marker in individuals who do not have lung cancer may be considered within a normal abundance level range. These are merely exemplary cut-offs which can be used to label an abundance level of a marker as "high"/"increased" or "low"/"decreased".

In alternative exemplary embodiments, the cut-offs for a "high"/"increased" or "low"/"decreased" abundance can be an abundance level that is greater that one standard deviation above or below the normal abundance level, or greater that three standard deviations above or below the normal abundance level, or any other desired standard deviation. In further alternative exemplary embodiments, the cut-offs for a "high"/"increased" or "low"/"decreased" abundance can be based directly on the expression ratio or fold difference, for example, a 2-fold increase/decrease, 3-fold increase/decrease, or 4-fold increase/decrease, or any other desired degree of increase/decrease. Further, the normal abundance level can be based on, for example, either the mean or median abundance level (e.g., of a given control sample set). Other exemplary methods for developing cut-offs for "high"/"increased" or "low"/"decreased" abundance levels include determining a normal abundance level range (such as by testing a panel of markers in a control sample set of normal lung tissue samples), and classifying any test samples above or below this normal range (or above/below a desired threshold relative to this normal range, such as outside a particular percentage of samples within this normal range such as above or below 95% of samples within the normal range) as "high"/ "increased" or "low"/"decreased", respectively.

A wide variety of further cut-offs for classifying the abundance level of a marker as "high"/"increased" or "low"/"decreased", and methods for formulating these cut-offs, are known in the art and/or can be implemented by one of ordinary skill in the art. For a given marker or panel of markers, various cut-offs can be applied, such as cut-offs that maximize sensitivity while maintaining a desired specificity, for example, or that maximize specificity while maintaining a desired sensitivity. For example, the classification of a sample as a tumor sample or normal sample can be accomplished using a variety of methods that may involve using a set of training data to produce a model that can then be used to classify a test sample (such as to diagnose lung cancer, for example). Tumor/normal cut-offs can be selected by manual inspection of multiple markers from the training data set, and these cut-offs can be applied to classifying test samples (such as to characterize patient samples with respect to lung cancer). Exemplary methods include, but are not limited to, split-point analysis (e.g., Mor et al., "Serum protein markers for early detection of ovarian cancer", Proc Natl Acad Sci USA. 2005 May 24; 102(21):7677-82, incorporated herein by reference), logistic regression analysis (e.g., Planque et al., "A multiparametric serum kallikrein panel for diagnosis of non-small cell lung carcinoma", Clin Cancer Res. 2008 Mar. 1; 14(5):1355-62, incorporated herein by reference), Naïve Bayes, multivariate analysis, decision tree modeling (e.g., Patz et al., "Panel of serum biomarkers for the diagnosis of lung cancer", J Clin Oncol (2007), 25, 5578-5583), and other classification methods (see, for example, Dudoit et al., "Classification in Microarray Experiments", Statistical Analysis of Gene Expression Microarray Data, 2003, Chapman & Hall/ CRC: 93-158, incorporated herein by reference).

The terms "sensitivity" and "specificity" are used herein with respect to the ability of one or more markers to correctly classify a sample as a tumor sample or a non-tumor sample (a non-tumor sample may be interchangeably referred to as a "normal", "control", or "healthy" sample), respectively. "Sensitivity" indicates the performance of the marker(s) with respect to correctly classifying tumor samples. "Specificity" indicates the performance of the marker(s) with respect to correctly classifying non-tumor samples. For example, 98% specificity and 85% sensitivity for a panel of markers used to test a set of control and tumor samples indicates that 98% of the control samples were correctly classified as control samples by the panel, and 85% of the tumor sample were correctly classified as tumor samples by the panel.

Area under the curve (AUC) refers to the area under the curve of a receiver operating characteristic (ROC) curve, which are well known in the art (see, e.g., Planque et al., "A multiparametric serum kallikrein panel for diagnosis of non-small cell lung carcinoma", Clin Cancer Res. 2008 Mar. 1; 14(5):1355-62, incorporated herein by reference). AUC measures are useful for comparing the accuracy of a classification algorithm across the complete data range. Classification algorithms with a greater AUC have a greater capacity to classify unknowns correctly between two groups of interest (e.g., lung cancer samples and normal samples). ROC curves are useful for plotting the performance of a particular feature (e.g., an LCM and/or a supplemental biomedical parameter) in distinguishing between two populations (e.g., cases having lung cancer and controls without lung cancer). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (specificity) of the test.

Exemplary embodiments of the invention, which are discussed in greater detail below, provide antibodies, proteins, carbohydrate antigens, immunogenic peptides (e.g., peptides which induce a T-cell response), or other biomolecules, as well as small molecules, nucleic acid agents (e.g., RNAi and antisense nucleic acid agents), and other compositions that modulate the markers (e.g., agonists and antagonists), such as by binding to or otherwise interacting with or affecting the markers. These compositions can be used for assessing, treating, and preventing diseases, especially cancer, and particularly lung cancer, as well as other uses. Moreover, the invention provides methods for assessing, treating, and preventing diseases such as lung cancer, particularly by using these compositions. Further provided are methods of screening for agents that modulate LCM, such as by affecting the function, activity, and/or expression level of LCM, and agents identified by these screening methods.

Exemplary embodiments of the invention also provide methods of modulating cell function, especially lung cell function. In particular, the invention provides methods of modulating cell proliferation and/or apoptosis. For example, for cancer/tumor cells, the invention provides methods of inhibiting cell proliferation and/or stimulating apoptosis. Such methods can be applied to the treatment of diseases, especially cancer, and particularly lung cancer. In certain exemplary embodiments, the invention provides methods of treating lung cancer by targeting LCM to thereby inhibit proliferation of lung cancer cells and/or stimulate apoptosis of lung cancer cells.

Exemplary embodiments of the invention further provide methods of determining or predicting effectiveness or response to a particular treatment, and methods of selecting a treatment for an individual, particularly a lung cancer treatment. For example, markers that are differentially expressed by cells (e.g., lung cancer cells) that are more or less responsive (sensitive) or resistant to a particular treatment, such as a cancer treatment, are useful for determining or predicting effectiveness or response to the treatment or for selecting a treatment for an individual.

Exemplary embodiments of the invention also provide methods of selecting individuals for a clinical trial of a therapeutic agent, particularly a clinical trial for lung cancer or other cancer. For example, the markers can be used to identify individuals for inclusion in a clinical trial who are more likely to respond to a particular therapeutic agent.

Alternatively, the markers can be used to exclude individuals from a clinical trial who are less likely to respond to a particular therapeutic agent or who are more likely to experience toxic or other undesirable side effects from a particular therapeutic agent. Furthermore, such individuals who are determined to be less likely to respond to a particular therapeutic agent can be selected for inclusion in a clinical trial of a different therapeutic agent that may potentially benefit them.

In certain exemplary embodiments, the various individual LCM and LCM panels described herein are provided as compositions. For example, in certain embodiments, each of the members of an LCM panel, and/or reagents for detecting each of these members, are provided as individual compositions, such as in the form of reagents for detecting each member of an LCM panel by ELISA assays (which may be referred to herein as "ELISA reagents"). Furthermore, in certain embodiments, compositions that comprise multiple members of a panel or an entire panel (and/or reagents for detecting each of these multiple members), are provided, such as in the form of kits that contain reagents (such as ELISA reagents) for detecting multiple members of a panel or an entire panel. Other compositions of the invention include arrays or other platforms that have multiple LCM, or multiple reagents (e.g., antibodies) for detecting multiple LCM, coupled to a substrate. In various compositions of the invention, the LCM, or reagents for detecting LCM (e.g., antibodies), are labeled with a detectable moiety (such as a fluorescent label).

Exemplary LCM Combinations/Panels

For example, using a panel of sera from 12 lung cancer patients and 12 healthy control individuals, a group of 8 markers made up of TFPI, SCC, CEA, CA242, MN/CAIX, OPN, Cyfra 21-1, and MIF (FIG. 2) detected all the cancer samples except a bronchioalveolar cancer sample (which is biologically distinct from other samples in the panel), and only a few of these markers were detected at levels above the threshold in the healthy control samples. When a simple algorithm was applied (i.e., markers greater than or equal to two standard deviations were scored "positive", using the criterion stated above), this group of eight markers had a sensitivity of 92% and specificity of 100% among the 12 sera from lung cancer patients and 12 sera from healthy controls (no false positives, 11 true positives, 1 false negative, and 12 true negatives) (FIG. 3).

An alternate panel was configured that was made up of following markers: SLPI, TFPI, OPN, MIF, TIMP1, and MMP2 (FIG. 4). Any or all of these markers can also be used in any combination with any or all of the following markers: CA242, SCC, CEA, NSE, CA72-4, CA19-9, Cyfra 21-1, and MN/CAIX (FIG. 4).

Figure 5:
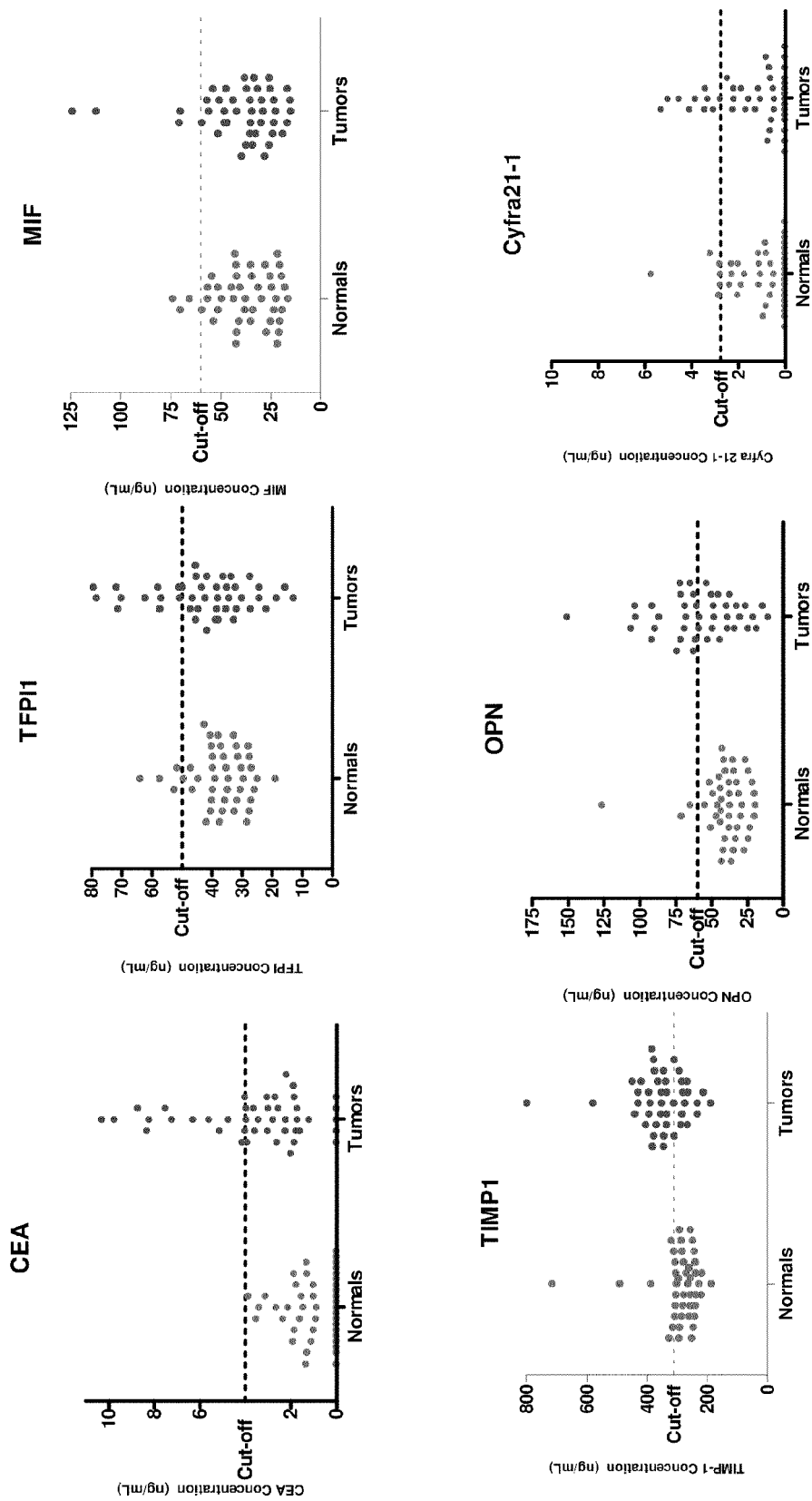
FIG. 5. Shows scatter plots of ELISA data for the six markers CEA, TFPI, MIF, TIMP1, OPN, and Cyfra 21-1 in 44 normal and 44 lung tumor samples, with exemplary cut-offs indicated (dotted lines). Cut-offs can be applied that maximize sensitivity while not compromising specificity of the panel, for example.

Further, a six-marker panel made-up of Cyfra 21-1, TIMP-1, MIF, TFPI, CEA, and OPN was also configured (FIG. 5). This six-marker panel, when tested on a larger group of 44 lung tumor sera and 44 normal sera, resulted in 75% sensitivity at 95% specificity.

Figure 6:
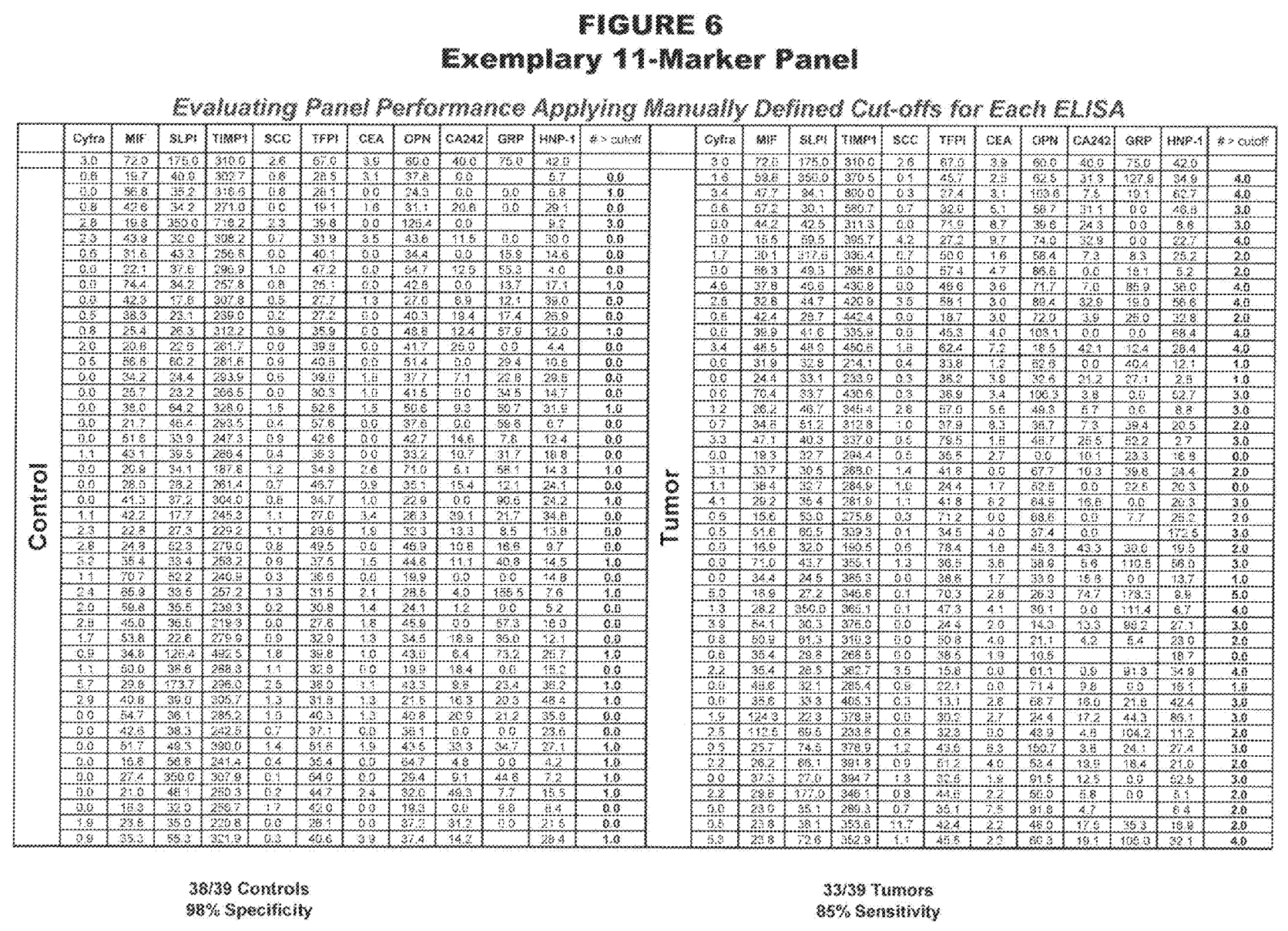

Further, an 11-marker panel made-up of Cyfra, MIF, TIMP1, TFPI, CEA, OPN, SCC, SLPI, HNP-1, GRP, and CA242 was also configured (FIG. 6). This 1-marker panel, when tested on a group of 39 lung tumor sera and 39 normal sera, resulted in 98% specificity for controls (38/39 controls) and 85% sensitivity for tumor sera (33/39 tumors) (FIG. 6).

Table 3 shows further examples of various 1'-marker panels. Specifically, Table 3 provides 35 different panels of 11 markers (each row of 11 markers represents a panel) that have at least 98% specificity and 82% sensitivity for detecting lung cancer. Seven markers (SLPI, TIMP1, TFPI, SCC, OPN, CEA and CA242) appear in all 35 of these panels, GRP appears in 33 of the 35 panels, MIF appears in 29 of the 35 panels, and NSE and HNP-1 each appear in 15 of the 35 panels. AMBP, Cyfra, MMP2, Ca72-4, Ca19-9, and CAIX each appear in 7-9 of the panels, as indicated in Table 3.

Further, a 9-marker panel made-up of Cyfra, SLPI, TIMP1, SCC, TFPI, CEACAM5, MMP2, OPN, and MDK was also configured (e.g., FIG. 17 and Table 5). This 9-marker panel demonstrated 98% specificity (49/50 controls) and 96% sensitivity (48/50 tumors) (FIG. 17). Additionally, a 6-marker subset of this 9-marker panel was also configured that was made-up of Cyfra, SLPI, TIMP1, TFPI, CEACAM5, and MDK (Table 5).

Other markers, which are also referred to herein as LCM and which may be used either alone or in combination with any of the other LCM described herein in any combination, include a group of antigens to which "self-made" or "autoantibodies" are often found in the circulation of patients with various diseases, particularly cancer (Table 2 and FIGS. 11-14). Examples of these autoantibody markers include the following: KLKB1, CFL1, LGAGS1, EEF1G, RTN4, ALDOA, HSPCA, PABPC4, NAGK, CFHL1, CSF1R, and RANBP2 (FIG. 12), and other autoantibody markers as shown in Table 2. Detection of autoantibody LCM such as these may complement other LCM and enhance the performance of LCM panels, particularly for assessing lung cancer.

The following are exemplary panels of LCM. Various exemplary embodiments of the invention provide, for example, compositions based on these panels and methods of using these panels, particularly for uses related to lung cancer such as diagnosis of lung cancer (e.g., differential levels, such as elevated or low levels as compared to control/normal levels, of a plurality of markers in a panel, or all markers in panel, can indicate the presence of lung cancer). These exemplary panels may consist of, consist essentially of, or comprise the following combinations of markers:

1) Cyfra, SLPI, TIMP1, SCC, TFPI, CEACAM5, MMP2, OPN, and MDK (which may be referred to herein as the "9-marker panel" and is shown in FIG. 17 and Table 5).
2) Cyfra, SLPI, TIMP1, TFPI, CEACAM5, and MDK (which may be referred to herein as the "6-marker subset of the 9-marker panel" and is shown in Table 5).
3) Cyfra, SLPI, TIMP1, SCC, TFPI, CEACAM5, MMP2, OPN, and MDK (the "9-marker panel"), which may optionally be in combination with one or more other markers (which may be added to this 9-marker panel and/or replace one or more members of this 9-marker panel), wherein these other markers may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12, particularly those markers that are shown in Table 4.
4) Cyfra, SLPI, TIMP1, TFPI, CEACAM5, and MDK (the "6-marker subset of the 9-marker panel"), which may optionally be in combination with one or more other markers (which may be added to this 6-marker subset of the 9-marker panel and/or replace one or more members of this 6-marker subset of the 9-marker panel), wherein these other markers may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12, particularly those markers that are shown in Table 4.
5) Any of the panels (which may include single markers) provided in Table 5 (which provides the 9-marker panel and all subcombinations thereof; each row of Table 5 represents a different panel), which may optionally be in combination with one or more other markers (which may be added to any panel in Table 5 and/or replace one or more members of any panel in Table 5), wherein these other markers may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12, particularly those markers that are shown in Table 4.

6) Any of the panels provided in Table 5 or Table 6 (particularly the 9-marker panel of Cyfra, SLPI, TIMP1, SCC, TFPI, CEACAM5, MMP2, OPN, and MDK, as well as subsets thereof, and panels comprising this 9-marker panel or subsets thereof that further include one or more additional markers such as those panels set forth in Table 6), particularly for use in methods for distinguishing lung tumor samples versus normal (i.e., control/healthy) samples. These panels are particularly useful for determining whether an individual has lung cancer (i.e., detecting lung cancer), for example.

7) Any of the panels provided in Table 7 (particularly the 9-marker panel of Cyfra, SLPI, TIMP1, SCC, TFPI, CEACAM5, MMP2, OPN, and MDK, as well as subsets thereof), particularly for use in methods for distinguishing adenocarcinoma versus squamous cell carcinoma. These panels are particularly useful for determining whether an individual's lung cancer is adenocarcinoma or squamous cell carcinoma, for example.

8) Any of the panels provided in Table 8 (particularly the 9-marker panel of Cyfra, SLPI, TIMP1, SCC, TFPI, CEACAM5, MMP2, OPN, and MDK, as well as subsets thereof), particularly for use in methods for distinguishing between any stages of lung cancer (e.g., any of stages I, II, III, and IV), particularly between early stage (stage I or II) and late stage (stage III or IV) lung cancer, and especially between stage I and stage III lung cancer. These panels are particularly useful for determining the stage of an individual's lung cancer, for example.

9) Any of the panels provided in Table 9, particularly for use in methods for distinguishing SCLC versus other types of lung cancer (e.g., NSCLC). These panels are particularly useful for determining whether an individual's lung cancer is SCLC or NSCLC, for example.

10) Any of the panels provided in Table 10 (particularly the 9-marker panel of Cyfra, SLPI, TIMP1, SCC, TFPI, CEACAM5, MMP2, OPN, and MDK, as well as subsets thereof), particularly for use in methods for distinguishing malignant lung tumors versus benign lung lesions. These panels are particularly useful for determining whether a lung lesion identified in an individual (such as by CT screening) is a malignant tumor or a benign lesion, for example.

11) Any of the panels provided in Table 11, particularly for use in methods for distinguishing SCLC versus normal (i.e., control/healthy) samples. These panels are particularly useful for determining whether an individual has SCLC, for example.

12) Any of the panels provided in Table 12, particularly for use in methods for distinguishing lung cancer (including both SCLC and NSCLC) versus normal (i.e., control/healthy) samples. These panels are particularly useful for determining whether an individual has lung cancer such as SCLC or NSCLC, for example.

13) Panels that include any or all of the 11 markers provided in FIG. 19 (and subsets thereof, as well as panels comprising these 11 markers or subsets thereof that further include one or more additional markers), particularly for use in methods of monitoring for lung tumor regression and/or recurrence. These panels are particularly useful for monitoring for lung tumor regression and/or recurrence, for example.

14) Cyfra 21-1, MIF, TIMP1, TFPI, CEA, OPN, SCC, SLPI, HNP-1, GRP, and CA242 (which may be referred to herein as the "1'-marker panel" and is shown in FIG. 6).

15) TFPI, CEA, MIF, TIMP1, OPN, and Cyfra 21-1 (which may be referred to herein as the "6-marker panel" and is shown in FIG. 5).

Figure 2:
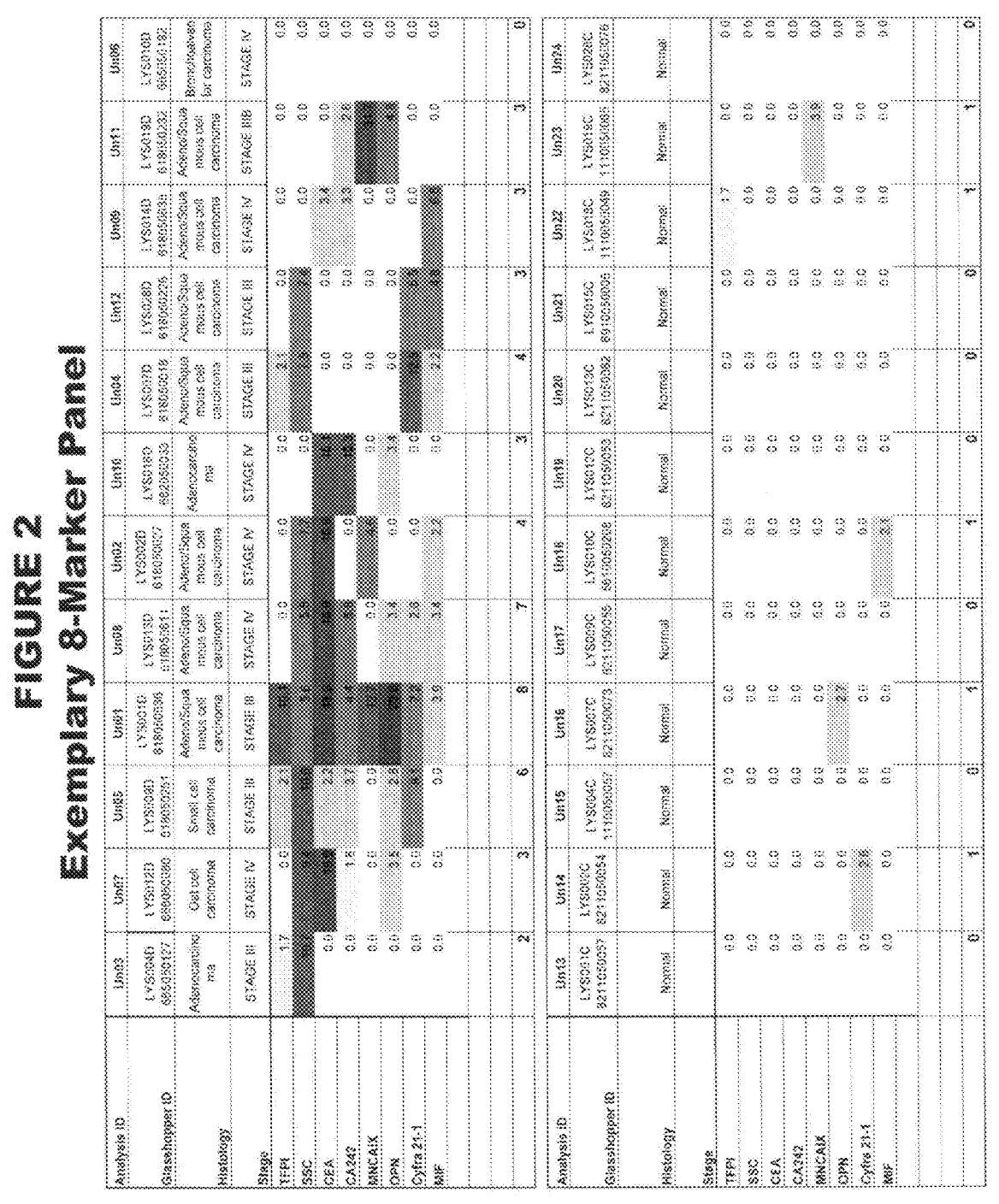

16) TFPI, SCC, CEA, CA242, MN/CAIX, OPN, Cyfra 21-1 and MIF (which may be referred to herein as the "8-marker panel" and is shown in FIGS. 2-3).

17) TFPI, SLPI, OPN, MIF, TIMP1, and MMP2, any or all of which can optionally be used in combination with any or all of the following additional markers: CA242, SCC, CEA, NSE, CA724, CA199, Cyfra 21-1, and MN/CAIX (see FIG. 4).

Figure 7:
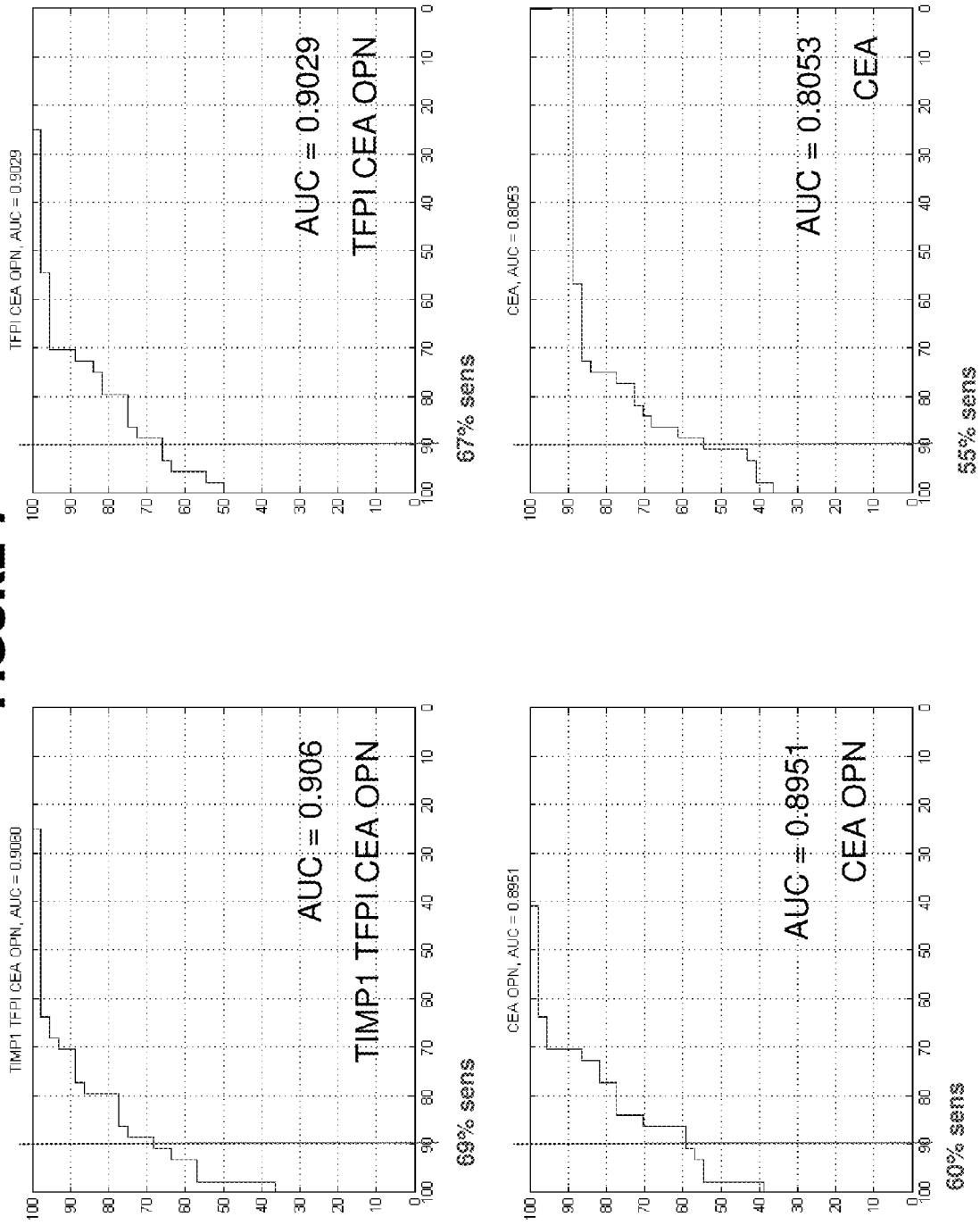
FIG. 7. Shows performance of exemplary panels of markers, demonstrating that increased sensitivity can be achieved by including additional markers. The marker CEA provides 55% sensitivity and 90% specificity, the two markers CEA and OPN provide 60% sensitivity and 90% specificity, the three markers TFPI, CEA, and OPN provide 67% sensitivity and 90% specificity, and the four markers TIMP1, TFPI, CEA, and OPN provide 69% sensitivity and 90% specificity. The score is the sum of the $\log_2$ of the ratios of the tumor concentration to the mean concentration in normal serum. ROC curves can be constructed by varying the cut-off of the score needed to call a sample a tumor.

18) TFPI, TIMP1, CEA, and OPN (see FIG. 7).

19) TFPI, CEA, and OPN (see FIG. 7).

20) CEA and OPN (see FIG. 7).

Figure 9:
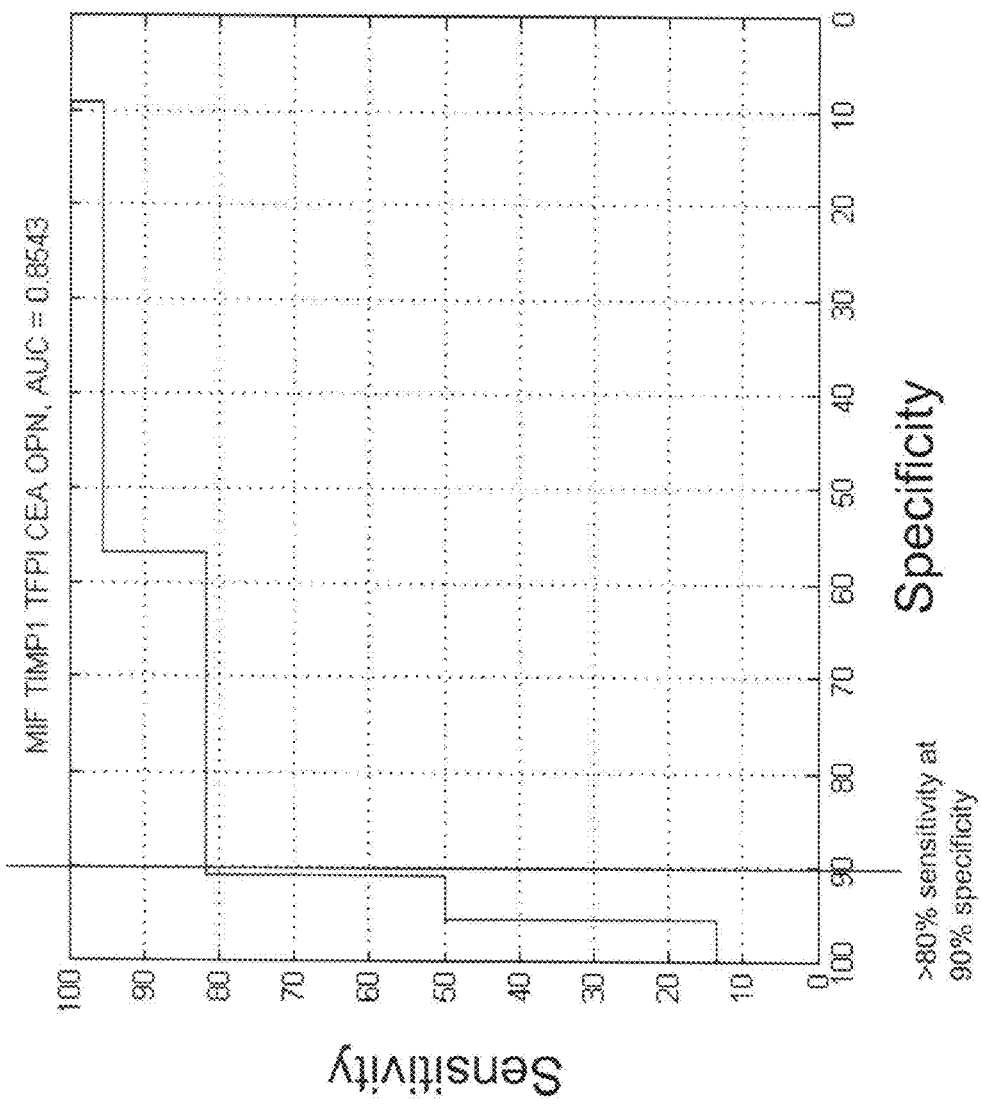
FIGS. 9-10. Shows AUC (area under curve)=0.8543 for markers MIF, TIMP1, TFPI, CEA, and OPN (FIG. 9), and AUC=0.8518 for markers TIMP1, NSE, CEA, and OPN. Score is the number of markers greater than the cutoff that best separates tumor samples from normal samples for each marker. ROC curve can be constructed by varying the cut-off of the score needed to call a sample a tumor.

21) TFPI, MIF, MIMP1, CEA, and OPN (see FIG. 9).

Figure 10:
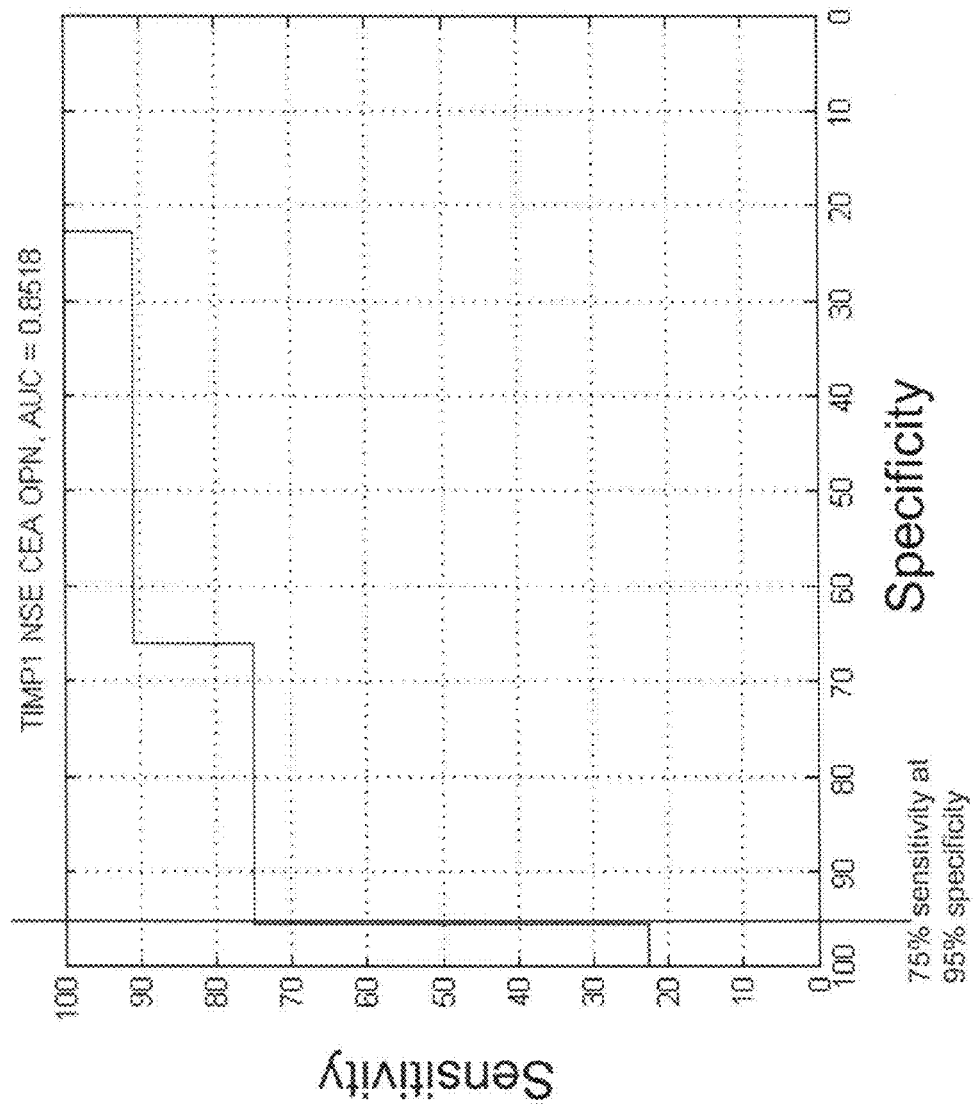

22) TIMP1, NSE, CEA, and OPN (see FIG. 10).

23) TFPI, CEA, TIMP-1, NSE, SLPI, SCC, Cyfra 21-1, and MIF, any or all of which can optionally be in combination with any or all of the following autoantibody markers: p53, KLKB1, LGALS1, CFLN, EEF1G, HSP90α, RTN4, ALDOA, GLG1, PTK7, EFEMP1, CD98, CHGB, B7H3, and CEACAM1 (see FIG. 11).

24) TFPI, SLPI, TFPI2, CEA, and TIMP1.

25) TFPI, SLPI, and TIMP1.

Figure 13C:
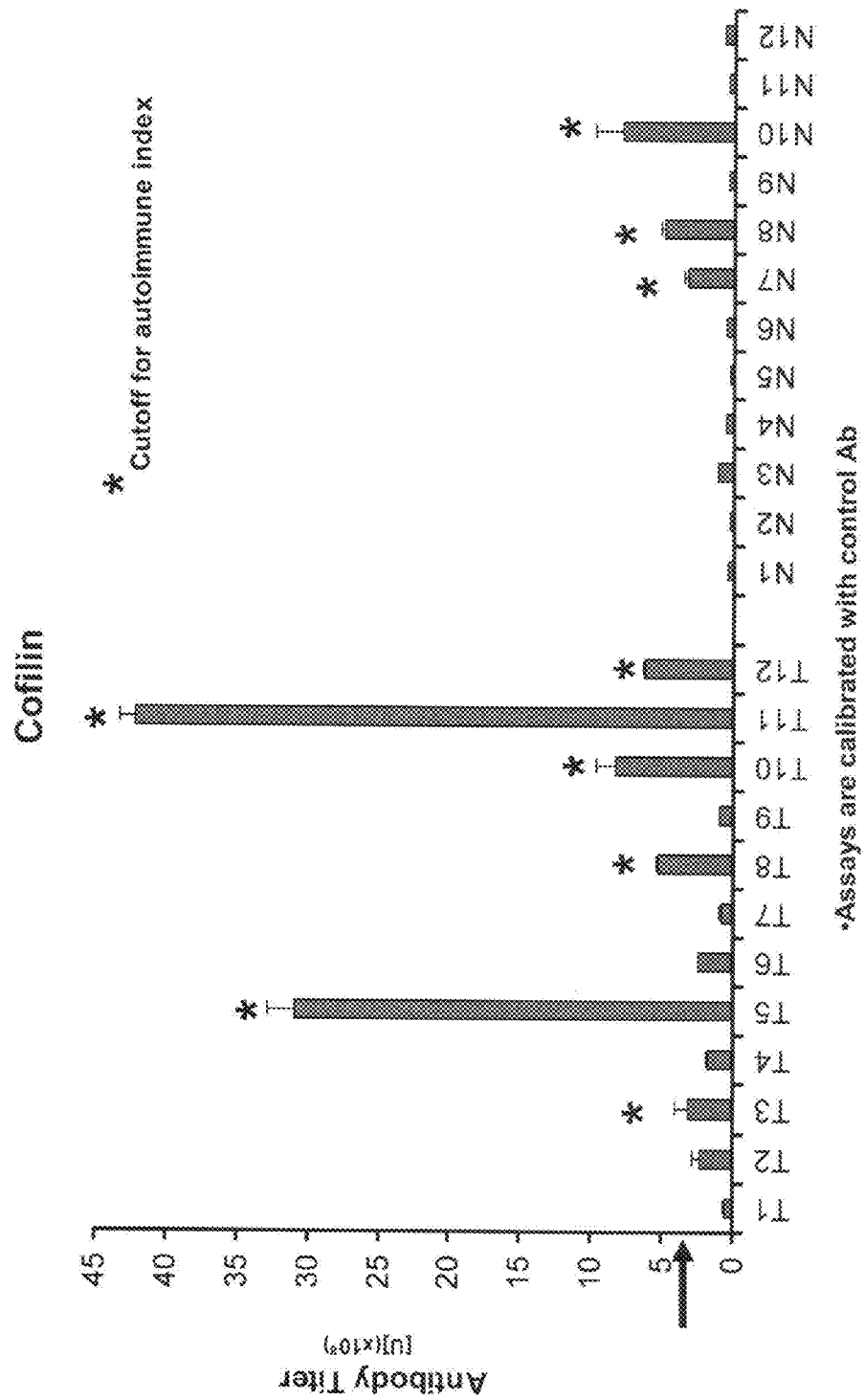
FIG. 13. Shows autoantibody responses observed in lung cancer and normal serum samples for the autoantibody markers KLKB1, cofilin, and LGALS1, as well as p53. Along the horizontal axis, T1 through T12 indicate tumor samples and N1 through N12 indicate normal samples.
Figure 15:
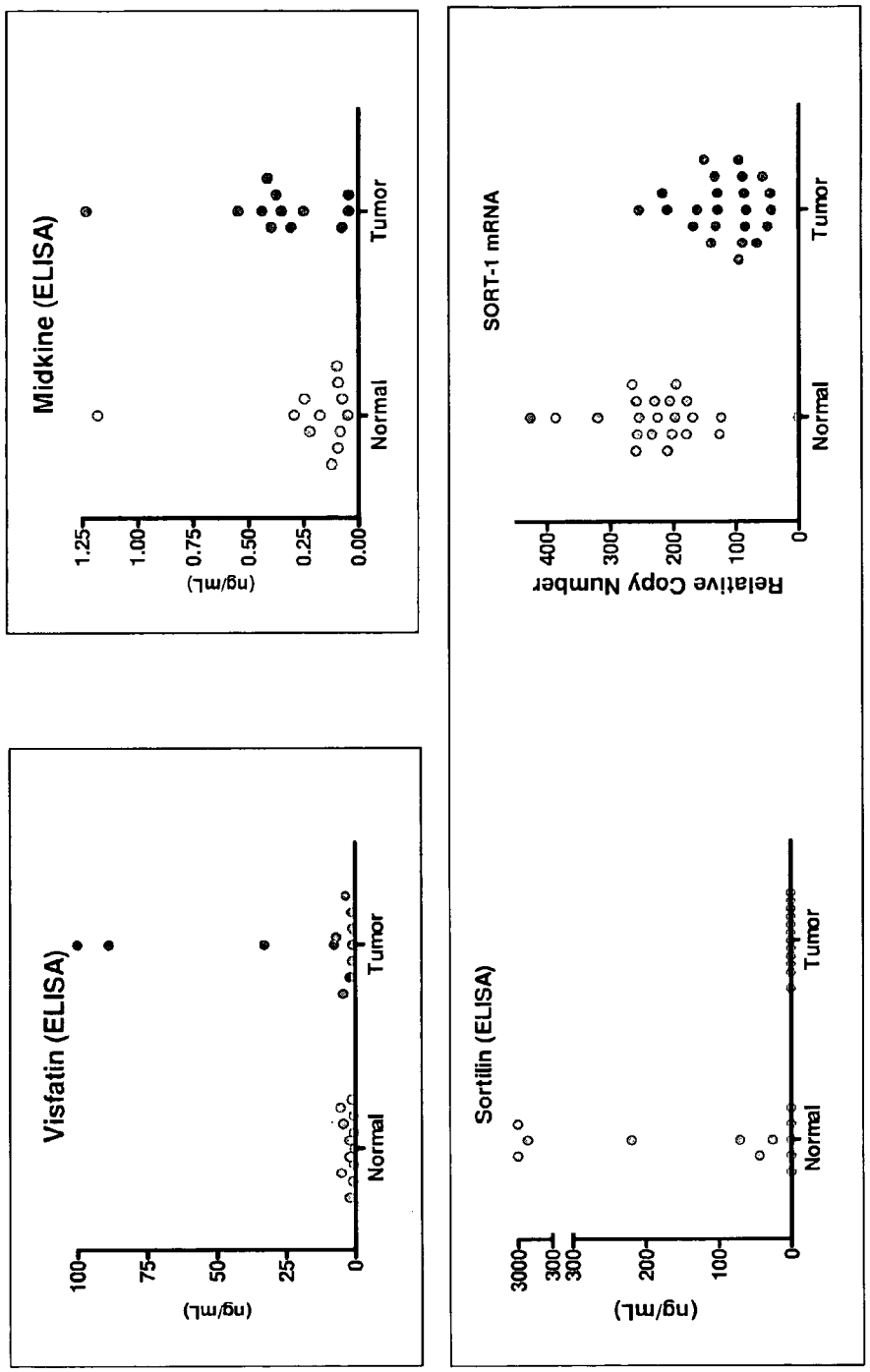
FIG. 15. Shows three additional LCM: visfatin (PBEF), sortilin (SORT-1), and midkine (MDK). Any or all of these three LCM can be implemented in a panel of markers for lung cancer diagnosis, for example.
Figure 18:
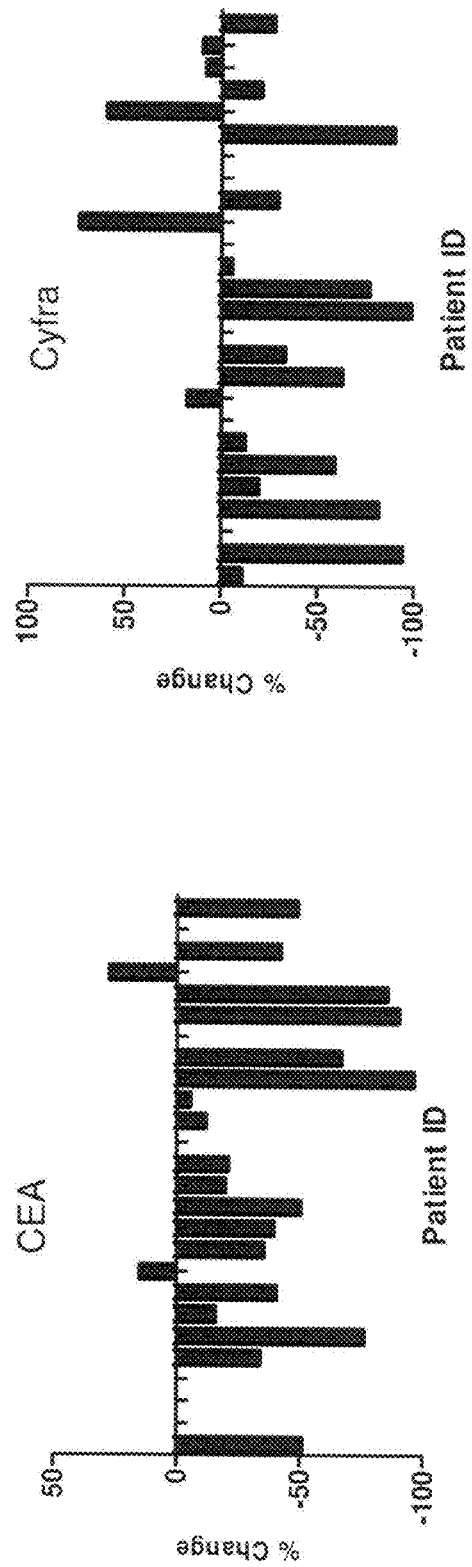
FIG. 18. Describes the analysis of markers to monitor lung tumor regression/recurrence, with CEA and Cyfra as examples. In particular, levels of biomarkers in patient serum 2-4 weeks following surgery were compared to pre-surgical marker levels.

26) KLKB1 and cofilin (CFLN) (see FIG. 13).

27) KLKB1, cofilin (CFLN), and CA12 (see FIG. 14).

28) TFPI, either alone or in combination with one or more other markers, which may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12.

29) One or more markers selected from the group consisting of defensin (DEFA1, HNP-1), ICAM3, CTGF, LCN2, biglycan, and HGF, either alone or in combination with one or more other markers, which may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12.

30) Two or more markers selected from the group consisting of TFPI, defensin, ICAM3, CTGF, LCN2, biglycan, and HGF, either alone or in combination with one or more other markers, which may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12.

31) One or more markers shown in Table 1 (SEQ ID NOS: 1-38 and 56-65 and the carbohydrate antigens CA 242, CA 19-9, and CA 72-4) and/or FIG. 1, in combination with one or more autoantibody markers shown in Table 2 (SEQ ID NOS:39-55) and/or FIG. 12.

32) Any of the 1'-marker panels provided in Table 3 (each row of Table 3 represents a different 11-marker panel).

33) SLPI, TIMP1, TFPI, SCC, OPN, CEA, and CA242, which may optionally be in combination with GRP and/or MIF (see Table 3).

34) SLPI, TIMP1, TFPI, SCC, OPN, CEA, and CA242, which may optionally be in combination with GRP and/or MIF, and which may optionally further be in combination with HNP-1 and/or NSE (see Table 3).

35) SLPI, TIMP1, TFPI, SCC, OPN, CEA, and CA242, which may optionally be in combination with any or all of GRP, MIF, HNP-1, and NSE, and which may optionally further be in combination with any or all of CAIN, Ca19-9, Ca72-4, MMP2, Cyfra 21-1, and AMBP (see Table 3).

36) SLPI, TIMP1, TFPI, SCC, OPN, CEA, and CA242, which may optionally be in combination with any or all of GRP, MIF, HNP-1, NSE, and Cyfra 21-1.

37) One or more markers selected from the group consisting of visfatin, sortilin, and midkine, either alone or in combination with one or more other markers, which may optionally be selected from the group consisting of the markers shown in Tables 1-2 (SEQ ID NOS:1-65 and the carbohydrate antigens CA 242, CA 19-9, and CA 72-4), Table 4, FIG. 1, and FIG. 12.

Exemplary Uses of LCM

Certain exemplary embodiments of the invention relate to methods of detecting the presence of lung cancer in an individual by measuring the amounts of circulating LCM, such as in serum, by immunological methods or other methods. These LCM are, for example, differentially expressed (over- or under-expressed) in individuals with lung cancer as compared to individuals without lung cancer (individuals without lung cancer are interchangeably referred to herein as "normal", "control", or "healthy" individuals).

Detection of variation from a "normal" expression level, or differential expression, can be used for, for example, early diagnosis of lung cancer, distinguishing between a benign and malignant lung lesion (such as a lesion observed on a CT scan), monitoring lung cancer recurrence, or other clinical indications.

LCM may be used in a variety of clinical indications for lung cancer, including, but not limited to, detection of lung cancer (such as in a high-risk individual or population), characterizing lung cancer (e.g., determining lung cancer type, sub-type, or stage) such as distinguishing between non-small cell lung cancer (NSCLC) and small cell lung cancer (SCLC) and/or between adenocarcinoma and squamous cell carcinoma (or otherwise facilitating histopathology), determining whether a lung lesion is a benign lesion or a malignant lung tumor, lung cancer prognosis, monitoring lung cancer progression or remission, monitoring for lung cancer recurrence, monitoring metastasis, treatment selection, monitoring response to a therapeutic agent or other treatment, stratification of patients for computed tomography (CT) screening (e.g., identifying those patients at greater risk of lung cancer and thereby most likely to benefit from spiral-CT screening, thus increasing the positive predictive value of CT), combining LCM testing with supplemental biomedical parameters such as smoking history, etc., or with nodule size, morphology, etc. (such as to provide an assay with increased diagnostic performance compared to CT testing or LCM testing alone), facilitating the diagnosis of a pulmonary nodule as malignant or benign, facilitating clinical decision making once a lung cancer lesion is observed on CT (e.g., ordering repeat CT scans if the lesion is deemed to be low risk, such as if an LCM-based test is negative, with or without categorization of lesion size, or considering biopsy if the lesion is deemed medium to high risk, such as if an LCM-based test is positive, with or without categorization of lesion size), and facilitating decisions regarding clinical follow-up (e.g., whether to implement repeat CT scans, fine needle biopsy, or thoracotomy after observing a non-calcified lesion on CT). LCM testing may improve positive predictive value (PPV) over CT screening alone. In addition to their utilities in conjunction with CT screening, LCM can also be used in conjunction with any other imaging modalities used for lung cancer, such as chest X-ray. Furthermore, LCM may also be useful for enabling certain of these uses to be achieved before indications of lung cancer are detected by imaging modalities or other clinical correlates, or before symptoms appear.

As examples of how LCM may be useful for diagnosing lung cancer, a high or low abundance level (i.e., a "differential" abundance level) of one or more LCM in an individual who is not known to have lung cancer may indicate that the individual has lung cancer, thereby enabling early detection of lung cancer at an early stage of the disease when treatment is most effective, perhaps before the lung cancer is detected by other means or before symptoms appear. An increase in the abundance of one or more LCM during the course of lung cancer may be indicative of lung cancer progression, e.g., a lung tumor is growing and/or metastasizing (and thus a poor prognosis), whereas a decrease in the abundance of one or more LCM may be indicative of lung cancer remission, e.g., a lung tumor is shrinking (and thus a good prognosis). Similarly, an increase in the abundance of one or more LCM during the course of lung cancer treatment may indicate that the lung cancer is progressing and therefore indicate that the treatment is ineffective, whereas a decrease in the abundance of one or more LCM during the course of lung cancer treatment may be indicative of lung cancer remission and therefore indicate that the treatment is working successfully. Additionally, an increase or decrease in the abundance of one or more LCM after an individual has apparently been cured of lung cancer may be indicative of lung cancer recurrence. In a situation such as this, for example, the individual can be re-started on therapy (or the therapeutic regimen modified such as to increase dosage amount and/or frequency, if the patient has maintained therapy) at an earlier stage than if the recurrence of lung cancer was not detected until later. Furthermore, a differential abundance level of one or more LCM in an individual may be predictive of the individual's response to a particular therapeutic agent. In monitoring for lung cancer recurrence or progression, changes in LCM levels may indicate the need for repeat imaging (e.g., repeat CT scanning), such as to determine lung cancer activity, or the need for changes in treatment.

Detection of LCM may be particularly useful following, or in conjunction with, lung cancer treatment, such as to evaluate the success of the treatment or to monitor lung cancer remission, recurrence, and/or progression (including metastasis) following treatment. Lung cancer treatment may include, for example, administration of a therapeutic agent to a patient, surgery (e.g., surgical resection of at least a portion of a lung tumor), radiation therapy, or any other type of lung cancer treatment used in the art, and any combination of these treatments. For example, LCM may be detected at least once after treatment or may be detected multiple times after treatment (such as at periodic intervals), or may be detected both before and after treatment. A differential abundance level of LCM, such as an increase or decrease in the abundance level of LCM after treatment compared with the abundance level of LCM before treatment, or an increase or decrease in the abundance level of LCM at a later time point after treatment compared with the abundance level of LCM at an earlier time point after treatment, or a differential abundance level of LCM at a single time point after treatment compared with normal levels of LCM, may be indicative of lung cancer progression, remission, or recurrence.

As a specific example, ELISA analysis of LCM levels in pre-surgery and post-surgery (e.g., 2-4 weeks after surgery) serum samples can be carried out. An increase in the level of LCM in the post-surgery sample compared with the pre-surgery sample can indicate progression of lung cancer (e.g., unsuccessful surgery), whereas a decrease in the level of LCM in the post-surgery sample compared with the pre-surgery sample can indicate regression of lung cancer (e.g., the surgery successfully removed the lung tumor). Similar analyses of LCM levels can be carried out before and after other forms of treatment, such as before and after radiation therapy or administration of a therapeutic agent or cancer vaccine.

In addition to the utilities of testing LCM levels as stand-alone screening tests, testing of LCM levels can also be done in conjunction with CT screening. For example, LCM may facilitate the medical and economic justification for implementing CT screening, such as to screen large asymptomatic populations at risk for lung cancer (e.g., smokers). For example, a "pre-CT" test of LCM levels could be used to stratify high-risk individuals for CT screening, such as to identify those who are at highest risk for lung cancer based on their LCM levels and who should be prioritized for CT screening. If a CT test is implemented, LCM levels (e.g., as determined by immunoassay of serum samples) of one or more LCM can be measured and the scores added to scores for supplemental biomedical parameters (e.g., tumor parameters determined by CT testing) to create a combined score, such as to enhance positive predictive value (PPV) over CT or LCM testing alone. A "post-CT" immunoassay panel for determining LCM levels can be used to determine the likelihood that a pulmonary lesion observed by CT (or other imaging modality) is malignant or benign.

Detection of LCM may be useful for post-CT testing. For example, LCM testing may eliminate a significant number of false positive tests over CT alone. Further, LCM testing may facilitate treatment of patients. As an example, if a lung tumor is less than 5 mm in size, results of LCM testing may move patients from "watch and wait" to biopsy at an earlier time, if a lung tumor is 5-9 mm, LCM testing may eliminate biopsy or thoracotomy on false positive scans, and if a lung tumor is larger than 10 mm, LCM testing may eliminate surgery for sub-population of these patients with benign lesions. Eliminating the need for biopsy in some patients based on LCM testing would be beneficial because there is significant morbidity associated with nodule biopsy and difficulty in obtaining nodule tissue depending on location of nodule. Similarly, eliminating the need for surgery in some patients, such as those whose lesions are actually benign, would avoid unnecessary risks and costs associated with surgery.

In addition to testing LCM levels in conjunction with CT screening (e.g., assessing LCM levels in conjunction with size or other characteristics of a lung nodule observed on a CT scan), information regarding LCM can also be evaluated in conjunction with other types of data, particularly data that indicates an individual's risk for lung cancer (e.g., patient clinical history, symptoms, family history of cancer, risk factors such as whether or not the individual is a smoker, and/or status of other biomarkers, etc.). These various data can be assessed by automated methods, such as a computer program/software, which can be embodied in a computer or other apparatus/device.

The various methods described herein, such as correlating the level of LCM in an individual with an altered (e.g., increased or decreased) risk (or no altered risk) for lung cancer, can be carried out by automated methods such as by using a computer (or other apparatus/devices such as bio-medical devices, laboratory instrumentation, or other apparatus/devices having a computer processor) programmed to carry out any of the methods described herein. For example, computer software (which may be interchangeably referred to herein as a computer program) can perform the step of correlating the level of LCM in an individual with an altered (e.g., increased or decreased) risk (or no altered risk) of lung cancer for the individual. Accordingly, certain embodiments of the invention provide a computer (or other apparatus/device) programmed to carry out any of the methods described herein.

LCM may also be used in imaging tests. For example, an imaging agent can be coupled to an LCM, which can be used to aid in lung cancer diagnosis, to monitor disease progression/remission or metastasis, to monitor for disease recurrence, or to monitor response to therapy, among other uses.

LCM can be detected using a variety of platforms. For example, LCM may be detected using singleplex ELISAs, ultrasensitive detection technologies, multiplex formats, and/or automated immunoanalyzers.

In addition to detecting LCM in serum, LCM may also be detected in, for example, plasma and bronchial lavage.

LCM may be used for pharmacoproteomic or pharmacogenomic applications; for example, detection of LCM may be used for treatment selection or stratification. Differential expression of LCM in, for example, tumor cells that are resistant to a treatment (e.g., a particular therapeutic agent) and tumor cells that are sensitive to a treatment can be used to predict resistance or sensitivity of an individual's lung cancer to the treatment. As specific examples, CTGF is secreted at elevated levels by cell lines that are resistant to the chemotherapeutic agent Topotecan. In contrast, TIMP1, TFPI, and TIMP2 are secreted at elevated levels by cell lines that are sensitive to the chemotherapeutic agent Iressa. LCM may also be used as treatment response markers for a particular therapeutic agent. For example, certain LCM may be used as surrogate markers of cisplatin or Iressa treatment response.

Thus, the LCM profile of an individual having lung cancer can be used to determine which treatment(s) are best suited for that particular individual. For example, treatments to which an individual's lung cancer is predicted to be sensitive can be selected for the individual rather than treatments to which the individual's lung cancer is predicted to be resistant. As a further example, LCM levels can be used by a medical practitioner to distinguish between types of lung cancer (e.g., non-small cell lung cancer (NSCLC) versus small cell lung cancer (SCLC), adenocarcinoma versus squamous cell carcinoma, different stages of lung cancer, or other lung cancer characteristics) in order to adjust therapy options (e.g., to select a particular therapeutic agent or a particular form of treatment, such as chemotherapy, surgery, or radiation therapy, that is best suited for that particular subtype of lung cancer).

Tables 5-6 and 11-12 provide panels that are particularly well-suited for diagnosing/detecting lung cancer, among other lung cancer-related uses. For example, Tables 5 and 6 provides LCM panels that are particularly well-suited for distinguishing lung tumor samples versus normal (i.e., control/healthy) samples, Table 11 provides LCM panels that are particularly well-suited for distinguishing SCLC versus normal samples, Table 12 provides LCM panels that are particularly well-suited for distinguishing lung cancer (including both SCLC and NSCLC) versus normal samples.

Any of the LCM and the various exemplary LCM panels disclosed herein (such as any of the panels provided in Tables 5-6, such as the 9-marker panel or the 6-marker subset of this 9-marker panel, as well as any LCM provided in Tables 1-2

(SEQ ID NOS:1-65 and the carbohydrate antigens CA 242, CA 19-9, and CA 72-4), Table 4, FIG. 1, and FIG. 12, and any panels that include one or more of these LCM, particularly panels that include one or more markers provided in Table 4) may be used for any of the various lung cancer-related uses disclosed herein. However, certain LCM panels are particularly well-suited for certain specific lung cancer-related uses ("indications"); these specific uses may be referred to herein as determining or assessing various "characteristics" of lung cancer. Examples of such LCM panels that are particularly well-suited for certain specific lung cancer-related uses are provided in Tables 7-10 and FIG. 19. For example, Table 7 provides LCM panels that are particularly well-suited for distinguishing adenocarcinoma versus squamous cell carcinoma types of lung cancer, Table 8 provides LCM panels that are particularly well-suited for distinguishing between different stages of lung cancer (such as between early-stage and late-stage lung cancer such as stage I versus stage III lung cancer, or between any other of stages I, II, III, and IV) such as to determine the stage of lung cancer in a patient, Table 9 provides LCM panels that are particularly well-suited for distinguishing SCLC versus other types of lung cancer (e.g., NSCLC), Table 10 provides LCM panels that are particularly well-suited for distinguishing malignant lung tumors versus benign lung lesions, and FIG. 19 provides LCM that are particularly well-suited for monitoring for lung tumor regression and/or recurrence.

Tables 5-12 provide a variety of exemplary LCM panels, together with performance characterisitics for each panel (AUC, sensitivity, and specificity). In certain embodiments, LCM panels are provided that have at least 70% sensitivity at 95% specificity, or at least 70% specificity at 95% sensitivity. In certain embodiments, LCM panels are provided that have at least 85% sensitivity at 95% specificity, or at least 85% specificity at 95% sensitivity. In further embodiments, LCM panels are provided that have at least 90% sensitivity or at least 90% specificity, or that have at least 95% sensitivity or at least 95% specificity. In yet further embodiments, LCM panels are provided that have at least 70, 75, 80, 85, 90, 91, 92, 93, 94, 95, 96, 97, 98, or 99% (or any other percentage in-between) sensitivity and 70, 75, 80, 85, 90, 91, 92, 93, 94, 95, 96, 97, 98, or 99% (or any other percentage in-between) specificity. In yet further embodiments, LCM panels are provided that have at least 0.7, 0.75, 0.8, 0.85, 0.9, 0.91, 0.92, 0.93, 0.94, 0.95, 0.96, 0.97, 0.98, or 0.99 (or any other value in-between) AUC values. Any of these panels are particularly useful for lung-cancer related uses such as those described herein (e.g., diagnosing lung cancer), such as in clinical practice. However, the desired performance for clinical use of an assay may vary depending on such factors as the particular use, point of implementation, or other factors.

Distinguishing NSCLC and SCLC

The following panels of LCM are particularly useful for distinguishing (which may be interchangeably referred to as "resolving") non-small cell lung carcinoma (NSCLC) and small cell lung carcinoma (SCLC) from each other and/or from normal (i.e., control/healthy) samples. These panels may consist of, consist essentially of, or comprise the following combinations of markers:

1) Any of the panels provided in Table 9, particularly for distinguishing NSCLC versus SCLC.
2) Any of the panels provided in Table 11, particularly for distinguishing SCLC versus normal samples.
3) Any of the panels provided in Table 12, particularly for distinguishing SCLC and NSCLC versus normal samples.
4) OPN (either alone or in combination with one or more other markers), particularly for distinguishing NSCLC from SCLC and for distinguishing SCLC from NSCLC.
5) SCC, OPN, AMBP, and Ca72-4, particularly for distinguishing NSCLC from SCLC (levels of these LCM are higher in NSCLC as compared to SCLC).
6) ENO2, MMP2, Ca19-9, CAIX, and GRP, particularly for distinguishing SCLC from NSCLC (levels of these LCM are higher in SCLC as compared to NSCLC).
7) Cyfra, SLPI, TIMP1, TFPI, CEACAM5, MMP2, and CA242, particularly for distinguishing SCLC from normal samples (particularly by using split-point analysis).
8) SLPI, TIMP1, TFPI, CEACAM5, MMP2, OPN, and CA242, particularly for distinguishing SCLC from normal samples (particularly by using split-point analysis).
9) Cyfra, TIMP1, ENO2, TFPI, CEACAM5, MMP2, OPN, and DEFA1, particularly for distinguishing NSCLC and SCLC from normal samples (particularly by using split-point analysis).
10) Cyfra, MIF, TIMP1, SCC, TFPI, CEACAM5, OPN, and DEFA1, particularly for distinguishing NSCLC and SCLC from normal samples (particularly by using split-point analysis).
11) TIMP1, ENO2, TFPI, CEACAM5, MMP2, OPN, AMBP, and DEFA1, particularly for distinguishing NSCLC and SCLC from normal samples (particularly by using split-point analysis).

Supplemental Biomedical Parameters

The term "supplemental biomedical parameters" refers to one or more assessments of an individual, other than LCM, that are associated with lung cancer risk. "Supplemental biomedical parameters" include, but are not limited to, physical descriptors of a patient, physical descriptors of a pulmonary nodule observed by CT imaging, the height and/or weight of a patient, the gender of a patient, smoking history, occupational history, exposure to carcinogens, exposure to secondhand smoke, family history of lung cancer (or other cancer), the presence of pulmonary nodules, size of nodules, location of nodules, morphology of nodules (e.g., nodules may be observed by CT imaging), etc. Smoking history is usually quantified in terms of "pack years", which refers to the number of years a person has smoked multiplied by the average number of packs smoked per day. For example, a person who has smoked, on average, one pack of cigarettes per day for 35 years is referred to as having 35 pack years of smoking history. Supplemental biomedical parameters can be obtained from an individual using routine techniques known in the art, such as from the individual themselves by use of a routine patient questionnaire or health history questionnaire, etc., or from a medical practitioner, etc. Alternately, supplemental biomedical parameters can be obtained from routine imaging techniques including CT imaging (e.g., low-dose CT imaging) and X-ray.

Testing of LCM in combination with an assessment of supplemental biomedical parameters may, for example, improve sensitivity, specificity, and/or AUC for detecting lung cancer (or other lung cancer-related uses) as compared to LCM testing alone or assessing supplemental biomedical parameters alone (e.g., CT imaging alone).

Accordingly, any of the LCM, and panels of LCM, can be used in combination with supplemental biomedical parameters. Furthermore, supplemental biomedical parameters may serve to replace one or more markers of a panel, such as to enable the use of smaller panels (i.e., panels with fewer biomarkers) while retaining similar performance (e.g., sensitivity, specificity, and/or AUC for detecting lung cancer). Thus, supplemental biomedical parameters can be used in addition to a panel, or in addition to one or more markers of a panel, or as a substitute for one or more markers of a panel. As a specific example, one or more supplemental biomedical parameters can be used in addition to the 9-marker panel of Cyfra, SLPI, TIMP1, SCC, TFPI, CEACAM5, MMP2, OPN, and MDK or the 6-marker subset of this 9-marker panel (Cyfra, SLPI, TIMP1, TFPI, CEACAM5, and MDK). As another specific example, one or more supplemental biomedical parameters can replace one or more members of the 9-marker panel of Cyfra, SLPI, TIMP1, SCC, TFPI, CEACAM5, MMP2, OPN, and MDK or the 6-marker subset of this 9-marker panel (Cyfra, SLPI, TIMP1, TFPI, CEACAM5, and MDK). Furthermore, one or more supplemental biomedical parameters can be used in addition to any of the panels provided in Table 5 and/or can replace one or more members of any of the panels provided in Table 5. Moreover, one or more supplemental biomedical parameters can be used in addition to any of the markers or panels provided herein and/or can replace one or more members of any of the panels provided herein, including the markers provided in Tables 1-2 (SEQ ID NOS:1-65 and the carbohydrate antigens CA 242, CA 19-9, and CA 72-4), Table 4, FIGS. 1, 12, and 19, and the panels provided in Tables 3 and 6-12. Furthermore, supplemental biomedical parameters can be incorporated into algorithms and scoring systems/classifiers, together with biomarker assessments (e.g., biomarker levels), for assessing lung cancer (e.g., diagnosing lung cancer).

Examples of supplemental biomedical parameters include, but are not limited to, any of the following. Any or all of these supplemental biomedical parameters can be used, in any combination, with any of the LCM and LCM panels disclosed herein. For example, any of the LCM and LCM panels disclosed herein can be assessed alone (without considering supplemental biomedical parameters) or can be assessed in combination with CT results (for example), or can be assessed in combination with any other supplemental biomedical parameters, or can be assessed in combination with CT results plus any other supplemental biomedical parameters, or any other combination of supplemental biomedical parameters can be assessed in combination with any of the LCM and LCM panels disclosed herein. Any of these supplemental biomedical parameters can be assessed as part of an algorithm or scoring system/classifier, together with biomarker assessments (e.g., biomarker levels), such as for assessing lung cancer (e.g., diagnosing lung cancer).

1) age, gender, and/or ethnicity;
2) family history of lung cancer or other type of cancer;
3) smoking history (e.g., whether or not an individual previously and/or currently smokes);
4) smoking level (e.g., "pack year": number of cigarettes smoked per day multiplied by number of years of smoking at this rate);
5) size of lesion;
6) location of lesion;
7) lesion morphology (ground glass opacity (GGO), solid, non-solid);
8) edge characteristics of lesion (smooth, lobulated, sharp and smooth, spiculated, infiltrating);
9) any other parameters determined from computed tomography (CT) screening;
10) exposure to second-hand smoke; and
10) any known carcinogen exposure (including, but not limited to, exposure to any of asbestos, radon gas, chemicals, smoke from fires, and air pollution, which can include emissions from stationary or mobile sources such as industrial/factory or auto/marine/aircraft emissions).

Exemplary methods of combining LCM with supplemental biomedical parameters can comprise the steps of obtaining a value for at least one supplemental biomedical parameter (e.g., smoking history) from an individual, comparing the value of each of the supplemental biomedical parameter(s) to one or more predetermined cutoffs, assigning a score for each supplemental biomedical parameter based on said comparison, combining the assigned score for each supplemental biomedical parameter with the assigned score for each LCM to obtain a total score for said individual, comparing the total score with a predetermined total score cutoff, and classifying said individual as having or not having lung cancer (or the likelihood thereof) based on whether the individual's total score is above or below (or equal to) the predetermined total score cutoff. In certain embodiments, if the individual's total score is above (or equal to) the predetermined total score cutoff, then the individual is classified as having lung cancer.

Further exemplary methods can comprise the steps of:
a) obtaining a value for at least one supplemental biomedical parameter of an individual;
b) comparing the value of each supplemental biomedical parameter against one or more predetermined cutoffs and assigning a score for each supplemental biomedical parameter based on said comparison;
c) quantifying in a test sample obtained from the individual, the levels of one or more LCM or LCM panels (e.g., the 9-marker panel of Cyfra, SLPI, TIMP1, SCC, TFPI, CEACAM5, MMP2, OPN, and MDK, or the 6-marker subset of Cyfra, SLPI, TIMP1, TFPI, CEACAM5, and MDK);
d) comparing the amount of each LCM quantified to a predetermined cutoff and assigning a score for each LCM based on said comparison;
e) combining the assigned score for each supplemental biomedical parameter determined in step b with the assigned score for each LCM determined in step d to obtain a total score for said individual;
f) comparing the total score determined in step e with a predetermined total score cutoff; and
g) classifying the individual (or the test sample from the individual) as having or not having lung cancer (or the likelihood thereof) based on whether the individual's total score is above or below (or equal to) the predetermined total score cutoff (in certain embodiments, if the individual's total score is above (or equal to) the predetermined total score cutoff, then the individual is classified as having lung cancer).

In the above exemplary methods, the supplemental biomedical parameter obtained from the individual can be, for example, the individual's smoking history, age, carcinogen exposure, gender, nodule size, nodule morphology, and/or nodule location (nodule characteristics, such as size, morphology, and/or location, may be determined by CT imaging, as well as X-ray or other imaging methods). Preferably, the supplemental biomedical parameter is related to nodule mophology.

Exemplary Scoring Systems and Cutoffs

A variety of methodologies can be used to classify a sample based on assaying one or more LCM disclosed herein. Classifying a sample can be based on a score derived from assessing one or more LCM disclosed herein, optionally in combination with one or more supplemental biomedical parameters (including, but not limited to, the supplemental biomedical parameters disclosed in the preceding section). A score or other classification system can be based on, for example, determining whether the level of one or more LCM is above or below a cutoff level (which may be referred to as a "cutoff value" or just "cutoff"), or is above or below a cutoff value by a certain amount (e.g., by a certain number of standard deviations such as two standard deviations), or the magnitude/extent of how high or low the level of one or more LCM is (which may optionally be in relation to a cutoff value). A wide variety of scoring systems and methodologies for establishing cutoff values are known in the art, and one of ordinary skill in the art would know how to implement a known scoring system or method of establishing cutoff values (or devise a new scoring system or method for establishing cutoff values) that is best suited for the intended use, such as assessing lung cancer based on one or more LCM or LCM panels (optionally in combination with one or more supplemental biomedical parameters). Accordingly, one of ordinary skill in the art could establish and adjust cutoff values to suit the intended use, and could incorporate these cutoff values into any desirable scoring system. For example, cutoff values can be adjusted based on whether increased sensitivity (for detecting tumor samples and avoiding false-negatives) or increased specificity (for avoiding false-positives) is considered more important. For example, cutoffs can be selected such as to achieve at least 70% sensitivity at 95% specificity, or at least 70% specificity at 95% sensitivity, or at least 85% sensitivity at 95% specificity, or at least 85% specificity at 95% sensitivity, or at least 90% or 95% sensitivity, or at least 90% or 95% specificity, or any other desired sensitivity and/or specificity (such as the sensitivity and specificity values described above). As another example, cutoffs can be set lower while requiring more markers in a panel to be above the cutoff levels in order to classify a sample as a tumor sample, or cutoffs can be set higher while requiring fewer markers in a panel to be above the cutoff levels in order to classify a sample as a tumor sample. When a cutoff value is set and applied to testing, it may be interchangeably referred to herein as a "predetermined" or "established" cutoff value. Furthermore, various analysis methods can be applied, including, but not limited to, split-point analysis (such as for setting discrete cutoffs), logistic regression analysis (such as for factoring in the magnitude/extent by which a marker level is elevated or low), Naïve Bayes, multivariate analysis, decision tree modeling, etc.

A representative example is shown in FIG. 17 for the 9-marker panel of Cyfra, SLPI, TIMP1, SCC, TFPI, CEACAM5, MMP2, OPN, and MDK. In FIG. 17, exemplary cutoffs for each of these 9-markers are shown just below each marker symbol, as follows (levels/concentrations, in ng/ml, were determined by ELISA): Cyfra=1.20 ng/ml, CEA=5.00 ng/ml, SLPI=52 ng/ml, OPN=32 ng/ml, MDK=0.15 ng/ml, TFPI=150 ng/ml, TIMP1=385 ng/ml, MMP2=210 ng/ml, and SCC=2.2 ng/ml. These cutoff values were established by examining the levels of these markers in both normal (control) samples and lung tumor samples in the 50×50 sample set and determining appropriate cutoff values that would best distinguish lung tumor versus normal samples (e.g., cutoff values were selected for which the levels of a majority of lung tumor samples are above and the levels of a majority of normal samples are below, so as to maximize sensitivity and specificity). These cutoffs were then applied to the same 50×50 sample set (i.e., the 50×50 sample set was used for both training and testing in this example). In this example, if the levels of two or more of the nine markers was greater than or equal to the established cutoff value for each marker, then the sample was classified as a lung tumor sample (thus, if the levels of none, or only one, of the nine markers was greater than or equal to the established cutoff value for each marker, then the sample was classified as a normal sample). Using this exemplary scoring system in this exemplary sample set, 48 out of 50 tumor samples were correctly classified, whereas the $42^{nd}$ and $43^{rd}$-listed samples were mis-classified as not being tumor samples since the level of only one of the nine markers (rather than the minimum of two or more) in each of these two sample sets was greater than or equal to the cutoff level (96% sensitivity; right-side of FIG. 17). Similarly, using this exemplary scoring system in this exemplary sample set, 49 out of 50 normal (control) samples were correctly classified, whereas the $2^{nd}$-listed sample was mis-classified as being a tumor sample since the levels of three of the nine markers (which meets the minimum of two or more) in this sample set were greater than or equal to the cutoff levels (98% specificity; left-side of FIG. 17). However, one of skill in the art would appreciate that no assay would be expected to correctly classify every single sample; rather, some misclassification is expected in the art. The goal is generally to minimize, rather than eliminate, misclassifications. Further, an assay (such as an assay of LCM levels) can be combined with other types of tests (such as CT screening) to further minimize misclassifications.

In other exemplary scoring systems, if the levels of one or more, three of more, four or more, five of more, six or more, seven or more, eight or more, or all nine markers of the 9-marker panel of Cyfra, SLPI, TIMP1, SCC, TFPI, CEACAM5, MMP2, OPN, and MDK are greater than or equal to the established cutoff value for each marker, then the sample can be classified as a lung tumor sample. In certain exemplary scoring systems, if the level of a marker is greater than or equal to the established cutoff value for that marker, it can be assigned a value of one (for example) and if the level of a marker is below the established cutoff value for that marker, it can be assigned a value of zero (for example). However, any desired values can be assigned to the various outcomes. Furthermore, these values can be added together (or otherwise combined) to determine a total score for a sample, and a classification of the sample as a tumor or normal sample (for example) can be assigned based on this total score. For example, in the example described above and depicted in FIG. 17, a score of two or greater can be used to classify a sample as a tumor sample (and a score below two could be used to classify a sample as a normal sample) if the level of each marker that is greater than or equal to its established cutoff value is assigned a value of one. Any other scoring system can be used, and one of ordinary skill in the art would know how to select or devise a scoring system best suited for the intended use.

A scoring system and cutoff values such as those exemplified in FIG. 17, or any other desirable scoring system and cutoff values, can be applied to any of the other LCM and LCM panels disclosed herein, such as the 6-marker subset of the 9-marker panel (Cyfra, SLPI, TIMP1, TFPI, CEACAM5, and MDK) and any of the other panels provided in Table 5, and can optionally incorporate any supplemental biomedical parameters. For example, any supplemental biomedical parameters can be assigned a value in a scoring system (e.g., a history of smoking can be assigned a value of one or other value, and no smoking history can be assigned a value of zero, negative one, or other value), and such values can be combined with the values assigned to marker levels being above a predetermined cutoff level (for example), such as to generate a total score for classifying a sample as a lung tumor or normal sample. Furthermore, these various scoring systems and cutoff values can be applied to any of the lung cancer-related uses disclosed herein, including specific uses such as those disclosed in Tables 7-10.

Figure 21:
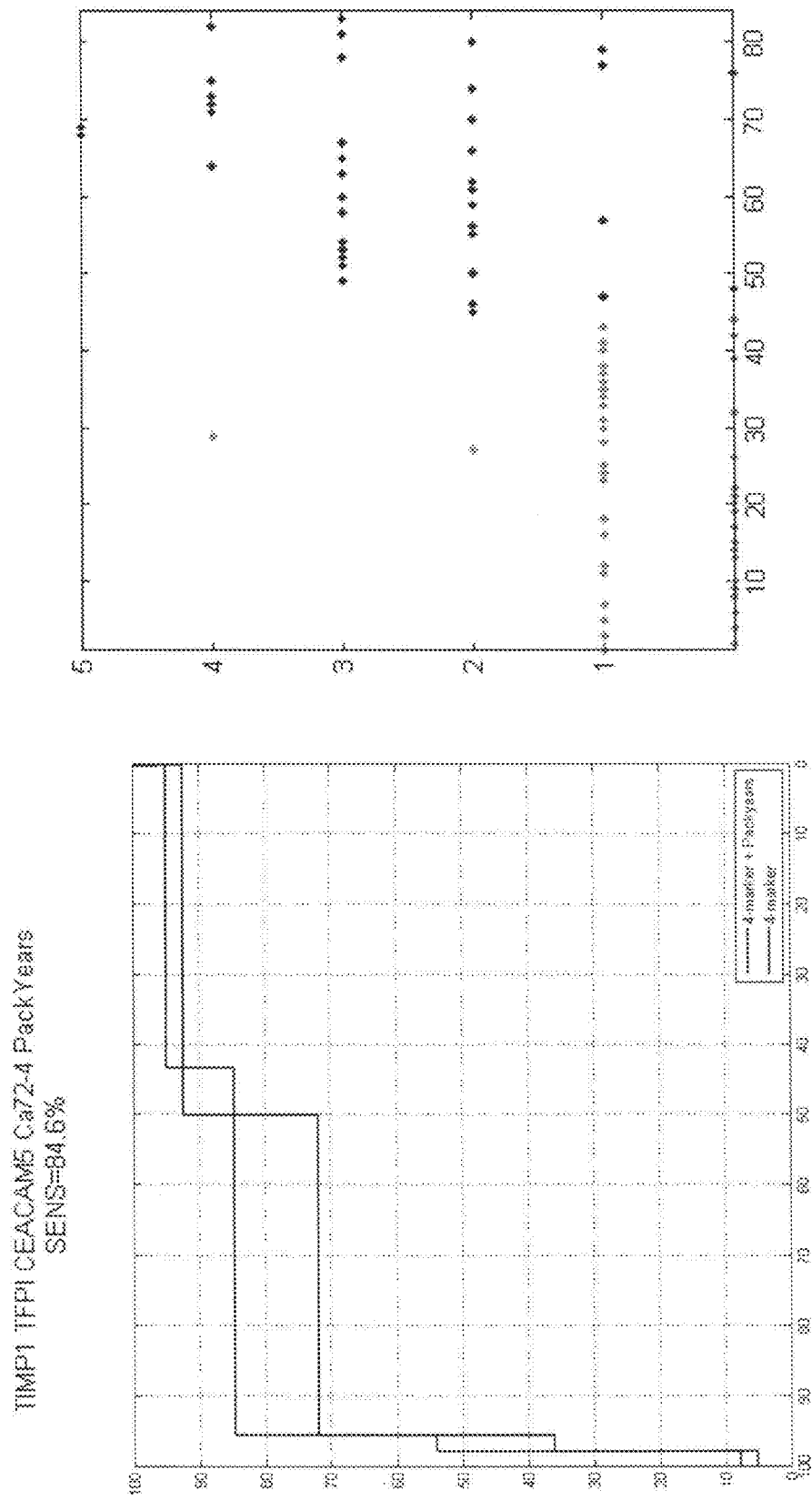
FIG. 21. Shows an analysis of integrating an exemplary supplemental biomedical parameter (smoking history) with an exemplary LCM panel (TIMP1, TFPI, CEACAM5, and Ca72-4) plus pack years ("pack year": number of cigarettes smoked per day multiplied by number of years of smoking at this rate). The left-side graph shows that performance of a 5-marker panel (represented by the line that includes a vertical portion at 50 of the x-axis) is enhanced with addition of smoking history (pack years) (represented by the line that includes a vertical portion at about 43 of the x-axis). Sensitivity increases from 71.5% to 84.6%. The right-side graph shows split-point analysis performed following the addition of smoking history (split at about 45 of the x-axis).

Any of the scoring systems disclosed herein or known in the art, or which may be devised by one of ordinary skill in the art, can be incorporated into a computer program, and such a computer program can be embodied on computer readable medium. For example, a computer program can generate a total score from a sample based on, for example, the number of markers in a panel for which the levels are above predetermined cutoff levels, together with parameters from CT screening (e.g., tumor volume/size, tumor morphology, tumor location, and/or other tumor characteristics, etc.) and/or other supplemental biomedical parameters (e.g., smoking history, age of the individual, etc.), and this total score can be used to classify a sample as a lung tumor or normal sample, for example. A single total score can be generated that represents the combination of multiple different types of assessments (e.g., a combination of LCM levels and supplemental biomedical parameters), or multiple individual scores can be generated for evaluation individually (e.g., a score based on assessment of LCM levels, and one or more separate scores based on supplemental biomedical parameters). An example of this type of integrated approach of combining LCM levels (using the exemplary panel of TIMP1, TFPI, CEACAM5, and Ca72-4) with a supplemental biomedical parameter (smoking history, as indicated by "pack years") is shown in FIG. 21.

Kits

Any combination of LCM and LCM panels (as well as supplemental biomedical parameters) can be provided in the form of kits, such as for use in performing the methods disclosed herein. Furthermore, any kit can contain one or more detectable labels (e.g., detactably labeled reagents such as antibodies), such as a fluorescent moiety, etc.

For example, a kit can comprise (a) reagents comprising at least one antibody for quantifying one or more LCM in a test sample, wherein said LCM comprise: Cyfra, SLPI, TIMP1, SCC, TFPI, CEACAM5, MMP2, OPN, and MDK (or just Cyfra, SLPI, TIMP1, TFPI, CEACAM5, and MDK; or any other LCM or LCM panels disclosed herein, such as the panels disclosed in Tables 5-12), and optionally (b) one or more algorithms or computer programs for performing the steps of comparing the amount of each LCM quantified in the test sample to one or more predetermined cutoffs and assigning a score for each LCM quantified based on said comparison, combining the assigned score for each LCM quantified to obtain a total score, comparing the total score with a predetermined total score, and using said comparison to determine whether an individual has lung cancer. Alternatively, rather than one or more algorithms or computer programs, one or more instructions for manually performing the above steps by a human can be provided.

In certain embodiments, a kit can contain: (a) reagents comprising at least one antibody for quantifying one or more LCM in a test sample, wherein said LCM are Cyfra, SLPI, TIMP1, SCC, TFPI, CEACAM5, MMP2, OPN, and MDK, and (b) reagents containing one or more LCM for quantifying at least one antibody in a test sample; wherein said antibodies are: TP53 (p53), KLKB1, CFL1 (CFLN), EEF1G, HSP90α (HSP90AA1), RTN4, ALDOA, GLG1, PTK7, EFEMP1, SLC3A2 (CD98), CHGB, CEACAM1, ALCAM, HSPB1 (HSP27), LGALS1, and B7H3, and optionally (c) one or more algorithms or computer programs for performing the steps of comparing the amount of each LCM and antibody quantified in the test sample to one or more predetermined cutoffs and assigning a score for each LCM and antibody quantified based on said comparison, combining the assigned score for each LCM and antibody quantified to obtain a total score, comparing the total score with a predetermined total score, and using said comparison to determine whether an individual has lung cancer. Alternatively, rather than one or more algorithms or computer programs, one or more instructions for manually performing the above steps by a human can be provided.

Translating LCM Assessments to Lung Cancer Assessments, and Systems Therefor

An assessment of LCM in an individual, such as LCM levels determined by assaying a serum sample (or other sample) from the individual, can be translated to an assessment of lung cancer for the individual. For example, the levels of multiple LCM (such as each of the LCM in the 9-marker panel of Cyfra, SLPI, TIMP1, SCC, TFPI, CEACAM5, MMP2, OPN, and MDK) can be translated to a score or other identifier that indicates whether an individual has lung cancer (or that indicates the likelihood that the individual has lung cancer), for example. Similarly, the score or other identifier may indicate a specific type of lung cancer assessment, such as the assessments of various lung cancer characteristics described herein, including (but not limited to), determination of whether an individual's lung cancer is adenocarcinoma or squamous cell carcinoma, determination of the stage of an individual's lung cancer (such as distinguishing between stage I and stage III lung cancer), determination of whether an individual's lung cancer is SCLC or NSCLC, determining whether a lung lesion identified in an individual (such as by CT screening) is a malignant tumor or a benign lesion, and determining lung tumor regression and/or recurrence. Any of these determinations may be expressed in a discrete (e.g., absolute) or continuous (e.g., likelihood) manner, for example.

Furthermore, the assessment of LCM in an individual, such as LCM levels, can be translated to a tangible report. Thus, a score or other identifier that indicates the lung cancer assessment can be provided in the form of a tangible report.

Additionally, the translation, such as the translation of LCM levels to a lung cancer assessment (such as a score or other identifier), can be performed by a computer. Furthermore, certain embodiments provide computer readable medium having a computer program code embodied thereon for translating LCM levels to a lung cancer assessment.

In certain embodiments, the invention provides systems for assessing one or more LCM, particularly the levels of multiple LCM, and translating this LCM assessment to an assessment of lung cancer, such as a determination of whether an individual has (or is likely to have) lung cancer (which may be indicated by a score or other identifier). In certain embodiments, these systems include one or more computers to receive an LCM assessment, translate the LCM assessment to a lung cancer assessment, and output the lung cancer assessment (e.g., as a score or other identifier). These systems may optionally comprise multiple computers that communicate via the internet (or any other mode of communication used in the art for inter-computer communication).

Accordingly, certain embodiments of the invention provide methods of translating an assessment of LCM (e.g., LCM levels) to an assessment of lung cancer (e.g., a score or other indication of whether an individual has lung cancer, or their likelihood of having lung cancer, or other specific lung cancer assessment). In certain embodiments, this assessment of lung cancer is provided in the form of a tangible report. In certain embodiments, the translation is performed by a computer. Furthermore, certain embodiments of the invention provide computers programmed to translate an LCM assessment to a lung cancer assessment. Certain embodiments provide computer readable medium having a computer program code embodied thereon for translating LCM levels to a lung cancer assessment. In certain embodiments, a system is provided for receiving an LCM assessment, translating the LCM assessment to a lung cancer assessment, and outputting the lung cancer assessment (e.g., as a score or other identifier). In various embodiments, the system comprises one or more computers (which may optionally communicate via the internet or other mode of communication).

Reports, Transmission of Reports, and Programmed Computers

The results of a test (e.g., a diagnosis of lung cancer for an individual based on the level, or other assay, of one or more LCM disclosed herein, or assessment of tumor progression/regression/recurrence, lung cancer stage, type of lung cancer such as NSCLC versus SCLC or adenocarcinoma versus squamous cell carcinoma, malignant tumor versus benign lung lesion, etc.), and/or any other information pertaining to a test (e.g., the levels of one or more LCM disclosed herein in a sample from an individual, which may optionally be provided in the absence of explicit disease or diagnostic information), may be referred to herein as a "report". A tangible report can optionally be generated as part of a testing process (which may be interchangeably referred to herein as "reporting", or as "providing" a report, "producing" a report, or "generating" a report).

Examples of tangible reports may include, but are not limited to, reports in paper (such as computer-generated printouts of test results) or equivalent formats and reports stored on computer readable medium (such as a CD, USB flash drive or other removable storage device, computer hard drive, or computer network server, etc.). Reports, particularly those stored on computer readable medium, can be part of a database, which may optionally be accessible via the internet (such as a database of patient records or biomedical information stored on a computer network server, which may be a "secure database" that has security features that limit access to the report, such as to allow only the patient and the patient's medical practioners to view the report while preventing other unauthorized individuals from viewing the report, for example). In addition to, or as an alternative to, generating a tangible report, reports can also be displayed on a computer screen (or the display of another electronic device or instrument).

A report can further be "transmitted" or "communicated" (these terms may be used herein interchangeably), such as to the individual who was tested, a medical practitioner (e.g., a doctor, nurse, clinical laboratory practitioner, etc.), a healthcare organization, a clinical laboratory, and/or any other party or requester intended to view or possess the report. The act of "transmitting" or "communicating" a report can be by any means known in the art, based on the format of the report. Furthermore, "transmitting" or "communicating" a report can include delivering a report ("pushing") and/or retrieving ("pulling") a report. For example, reports can be transmitted/communicated by various means, including being physically transferred between parties (such as for reports in paper format) such as by being physically delivered from one party to another, or by being transmitted electronically or in signal form (e.g., via e-mail or over the internet, by facsimile, and/or by any wired or wireless communication methods known in the art) such as by being retrieved from a database stored on a computer network server, etc.

In certain exemplary embodiments, the invention provides computers (or other apparatus/devices such as biomedical devices or laboratory instrumentation) programmed to carry out the methods described herein. For example, in certain embodiments, the invention provides a computer programmed to receive (i.e., as input) the levels of one or more LCM disclosed herein and provide (i.e., as output) a lung cancer diagnosis or other result (e.g., assessment of tumor progression/regression/recurrence, lung cancer stage, type of lung cancer such as NSCLC versus SCLC or adenocarcinoma versus squamous cell carcinoma, malignant tumor versus benign lung lesion, etc.) based on the levels of one or more LCM. Such output (e.g., communication of lung cancer diagnosis, etc.) may be, for example, in the form of a report on computer readable medium, printed in paper form, and/or displayed on a computer screen or other display.

Further exemplary embodiments of the invention are described in greater detail below.

1. LCM Proteins

Exemplary embodiments of the invention provide LCM proteins that consist of, consist essentially of, or comprise the amino acid sequences of SEQ ID NOS:1-65 (additionally, carbohydrate antigens CA 242, CA 19-9, and CA 72-4 are also provided, which may also be encompassed by references herein to proteins/polypeptides), as well as all known variants and fragments of these proteins, and nucleic acid molecules that are within the art to make and use. Examples of such obvious variants include, but are not limited to, naturally-occurring allelic variants, pre-processed or mature processed forms of a protein, non-naturally occurring recombinantly-derived variants, orthologs, and paralogs. Such variants can readily be generated using art-known techniques in the fields of recombinant nucleic acid technology and protein biochemistry.

A protein is said to be "isolated" or "purified" when it is substantially free of cellular material or free of chemical precursors or other chemicals. LCM proteins can be purified to homogeneity or other degrees of purity. The level of purification can be based on the intended use. The primary consideration is that the preparation allows for the desired function of the protein, even if in the presence of considerable amounts of other components.

In some uses, "substantially free of cellular material" includes preparations of a protein having less than about 30% (by dry weight) other proteins (i.e., contaminating protein), less than about 20% other proteins, less than about 10% other proteins, or less than about 5% other proteins. When the protein is recombinantly produced, it can also be substantially free of culture medium, i.e., culture medium represents less than about 20% of the volume of the protein preparation.

The language "substantially free of chemical precursors or other chemicals" includes preparations of a protein in which the protein is separated from chemical precursors or other chemicals that are involved in the protein's synthesis. In one embodiment, the language "substantially free of chemical precursors or other chemicals" includes preparations of a LCM protein having less than about 30% (by dry weight) chemical precursors or other chemicals, less than about 20% chemical precursors or other chemicals, less than about 10% chemical precursors or other chemicals, or less than about 5% chemical precursors or other chemicals.

Isolated LCM proteins can be purified from cells that naturally express it, purified from cells that have been altered to express it (recombinant), or synthesized using known protein synthesis methods (e.g., Sambrook et al., Molecular Cloning: A Laboratory Manual. 3rd. ed., Cold Spring Harbor Laboratory Press, Cold Spring Harbor, N.Y., (2001)). For example, a nucleic acid molecule encoding a LCM protein can be cloned into an expression vector, the expression vector introduced into a host cell, and the protein expressed in the host cell. The protein can then be isolated from the cells by an appropriate purification scheme using standard protein purification techniques.

A LCM protein or fragment thereof can be attached to heterologous sequences to form chimeric or fusion proteins. Such chimeric and fusion proteins comprise a protein operatively linked to a heterologous protein having an amino acid sequence not substantially homologous to the protein.

"Operatively linked" indicates that the protein and the heterologous protein are fused in-frame. The heterologous protein can be fused to the N-terminus or C-terminus of the protein.

In some uses, the fusion protein does not affect the activity of the protein per se. For example, the fusion protein can include, but is not limited to, beta-galactosidase fusions, yeast two-hybrid GAL fusions, poly-His fusions, MYC-tagged, HI-tagged, and Ig fusions. Such fusion proteins, particularly poly-His fusions, can facilitate the purification of recombinant LCM proteins. In certain host cells (e.g., mammalian host cells), expression and/or secretion of a protein can be increased by using a heterologous signal sequence.

A chimeric or fusion LCM protein can be produced by standard recombinant DNA techniques. For example, DNA fragments coding for different protein sequences can be ligated together in-frame in accordance with conventional techniques. In another embodiment, a fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (Ausubel et al., Current Protocols in Molecular Biology, 1992-2006). Moreover, many expression vectors are commercially available that already encode a fusion moiety (e.g., a GST protein). A LCM-encoding nucleic acid can be cloned into such an expression vector such that the fusion moiety is linked in-frame to the LCM protein.

To determine the percent identity of two amino acid sequences or two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In an exemplary embodiment, at least 30%, 40%, 50%, 60%, 70%, 80%, or 90% or more of the length of a reference sequence can be aligned for comparison purposes. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps, and the length of each gap, that are introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., Stockton Press, New York, 1991). In an exemplary embodiment, the percent identity between two amino acid sequences is determined using the Needleman and Wunsch (*J. Mol. Biol.* (48):444-453 (1970)) algorithm which has been incorporated into the GAP program in the GCG software package, using either a Blossom 62 matrix or a PAM250 matrix, a gap weight of 16, 14, 12, 10, 8, 6, or 4, and a length weight of 1, 2, 3, 4, 5, or 6. In another exemplary embodiment, the percent identity between two nucleotide sequences can be determined using the GAP program in the GCG software package (Devereux et al., *Nucleic Acids Res.* 12(1):387 (1984)) using a NWSgapdna.CMP matrix and a gap weight of 40, 50, 60, 70, or 80, and a length weight of 1, 2, 3, 4, 5, or 6. In another exemplary embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM 120 weight residue table, a gap length penalty of 12, and a gap penalty of 4.

The sequences of the proteins and nucleic acid molecules of the invention can further be used as a "query sequence" to perform a search against sequence databases to, for example, identify other protein family members or related sequences. Such searches can be performed using the NBLAST and XBLAST programs (version 2.0) of Altschul et al. (*J. Mol. Biol.* 215:403-10 (1990)). BLAST nucleotide searches can be performed with the NBLAST program, score=100, wordlength=12, to obtain nucleotide sequences homologous to the query nucleic acid molecule. BLAST protein searches can be performed with the XBLAST program, score=50, wordlength=3, to obtain amino acid sequences homologous to the query proteins. To obtain gapped alignments for comparison purposes, Gapped BLAST can be utilized as described in Altschul et al. (*Nucleic Acids Res.* 25(17):3389-3402 (1997)). When utilizing BLAST and gapped BLAST programs, the default parameters of the respective programs (e.g., XBLAST and NBLAST) can be used.

As used herein, two proteins (or a region or domain of the proteins) have significant homology/identity (also referred to as substantial homology/identity) when the amino acid sequences are typically at least about 70-80%, 80-90%, 90-95%, 96%, 97%, 98%, or 99% identical A significantly homologous amino acid sequence can be encoded by a nucleic acid molecule that hybridizes to a LCM protein-encoding nucleic acid molecule under stringent conditions, as more fully described below.

Orthologs of a LCM protein typically have some degree of significant sequence homology to at least a portion of a LCM protein and are encoded by a gene from another organism. Preferred orthologs are isolated from mammals, preferably non-human primates, for the development of human therapeutic markers and agents. Such orthologs can be encoded by a nucleic acid molecule that hybridizes to a LCM protein-encoding nucleic acid molecule under moderate to stringent conditions, as more fully described below, depending on the degree of relatedness of the two organisms yielding the proteins.

Non-naturally occurring variants of the LCM proteins can readily be generated using recombinant techniques. Such variants include, but are not limited to, deletions, additions, and substitutions in the amino acid sequence of the LCM protein. For example, one class of substitutions is conserved amino acid substitutions. Such substitutions are those that substitute a given amino acid in a LCM protein by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306-1310 (1990).

Variant LCM proteins can be fully functional or can lack function in one or more activities, e.g., ability to bind substrate, ability to phosphorylate substrate, ability to mediate signaling, etc. Fully functional variants typically contain only conservative variations or variation in non-critical residues or in non-critical regions.

Non-functional variants typically contain one or more non-conservative amino acid substitutions, deletions, insertions, inversions, or truncations, or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081-1085 (1989)). The latter procedure introduces single alanine mutations at every residue in the molecule. The resulting mutant molecules are then tested for biological activity or in assays such as in vitro proliferative activity. Sites that are critical for binding partner/substrate binding can also be determined by structural analysis such as crystallization, nuclear magnetic resonance, or photoaffinity labeling (Smith et al., *J. Mol. Biol.* 224:899-904 (1992); de Vos et al., *Science* 255:306-312 (1992)).

LCM of the invention include fragments of LCM, and peptides that comprise and consist of such fragments. Such fragments of LCM may be naturally-occurring in the human body. An exemplary fragment typically comprises at least about 5, 6, 8, 10, 12, 14, 16, 18, 20 or more contiguous amino acid residues of a LCM protein. Such fragments can be chosen based on the ability to retain one or more of the biological activities of LCM or can be chosen for the ability to perform a function, e.g., bind a substrate or act as an immunogen. Particularly important fragments are biologically active fragments, such as peptides that are, for example, about 8 or more amino acids in length. Such fragments can include a domain or motif of a LCM, e.g., an active site, a transmembrane domain, or a binding domain. Further, possible fragments include, but are not limited to, soluble peptide fragments and fragments containing immunogenic structures. Domains and functional sites can readily be identified, for example, by computer programs well known and readily available to those of skill in the art (e.g., PROSITE analysis).

Proteins can contain amino acids other than the 20 amino acids commonly referred to as the 20 naturally-occurring amino acids. Further, many amino acids, including the terminal amino acids, can be modified by natural processes, such as processing and other post-translational modifications, or by chemical modification techniques well known in the art. Common modifications that occur naturally in proteins are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, tRNA-mediated addition of amino acids to proteins such as arginylation, and ubiquitination.

Such modifications are well known to those of skill in the art and have been described in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins-Structure and Molecular Properties, 2nd Ed., T. E. Creighton, W. H. Freeman and Company, New York (1993). Many detailed reviews are available on this individual, such as by Wold (Posttranslational Covalent Modification of Proteins, B. C. Johnson, Ed., Academic Press, New York 1-12 (1983)); Seifter et al. (Meth. Enzymol. 182: 626-646 (1990)); and Rattan et al. (Ann. N.Y. Acad. Sci. 663:48-62 (1992)).

Accordingly, exemplary LCM proteins and fragments thereof of the invention can also encompasses derivatives or analogs in which, for example, a substituted amino acid residue is not one encoded by the genetic code, in which a substituent group is included, in which a mature LCM is fused with another composition, such as a composition to increase the half-life of a LCM (e.g., polyethylene glycol or albumin), or in which additional amino acids are fused to a mature LCM, such as a leader or secretory sequence or a sequence for purification of a mature LCM or a pro-protein sequence.

2. Antibodies to LCM Proteins

Exemplary embodiments of the invention provide antibodies to LCM proteins, including, for example, monoclonal and polyclonal antibodies; chimeric, humanized, and fully human antibodies; and antigen-binding fragments and variants thereof, as well as other embodiments.

Antibodies that selectively bind to a LCM protein can be made using standard procedures known to those of ordinary skills in the art. The term "antibody" is used in the broadest sense, and specifically covers, for example, monoclonal antibodies, polyclonal antibodies, multispecific antibodies (e.g., bispecific antibodies), chimeric antibodies, humanized antibodies, fully human antibodies, and antibody fragments (e.g., Fab, F(ab')$_2$, Fv and Fv-containing binding proteins), so long as they exhibit LCM-binding activity. Antibodies (Ab's) and immunoglobulins (Ig's) are glycoproteins typically having the same structural characteristics. Antibodies can be of the IgG, IgE, IgM, IgD, and IgA class or subclass thereof (e.g., IgG1, IgG2, IgG3, IgG4, IgA1 and IgA2). Antibodies may be interchangeably referred to as "LCM-binding molecules".

The term "monoclonal antibody", as used herein, refers to an antibody obtained from a population of substantially homogeneous antibodies, i.e., the individual antibodies comprising the population are substantially identical except for possible naturally occurring mutations that may be present in minor amounts. Monoclonal antibodies are highly specific and are typically directed against a single antigenic site. Furthermore, in contrast to polyclonal antibody preparations, which typically include different antibodies directed against different determinants (epitopes), each monoclonal antibody is typically directed against a single determinant on an antigen. In addition to their specificity, monoclonal antibodies are advantageous in that substantially homogenous antibodies can be produced by a hybridoma culture which is uncontaminated by other immunoglobulins or antibodies. The modifier "monoclonal" antibody indicates the character of the antibody as being obtained from a substantially homogeneous population of antibodies, and is not to be construed as requiring production of the antibody by any particular method. For example, monoclonal antibodies can be made by hybridoma methods such as described by Kohler and Milstein, *Nature* 256: 495-497 (1975), by recombinant methods (e.g., as described in U.S. Pat. No. 4,816,567), or can be isolated from phage antibody libraries such as by using the techniques described in Clackson et al., *Nature* 352: 624-628 (1991) or Marks et al., *J. Mol. Biol.* 222: 581-597 (1991).

"Humanized" forms of non-human (e.g., murine or rabbit) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Typically, humanized antibodies are human immunoglobulins (a recipient antibody) in which residues from a complementarity determining regions ("CDR") of the recipient are replaced by residues from a CDR of a non-human species (a donor antibody) such as mouse, rat, or rabbit having the desired specificity, affinity, and capacity. In some instances, Fv framework residues of the human immunoglobulin are replaced by corresponding non-human residues. Furthermore, a humanized antibody may comprise residues which are found neither in the recipient antibody nor in the imported CDR or framework region (FR) sequences. These modifications can be made to further refine and optimize antibody performance. In general, a humanized antibody can comprise substantially all of at least one, and typically two, variable domains, in which all or substantially all of the CDRs correspond to those of a non-human immunoglobulin and all or substantially all of the FRs are those of a human immunoglobulin consensus sequence.

A humanized antibody can also comprise at least a portion of an immunoglobulin constant region (Fc), typically that of a human immunoglobulin. For further details concerning humanized antibodies, see: Jones et al., *Nature* 321:522-525 (1986); Reichmann et al., *Nature* 332:323-327 (1988); Presta, *Curr. Op. Struct. Biol.* 2:593-596 (1992); Queen et al., U.S. Pat. Nos. 5,530,101; 5,585,089; 5,693,762; and 6,180,370; and Winter, U.S. Pat. No. 5,225,539.

Antibodies, as used herein, include antibody fragments, particularly antigen-binding fragments, as well as other modified antibody structures and antigen-binding scaffolds (such as modified antibody structures that are smaller or have less than all domains or chains compared with a typical naturally occurring, full-size human antibody). Examples of antibody fragments and other modified antibody structures and antigen-binding scaffolds are known in the art by such terms as minibodies (e.g., U.S. Pat. No. 5,837,821), Nanobodies (llama heavy chain antibodies; Ablynx, Ghent, Belgium), Adnectins (fibronectin domains; Adnexus Therapeutics, Waltham, Mass.), Affibodies (protein-binding domain of *Staphylococcus aureus* protein A; Affibody, Stockholm, Sweden), peptide aptamers (synthetic peptides; Aptanomics, Lyon, France), Avimers (A-domains derived from cell surface receptors; Avidia, Mountain View, Calif. (acquired by Amgen)), Transbodies (transferrin; BioRexis Pharmaceuticals, King of Prussia, Pa. (acquired by Pfizer)), trimerized tetranectin domains (Borean Pharma, Aarhus, Denmark), Domain antibodies (heavy or light chain antibodies; Domantis, Cambridge, UK (acquired by GlaxoSmithKline)), Evibodies (derived from V-like domains of T-cell receptors CTLA-4, CD28 and inducible T-cell costimulator; EvoGenix Therapeutics, Sydney, Australia), scFV fragments (stable single chain antibody fragments; ESBATech, Zurich, Switzerland), Unibodies (monovalent IgG4 mAbs fragments; Genmab, Copenhagen, Denmark), BiTEs (bispecific, T-cell activating single-chain antibody fragments; Micromet, Munich, Germany), DARPins (designed ankyrin repeat proteins; Molecular Partners, Zurich, Switzerland), Anticalins (derived from lipocalins; Pieris, Freising-Weihenstephan, Germany), Affilins (derived from human lens protein gamma crystalline; Scil Proteins, Halle, Germany), and SMIPs (small modular immunopharmaceuticals; Trubion Pharmaceuticals, Seattle, Wash.) (Sheridan, *Nature Biotechnology,* 2007 April; 25(4):365-6).

An "isolated" or "purified" antibody is one that has been identified and separated and/or recovered from a component of the environment in which it is produced. Contaminant components of its production environment are materials that would interfere with diagnostic or therapeutic uses for the antibody, and may include enzymes, hormones, and other proteinaceous or nonproteinaceous solutes. In exemplary embodiments, the antibody can be purified as measurable by any of at least three different methods: 1) to greater than 95% by weight of antibody as determined by the Lowry method, preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or silver stain. Isolated antibody can include an antibody in situ within recombinant cells since at least one component of the antibody's natural environment will not be present. Ordinarily, however, an isolated antibody can be be prepared by at least one purification step.

An "antigenic region", "antigenic determinant", or "epitope" includes any protein determinant capable of specific binding to an antibody. This is the site on an antigen to which each distinct antibody molecule binds. Epitopic determinants can be active surface groupings of molecules such as amino acids or sugar side chains and may have specific three-dimensional structural characteristics or charge characteristics.

"Antibody specificity" refers to an antibody that has a stronger binding affinity for an antigen from a first individual species than it has for a homologue of that antigen from a second individual species. Typically, an antibody "binds specifically" to a human antigen (e.g., has a binding affinity (Kd) value of no more than about $1 \times 10^{-7}$ M, preferably no more than about $1 \times 10^{-8}$ M, and most preferably no more than about $1 \times 10^{-9}$ M) but has a binding affinity for a homologue of the antigen from a second individual species which is at least about 50-fold, or at least about 500-fold, or at least about 1000-fold, weaker than its binding affinity for the human antigen. The antibodies can be of any of the various types of antibodies as described herein, such as humanized or fully human antibodies.

An antibody "selectively" or "specifically" binds a marker protein when the antibody binds the marker protein and does not significantly bind to unrelated proteins. An antibody can still be considered to selectively or specifically bind a marker protein even if it also binds to other proteins that are not substantially homologous with the marker protein as long as such proteins share homology with a fragment or domain of the marker protein. In this case, it would be understood that antibody binding to the marker protein is still selective despite some degree of cross-reactivity.

Exemplary embodiments of the invention provide an "antibody variant", which refers to an amino acid sequence variant of an antibody wherein one or more of the amino acid residues have been modified. Such variants necessarily have less than 100% sequence identity with the amino acid sequence of the antibody, and have at least 75%, 80%, 85%, 90%, 95%, 96%, 97%, 98%, or 99% amino acid sequence identity with the amino acid sequence of either the heavy or light chain variable domain of the antibody.

The term "antibody fragment" refers to a portion of a full-length antibody, including the antigen binding or variable region or the antigen-binding portion thereof. Examples of antibody fragments include Fab, Fab', F(ab')$_2$ and Fv fragments. Papain digestion of antibodies typically produces two identical antigen binding fragments, called the Fab fragment, each with a single antigen binding site, and a residual "Fc"

fragment. Pepsin treatment typically yields an F(ab')$_2$ fragment that has two antigen binding fragments which are capable of crosslinking antigen, and a residual other fragment (which is termed pFc'). Examples of additional antigen-binding fragments can include diabodies, triabodies, tetrabodies, single-chain Fv, single-chain Fv-Fc, SMIPs, and multispecific antibodies formed from antibody fragments. A "functional fragment", with respect to antibodies, typically refers to an Fv, F(ab), F(ab')$_2$ or other antigen-binding fragments comprising one or more CDRs that has substantially the same antigen-binding specificity as an antibody.

An "Fv" fragment is an example of an antibody fragment that contains a complete antigen recognition and binding site. This region typically consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen.

An "Fab" fragment (also designated as "F(ab)") also contains the constant domain of the light chain and the first constant domain (CH1) of the heavy chain. Fab' fragments differ from Fab fragments by the addition of a few residues at the carboxyl terminus of the heavy chain CH1 domain, including one or more cysteines from the antibody hinge region. Fab'-SH is the designation for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

A "single-chain Fv" or "scFv" antibody fragment contains $V_H$ and $V_L$ domains, wherein these domains are present in a single polypeptide chain. Typically, the Fv polypeptide further comprises a polypeptide linker between the $V_H$ and $V_L$ domains that enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994). A single chain Fv-Fc is an scFv linked to a Fc region.

A "diabody" is a small antibody fragment with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., Proc. Natl. Acad. Sci. USA 90:6444-6448 (1993). Triabodies, tetrabodies and other antigen-binding antibody fragments have been described by Hollinger and Hudson, 2005, Nature Biotechnology 23:1126.

A "small modular immunopharmaceutical" (or "SMIP") is a single-chain polypeptide including a binding domain (e.g., an scFv or an antigen binding portion of an antibody), a hinge region, and an effector domain (e.g., an antibody Fc region or a portion thereof). SMIPs are described in published U.S. Patent Application No. 20050238646.

Many methods are known for generating and/or identifying antibodies to a given marker protein. Several such methods are described by Kohler et al., 1975, Nature 256: 495-497; Lane, 1985, J. Immunol. Meth. 81:223-228; Harlow et al., 1988, Antibodies: A Laboratory Manual. Cold Spring Harbor Laboratory Press; Harlow et al., 1998, Using Antibodies, Cold Spring Harbor Press; Zhong et al., 1997, J. Indust. Microbiol. Biotech. 19(1):71-76; and Berry et al., 2003, Hybridoma and Hybridomics 22(1): 23-31.

Polyclonal antibodies can be prepared by any known method or modifications of these methods, including obtaining antibodies from patients. In certain exemplary methods for generating antibodies such as polyclonal antibodies, an isolated protein can be used as an immunogen which is administered to a mammalian organism, such as a rat, rabbit, or mouse. For example, a complex of an immunogen such as a LCM protein (or fragment thereof) and a carrier protein can be prepared and an animal immunized by the complex. Serum or plasma containing antibodies against the protein can be recovered from the immunized animal and the antibodies separated and purified (in the same manner as for monoclonal antibodies, for example). The gamma globulin fraction or the IgG antibodies can be obtained, for example, by use of saturated ammonium sulfate or DEAE SEPHADEX, or other techniques known to those skilled in the art. The antibody titer in the antiserum can be measured in the same manner as in the supernatant of a hybridoma culture.

A marker such as a full-length LCM protein, an antigenic peptide fragment, a fusion protein thereof, or a carbohydrate antigen or fragment thereof, can be used as an immunogen. A marker used as an immunogen is not limited to any particular type of immunogen. In one aspect, antibodies can be prepared from regions or discrete fragments (e.g., functional domains, extracellular domains, or portions thereof) of a LCM. Antibodies can be prepared from any region of a marker as described herein. In particular, the markers can be selected from the group consisting of SEQ ID NOS:1-65, the carbohydrate antigens CA 242, CA 19-9, and CA 72-4, and fragments thereof. An antigenic fragment can typically comprise at least 8, 10, 12, 14, 16, or more contiguous amino acid residues, for example. Such fragments can be selected based on a physical property, such as fragments that correspond to regions located on the surface of a marker (e.g., hydrophilic regions) or can be selected based on sequence uniqueness.

Antibodies can also be produced by inducing production in a lymphocyte population or by screening antibody libraries or panels of highly specific binding reagents, such as disclosed in Orlandi et al. (Proc. Natl. Acad. Sci. 86:3833-3837 (1989)) or Winter et al. (Nature 349:293-299 (1991)). A protein can be used in screening assays of phagemid or B-lymphocyte immunoglobulin libraries to identify antibodies having a desired specificity. Numerous protocols for competitive binding or immunoassays using either polyclonal or monoclonal antibodies with established specificities are well known in the art (e.g., Smith, Curr. Opin. Biotechnol. 2: 668-673 (1991)).

Antibodies can also be generated using various phage display methods known in the art. In representative phage display methods, functional antibody domains are displayed on the surface of phage particles which carry nucleic acid molecules that encode the antibody domains. In particular, such phage can be utilized to display antigen-binding domains expressed from a repertoire or combinatorial antibody library (e.g., human or murine). Phage expressing an antigen binding domain that binds an antigen of interest can be selected or identified with the antigen, e.g., using labeled antigen or antigen bound or captured to a solid surface or bead. Phage used in methods such as these can typically be filamentous phage including fd and M13 binding domains expressed from phage with Fab, Fv, or disulfide stabilized Fv antibody domains recombinantly fused to either the phage gene III or gene VIII protein. Examples of phage display methods that can be used to make antibodies include methods described in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Antibodies, antigen binding fragments, and/or antibody variants can be produced by recombinant and genetic engineering methods well known in the art. For example, methods of expressing heavy and light chain genes in *E. coli* are described in PCT publication numbers WO901443, WO901443, and WO9014424, and in Huse et al., 1989 *Science* 246:1275-1281. When using recombinant techniques, such as to produce an antibody variant, the antibody variant can be produced intracellularly, in the periplasmic space, or directly secreted into the medium. If an antibody variant is produced intracellularly, as a first step, the particulate debris, either host cells or lysed fragments, can be removed, for example, by centrifugation or ultrafiltration. Carter et al. (*Bio/Technology* 10: 163-167 (1992)) describe a procedure for isolating antibodies that are secreted to the periplasmic space of *E. coli*. Briefly, cell paste can be thawed in the presence of sodium acetate (pH 3.5), EDTA, and phenylmethylsulfonylfluoride (PMSF) over about 30 minutes. Cell debris can be removed by centrifugation. Where an antibody variant is secreted into the medium, supernatants from such expression systems can first be concentrated using a commercially available protein concentration filter (e.g., an Amicon or Millipore PELLICON ultrafiltration unit). A protease inhibitor such as PMSF can be included in any of the foregoing steps to inhibit proteolysis, and antibiotics can be included to prevent the growth of contaminating microorganisms.

An antibody composition prepared from cells can be purified using, for example, affinity chromatography, hydroxylapatite chromatography, gel electrophoresis, and/or dialysis. The suitability of protein A as an affinity ligand typically depends on the species and isotype of the immunoglobulin Fc domain of an antibody. Protein A can be used to purify antibodies that are based on human delta1, delta2, or delta4 heavy chains (Lindmark et al., *J. Immunol. Meth.* 62: 1-13 (1983)). Protein G can be used for all mouse isotypes and for human delta3 (Guss et al., *EMBO J.* 5: 1567-1575 (1986)). The matrix to which the affinity ligand is attached can be, for example, agarose or mechanically stable matrices such as controlled pore glass or poly(styrenedivinyl)benzene. Where the antibody comprises a CH3 domain, the BAKERBOND ABX™ resin (J. T. Baker, Phillipsburg, N.J.) can be used for purification. Other exemplary techniques for antibody purification include, but are not limited to, fractionation on an ion-exchange column, ethanol precipitation, reverse phase HPLC, chromatography on silica, chromatography on heparin hepharos, chromatography on an anion or cation exchange resin (such as a polyaspartic acid column), chromatofocusing, SDS-PAGE, and ammonium sulfate precipitation.

Following any preliminary purification step(s), contaminants in a mixture containing an antibody of interest can be removed by low pH hydrophobic interaction chromatography using an elution buffer at a pH between about 2.5-4.5, preferably performed at low salt concentrations (e.g., from about 0-0.25M salt).

Full-length antibodies, as well as antibody fragments, can also be expressed and isolated from bacteria such as *E. coli*, such as described in Mazor et al., "Isolation of engineered, full-length antibodies from libraries expressed in *Escherichia coli*", *Nat. Biotechnol.* 2007 May; 25(5):563-5 and Sidhu, "Full-length antibodies on display", *Nat. Biotechnol.* 2007 May; 25(5):537-8.

Further details regarding antibodies are set forth in the following U.S. Pat. No. 6,248,516 (Winter et al.); U.S. Pat. No. 6,291,158 (Winter et al.); U.S. Pat. No. 5,885,793 (Griffiths et al.); U.S. Pat. No. 5,969,108 (McCafferty et al.); U.S. Pat. No. 5,939,598 (Kucherlapati et al.); U.S. Pat. No. 4,816,397 (Boss et al.); U.S. Pat. No. 4,816,567 (Cabilly et al.); U.S. Pat. No. 6,331,415 (Cabilly et al.); U.S. Pat. No. 5,770,429 (Lonberg et al.); U.S. Pat. No. 5,639,947 (Hiatt et al.); and 5,260,203 (Ladner et al.), each of which is incorporated herein by reference, and in the following published U.S. patent applications: US20040132101 (Lazar et al.), US20050064514 (Stavenhagen et al.), US20040261148 (Dickey et al.), and US20050014934 (Hinton et al.), each of which is incorporated herein by reference. Antibody engineering is further described in Jain et al., "Engineering antibodies for clinical applications", *Trends Biotechnol.* 2007 July; 25(7):307-16.

3. Antibody-Drug Conjugates to LCM Proteins

An antibody against LCM can be coupled (e.g., covalently bonded) to a suitable therapeutic agent (as further discussed herein) either directly or indirectly (e.g., via a linker group). A direct reaction between an antibody and a therapeutic agent is possible when each possesses a substituent capable of reacting with the other. For example, a nucleophilic group, such as an amino or sulfhydryl group, on one molecule may be capable of reacting with a carbonyl-containing group, such as an anhydride or an acid halide, or with an alkyl group containing a good leaving group (e.g., a halide) on the other molecule.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

A variety of bifunctional or polyfunctional reagents, both homo- and hetero-functional (such as those described in the catalog of the Pierce Chemical Co., Rockford, Ill.), can be employed as the linker group. Coupling can be effected, for example, through amino groups, carboxyl groups, sulfhydryl groups, or oxidized carbohydrate residues (e.g., U.S. Pat. No. 4,671,958).

Where a therapeutic agent is more potent when free from the antibody portion of an immunoconjugate, it may be desirable to use a linker group that is cleavable during or upon internalization into a cell. A number of different cleavable linker groups have been described. Mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), by protease cleavable linker (e.g., U.S. Pat. No. 6,214,345), and by acid-catalyzed hydrolysis (e.g., U.S. Pat. No. 4,569,789).

It may be desirable to couple more than one agent to an antibody. Multiple molecules of an agent can be coupled to one antibody molecule, and more than one type of agent can be coupled to the same antibody. For example, about 1, 2, 4, 6, 8, 10, 12, 14, 16, 18, 20, or 22 (or any other number in-between) molecules of therapeutic agents can be coupled to an antibody. The average number or quantitative distribution of therapeutic agent molecules per antibody molecule in a preparation of conjugation reactions can be determined by conventional means such as mass spectroscopy, ELISA, or HPLC. Separation, purification, and characterization of homogeneous antibody-drug conjugates having a certain number of therapeutic agents conjugated thereto can be achieved by means such as reverse phase HPLC or electrophoresis (see, e.g., Hamblett et al., *Clinical Cancer Res.* 10:7063-70 (2004).

Examples of suitable therapeutic agents that can be conjugated to an antibody include, but are not limited to, chemotherapeutic agents (e.g., cytotoxic or cytostatic agents or immunomodulatory agents), radiotherapeutic agents, therapeutic antibodies, small molecule drugs, peptide drugs, immunomodulatory agents, differentiation inducers, and toxins.

Examples of useful classes of cytotoxic or immunomodulatory agents include, but are not limited to, antitubulin agents, auristatins, DNA minor groove binders, DNA replication inhibitors, alkylating agents (e.g., platinum complexes such as cis-platin, mono(platinum), bis(platinum) and trinuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Examples of individual cytotoxic or immunomodulatory agents include, but are not limited to, androgen, anthramycin (AMC), asparaginase, 5-azacytidine, azathioprine, bleomycin, busulfan, buthionine sulfoximine, calicheamicin or calicheamicin derivatives, camptothecin or camptothecins derivatives, carboplatin, carmustine (BSNU), CC-1065, chlorambucil, cisplatin, colchicine, cyclophosphamide, cytidine arabinoside (cytarabine), cytochalasin B, dacarbazine, dactinomycin (formerly actinomycin), daunorubicin, decarbazine, docetaxel, doxorubicin, etoposide, estrogen, 5-fluorodeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16, and VM-26.

Examples of other suitable cytotoxic agents include, but are not limited to, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, a maytansinoid, discodermolide, eleutherobin, and mitoxantrone.

Examples of other suitable agents include, but are not limited to, radionuclides, differentiation inducers, drugs, toxins, and derivatives thereof. Exemplary radionuclides include $^{90}$Y, $^{123}$I, $^{125}$I, $^{131}$I, $^{186}$Re, $^{188}$Re, $^{211}$At, and $^{212}$Bi. Exemplary drugs include methotrexate, and pyrimidine and purine analogs. Exemplary differentiation inducers include phorbol esters and butyric acid. Exemplary toxins include ricin, abrin, diptheria toxin, cholera toxin, gelonin, *Pseudomonas* exotoxin, *Shigella* toxin, and pokeweed antiviral protein.

In some embodiments, the therapeutic agent used in an antibody-drug conjugate is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophysins, cemadotin, maytansinoid, combretastatins, discodermolide, and eleutherobin.

In certain embodiments, the cytotoxic agent is a maytansinoid, another group of anti-tubulin agents. For example, in specific embodiments, the maytansinoid is maytansine, DM-1 (ImmunoGen, Inc.; see also Chari et al., *Cancer Res.* 52:127-131 (1992)) or DM-4.

In some embodiments, the therapeutic agent is an auristatin, such as auristatin E (also known in the art as dolastatin-10) or a derivative thereof. Typically, an auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; PCT Publication Nos WO 04/010957 and WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

4. LCM Nucleic Acid Molecules

Exemplary isolated LCM nucleic acid molecules of the invention consist of, consist essentially of, or comprise a nucleotide sequence that encodes a LCM protein of the invention, an allelic variant thereof, or an ortholog or paralog thereof, for example. As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 kilobases (KB), 4 KB, 3 KB, 2 KB, or 1 KB or less, particularly contiguous protein-encoding sequences and protein-encoding sequences within the same gene but separated by introns in the genomic sequence, and flanking nucleotide sequences that contain regulatory elements. The primary consideration is that the nucleic acid is isolated from remote and unimportant flanking sequences such that it can be individualed to the specific manipulations described herein such as recombinant expression, preparation of probes and primers, and other uses specific to the nucleic acid molecules. Moreover, an "isolated" nucleic acid molecule, such as a transcript/cDNA molecule, can be substantially free of other cellular material, or culture medium when produced by recombinant techniques, or chemical precursors or other chemicals when chemically synthesized.

A nucleic acid molecule can be fused to other coding or regulatory sequences and still be considered isolated. Isolated nucleic acid molecules can include heterologous nucleotide sequences, such as heterologous nucleotide sequences that are fused to a nucleic acid molecule by recombinant techniques. For example, recombinant DNA molecules contained in a vector are considered isolated. Further examples of isolated DNA molecules include recombinant DNA molecules maintained in heterologous host cells, or purified (partially or substantially) DNA molecules in solution. Isolated RNA molecules include in vivo or in vitro RNA transcripts of isolated DNA molecules. Isolated nucleic acid molecules further include such molecules produced synthetically.

Isolated nucleic acid molecules can encode a mature protein plus additional amino or carboxyl-terminal amino acids, or amino acids interior to the mature protein (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, additional amino acids may be processed away from the mature protein by cellular enzymes.

Isolated nucleic acid molecules include, but are not limited to, sequences encoding a LCM protein alone, sequences encoding a mature protein with additional coding sequences (such as a leader or secretory sequence (e.g., a pre-pro or pro-protein sequence)), and sequences encoding a mature protein (with or without additional coding sequences) plus additional non-coding sequences (e.g., introns and non-coding 5' and 3' sequences such as transcribed but non-translated sequences that play a role in transcription, mRNA processing (including splicing and polyadenylation signals), ribosome binding, and/or stability of mRNA). In addition, nucleic acid molecules can be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. Nucleic acid molecules, especially DNA, can be double-stranded or single-stranded. Single-stranded nucleic acid can be the coding strand (sense strand) or the non-coding strand (anti-sense strand).

Exemplary embodiments of the invention further provide isolated nucleic acid molecules that encode fragments of a LCM protein as well as nucleic acid molecules that encode obvious variants of a LCM protein. Such nucleic acid molecules may be naturally occurring, such as allelic variants (same locus), paralogs (different locus), and orthologs (different organism), or can be constructed by recombinant DNA methods or by chemical synthesis. Such non-naturally occurring variants can be made by mutagenesis techniques, including those applied to nucleic acid molecules, cells, or organisms. Accordingly, nucleic acid molecule variants can contain nucleotide substitutions, deletions, inversions, and/or insertions. Variations can occur in either or both the coding and non-coding regions, and variations can produce conservative and/or non-conservative amino acid substitutions.

A fragment of a nucleic acid molecule typically comprises a contiguous nucleotide sequence at least 8, 10, 12, 15, 16, 18, 20, 22, 25, 30, 40, 50, 100, 150, 200, 250, 500 (or any other number in-between) or more nucleotides in length. The length of a fragment can be based on its intended use. For example, a fragment can encode epitope bearing regions of a protein, or can be used as DNA probes and primers. Isolated fragments can be produced by synthesizing an oligonucleotide probe using known techniques, for example, and can optionally be labeled and used to screen a cDNA library, genomic DNA, or mRNA, for example. Primers can be used in PCR reactions to clone specific regions of a gene.

A probe/primer typically comprises substantially a purified oligonucleotide or oligonucleotide pair. An oligonucleotide typically comprises a nucleotide sequence that hybridizes under stringent conditions to at least about 8, 10, 12, 14, 15, 16, 17, 18, 19, 20, 21, 22, 23, 24, 25, 30, 40, 50 (or any other number in-between) or more contiguous nucleotides.

Allelic variants, orthologs, and homologs can be identified using methods well known in the art. These variants can comprise a nucleotide sequence encoding a protein that is typically 60-70%, 70-80%, 80-90%, 90-95%, 96%, 97%, 98%, or 99% homologous to the nucleotide sequence. Such nucleic acid molecules can readily be identified as being able to hybridize under moderate to stringent conditions, to a nucleotide sequence shown in the Sequence Listing or a fragment thereof.

As used herein, the term "hybridizes under stringent conditions" is intended to describe conditions for hybridization and washing under which nucleotide sequences encoding a protein at least 60-70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in, for example, Current Protocols in Molecular Biology, John Wiley & Sons, N.Y. (1989-2006), 6.3.1-6.3.6. One example of stringent hybridization conditions is hybridization in 6× sodium chloride/sodium citrate (SSC) at about 45° C., followed by one or more washes in 0.2×SSC, 0.1% SDS at 50-65° C. Examples of moderate to low stringency hybridization conditions are well known in the art.

Exemplary embodiments of the invention also include kits for detecting the presence of LCM nucleic acid (e.g., DNA or mRNA) in a biological sample. For example, a kit can comprise reagents such as a labeled or labelable nucleic acid and/or other agents capable of detecting LCM nucleic acid in a biological sample; means for determining the amount of LCM nucleic acid in the sample; and means for comparing the amount of LCM nucleic acid in the sample with a standard. The nucleic acid and/or other agent can be packaged in one or more suitable containers. The kit can further comprise instructions for using the kit to detect LCM nucleic acid.

5. Vectors and Host Cells

Exemplary embodiments of the invention also provide vectors containing LCM nucleic acid molecules. The term "vector" refers to a vehicle, such as a nucleic acid molecule, which can transport the LCM nucleic acid molecules. When the vector is a nucleic acid molecule, the LCM nucleic acid molecules are covalently linked to the vector nucleic acid. A vector can be, for example, a plasmid, single or double stranded phage, a single or double stranded RNA or DNA viral vector, or artificial chromosome, such as a BAC, PAC, YAC, OR MAC.

A vector can be maintained in a host cell as an extrachromosomal element where it replicates and produces additional copies of the LCM nucleic acid molecules. Alternatively, a vector can integrate into a host cell genome and produce additional copies of the LCM nucleic acid molecules when the host cell replicates.

Exemplary embodiments of the invention provide vectors for maintenance (cloning vectors) and vectors for expression (expression vectors) of the nucleic acid molecules, for example. Expression vectors can express a portion of, or all of, a protein sequence. Vectors can function in prokaryotic or eukaryotic cells or in both (shuttle vectors). Vectors also include insertion vectors, which integrate a nucleic acid molecule into another nucleic acid molecule, such as into the cellular genome (such as to alter in situ expression of a gene and/or gene product). For example, an endogenous protein-coding sequence can be entirely or partially replaced via homologous recombination with a protein-coding sequence containing one or more specifically introduced mutations.

Expression vectors can contain cis-acting regulatory regions that are operably-linked in the vector to the nucleic acid molecules such that transcription of the nucleic acid molecules is allowed in a host cell. The nucleic acid molecules can be introduced into the host cell with a separate nucleic acid molecule capable of affecting transcription. The separate nucleic acid molecule may provide, for example, a trans-acting factor interacting with the cis-regulatory control region to allow transcription of the nucleic acid molecules from the vector. Alternatively, a trans-acting factor may be supplied by a host cell. Additionally, a trans-acting factor can be produced from a vector itself. It is understood, however, that transcription and/or translation of nucleic acid molecules can occur in cell-free systems.

Regulatory sequences to which LCM nucleic acid molecules can be operably linked include, for example, promoters for directing mRNA transcription. These include, but are not limited to, the left promoter from bacteriophage, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors can also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region, a ribosome binding site for translation. Other regulatory control elements for expression include initiation and termination codons as well as polyadenylation signals. Numerous regulatory sequences useful in expression vectors are well known in the art (e.g., Sambrook et al., Molecular Cloning: A Laboratory Manual. 3rd. ed., Cold Spring Harbor Laboratory Press, Cold Spring Harbor, N.Y. (2001)).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., Molecular Cloning: A Laboratory Manual. 3rd. ed., Cold Spring Harbor Laboratory Press, Cold Spring Harbor, N.Y. (2001).

A regulatory sequence can provide constitutive expression in one or more host cells (e.g., tissue specific) or can provide for inducible expression in one or more cell types such as by temperature, nutrient additive, or exogenous factors such as a hormone or other ligand. A variety of vectors providing for constitutive and inducible expression in prokaryotic and eukaryotic hosts are well known in the art.

Nucleic acid molecules can be inserted into vector nucleic acid by well-known methodology. For example, the DNA sequence that will ultimately be expressed can be joined to an expression vector by cleaving the DNA sequence and the expression vector with one or more restriction enzymes and then ligating the fragments together. Procedures for restriction enzyme digestion and ligation are well known in the art.

A vector containing a nucleic acid molecule of interest can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells (e.g., DG44 or CHO-s), and plant cells.

As described herein, it may be desirable to express a protein as a fusion protein. Accordingly, exemplary embodiments of the invention provide fusion vectors that allow for the production of fusion proteins. Fusion vectors can, for example, increase the expression of a recombinant protein; increase the solubility of a recombinant protein, and/or aid in the purification of a protein such as by acting as a ligand for affinity purification. A proteolytic cleavage site can be introduced at the junction of the fusion moiety so that the desired protein can ultimately be separated from the fusion moiety. Proteolytic enzymes include, but are not limited to, factor Xa, thrombin, and enteroenzyme. Typical fusion expression vectors include pGEX (Smith et al., Gene 67:31-40 (1988)), pMAL (New England Biolabs, Beverly, Mass.) and pRIT5 (Pharmacia, Piscataway, N.J.), which fuse glutathione S-transferase (GST), maltose E binding protein, or protein A, respectively, to a recombinant marker protein. Examples of suitable inducible non-fusion *E. coli* expression vectors include pTrc (Amann et al., Gene 69:301-315 (1988)) and pET 11d (Studier et al., Gene Expression Technology: Methods in Enzymology 185:60-89 (1990)).

Recombinant protein expression can be maximized in host bacteria by providing a genetic background wherein the host cell has an impaired capacity to proteolytically cleave the recombinant protein (Gottesman, S., Gene Expression Technology: Methods in Enzymology 185, Academic Press, San Diego, Calif. (1990), pp. 119-128). Alternatively, the sequence of a nucleic acid molecule of interest can be altered to provide preferential codon usage for a specific host cell, such as *E. coli* (Wada et al., Nucleic Acids Res. 20:2111-2118 (1992)).

LCM nucleic acid molecules can, for example, be expressed by expression vectors in a yeast host. Examples of vectors for expression in yeast (e.g., *S. cerevisiae*) include pYepSec1 (Baldari, et al., EMBO J. 6:229-234 (1987)), pMFa (Kurjan et al., Cell 30:933-943 (1982)), pJRY 88 (Schultz et al., Gene 54:113-123 (1987)), and pYES2 (Invitrogen Corporation, San Diego, Calif.). Nucleic acid molecules can also be expressed in insect cells using, for example, baculovirus expression vectors. Baculovirus vectors available for expression of proteins in cultured insect cells (e.g., Sf 9 cells) include the pAc series (Smith et al., Mol. Cell. Biol. 3:2156-2165 (1983)) and the pVL series (Lucklow et al., Virology 170:31-39 (1989)). Nucleic acid molecules can also be expressed in mammalian cells using mammalian expression vectors. Examples of mammalian expression vectors include pCDM8 (Seed, B. Nature 329:840 (1987)), pMT2PC (Kaufman et al., EMBO J. 6:187-195 (1987)), and CHEF (U.S. Pat. No. 5,888,809).

The expression vectors listed herein are provided by way of example only of well-known vectors available to those of ordinary skill in the art that would be useful to express LCM nucleic acid molecules. The person of ordinary skill in the art would be aware of other vectors suitable for maintenance, propagation, and/or expression of LCM nucleic acid molecules (e.g., Sambrook et al. Molecular Cloning: A Laboratory Manual. 3rd. ed., Cold Spring Harbor Laboratory Press, Cold Spring Harbor, N.Y. (2001).

Exemplary embodiments of the invention also encompasses vectors in which LCM nucleic acid molecules are cloned into a vector in reverse orientation, but operably linked to a regulatory sequence that permits transcription of antisense RNA. Thus, an antisense transcript can be produced to all, or to a portion, of a LCM nucleic acid molecule, including coding and non-coding regions. Expression of this antisense RNA may be individual to each of the parameters described above in relation to expression of the sense RNA (e.g., regulatory sequences, constitutive or inducible expression, tissue-specific expression).

Exemplary embodiments of the invention provide recombinant host cells containing the vectors described herein. Host cells include, for example, prokaryotic cells, lower eukaryotic cells such as yeast, other eukaryotic cells such as insect cells, and higher eukaryotic cells such as mammalian cells.

Recombinant host cells can be prepared by introducing vector constructs, such as described herein, into cells by techniques readily available to a person of ordinary skill in the art. These techniques include, but are not limited to, calcium phosphate transfection, DEAE-dextran-mediated transfection, cationic lipid-mediated transfection, electroporation, transduction, infection, lipofection, microinjection, and other techniques such as those found in Sambrook, et al. (Molecular Cloning: A Laboratory Manual. 3rd. ed., Cold Spring Harbor Laboratory Press, Cold Spring Harbor, N.Y. (2001).

For example, using techniques such as these, a retroviral or other viral vector can be introduced into mammalian cells. Examples of mammalian cells into which a retroviral vector can be introduced include, but are not limited to, primary mammalian cultures or continuous mammalian cultures, COS cells, NIH3T3, 293 cells (ATCC #CRL 1573), and dendritic cells.

Host cells can contain more than one vector. Thus, different nucleotide sequences can be introduced on different vectors of the same cell. Similarly, nucleic acid molecules of interest can be introduced either alone or with other unrelated nucleic acid molecules such as those providing trans-acting factors for expression vectors. When more than one vector is introduced into a cell, the vectors can be introduced independently, co-introduced, or joined to the nucleic acid molecule vector.

Bacteriophage and viral vectors can be introduced into cells as packaged or encapsulated virus by standard procedures for infection and transduction. Viral vectors can be replication-competent or replication-defective. If viral replication is defective, replication can occur in host cells that provide functions that complement the defects.

Vectors can include selectable markers that enable the selection of a subpopulation of cells that contain the recombinant vector constructs. Markers can be contained in the same vector that contains the nucleic acid molecules of interest or can be on a separate vector. Exemplary markers include tetracycline or ampicillin-resistance genes for prokaryotic host cells, and dihydrofolate reductase or neomycin resistance for eukaryotic host cells. However, any marker that provides selection for a phenotypic trait can be used.

While mature proteins can be produced in bacteria, yeast, mammalian cells, and other cells under the control of appropriate regulatory sequences, cell-free transcription and translation systems can also be used to produce these proteins using RNA derived from the DNA constructs described herein.

If secretion of a protein is desired, appropriate secretion signals can be incorporated into a vector. The signal sequence can be endogenous or heterologous to the protein.

If a protein is not secreted into a medium, the protein can be isolated from a host cell by standard disruption procedures, including freeze/thaw, sonication, mechanical disruption, use of lysing agents, and the like. A protein can then be recovered and purified by well-known purification methods including, for example, ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that, depending upon the host cell used in recombinant production of a protein, proteins can have various glycosylation patterns or can be non-glycosylated, such as when produced in bacteria. In addition, proteins can include an initial modified methionine in some instances as a result of a host-mediated process.

Recombinant host cells that express a LCM protein have a variety of uses. For example, such host cells are useful for producing LCM proteins, which can be further purified to produce desired amounts of the protein or fragments thereof. Thus, host cells containing expression vectors are useful for protein production.

Host cells are also useful for conducting cell-based assays involving a LCM protein or fragments thereof. For example, a recombinant host cell expressing a LCM protein can be used to assay compounds that stimulate or inhibit the protein's function.

Host cells are also useful for identifying mutant LCM proteins in which the protein's function is affected. Host cells expressing mutant proteins are useful for assaying compounds that have a desired effect on the mutant proteins (e.g., stimulating or inhibiting function), particularly if the mutant proteins naturally occur and give rise to a pathology.

6. Diagnosis and Treatment in General

The following terms, as used in the present specification and claims, are intended to have the meaning as defined below, unless indicated otherwise.

As used herein, a "biological sample" (or just "sample") can comprise, for example, tissue, blood, sera, cells, cell lines, or biological fluids such as plasma, interstitial fluid, urine, cerebrospinal fluid, and the like. A biological sample is typically, although not necessarily, obtained from an individual by a medical practitioner.

As used herein, a "individual" can be a mammalian individual or non-mammalian individual, preferably a mammalian individual. A mammalian individual can be a human or non-human, preferably a human. The terms "individual", "individual", and "patient" are used herein interchangeably.

A "healthy" or "normal" individual or biological sample is a individual or biological sample in which the disease of interest (e.g., lung cancer) is not detectable, as ascertained by using conventional diagnostic methods (such a biological sample can interchangeably be referred to as a "control" sample).

As used herein, "disease(s)" include cancer, especially aerodigestive cancers, and particularly lung cancer, as well as associated diseases and pathologies, such as other lung diseases.

The term "diagnose" (or "diagnosing", etc.) refers to determining the current state or status (e.g., the presence/absence or characteristics) of a disease condition, such as initially detecting the presence of a disease, characterizing/classifying a disease, or detecting disease progression, remission, or recurrence.

The term "prognose" (or "prognosing", etc.) refers to predicting the future course of a disease in a patient who has the disease (e.g., predicting patient survival).

The term "assess" (or "assessing", etc.) can encompass "diagnose" and "prognose" but can also encompass making future determinations/predictions about the disease in an individual who does not have the disease or determining/predicting the likelihood that a disease will recur in an individual who apparently has been cured of the disease. The term "assess" can also encompass making assessments of an individual's response to a therapy, such as predicting whether an individual is likely to respond favorably to a therapeutic agent or is unlikely to respond to a therapeutic agent (or will experience toxic or other undesirable side effects, for example), selecting a therapeutic agent for administration to an individual, or monitoring or determining an individual's response to a therapy that has been administered to the individual.

Thus, "assessing" lung cancer can include, for example, prognosing the future course of lung cancer; predicting recurrence of lung cancer in an individual who apparently has been cured of lung cancer; and/or determining or predicting an individual's response to a lung cancer treatment or selecting a lung cancer treatment to administer to an individual based on the individual's LCM profile (i.e., the differential abundance level of one or more LCM in the individual).

The following examples may be referred to as either "diagnosing" or "assessing" lung cancer: initially detecting the presence of lung cancer; determining a specific stage, type or sub-type, or other classification or characteristic of lung cancer; determining whether a lung lesion is a benign lesion or a malignant lung tumor; and/or detecting/monitoring lung cancer progression (e.g., monitoring lung tumor growth or metastatic spread), remission, or recurrence.

LCM are therefore useful as "prognostic markers" (e.g., predicting disease progression) and "predictive markers" (e.g., predicting drug response), among other uses.

"Treat", "treating", or "treatment" of a disease includes: (1) inhibiting the disease, i.e., arresting or reducing the development of the disease or its clinical symptoms, or (2) relieving the disease, i.e., causing regression of the disease or its clinical symptom(s).

The term "prophylaxis" is used to distinguish from "treatment," and to encompass both "preventing" and "suppressing." It is not always possible to distinguish between "preventing" and "suppressing," as the ultimate inductive event or events may be unknown, latent, or the patient is not ascertained until well after the occurrence of the event or events. Therefore, the term "protection", as used herein, is meant to include "prophylaxis."

A "therapeutically effective amount" means the amount of an agent that, when administered to a individual for treating a disease, is sufficient to effect such treatment for the disease. The "therapeutically effective amount" can vary depending on such factors as the agent, the disease and its severity, and the age, weight, etc., of the individual to be treated.

Exemplary embodiments of the invention provide methods for treating diseases, especially cancer, and particularly lung cancer, comprising administering to a patient a therapeutically effective amount of an antagonist, agonist, or a pharmaceutical composition thereof. Exemplary embodiments of the invention further provide agonists and antagonists to LCM proteins, as well as pharmaceutical compositions that comprise an agonist or antagonist with a suitable carrier such as a pharmaceutically acceptable excipient.

Exemplary agonists or antagonists include antibodies that specifically bind to a LCM protein. Antibodies can be used alone or in combination with one or more other therapeutic agents (e.g., as an antibody-drug conjugate or a combination therapy). Further examples of molecules that can be used as antagonists include, but are not limited to, small molecules that inhibit the function or abundance level of LCM, and inhibitory nucleic acid molecules such as RNAi or antisense nucleic acid molecules that specifically hybridize to LCM nucleic acid.

Exemplary embodiments of the invention further encompass novel agents identified by screening assays using LCM, such as the screening assays described herein, as well as methods of using these agents, such as for treatment or diagnostic purposes. For example, an agent identified as described herein (e.g., a LCM-modulating agent, a LCM-specific nucleic acid molecule such as an RNAi or antisense molecule, a LCM-specific antibody, a LCM-specific antibody-drug conjugate, or a LCM-binding partner) can be used in an animal or other model, such as to determine efficacy, toxicity, or side effects of treatment with the agent.

Modulators of LCM protein activity, such as modulators identified according to the drug screening assays described herein, can be used to treat a individual with a disorder mediated by a LCM, e.g., by treating cells or tissues that express LCM at a differential level. Methods of treatment can include the step of administering a modulator of LCM activity in a pharmaceutical composition to a individual in need of such treatment.

In certain exemplary embodiments, if decreased expression or activity of a protein is desired, an antibody to the protein or an inhibitor/antagonist and the like, or a pharmaceutical agent containing one or more of these molecules, can be administered to an individual. In other exemplary embodiments, if increased expression or activity of a protein is desired, the protein itself or an agonist/enhancer and the like, or a pharmaceutical agent containing one or more of these molecules, can be administered. Administration can be effected by methods well known in the art and may include delivery by an antibody specifically targeted to the protein. Neutralizing antibodies, which inhibit dimer formation, can be used when decreased expression or activity of a protein is desired.

Although modulating agents can be administered in a pure or substantially pure form, modulating agents can also be administered as pharmaceutical compositions, formulations, or preparations with a carrier. Exemplary formulations of the invention, such as for human or veterinary use, comprise a suitable active LCM-modulating agent, together with one or more pharmaceutically acceptable carriers and, optionally, other therapeutic ingredients. The carrier(s) are "acceptable" in the sense of being compatible with other ingredients of a formulation and not deleterious to the recipient thereof. The formulations can be presented in unit dosage form and can be prepared by any method known to the skilled artisan.

Examples of suitable pharmaceutical carriers include proteins such as albumins (e.g., U.S. Pat. No. 4,507,234), peptides and polysaccharides such as aminodextran (e.g., U.S. Pat. No. 4,699,784), and water. A carrier can also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate can be formed from chelating compounds that include those containing nitrogen and sulfur atoms as the donor atoms for binding the metal, metal oxide, radionuclide. For example, U.S. Pat. No. 4,673,562 discloses representative chelating compounds and their synthesis.

Methods of preparing pharmaceutical formulations typically include the step of bringing into association the active ingredient with the carrier, which constitutes one or more accessory ingredients. Formulations can be prepared by uniformly and intimately bringing into association the active ingredient with liquid carriers or finely divided solid carriers, or both, and then, if necessary, shaping the product into the desired formulation.

Formulations suitable for intravenous, intramuscular, subcutaneous, or intraperitoneal administration can comprise sterile aqueous solutions of the active ingredient with solutions, which can be isotonic with the blood of the recipient. Such formulations can be prepared by dissolving solid active ingredient in water containing physiologically compatible substances such as sodium chloride (e.g., 0.1-2.0 M), glycine, and the like, and having a buffered pH compatible with physiological conditions to produce an aqueous solution, and rendering the solution sterile. These may be present in unit or multi-dose containers, for example, sealed ampoules or vials.

Exemplary formulations of the invention can incorporate a stabilizer. Exemplary stabilizers include polyethylene glycol, proteins, saccharides, amino acids, inorganic acids, detergents, and organic acids, which can be used either alone or as admixtures. These stabilizers can be incorporated in an amount of, for example, 0.11-10,000 parts by weight per part by weight of an agent. If two or more stabilizers are to be used, their total amount can be within the range specified above. These stabilizers can be used in aqueous solutions at an appropriate concentration and pH. The specific osmotic pressure of such aqueous solutions can be in the range of 0.1-3.0 osmoles, preferably in the range of 0.8-1.2. The pH of the aqueous solution can be adjusted to be within the range of 5.0-9.0, preferably within the range of 6-8. In formulating an antibody or antibody-drug conjugate, an anti-adsorption agent can be used.

Additional pharmaceutical methods can be employed to control duration of action. Controlled release can be achieved through the use of polymer to complex or absorb the proteins or their derivatives. Controlled delivery can be achieved by selecting appropriate macromolecules (e.g., polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate an anti-LCM antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions can be combined with typical carriers, such as lactose, sucrose, starch, talc magnesium stearate, crystalline cellulose, methyl cellulose, carboxymethyl cellulose, glycerin, sodium alginate or gum arabic, among others.

Any of the therapeutic agents provided herein may be administered in combination with other therapeutic agents. Selection of agents for use in combination therapy can be made by one of ordinary skill in the art according to conventional pharmaceutical principles. A combination of therapeutic agents may act synergistically to affect treatment of a particular disorder at a lower dosage of each agent.

7. Methods of Detection and Diagnosis Based on LCM Proteins

LCM proteins are useful for diagnosing a disease, particularly diseases in which the protein is over- or under-expressed, especially cancer, and particularly lung cancer. The diagnostic methods may be further suitable for monitoring disease progression in patients undergoing treatment, or for testing for reoccurrence of disease in patients who were previously treated for a disease, for example. Accordingly, exemplary embodiments of the invention provide methods for detecting the presence of, or abundance levels of, a LCM protein in a biological sample.

In vitro techniques for detection of proteins include, but are not limited to, enzyme linked immunosorbent assays (ELISAs), Western blots, immunoprecipitations, and immunofluorescence using a detection reagent, such as an antibody or protein binding agent. Alternatively, a protein can be detected in vivo in a individual by introducing into the individual a labeled antibody (or other types of detection agent) specific for the protein marker. For example, an antibody can be labeled with a radioactive marker whose presence and location in a individual can be detected by standard imaging techniques. Also useful are methods that detect variants of a protein (e.g., allelic variants or mutations) and methods that detect fragments of a protein in a sample.

Examples of immunoassays that can be used in accordance with exemplary embodiments of the invention include, but are not limited to, competitive and non-competitive assays using techniques such as Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays, as well as fluorescence polarization immunoassay (FPIA), fluorescence immunoassay (FIA), enzyme immunoassay (EIA), and nephelometric inhibition immunoassay (NIA). Immunoassays such as these are well known in the art and are described in, for example, Ausubel et al., Current Protocols in Molecular Biology, 1992-2006.

For example, ELISA can be used to detect or quantify one or more LCM. For example, ELISA (or other types of LCM assays) can be used to detect LCM in, for example, a high-risk individual or population, in an individual suspected of having lung cancer, or in an individual with no suspicion of having lung cancer (e.g., an individual undergoing routine screening for lung cancer).

In certain exemplary ELISA methods, an antibody that specifically binds to an LCM antigen may be coated to the well of a suitable container (e.g., a 96 well microtiter plate), a patient sample (e.g., a serum sample) can be added to the well and incubated for a period of time, and the presence of the LCM antigen in the patient sample can be detected upon binding of the LCM antigen in the patient sample to the antibody that is coated to the well. In this instance, a second antibody conjugated to a detectable moeity may optionally be added following the addition of the patient sample to the coated well. ELISA methods such as these may be modified or optimized as desired.

Further, instead of coating the well with an antibody to an LCM antigen, the LCM antigen itself may be coated to the well. Thus, in certain exemplary ELISA methods, an LCM antigen can be coated to the well of a suitable container (e.g., a 96 well microtiter plate), an antibody (which may optionally be conjugated to a detectable moiety such as an enzymatic substrate like horseradish peroxidase or alkaline phosphatase) to the LCM antigen can be added to the well and incubated for a period of time, and the presence of the LCM antigen can be detected. The antibody to the LCM antigen does not have to be conjugated to a detectable moiety; for example, a second antibody (which recognizes the antibody to the LCM antigen) conjugated to a detectable moeity may be added to the well. ELISA methods such as these may be modified or optimized as desired.

Proteins can be isolated from a biological sample (such as from a patient having a disease) and assayed for the presence of a mutation. A mutation can include, for example, one or more amino acid substitutions, deletions, insertions, rearrangements (such as from aberrant splicing events), or inappropriate post-translational modifications. Examples of analytic methods useful for detecting mutations in a protein include, but are not limited to, altered electrophoretic mobility, altered tryptic peptide digest, altered protein activity in cell-based or cell-free assays, alteration in substrate or antibody-binding patterns, altered isoelectric point, and direct amino acid sequencing.

Information obtained by detecting a protein can be used, for example, to determine prognosis and appropriate course of treatment for a disease. For example, individuals with a particular LCM expression level or stage of disease may respond differently to a given treatment that individuals lacking LCM expression, or individuals over- or under-expressing LCM. Information obtained from diagnostic methods of the invention can provide for the personalization of diagnosis and treatment.

In exemplary embodiments, the invention provides methods for diagnosing disease (including, for example, monitoring treatment response or recurrence of disease following treatment) in an individual comprising: determining the abundance level of LCM (e.g., LCM protein or nucleic acid, or protein or nucleic acid fragments thereof) in a test sample from the individual; wherein a difference in the abundance level of LCM relative to the abundance level of LCM in a test sample from a healthy individual, or the level established for a healthy individual, is indicative of disease.

Exemplary embodiments of the invention provide methods for diagnosing diseases having differential protein expression. For example, normal, control, or standard values (e.g., that represent typical expression levels of a protein in healthy individuals) can be established, such as by combining body fluids, tissues, or cell extracts taken from a normal healthy mammalian or human individual with specific antibodies to a protein under conditions for complex formation. Standard values for complex formation in normal and disease tissues can be established by various methods, such as photometric means. Complex formation, as it is expressed in a test sample, can be compared with the standard values. Deviation from a normal standard and toward a disease standard can provide parameters for disease diagnosis or prognosis while deviation away from a disease standard and toward a normal standard can be used to evaluate treatment efficacy, for example.

Immunological methods for detecting and measuring complex formation as a measure of protein expression using either specific polyclonal or monoclonal antibodies are known in the art. Examples of such techniques include ELISAs, radioimmunoassays (RIAs), flow cytometry (also referred to as fluorescence-activated cell sorting, or FACS), and antibody arrays. Such immunoassays typically involve the measurement of complex formation between a protein and its specific antibody. These assays and their quantitation against purified, labeled standards are well known in the art (Ausubel, supra, unit 10.1-10.6). For example, a two-site, monoclonal-based immunoassay utilizing antibodies reactive to two non-interfering epitopes can be utilized, and competitive binding assay can also be utilized (Pound (1998) Immunochemical Protocols, Humana Press, Totowa N.J.).

For diagnostic applications, an antibody can be labeled with a detectable moiety (interchangeably referred to as a "label" or "detectable substance"), such as to facilitate detection by various imaging methods. Methods for detection of labels include, but are not limited to, fluorescence, light, confocal, and electron microscopy; magnetic resonance imaging and spectroscopy; fluoroscopy, computed tomography and positron emission tomography. Examples of suitable labels include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, labels may be bi- or multi-functional and be detectable by more than one of the methods listed. Antibodies may be directly or indirectly labeled. Attachment of labels to antibodies includes covalent attachment of a label, incorporation of a label into an antibody, and covalent attachment of a chelating compound for binding of a label, among others well known in the art.

Numerous detectable moieties are available for labeling antibodies, including, but not limited to, those in the following categories:

(a) Radioisotopes, such as $^{36}S$, $^{14}C$, $^{125}I$, $^{3}H$, and $^{131}I$. An antibody can be labeled with a radioisotope using the techniques described in Current Protocols in Immunology, vol 1-2, Coligen et al., Ed., Wiley-Interscience, New York, Pubs. (1991-2006), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. Fluorescent labels can be conjugated to an antibody using the techniques disclosed in Current Protocols in Immunology, supra, for example. Fluorescence can be quantified using a fluorometer.

(c) Various enzyme-substrate labels are available (e.g., U.S. Pat. Nos. 4,275,149 and 4,318,980). An enzyme generally catalyzes a chemical alteration of a chromogenic substrate which can be measured using various techniques. For example, an enzyme may catalyze a color change in a substrate, which can be measured spectrophotometrically. Alternatively, an enzyme may alter the fluorescence or chemiluminescence of a substrate. Techniques for quantifying a change in fluorescence are described herein and well known in the art A chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzyme. (Ed. J. Langone & H. Van Vunakis), Academic press, New York, 73: 147-166 (1981).

A label can be indirectly conjugated with an antibody. The skilled artisan will be aware of various techniques for achieving this. For example, an antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of a label with an antibody, an antibody can be conjugated with a small hapten (e.g., digoxin) and one of the different types of labels mentioned above can be conjugated with an anti-hapten antibody (e.g., anti-digoxin antibody). Thus, indirect conjugation of a label with an antibody can be achieved.

Antibodies can be used to isolate LCM proteins by standard techniques, such as affinity chromatography or immunoprecipitation, and antibodies can facilitate the purification of the natural protein from cells and recombinantly-produced protein expressed in host cells. Biological samples can be tested directly for the presence of a LCM protein by assays (e.g., ELISA or radioimmunoassay) and format (e.g., microwells, dipstick, etc., as described in International Patent Publication WO 93/03367). Alternatively, proteins in a sample can be size separated (e.g., by polyacrylamide gel electrophoresis (PAGE)), in the presence or absence of sodium dodecyl sulfate (SDS), and the presence of a LCM detected by immunoblotting (e.g., Western blotting).

Antibody binding can also be detected by "sandwich" immunoassays, immunoradiometric assays, gel diffusion precipitation reactions, immunodiffusion assays, in situ immunoassays (e.g., using colloidal gold, enzyme or radioisotope labels, for example), precipitation reactions, agglutination assays (e.g., gel agglutination assays, hemagglutination assays, etc.), complement fixation assays, immunofluorescence assays, protein A assays, and immunoelectrophoresis assays, etc.

In certain exemplary embodiments, antibody binding can be detected by detecting a label on the primary antibody. In other exemplary embodiments, a primary antibody can be detected by detecting binding of a secondary antibody or reagent to the primary antibody. In further exemplary embodiments, the secondary antibody is labeled. Numerous means are known in the art for detecting binding in an immunoassay and are within the scope of the invention. In some embodiments, an automated detection assay is utilized. Methods for the automation of immunoassays are well known in the art (e.g., U.S. Pat. Nos. 5,885,530; 4,981,785; 6,159,750; and 5,358,691, each of which is herein incorporated by reference). In some embodiments, the analysis and presentation of results are also automated. For example, in some embodiments, software that generates a prognosis based on the presence or absence of one or more antigens can be implemented.

Competitive binding assays typically rely on the ability of a labeled standard to compete with a test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies can be separated from the standard and test sample that remain unbound.

Sandwich assays typically involve the use of two antibodies, each capable of binding to a different immunogenic portion, or epitope, of the protein to be detected. In typical sandwich assays, the test sample to be analyzed is bound by a first antibody, which is immobilized on a solid support, and thereafter a second antibody binds to the test sample, thus forming an insoluble three-part complex (e.g., U.S. Pat. No. 4,376,110). The second antibody can itself be labeled with a detectable moiety (direct sandwich assays) or can be measured using an anti-immunoglobulin antibody that is labeled with a detectable moiety (indirect sandwich assay). For example, one type of sandwich assay is an ELISA assay, in which case the detectable moiety is an enzyme.

Antibodies can also be used for in vivo diagnostic assays. Generally, an antibody can be labeled with a radionuclide (such as $^{111}$In, $^{99}$Tc, $^{14}$C, $^{131}$I, $^{3}$H, $^{32}$P or $^{35}$S) so that disease cells or tissues can be localized using immunoscintiography, for example. In certain embodiment, antibodies or fragments thereof bind to the extracellular domains of two or more LCM proteins and the affinity value (Kd) is less than $1 \times 10^8$ M.

For immunohistochemistry, a disease tissue sample may be, for example, fresh or frozen or may be embedded in paraffin and fixed with a preservative such as formalin. A fixed or embedded section can be contacted with a labeled primary antibody and secondary antibody, wherein the antibody is used to detect LCM protein expression in situ.

Antibodies can be used to detect a marker protein in situ, in vitro, or in a cell lysate or supernatant in order to evaluate the abundance and pattern of expression. Also, antibodies can be used to assess abnormal tissue distribution or abnormal expression during development or progression of a biological condition. Antibodies against LCM proteins are useful for detecting the presence of the proteins in cells or tissues to determine the pattern of expression of the proteins among various tissues in an organism and over the course of the organism's development.

Further, antibodies can be used to assess expression in disease states such as in active stages of a disease or in an individual with a predisposition toward disease related to the protein's function. When a disorder is caused by inappropriate tissue distribution, developmental expression, or level of expression of a protein, or expressed/processed form, for example, an antibody can be prepared against the normal protein. If a disorder is characterized by a specific mutation in a protein, antibodies specific for the mutant protein can be used to assay for the presence of the specific mutant protein and to target the mutant protein for therapeutic purposes. Antibodies are also useful as diagnostic tools, as immunological markers for aberrant protein analyzed by electrophoretic mobility, isoelectric point, tryptic peptide digest, and other physical assays known in the art.

Certain exemplary diagnostic methods of the invention can also include monitoring a treatment modality. Accordingly, where treatment is ultimately aimed at correcting, for example, the function, activity, expression level, tissue distribution, or developmental expression of a protein, antibodies directed against the protein can be used to monitor therapeutic efficacy and to modify a treatment regimen as necessary.

Additionally, antibodies to a marker protein are useful in pharmacogenomic analysis. For example, antibodies prepared against polymorphic proteins can be used to identify individuals that require modified treatment modalities. Moreover, the marker proteins and antibodies thereto can be used for clinical trials, such as to identify individuals that should be included (e.g., individuals more likely to respond to a therapy) or excluded (e.g., individuals less likely to respond to a therapy, or individuals more likely to experience harmful side effects from a therapy) from a clinical trial.

The invention also encompasses kits for using antibodies to detect the presence of a marker protein in a biological sample. An exemplary kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be configured to detect a single marker protein or epitope or can be configured to detect one of a multitude of epitopes, such as in an antibody detection array.

LC/MS and ICAT

In certain exemplary embodiments, the invention provides detection or diagnostic methods of a LCM by using LC/MS. Proteins can be prepared from cells by methods known in the art (e.g., Zhang et al., *Nature Biotechnology* 21(6):660-666 (2003)). The differential expression of proteins in disease and healthy (or drug-resistant and drug-sensitive, for example) samples can be quantitated using mass spectrometry and ICAT (Isotope Coded Affinity Tag) labeling, which is known in the art. ICAT is an isotope label technique that allows for discrimination between two populations of proteins, such as a healthy and a disease sample. Over-expression or under-expression of a LCM protein, as measured by ICAT, can indicate, for example, the likelihood of having or developing a disease or an associated pathology.

LC/MS spectra can be collected for labeled samples and processed as follows. The raw scans from the LC/MS instrument can be individualed to peak detection and noise reduction software. Filtered peak lists can then be used to detect 'features' corresponding to specific peptides from the original sample(s). Features are characterized by their mass/charge ratio, charge, retention time, isotope pattern, and/or intensity, for example.

The intensity of a peptide present in both healthy and disease samples can be used to calculate the differential expression, or relative abundance, of the peptide. The intensity of a peptide found exclusively in one sample can be used to calculate a theoretical expression ratio for that peptide (singleton). Expression ratios can be calculated for each peptide in an assay or experiment.

Statistical tests can be performed to assess the robustness of the data and select statistically significant differentials. To ensure the accuracy of data, the following steps can be taken: a) ensure that similar features are detected in all replicates of an experiment; b) assess the distribution of the log ratios of all peptides (a Gaussian is expected); c) calculate the overall pair wise correlations between ICAT LC/MS maps to ensure that the expression ratios for peptides are reproducible across multiple replicates; and d) aggregate multiple experiments in order to compare the expression ratio of a peptide in multiple diseases or disease samples.

8. Methods of Treatment Based on LCM Proteins a. Antibody Therapy

Antibodies of the invention can be used for therapeutic purposes. It is contemplated that antibodies of the invention may be used to treat a mammal, preferably a human, with a disease, especially cancer, and particularly lung cancer. The antibodies can be delivered alone, in a pharmaceutical composition (such as with a carrier), or conjugated to one or more therapeutic agents, for example.

Antibodies can be useful for modulating (e.g., agonizing or antagonizing) protein function, such as for therapeutic purposes. Antibodies can also be useful for inhibiting protein function by, for example, blocking the binding of a LCM protein to a binding partner such as a substrate, which can be useful therapeutically. Antibodies can be prepared against, for example, specific portions of a protein that contain domains required for protein function, or against intact protein that is associated with a cell membrane.

Antibodies of the invention can also be used for enhancing the immune response. The antibodies can be administered in amounts similar to those used for other therapeutic administrations of antibodies. For example, pooled gamma globulin can be administered at a range of about 1 mg to about 100 mg per patient.

Antibodies reactive with LCM proteins can be administered alone or in conjunction with other therapies, such as anti-cancer therapies, to a mammal afflicted with cancer or other disease. Examples of anti-cancer therapies include, but are not limited to, chemotherapy, radiation therapy, and adoptive immunotherapy therapy with TIL (tumor infiltrating lymphocytes).

The selection of an antibody subclass for therapy may depend upon the nature of the antigen to be acted upon. For example, an IgM may be preferred in situations where the antigen is highly specific for the disease marker and rarely occurs on normal cells. However, where the disease-associated antigen is also expressed in normal tissues, although at lower levels, the IgG subclass may be preferred. The IgG subclass may be preferred in these instances because the binding of at least two IgG molecules in close proximity is typically required to activate complement, and therefore less complement-mediated damage may occur in normal tissues that express smaller amounts of the antigen and thus bind fewer IgG antibody molecules. Furthermore, IgG molecules, by being smaller, may be more able than IgM molecules to localize to a diseased tissue.

A mechanism for antibody therapy can be that a therapeutic antibody recognizes a soluble or cell surface marker protein that is expressed (preferably, over-expressed) in a disease cell. By NK cell or complement activation, or conjugation of the antibody with an immunotoxin or radiolabel, the interaction of the antibody with the marker protein can abrogate ligand/receptor interaction or activation of apoptosis, for example.

Potential mechanisms of antibody-mediated cytotoxicity of diseased cells include phagocyte (antibody-dependent cellular cytotoxicity (ADCC)), complement (complement-dependent cytotoxicity (CDC)), naked antibody (receptor cross-linking apoptosis and growth factor inhibition), or targeted payload labeled with a therapeutic agent, such as a radionuclide, immunotoxin, or immunochemotherapeutic or other therapeutic agent.

In certain exemplary embodiments, an antibody is administered to a nonhuman mammal for the purposes of obtaining preclinical data, for example. Exemplary nonhuman mammals to be treated include nonhuman primates, dogs, cats, rodents, and other mammals in which preclinical studies are performed. Such mammals may be established animal models for a disease or may be used to study toxicity of an antibody of interest, for example. Dose escalation studies may be performed in the mammal, for example.

An antibody can be administered to an individual by any suitable means, including parenteral, subcutaneous, intraperitoneal, intrapulmonary, and intranasal, and, if desired for local immunomodulatory treatment, intralesional administration. Parenteral infusions include intramuscular, intravenous, intraarterial, intraperitoneal, or subcutaneous administration. In addition, an antibody can be administered by pulse infusion, particularly with declining doses of the antibody. The dosing can be given by injections, such as intravenous or subcutaneous injections, which may depend in part on whether the administration is brief or chronic.

For the prevention or treatment of a disease, the appropriate dosage of an antibody may depend on the type of disease to be treated, the severity and the course of the disease, whether the antibody is administered for preventive or therapeutic purposes, previous therapy, the patient's clinical history and response to the antibody, and the discretion of the attending physician.

Depending on the type and severity of disease, about 1 µg/kg to 150 mg/kg (e.g., 0.1-20 mg/kg) of antibody can be an initial candidate dosage for administration to a patient, whether, for example, by one or more separate administrations, or by continuous infusion. A typical daily dosage may range from about 1 µg/kg to 100 mg/kg or more, depending on such factors as those mentioned above. An antibody-drug conjugate can be administered from about 1 µg/kg to 50 mg/kg, typically from about 0.1-20 mg/kg, whether, for example, by one or more separate administrations, or by continuous infusion. A typical daily dosage may range from about 0.1 mg/kg to 10 mg/kg, or from about 0.3 mg/kg to about 7.5 mg/kg, depending on such factors as those mentioned above. For repeated administrations over several days or longer, depending on the condition, the treatment can be sustained until a desired suppression of disease symptoms occurs. However, other dosage regimens may be useful. Therapy progress can be monitored by conventional techniques and assays.

Antibody composition can be formulated, dosed, and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

An antibody may optionally be formulated with, or administered with, one or more therapeutic agents used to prevent or treat the disorder in question. For example, an antibody can be administered as a co-therapy with a standard of care therapeutic for the specific disease being treated.

b. Other Immunotherapy

An "immunogenic peptide" is a peptide that comprises an allele-specific motif such that the peptide typically will bind an MHC allele (HLA in human) and be capable of inducing a CTL (cytotoxic T-lymphocytes) response. Thus, immunogenic peptides typically are capable of binding to an appropriate class I or II MHC molecule and inducing a cytotoxic T cell or T helper cell response against the antigen from which the immunogenic peptide is derived.

Peptides derived from a LCM protein can be modified to increase their immunogenicity, such as by enhancing the binding of the peptide to the MHC molecules in which the peptide is presented. The peptide or modified peptide can be conjugated to a carrier molecule to enhance the antigenicity of the peptide. Examples of carrier molecules, include, but are not limited to, human albumin, bovine albumin, lipoprotein and keyhole limpet hemo-cyanin ("Basic and Clinical Immunology" (1991) Stites and Terr (eds) Appleton and Lange, Norwalk Conn., San Mateo, Calif.).

Further, amino acid sequence variants of a peptide can be prepared, such as by altering the nucleic acid sequence of the DNA which encodes the peptide, or by peptide synthesis. At the genetic level, these variants can be prepared by, for example, site-directed mutagenesis of nucleotides in the DNA encoding the peptide, thereby producing DNA encoding the variant, and thereafter expressing the DNA in recombinant cell culture. The variants can exhibit the same qualitative biological activity as the nonvariant peptide.

Exemplary embodiments of the invention provide peptides or modified peptides derived from a LCM protein that are differentially expressed in disease. Examples of peptide modifications include, but are not limited to, substitutions, deletions, or additions of one or more amino acids in a given immunogenic peptide sequence, or mutation of existing amino acids within a given immunogenic peptide sequence, or derivatization of existing amino acids within a given immunogenic peptide sequence. Any amino acid in an immunogenic peptide sequence may be modified. In some embodiments, at least one amino acid can be substituted or replaced within the given immunogenic peptide sequence. Any amino acid may be used to substitute or replace a given amino acid within the immunogenic peptide sequence. Modified peptides can include any immunogenic peptide obtained from differentially expressed proteins, which has been modified and exhibits enhanced binding to the MHC molecule with which it associates when presented to a T-cell. These modified peptides can be synthetically or recombinantly produced by conventional methods, for example.

In certain exemplary embodiments of the invention, the peptides comprise, or consist of, sequences of about 5-30 amino acids in length which are immunogenic (i.e., capable of inducing an immune response when injected into a individual).

In certain exemplary embodiments, the peptides may be used, for example, to treat T cell-mediated pathologies. The term "T cell-mediated pathologies" refers to any condition in which an inappropriate T cell response is a component of the pathology. The term is intended to encompass both T cell mediated diseases and diseases resulting from unregulated clonal T cell replication.

Modified (e.g., recombinant) or natural LCM proteins, or fragments thereof, can be used as a vaccine either prophylactically or therapeutically. When provided prophylactically, a vaccine can be provided in advance of any evidence of disease. The prophylactic administration of a disease vaccine may serve to prevent or attenuate a disease in a mammal such as a human.

An exemplary vaccine formulation can comprise an immunogen that induces an immune response directed against a disease-associated antigen such as a LCM protein. For example, a substantially or partially purified LCM protein or fragments thereof can be administered as a vaccine in a pharmaceutically acceptable carrier. An immunogen can be administered in a pure or substantially pure form, or can be administered as a pharmaceutical composition, formulation, or preparation. Exemplary doses of protein that can be administered are about 0.001 to about 100 mg per patient, or about 0.01 to about 100 mg per patient. Immunization can be repeated as necessary until a sufficient titer of anti-immunogen antibody or immune cells has been obtained.

Vaccine can be prepared using, for example, recombinant protein or expression vectors comprising a nucleic acid sequence encoding all or part of a LCM protein. Examples of vectors that can be used in vaccines include, but are not limited to, defective retroviral vectors, adenoviral vectors vaccinia viral vectors, fowl pox viral vectors, or other viral vectors (Mulligan, R. C., (1993) *Science* 260:926-932). The vectors can be introduced into a mammal (e.g., a human) either prior to any evidence of a disease or to mediate regression of a disease in a mammal afflicted with the disease. Examples of methods for administering a viral vector into mammals include, but are not limited to, exposure of cells to the virus ex vivo, or injection of the retrovirus or a producer cell line of the virus into the affected tissue, or intravenous administration of the virus. Alternatively, the vector can be administered locally by direct injection into a disease lesion or topical application in a pharmaceutically acceptable carrier. The quantity of viral vector to be administered can be based on the titer of virus particles. An exemplary range can be about $10^6$ to about $10^{11}$ virus particles per mammal.

After immunization, the efficacy of the vaccine can be assessed by, for example, the production of antibodies or immune cells that recognize the antigen, as assessed by specific lytic activity, specific cytokine production, or disease regression, which can be measured using conventional methods. If the mammal to be immunized is already afflicted with a disease, the vaccine can be administered in conjunction with other therapeutic treatments. Examples of other therapeutic treatments include, but are not limited to, adoptive T cell immunotherapy and coadministration of cytokines or other therapeutic drugs.

In certain embodiments, mammals, preferably humans, at high risk for disease, especially cancer, are prophylactically treated with vaccines of the invention. Examples include, but are not limited to, individuals with a family history of a disease, individuals who themselves have a history of disease (e.g., cancer that has been previously resected and at risk for reoccurrence), or individuals already afflicted with a disease. When provided therapeutically, a vaccine can be provided to enhance the patient's own immune response to a disease antigen. An exemplary vaccine, which acts as an immunogen, can be a cell, cell lysate from cells transfected with a recombinant expression vector, or a culture supernatant containing the expressed protein, for example. Alternatively, an immunogen can be, for example, a partially or substantially purified recombinant protein, peptide, or analog thereof, or a modified protein, peptide, or analog thereof. The proteins or peptides can be, for example, conjugated with lipoprotein or administered in liposomal form or with adjuvant.

Vaccination can be carried out using conventional methods. For example, an immunogen can be used in a suitable diluent such as saline or water, or complete or incomplete adjuvants. Further, an immunogen may or may not be bound to a carrier, including carriers to increase the immunogenicity of the immunogen. Examples of carrier molecules include, but are not limited to, bovine serum albumin (BSA), keyhole limpet hemocyanin (KLH), tetanus toxoid, and the like. An immunogen also may be coupled with lipoproteins or administered in liposomal form or with adjuvants. An immunogen can be administered by any route appropriate for antibody production such as intravenous, intraperitoneal, intramuscular, subcutaneous, and the like. An immunogen can be administered once or at periodic intervals until a significant titer of anti-LCM immune cells or anti-LCM antibody is produced. The presence of anti-LCM immune cells can be assessed by measuring the frequency of precursor CTL (cytotoxic T-lymphocytes) against LCM antigen prior to and after immunization by a CTL precursor analysis assay (Coulie et al., 1992, *International Journal Of Cancer* 50:289-297). An immunoassay can be used to detect antibody in serum.

The safety of a vaccine can be determined by examining the effect of immunization on the general health of an immunized animal (e.g., weight change, fever, change in appetite or behavior, etc.) and looking for pathological changes during autopsies. After initial testing in animals, a vaccine can be tested in patients having a disease of interest. Conventional methods can be used to evaluate the immune response of a patient to determine the efficiency of the vaccine.

In certain exemplary embodiments of the invention, a LCM protein or fragments thereof, or a modified LCM protein, can be exposed to dendritic cells cultured in vitro. The cultured dendritic cells provide a means of producing T-cell dependent antigens comprised of dendritic cell-modified antigen or dendritic cells pulsed with antigen, in which the antigen is processed and expressed on the antigen-activated dendritic cell. The antigen-activated dendritic cells or processed dendritic cell antigens can be used as immunogens for vaccines or for the treatment of diseases. The dendritic cells can be exposed to the antigen for sufficient time to allow the antigens to be internalized and presented on the surface of dendritic cells. The resulting dendritic cells or the dendritic cell-processed antigens can then be administered to an individual in need of therapy. Such methods are described in Steinman et al. (WO93/208185) and in Banchereau et al. (EPO Application 0563485A1).

In certain exemplary embodiments of the invention, T-cells isolated from individuals can be exposed to a LCM protein or fragment thereof, or a modified LCM protein, in vitro and then administered in a therapeutically effective amount to a patient in need of such treatment. Examples of where T-lymphocytes can be isolated include, but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami et al., 1989, *J. Immunol.* 142: 2453-3461). Lymphocytes can be cultured in media such as RPMI or RPMI 1640 or AIM V for 1-10 weeks. Viability can be assessed by trypan blue dye exclusion assay. Examples of how these sensitized T-cells can be administered to a mammal include, but are not limited to, intravenously, intraperitoneally, or intralesionally. Parameters that can be assessed to determine the efficacy of these sensitized T-lymphocytes include, but are not limited to, production of immune cells in the mammal being treated or tumor regression. Conventional methods can be used to assess these parameters. Such treatment can be given in conjunction with cytokines or gene-modified cells, for example (Rosenberg et al., 1992, *Human Gene Therapy*, 3: 75-90; Rosenberg et al., 1992, *Human Gene Therapy*, 3: 57-73).

9. Screening Methods Using LCM Proteins

Exemplary embodiments of the invention provide methods of screening for agents (interchangeably referred to by such terms as candidate agents, compounds, or candidate compounds) that modulate LCM protein activity (interchangeably referred to as protein function). Examples of candidate agents include, but are not limited to, proteins, peptides, antibodies, nucleic acids (such as antisense and RNAi nucleic acid molecules), and small molecules. Exemplary embodiments of the invention further provide agents identified by these screening methods, and methods of using these agents, such as for treating diseases, especially cancer, and particularly lung cancer.

Exemplary screening methods can typically comprise the steps of (i) contacting a LCM protein with a candidate agent, and (ii) assaying for LCM protein activity, wherein a change in protein activity in the presence of the agent relative to protein activity in the absence of the agent indicates that the agent modulates LCM protein activity.

Other exemplary screening methods can determine a candidate agent's ability to modulate LCM expression. Exemplary methods can typically comprise the steps of (i) contacting a candidate agent with a system that is capable of expressing LCM protein or LCM mRNA, and (ii) assaying for the level of LCM protein or LCM mRNA, wherein a change in the level in the presence of the agent relative to the level in the absence of the agent indicates that the agent modulates LCM expression levels.

Exemplary embodiments of the invention further provide methods to screen for agents that bind to LCM proteins. Exemplary methods can typically comprise the steps of contacting a LCM protein with a test agent and measuring the extent of binding of the agent to the LCM protein.

LCM proteins can be used to identify agents that modulate activity of a protein in its natural state or an altered form that causes a specific disease or pathology. LCM proteins and appropriate variants and fragments can be used in high-throughput screens to assay candidate compounds for their ability to bind to LCM. These compounds can be further screened against functional LCM proteins to determine the effect of the compound on the protein's activity. Further, these compounds can be tested in animal or invertebrate systems to determine activity/effectiveness. Compounds can be identified that activate (agonist) or inactivate (antagonist) LCM proteins to a desired degree.

LCM proteins can be used to screen agents for their ability to stimulate or inhibit interaction between a LCM protein and a target molecule that normally interacts with the LCM protein (e.g., a substrate, an extracellular binding ligand, or a component of a signal pathway that a LCM protein normally interacts with such as a cytosolic signal protein).

Exemplary assays can include the steps of combining a LCM protein or fragment thereof with a candidate compound under conditions that allow the LCM protein (or fragment thereof) to interact with a target molecule, and detecting the formation of a complex between the LCM protein and the target molecule or detecting the biochemical consequence of the interaction between the LCM protein and the target molecule, such as any of the associated effects of signal transduction (e.g., protein phosphorylation, cAMP turnover, adenylate cyclase activation, etc.). Any of the biological or biochemical functions mediated by a LCM protein can be used as an endpoint assay to identify an agent that modulates LCM activity.

Candidate compounds or agents include, but are not limited to, 1) peptides such as soluble peptides, including Ig-tailed fusion peptides and members of random peptide libraries (see, e.g., Lam et al., *Nature* 354:82-84 (1991); Houghten et al., *Nature* 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767-778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

An exemplary candidate compound or agent is a soluble fragment of a LCM that competes for substrate binding. Other exemplary candidate compounds include mutant LCM proteins or appropriate fragments containing mutations that affect LCM function and thus compete for substrate. Accordingly, a fragment that competes for substrate, for example with a higher affinity, or a fragment that binds substrate but does not allow release, is encompassed by the invention.

Compounds can also be screened by using chimeric proteins in which any portion of a protein such as an amino terminal extracellular domain, a transmembrane domain (e.g., transmembrane segments or intracellular or extracellular loops), or a carboxy terminal intracellular domain can be replaced in whole or part by heterologous domains or subregions.

For example, a substrate-binding region can be used that interacts with a different substrate than the substrate that is recognized by a native marker protein. Accordingly, a different set of signal transduction components can be available as an end-point assay for activation, thereby allowing assays to be performed in other than the specific host cell from which a marker is derived.

Competition binding assays can also be used to screen for compounds that interact with a marker protein (e.g., binding partners and/or ligands). For example, a test compound can be exposed to a marker protein under conditions that allow the test compound to bind or otherwise interact with the marker protein. Soluble marker protein can also be added to the mixture. If the test compound interacts with the soluble marker protein, it can decrease the amount of complex formed or activity of the marker protein. This type of assay is particularly useful in instances in which compounds are sought that interact with specific regions of a marker protein. Thus, the soluble marker protein that competes with the marker protein can contain peptide sequences corresponding to the marker region of interest.

To perform cell-free drug screening assays, it may be desirable to immobilize either a LCM protein (or fragment thereof) or a molecule that binds the LCM protein (referred to herein as a "binding partner") to facilitate separation of complexes from uncomplexed forms, as well as to facilitate automation of the assays.

Techniques for immobilizing proteins on matrices can be utilized in exemplary drug screening assays. In exemplary embodiments, a fusion protein can be provided which adds a domain that allows a protein to be bound to a matrix. For example, glutathione-S-transferase fusion proteins can be adsorbed onto glutathione SEPHAROSE beads (Sigma Chemical, St. Louis, Mo.) or glutathione derivatized microtitre plates, which are then combined with cell lysates (e.g., $^{35}$S-labeled) and a candidate compound, and the mixture incubated under conditions conducive to complex formation (e.g., at physiological conditions for salt and pH). Following incubation, the beads can be washed to remove any unbound label, and the matrix immobilized and radiolabel determined directly, or in the supernatant after the complexes are dissociated. Alternatively, the complexes can be dissociated from the matrix, separated by SDS-PAGE, and the level of a binding partner found in the bead fraction quantitated from the gel using standard electrophoretic techniques. For example, either a marker protein or a binding partner can be immobilized by conjugation of biotin and streptavidin using techniques well known in the art. Alternatively, antibodies that are reactive with a marker protein but do not interfere with binding of the marker protein to its binding partner can be derivatized to the wells of a plate, and the marker protein trapped in the wells by antibody conjugation. Preparations of a binding partner and a candidate compound can be incubated in marker protein-presenting wells and the amount of complex trapped in the well can be quantitated. Methods for detecting such complexes, in addition to those described for GST-immobilized complexes, include immunodetection of complexes using antibodies reactive with a binding partner, or which are reactive with a marker protein and compete with the binding partner, as well as marker protein-linked assays which rely on detecting an enzymatic activity associated with a binding partner.

In exemplary embodiments of the invention, a LCM protein can be used as a "bait protein" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques*

14:920-924; Iwabuchi et al. (1993) *Oncogene* 8:1693-1696; and Brent WO94/10300), to identify other proteins, which bind to or interact with a LCM protein and are involved in the protein's activity. The two-hybrid system is based on the modular nature of most transcription factors, which typically consist of separable DNA-binding and activation domains. In exemplary embodiments, the two-hybrid assay can utilize two different DNA constructs. In one construct, a gene that encodes a LCM protein can be fused to a gene encoding the DNA binding domain of a known transcription factor (e.g., GAL-4). In the other construct, a DNA sequence from a library of DNA sequences that encode an unidentified protein ("prey" or "sample") can be fused to a gene that encodes the activation domain of the known transcription factor. If the "bait" and the "prey" proteins are able to interact in vivo, forming a LCM-dependent complex, the DNA-binding and activation domains of the transcription factor are brought into close proximity. This proximity allows transcription of a reporter gene (e.g., LacZ), which can be operably linked to a transcriptional regulatory site responsive to the transcription factor. Expression of the reporter gene can be detected and cell colonies containing the functional transcription factor can be isolated and used to obtain the cloned gene that encodes the protein that interacts with the LCM protein.

Agents that modulate a LCM protein can be identified using one or more of the above assays, alone or in combination. For example, a cell-based or cell free system can be used for initial identification of agents, and then activity of the agents can be confirmed in an animal or other model system. Such model systems are well known in the art and can readily be employed in this context.

10. Diagnosis, Treatment, and Screening Methods Using LCM Nucleic Acid Molecules The nucleic acid molecules of the invention are useful, for example, as probes, primers, chemical intermediates, and in biological assays. The nucleic acid molecules are useful as hybridization probes for messenger RNA, transcript/cDNA, and genomic DNA to detect or isolate full-length cDNA and genomic clones encoding a LCM protein, or variants thereof. The nucleic acid molecules are also useful as primers for PCR to amplify any given region of a nucleic acid molecule and are useful to synthesize antisense molecules of desired length and sequence. The nucleic acid molecules are also useful for producing ribozymes corresponding to all, or a part, of the mRNA produced from the nucleic acid molecules described herein.

The nucleic acid molecules are also useful for constructing recombinant vectors. Exemplary vectors include expression vectors that express a portion of, or all of, a LCM protein. The nucleic acid molecules are also useful for expressing antigenic portions of the proteins. The nucleic acid molecules are also useful for constructing host cells expressing a part, or all, of the proteins. The nucleic acid molecules are also useful for constructing transgenic animals expressing all, or a part, of the proteins.

A primer or probe can correspond to any sequence along the entire length of a LCM-encoding nucleic acid molecule. Accordingly, a primer or probe can be derived from 5' noncoding regions, coding regions, or 3' noncoding regions, for example.

Exemplary in vitro techniques for detection of mRNA include Northern hybridizations and in situ hybridizations. Exemplary in vitro techniques for detecting DNA include Southern hybridizations and in situ hybridization. Reverse transcriptase PCR amplification (RT-PCR) and the like can also be used for detecting RNA expression. A specific exemplary method of detection comprises using TaqMan technology (Applied Biosystems, Foster City, Calif.).

a. Methods of Diagnosis Using Nucleic Acids

Nucleic acid molecules of the invention are useful, for example, as hybridization probes for determining the presence, level, form, and/or distribution of nucleic acid expression. Exemplary probes can be used to detect the presence of, or to determine levels of, a specific nucleic acid molecule in cells, tissues, and in organisms. Accordingly, probes corresponding to a LCM described herein can be used to assess expression and/or gene copy number in a given cell, tissue, or organism, which can be applied to, for example, diagnosis of disorders involving an increase or decrease in LCM protein expression relative to normal LCM protein expression levels.

Probes can be used as part of a diagnostic test kit for identifying cells or tissues that express LCM protein differentially, such as by measuring a level of a LCM-encoding nucleic acid (e.g., mRNA or genomic DNA) in a sample of cells from a individual, or determining if a LCM-encoding nucleic acid is mutated.

Exemplary embodiments of the invention encompass kits for detecting the presence of LCM-encoding nucleic acid (e.g., mRNA or genomic DNA) in a biological sample. For example, an exemplary kit can comprise reagents such as a labeled or labelable nucleic acid or agent capable of detecting LCM nucleic acid in a biological sample; means for determining the amount of LCM nucleic acid in the sample; and means for comparing the amount of LCM nucleic acid in the sample with a standard. The compound or agent can be packaged in a suitable container. The kit can further comprise instructions for using the kit to detect LCM nucleic acid.

The nucleic acid molecules are useful in diagnostic assays for qualitative changes in LCM nucleic acid expression, and particularly in qualitative changes that lead to pathology. The nucleic acid molecules can be used to detect mutations in LCM genes and gene expression products such as mRNA. The nucleic acid molecules can be used as hybridization probes to detect naturally occurring genetic mutations in a LCM gene and to determine whether a individual with the mutation is at risk for a disorder caused by the mutation. Examples of mutations include deletions, additions, or substitutions of one or more nucleotides in a gene, chromosomal rearrangements (such as inversions or transpositions), and modification of genomic DNA such as aberrant methylation patterns or changes in gene copy number (such as amplification). Detection of a mutated form of a LCM gene associated with a dysfunction can provide a diagnostic tool for an active disease or susceptibility to disease in instances in which the disease results from overexpression, underexpression, or altered expression of a LCM protein, for example.

Mutations in a LCM gene can be detected at the nucleic acid level by a variety of techniques. For example, genomic DNA, RNA, or cDNA can be analyzed directly or can be amplified (e.g., using PCR) prior to analysis. In certain exemplary embodiments, detection of a mutation involves the use of a probe/primer in a PCR reaction (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077-1080 (1988) and Nakazawa et al., *PNAS* 91:360-364 (1994)), the latter of which can be particularly useful for detecting point mutations in a gene (see Abravaya et al., *Nucleic Acids Res.* 23:675-682 (1995)). Exemplary methods such as these can include the steps of collecting a sample of cells from a patient, isolating nucleic acid (e.g., genomic, mRNA, or both) from the cells of the sample, contacting the nucleic acid with one or more primers which specifically hybridize to a marker nucleic acid under conditions such that hybridization and amplification of the marker nucleic acid (if present) occurs, and detecting the presence or absence of an amplification product, or detecting the size of the amplification product and comparing the length to a control sample. Deletions and insertions can be detected by a change in size of the amplified product compared to a normal genotype. Point mutations can be identified by hybridizing amplified DNA to normal RNA or antisense DNA sequences, for example.

Alternatively, mutations in a LCM gene can be identified, for example, by alterations in restriction enzyme digestion patterns as determined by gel electrophoresis. Further, sequence-specific ribozymes (U.S. Pat. No. 5,498,531) can be used to identify the presence of specific mutations by development or loss of a ribozyme cleavage site. Perfectly matched sequences can be distinguished from mismatched sequences by nuclease cleavage digestion assays or by differences in melting temperature.

Sequence changes at specific locations can be assessed by nuclease protection assays such as RNase and S1 protection, or chemical cleavage methods. Furthermore, sequence differences between a mutant LCM gene and a corresponding wild-type gene can be determined by direct DNA sequencing. A variety of automated sequencing procedures can be utilized when performing diagnostic assays (Naeve, C. W., (1995) *Biotechniques* 19:448), including sequencing by mass spectrometry (e.g., PCT International Publication No. WO 94/16101; Cohen et al., *Adv. Chromatogr.* 36:127-162 (1996); and Griffin et al., *Appl. Biochem. Biotechnol.* 38:147-159 (1993)).

Other methods for detecting mutations in a nucleic acid include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286-295 (1992)), electrophoretic mobility of mutant and wild type nucleic acid is compared (Orita et al., *PNAS* 86:2766 (1989); Cotton et al., *Mutat. Res.* 285:125-144 (1993); and Hayashi et al., *Genet. Anal. Tech. Appl.* 9:73-79 (1992)), and movement of mutant or wild-type fragments in polyacrylamide gels containing a gradient of denaturant is assayed using denaturing gradient gel electrophoresis (DGGE) (Myers et al., *Nature* 313:495 (1985)). Examples of other techniques for detecting point mutations include selective oligonucleotide hybridization, selective amplification, and selective primer extension.

b. Methods of Monitoring Treatment and Pharmacogenomic Methods Using Nucleic Acids Nucleic acid molecules of the invention are also useful for monitoring the effectiveness of modulating agents on the expression or activity of a LCM gene, such as in clinical trials or in a treatment regimen. For example, the gene expression pattern of a LCM gene can serve as a barometer for the continuing effectiveness of treatment with a compound, particularly with compounds to which a patient can develop resistance. The gene expression pattern can also serve as a marker indicative of a physiological response of the affected cells to the compound. For example, based on monitoring nucleic acid expression, the administration of a compound can be increased or alternative compounds to which the patient has not become resistant can be administered instead. Similarly, if the level of nucleic acid expression falls below a desirable level, administration of the compound can be commensurately decreased.

The nucleic acid molecules are also useful for testing an individual for a genotype that, while not necessarily causing a disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules provided herein can be used to assess the mutation content of a marker gene in an individual in order to select an appropriate compound or dosage regimen for treatment. For example, marker nucleic acid molecules having genetic variations that affect treatment can provide diagnostic markers that can be used to tailor treatment to an individual. Accordingly, the production of recombinant cells and animals having these genetic variations allows effective clinical design of treatment compounds and dosage regimens, for example.

c. Methods of Treatment Using Nucleic Acids

Nucleic acid molecules of the invention are useful to design antisense constructs to control LCM gene expression in cells, tissues, and organisms. An antisense nucleic acid molecule typically blocks translation of mRNA into LCM protein by hybridizing to marker mRNA in a sequence-specific manner. Nucleic acid molecules of the invention can also be used to specifically suppress gene expression by methods such as RNA interference (RNAi). RNAi and antisense-based gene suppression are well known in the art (e.g., *Science* 288:1370-1372, 2000). RNAi typically operates on a post-transcriptional level and is sequence specific. RNAi and antisense nucleic acid molecules are useful for treating diseases, especially cancer. RNAi fragments, particularly double-stranded (ds) RNAi, as well as antisense nucleic acid molecules can also be used to generate loss-of-function phenotypes by suppressing gene expression. Accordingly, exemplary embodiments of the invention provide RNAi and antisense nucleic acid molecules, and methods of using these RNAi and antisense nucleic acid molecules, such as for therapy or for modulating cell function. Nucleic acid molecules may also be produced that are complementary to a region of a gene involved in transcription, such as to hybridize to the gene to prevent transcription.

Exemplary embodiments of the invention relate to isolated RNA molecules (double-stranded; single-stranded) that are about 17 to about 29 nucleotides (nt) in length, and more particularly about 21 to about 25 nt in length, which mediate RNAi (e.g., degradation of mRNA, and such mRNA may be referred to herein as mRNA to be degraded). With respect to RNAi, the terms RNA, RNA molecule(s), RNA segment(s), and RNA fragment(s) are used interchangeably to refer to RNA that mediates RNAi. These terms include double-stranded RNA, single-stranded RNA, isolated RNA (e.g., partially purified RNA, essentially pure RNA, synthetic RNA, recombinantly produced RNA), as well as altered RNA that differs from naturally occurring RNA by the addition, deletion, substitution, and/or alteration of one or more nucleotides. Such alterations can include, for example, addition of non-nucleotide material, such as to the end(s) of a 21-25 nt RNA or internally (at one or more nucleotides of the RNA). Nucleotides in exemplary RNA molecules of the invention can also comprise non-standard nucleotides, including non-naturally occurring nucleotides or deoxyribonucleotides. Collectively, all such altered RNAs are referred to as analogs or analogs of naturally-occurring RNA. RNA of 21-25 nt typically need only be sufficiently similar to natural RNA that it has the ability to mediate RNAi. As used herein, the phrase "mediates RNAi" refers to the ability to distinguish which RNAs are to be degraded by RNAi processes. RNA that mediates RNAi directs degradation of particular mRNAs by RNAi processes. Such RNA may include RNAs of various structures, including short hairpin RNA.

In certain exemplary embodiments, the invention relates to RNA molecules of about 21 to about 25 nt that direct cleavage of specific mRNA to which their sequence corresponds.

It is not necessary that there be a perfect correspondence (i.e., match) of the sequences, but the correspondence must be sufficient to enable the RNA to direct RNAi cleavage of the marker mRNA (Holen et al., *Nucleic Acids Res.* 33:4704-4710 (2005)). In an exemplary embodiment, the 21-25 nt RNA molecules of the invention comprise a 3' hydroxyl group.

Certain exemplary embodiments of the invention relate to 21-25 nt RNAs of specific genes, produced by chemical synthesis or recombinant DNA techniques, that mediate RNAi. As used herein, the term "isolated RNA" includes RNA obtained by any means, including processing or cleavage of dsRNA, production by chemical synthetic methods, and production by recombinant DNA techniques, for example. Exemplary embodiments of the invention further relate to uses of the 21-25 nt RNAs, such as for therapeutic or prophylactic treatment and compositions comprising 21-25 nt RNAs that mediate RNAi, such as pharmaceutical compositions comprising 21-25 nt RNAs and an appropriate carrier.

Further exemplary embodiments of the invention relate to methods of mediating RNAi of genes of a patient. For example, RNA of about 21 to about 25 nt which targets a specific mRNA to be degraded can be introduced into a patient's cells. The cells can be maintained under conditions allowing degradation of the mRNA, resulting in RNA-mediated interference of the mRNA of the gene in the cells of the patient. Treatment of cancer patients, for example, with RNAi may inhibit the growth and spread of the cancer and reduce tumor size. Treatment of patients using RNAi can also be in combination with other therapies. For example, RNAi can be used in combination with other treatment modalities, such as chemotherapy, radiation therapy, and other treatments. In an exemplary embodiment, a chemotherapy agent is used in combination with RNAi. In a further exemplary embodiment, GEMZAR (gemcitabine HCl) chemotherapy is used with RNAi.

Treatment of certain diseases by RNAi may require introduction of the RNA into the disease cells. RNA can be directly introduced into a cell, or introduced extracellularly into a cavity, interstitial space, into the circulation of a patient, or introduced orally, for example. Physical methods of introducing nucleic acids, such as injection directly into a cell or extracellular injection into a patient, may also be used. RNA may be introduced into vascular or extravascular circulation, the blood or lymph system, or the cerebrospinal fluid, for example. RNA may be introduced into an embryonic stem cell or another multipotent cell, which may be derived from a patient. Physical methods of introducing nucleic acids include injection of a solution containing the RNA, bombardment by particles covered by the RNA, soaking cells or tissue in a solution of the RNA, or electroporation of cell membranes in the presence of the RNA. A viral construct packaged into a viral particle may be used to introduce an expression construct into a cell, with the construct expressing the RNA. Other methods known in the art for introducing nucleic acids to cells may be used, such as lipid-mediated carrier transport, chemical-mediated transport, and the like. The RNA may be introduced along with components that perform one or more of the following activities: enhance RNA uptake by the cell, promote annealing of the duplex strands, stabilize the annealed strands, or otherwise increase inhibition of the marker gene.

Exemplary RNA of the invention can be used alone or as a component of a kit having at least one reagent for carrying out in vitro or in vivo introduction of the RNA to a cell, tissue/fluid, or patient. Exemplary components of a kit include dsRNA and a vehicle that promotes introduction of the dsRNA. A kit may also include instructions for using the kit.

Certain exemplary embodiments of the invention provide compositions and methods for cleavage of mRNA by ribozymes having nucleotide sequences complementary to one or more regions in the mRNA, thereby attenuating the translation of the mRNA. Examples of regions in mRNA that can be targeted by ribozymes include coding regions, particularly coding regions corresponding to catalytic or other functional activities of a marker protein, such as substrate binding. These compositions and methods may be used to treat a disorder characterized by abnormal or undesired marker nucleic acid expression.

In certain exemplary embodiments, nucleic acid molecules of the invention may be used for gene therapy in individuals having cells that are aberrant in gene expression of a marker. For example, recombinant cells that have been engineered ex vivo (which can include an individual's own cells) can be introduced into an individual where the cells produce the desired marker protein to thereby treat the individual.

d. Methods of Screening Using Nucleic Acids

Nucleic acid expression assays are useful for drug screening to identify compounds that modulate LCM nucleic acid expression.

Exemplary embodiments of the invention thus provide methods for identifying a compound that can be used to treat a disease associated with differential expression of a LCM gene, especially cancer. Exemplary methods can typically include assaying the ability of a compound to modulate the expression of a marker nucleic acid to thereby identify a compound that can be used to treat a disorder characterized by undesired marker nucleic acid expression. The assays can be performed in cell-based or cell-free systems. Examples of cell-based assays include cells naturally expressing marker nucleic acid or recombinant cells genetically engineered to express specific marker nucleic acid sequences.

Assays for marker nucleic acid expression can involve direct assay of marker nucleic acid levels, such as mRNA levels, or on collateral compounds involved in a signal pathway. Further, the expression of genes that are up- or down-regulated in response to a signal pathway can also be assayed. In these embodiments, the regulatory regions of these genes can be operably linked to a reporter gene such as luciferase.

Thus, in exemplary embodiments, modulators of gene expression of a marker can be identified in methods wherein a cell is contacted with a candidate agent and the expression of marker mRNA determined. The level of expression of marker mRNA in the presence of the candidate agent is compared to the level of expression of marker mRNA in the absence of the candidate agent. The candidate agent can then be identified as a modulator of marker nucleic acid expression based on this comparison and may be used, for example, to treat a disorder characterized by aberrant marker nucleic acid expression. When expression of marker mRNA is statistically significantly greater in the presence of the candidate agent than in its absence, the candidate agent is identified as a stimulator (agonist) of nucleic acid expression. When nucleic acid expression is statistically significantly less in the presence of the candidate agent than in its absence, the candidate compound is identified as an inhibitor (antagonist) of nucleic acid expression.

11. Arrays and Expression Analysis

"Array" (interchangeably referred to as "microarray") typically refers to an arrangement of at least one, but more typically at least two, nucleic acid molecules, proteins, or antibodies on a substrate. In certain exemplary arrangements, at least one of the nucleic acid molecules, proteins, or antibodies typically represents a control or standard, and other nucleic acid molecules, proteins, or antibodies are of diagnostic or therapeutic interest. In exemplary embodiments, the arrangement of nucleic acid molecules, proteins, or antibodies on the substrate is such that the size and signal intensity of each labeled complex (e.g., formed between each nucleic acid molecule and a complementary nucleic acid, or between each protein and a ligand or antibody, or between each antibody and a protein to which the antibody specifically binds) is individually distinguishable.

An "expression profile" is a representation of marker expression in a sample. A nucleic acid expression profile can be produced using, for example, arrays, sequencing, hybridization, or amplification technologies for nucleic acids from a sample. A protein expression profile can be produced using, for example, arrays, gel electrophoresis, mass spectrometry, or antibodies (and, optionally, labeling moieties) which specifically bind proteins. Nucleic acids, proteins, or antibodies can be attached to a substrate or provided in solution, and their detection can be based on methods well known in the art.

A substrate includes, but is not limited to, glass, paper, nylon or other type of membrane, filter, chip, metal, or any other suitable solid or semi-solid (e.g., gel) support.

Exemplary arrays can be prepared and used according to the methods described in U.S. Pat. No. 5,837,832; PCT application WO95/11995; Lockhart et al., 1996, *Nat. Biotech.* 14: 1675-1680; Schena et al., 1996; *Proc. Natl. Acad. Sci.* 93: 10614-10619; and U.S. Pat. No. 5,807,522. Exemplary embodiments of the invention also provide antibody arrays (see, e.g., de Wildt et al. (2000) *Nat. Biotechnol.* 18:989-94).

Certain exemplary embodiments of the invention provide a nucleic acid array for assaying marker expression, which can be composed of single-stranded nucleic acid molecules, usually either synthetic antisense oligonucleotides or fragments of cDNAs, fixed to a solid support. The oligonucleotides can be, for example, about 6-60 nucleotides in length, about 15-30 nucleotides in length, or about 20-25 nucleotides in length.

To produce oligonucleotides to a marker nucleic acid molecule for an array, the marker nucleic acid molecule of interest is typically examined using a computer algorithm to identify oligonucleotides of defined length that are unique to the nucleic acid molecule, have a GC content within a range suitable for hybridization, and lack predicted secondary structure that may interfere with hybridization. In certain instances, it may be desirable to use pairs of oligonucleotides on an array. In exemplary embodiments, the "pairs" can be identical, except for one nucleotide (which can be located in the center of the sequence, for example). The second oligonucleotide in the pair (mismatched by one) serves as a control. Any number of oligonucleotide pairs may be utilized.

Oligonucleotides can be synthesized on the surface of a substrate, such as by using a light-directed chemical process or by using a chemical coupling procedure and an ink jet application apparatus (e.g., PCT application WO95/251116).

In some exemplary embodiments, an array can be used to diagnose or monitor the progression of disease, for example, by assaying marker expression.

For example, an oligonucleotide probe specific for a marker can be labeled by standard methods and added to a biological sample from a patient under conditions that allow for the formation of hybridization complexes. After an incubation period, the sample can be washed and the amount of label (or signal) associated with hybridization complexes can be quantified and compared with a standard value. If complex formation in the patient sample is significantly altered (higher or lower) in comparison to a normal (e.g., healthy) standard, or is similar to a disease standard, this differential expression can be diagnostic of a disorder.

By analyzing changes in patterns of marker expression, disease may be diagnosed at earlier stages before a patient is symptomatic. In exemplary embodiments of the invention, arrays or marker expression analysis methods can be used to formulate a diagnosis or prognosis, to design a treatment regimen, and/or to monitor the efficacy of treatment. For example, a treatment dosage can be established that causes a change in marker expression patterns indicative of successful treatment, and marker expression patterns associated with the onset of undesirable side effects can be avoided. In further exemplary embodiments, assays of marker expression can be repeated on a regular basis to determine if the level of marker expression in a patient begins to approximate that which is observed in a normal individual. The results obtained from successive assays may be used to show the efficacy of treatment over a period ranging from several days to years, for example.

Exemplary arrays of the invention can also be used to screen candidate agents, such as to identify agents that produce a marker expression profile similar to that caused by known therapeutic agents, with the expectation that agents that cause a similar expression profile of a marker may have similar therapeutic effects and/or modes of action on the marker.

EXAMPLES

Exemplary embodiments of the invention are further described in the following examples, which do not limit the scope of the invention.

1. Tissue Samples and Cell Lines

Tissue Processing and Preparation of Single Cell Suspensions from Tissue

Tissue samples (e.g., normal tissues or disease tissues such as surgically resected neoplastic or metastatic lesions) can be procured from clinical sites and transported in transport buffer. Tissues can be collected as remnant tissues following surgical resection of cancer (or other disease) tissues. Remnant tissues are supplied following processing for pathological diagnosis according to proper standards of patient care. Normal tissue specimens can be normal tissue adjacent to tumors (or other disease tissue) that is collected during tumor resection. Normal tissue from healthy patients not having cancer (or other disease of interest) can also be included, such as to reduce the contribution from pre-neoplastic changes that may exist in normal adjacent tissue. Procurement of tissue samples is carried out in an anonymous manner in compliance with federally mandated ethical and legal guidelines (HIPAA) and in accordance with clinical institution ethical review board and internal institutional review board guidelines.

Tissue can be crudely minced and incubate for 20-30 minutes with periodic agitation at 37° C. in Enzyme Combination #1 (200 units collagenase, cat #C5894 Sigma; 126 μg DNAse I, cat #D4513 Sigma (in 10 mM Tris/HCl pH7.5); 50 mM NaCl; 10 mM MgCl2; 0.05% elastase, cat #E7885 Sigma) (additionally hyaluronidase enzyme may also be utilized). D-PBS is added at 3× the volume of the enzyme combination, the tissue finely minced, and disassociated cells passed through a 200 μm filter. The cells are washed twice with D-PBS. Red blood cells are lysed with PharMLyse (BD Biosciences) when necessary. Cell number and viability are determined by PI exclusion (GUAVA). Cells at a total cell number greater than 20×10⁶ are sorted using a high-speed sorter (MoFlo Cytomation) for epithelial cells (EpCAM positive).

The remaining undigested tissue is incubated for 20-30 minutes with periodic agitation at 37° C. in Enzyme Combination #2 (1× Liberase Blendzyme 1, cat #988-417 Roche; 1× Liberase Blendzyme 3, cat #814-184 Roche; 0.05% elastase, cat #E7885 Sigma). D-PBS is added at 3× the volume of the enzyme combination, and the tissue finely minced until tissue is completely disassociated. The cells are passed through a 200 μm filter, washed twice with D-PBS, and pooled with cells from the Enzyme Combination #1 digestion.

Cells are passed through a 70 μm filter for single cell suspension, and cell number and viability are determined by PI exclusion (GUAVA). When need, red blood cells are lysed with PharMLyse (BD Biosciences). Cells are incubated in 20 ml of 1× PharMLyse in D-PBS for 30 seconds with gentle agitation and cells pelleted at 300×g for 5 minutes at 4° C. Cells are washed once in D-PBS and cell number and viability are recalculated by PI exclusion using the GUAVA. Cells at a total cell number greater than 20×10⁶ are sorted using a high-speed sorter (MoFlo Cytomation) for epithelial cells (EpCAM positive).

Single cell suspensions can also be prepared from tissue samples as follows: specimens are washed in DTT for 15 min, digested with Dispase (30-60 min), then filtered twice (380 μm/74 μm) before red blood cells are removed through addition of ACK lysis buffer. Epithelial (EpCAM) and leukocyte (CD45) content and cellular viability (PI exclusion) can be determined through flow cytometry analysis (LSR I, BD Biosciences, San Jose, Calif.).

The epithelial content of both disease and normal specimens can be enriched through depletion of immune CD45-positive cells by flow cytometry or purification of Epithelial Cell Surface Antigen (ECSA/EpCam)-positive cells by bead capture.

Bead capture of epithelial cells can be performed using a Dynal CELLection Epithelial Enrich kit (Invitrogen, Carlsbad, Calif.) as follows. Dynal CELLection beads at a concentration of 2×10⁸ beads are incubated with 1×10⁸ cells in HBSS with 10% fetal calf serum for 30 minutes at 4° C. Cells and beads are placed in a magnet system Dynal MPC for 2 minutes. Bead/cell complexes are washed in RPMI 1640 media with 1% fetal calf serum. Cells are released from the bead complex with 15 minute incubation with DNase with agitation in RPMI with 1% fetal calf serum.

DynalBead cell depletion of CD45 cells can be carried out as follows. DynalBead M-450 CD45 beads and cells are incubated at a concentration of 250 μl beads per 2×10⁷ cells for 30 minutes at 4° C. Bead/cell complexes are washed in DPBS buffer with 2% fetal bovine serum. Cells and beads are placed in a magnet system Dynal MPC for 2 minutes. The supernatant contains EpCAM enriched cells.

Cell Line Culture

Cell lines can be obtained from the American Type Culture Collection (ATCC, Manassas, Va.). For example, lung cancer cell lines and normal control lung cell lines (e.g., Beas2B cells can be used as a normal control lung cell line) can be used, such as to determine the expression levels of markers (e.g., proteins or encoding mRNA transcripts) in lung cancer cells compared with normal lung cells. Cell lines can be grown in a culturing medium that is supplemented as necessary with growth factors and serum, in accordance with the ATCC guidelines for each particular cell line. Cultures established from frozen stocks in which the cells are suspended in a freezing medium (cell culture medium with 10% DMSO [v/v]) and flash frozen in liquid nitrogen. Frozen stocks prepared in this way are stored in liquid nitrogen vapor. Cell cultures are established by rapidly thawing frozen stocks at 37° C. Thawed stock cultures are slowly transferred to a culture vessel containing a large volume of supplemented culture medium. For maintenance of culture, cells are seeded at 1×10⁵ cells/per ml in medium and incubated at 37° C. until confluence of cells in the culture vessel exceeds 50% by area. At this time, cells are harvested from the culture vessel using enzymes or EDTA where necessary. The density of harvested, viable cells is estimated by hemocytometry and the culture reseeded as above. A passage of this nature is repeated no more than 25 times, at which point the culture is destroyed and reestablished from frozen stocks as described above.

Alternatively, for secreted protein analysis, cells can be grown under routine tissue culture conditions in 490 cm² roller bottles at an initial seeding density of approximately 15 million cells per roller bottle. When the cells reach ~70-80% confluence, the culturing media is removed, the cells are washed 3 times with D-PBS and once with CD293 protein-free media (Invitrogen cat #11913-019), and the culturing media is replaced with CD293 for generating conditioned media. Cells are incubated for 72 hours in CD293 and the media is collected for analysis, such as mass spectrometry analysis of secreted proteins (30-300 ml). Cell debris is removed from the conditioned media by centrifugation at 300 g for 5 minutes and filtering through a 0.2 micron filter prior to analysis.

2. Cloning and Expression of Marker Proteins cDNA Retrieval

Peptide sequences can be searched using the BLAST algorithm against relevant protein sequence databases to identify the corresponding full-length protein (reference sequence). Each full-length protein sequence can then be searched using the BLAST algorithm against a human cDNA clone collection. For each sequence of interest, clones can be pulled and streaked onto LB/Ampicillin (100 μg/ml) plates. Plasmid DNA is isolated using Qiagen spin mini-prep kit and verified by restriction digest. Subsequently, the isolated plasmid DNA is sequence verified against the reference full-length protein sequence. Sequencing reactions are carried out using Applied Biosystems BigDye Terminator kit followed by ethanol precipitation. Sequence data is collected using the Applied Biosystems 3700 Genetic Analyzer and analyzed by alignment to the reference full-length protein sequence using the Clone Manager alignment tool.

PCR

PCR primers are designed to amplify the region encoding the full-length protein and/or any regions of the protein that are of interest for expression (e.g., antigenic or hydrophilic regions as determined by the Clone Manager sequence analysis tool). Primers also contain 5' and 3' overhangs to facilitate cloning (see below). PCR reactions contain 2.5 units Platinum Taq DNA Polymerase High Fidelity (Invitrogen), 50 ng cDNA plasmid template, 1 μM forward and reverse primers, 800 μM dNTP cocktail (Applied Biosystems), and 2 mM MgSO₄. After 20-30 cycles (94° C. for 30 seconds, 55° C. for 1 minute, and 73° C. for 2 minutes), the resulting product is verified by sequence analysis and quantitated by agarose gel electrophoresis.

Construction of Entry Clones

PCR products are cloned into an entry vector for use with the Gateway recombination based cloning system (Invitrogen). These vectors include pDonr221, pDonr201, pEntr/D-TOPO, or pEntr/SD/D-TOPO and are used as described in the cloning methods below.

TOPO Cloning into pEntr/D-TOPO or pEntr/SD/D-TOPO

For cloning using this method, the forward PCR primer contains a 5' overhang containing the sequence "CACC". PCR products are generated as described above and cloned into the entry vector using the Invitrogen TOPO® cloning kit. Reactions are typically carried out at room temperature for 10 minutes and subsequently transformed into TOP10 chemically competent cells (Invitrogen, CA). Candidate clones are picked, and plasmid DNA is prepared using a Qiagen spin mini-prep kit and screened by restriction enzyme digestion. Inserts are subsequently sequence-verified as described above.

Gateway Cloning into pDonr201 or pDonr221

For cloning using this method, PCR primers contain forward and reverse 5' overhangs. PCR products are generated as described above. Protein-encoding nucleic acid molecules are recombined into the entry vector using the Invitrogen Gateway BP Clonase enzyme mix. Reactions are typically carried out at 25° C. for 1 hour, treated with Proteinase K at 37° C. for 10 minutes, and transformed into Library Efficiency DH5α chemically competent cells (Invitrogen, CA). Candidate clones are picked, plasmid DNA is prepared using a Qiagen spin mini-prep kit, and screened by restriction enzyme digestion. Inserts are subsequently sequence-verified as described above.

Construction of Expression Clones

Protein-encoding nucleic acid molecules are transferred from the entry construct into a series of expression vectors using the Gateway LR Clonase enzyme mix. Reactions are typically carried out for 1 hour at 25° C., treated with Proteinase K at 37° C. for 10 minutes, and subsequently transformed into Library Efficiency DH5a chemically competent cells (Invitrogen). Candidate clones are picked, plasmid DNA is prepared using a Qiagen spin mini-prep kit, and screened by restriction enzyme digestion. Expression vectors include, but are not limited to, pDest14, pDest15, pDest17, pDest8, pDest10 and pDest20. These vectors allow expression in systems such as E. coli and recombinant baculovirus. Other vectors not listed here allow expression in yeast, mammalian cells, or in vitro.

Expression of Recombinant Proteins in E. coli

Constructs are transformed into one or more of the following host strains: BL21 SI, BL21 AI, (Invitrogen), Origami B (DE3), Origami B (DE3) pLysS, Rosetta (DE3), Rosetta (DE3) pLysS, Rosetta-Gami (DE3), Rosetta-Gami (DE3) pLysS, or Rosetta-Gami B (DE3) pLysS (Novagen). The transformants are grown in LB with or without NaCl and with appropriate antibiotics, at temperatures in the range of 20-37° C., with aeration. Expression is induced with the addition of IPTG (0.03-0.30 mM) or NaCl (75-300 mM) when the cells are in mid-log growth. Growth is continued for one to 24 hours post-induction. Cells are harvested by centrifugation in a Sorvall RC-3C centrifuge in a H6000A rotor for 10 minutes at 3000 rpm at 4° C. Cell pellets are stored at −80° C.

Expression of Recombinant Proteins Using Baculovirus

Recombinant proteins are expressed using baculovirus in Sf21 fall army worm ovarian cells. Recombinant baculoviruses are prepared using the Bac-to-Bac system (Invitrogen) per the manufacturer's instructions. Proteins are expressed on the large scale in Sf900II serum-free medium (Invitrogen) in a 10 L bioreactor tank (27° C., 130 rpm, 50% dissolved oxygen for 48 hours).

3. Recombinant Protein Purification

Recombinant proteins can be purified from E. coli and/or insect cells using a variety of standard chromatography methods. Briefly, cells are lysed using sonication or detergents. The insoluble material is pelleted by centrifugation at 10,000×g for 15 minutes. The supernatant is applied to an appropriate affinity column. For example, His-tagged proteins are separated using a pre-packed chelating sepharose column (Pharmacia) or GST-tagged proteins are separated using a glutathione sepharose column (Pharmacia). After using the affinity column, proteins are further separated using various techniques, such as ion exchange chromatography (columns from Pharmacia) to separate on the basis of electrical charge or size exclusion chromatography (columns from Tosohaas) to separate on the basis of molecular weight, size, and shape.

Expression and purification of the protein can also be achieved using either a mammalian cell expression system or an insect cell expression system. The pUB6/V5-His vector system (Invitrogen, CA) can be used to express cDNA in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6×His) sequence for rapid purification on PROBOND resin (Invitrogen, CA). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6× His which enables purification as described above. Purified proteins can be used to produce antibodies.

4. Chemical Synthesis of Proteins

Proteins or portions thereof can be produced not only by recombinant methods (such as described above), but also by using chemical methods well known in the art. Solid phase peptide synthesis can be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-a-protected by acid labile Boc (t-butyloxycarbonyl) or base-labile Fmoc (9-fluorenylmethoxycarbonyl) groups. The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full-length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20).

Automated synthesis can also be carried out on machines such as the 431A peptide synthesizer (Applied Biosystems, Foster City, Calif.). A protein or portion thereof can be purified by preparative high performance liquid chromatography and its composition confirmed by amino acid analysis or by sequencing (Creighton, 1984, Proteins, Structures and Molecular Properties, W H Freeman, New York N.Y.).

5. Antibody Production

Polyclonal Antibodies

Polyclonal antibodies against recombinant proteins can be raised in rabbits (Green Mountain Antibodies, Burlington, Vt.). Briefly, two New Zealand rabbits are immunized with 0.1 mg of antigen in complete Freund's adjuvant. Subsequent immunizations are carried out using 0.05 mg of antigen in incomplete Freund's adjuvant at days 14, 21, and 49. Bleeds are collected and screened for recognition of the antigen by solid phase ELISA and Western blot analysis. The IgG fraction is separated by centrifugation at 20,000×g for 20 minutes followed by a 50% ammonium sulfate cut. The pelleted protein is resuspended in 5 mM Tris and separated by ion exchange chromatography. Fractions are pooled based on IgG content. Antigen-specific antibody is affinity purified using Pierce AminoLink resin coupled to the appropriate antigen.

Isolation of Antibody Fragments Directed Against a Marker Protein from a Library of scFvs Naturally occurring V-genes isolated from human PBLs can be constructed into a library of antibody fragments which contain reactivities against a marker protein to which the donor may or may not have been exposed (see, for example, U.S. Pat. No. 5,885,793, incorporated herein by reference in its entirety).

Rescue of the library: A library of scFvs is constructed from the RNA of human PBLs, as described in PCT publication WO 92/01047. To rescue phage displaying antibody fragments, approximately $10^9$ E. coli harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×$10^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 rpm. for 10 min. and the pellet resuspended in 2 liters of 2×TY containing 100 μg/ml ampicillin and 50 μg/ml kanamycin and grown overnight. Phage are prepared as described in PCT publication WO 92/01047.

Preparation of M13 delta gene III: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 rpm for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 2001, Molecular Cloning: A Laboratory Manual. 3rd. ed., Cold Spring Harbor Laboratory Press, Cold Spring Harbor, N.Y.), resuspended in 2 ml PBS and passed through a 0.45 μm filter (Minisart NML; Sartorius) to give a final concentration of approximately $10^{13}$ transducing units/ml (ampicillin-resistant clones).

Panning of the library: Immunotubes (Nunc) are coated overnight in PBS with 4 ml of either 100 μg/ml or 10 μg/ml of a marker protein of interest. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over-and-under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under-and-over turntable after which the solution is immediately neutralized with 0.5 ml of 1.0 M Tris-HCl, pH 7.4. Phages are then used to infect 10 ml of mid-log E. coli TG1 by incubating eluted phage with bacteria for 30 minutes at 37° C. The E. coli are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of binders: Eluted phage from the 3rd and 4th rounds of selection are used to infect E. coli HB 2151 and soluble scFv is produced (Marks et al., 1991, *J. Mol. Biol.* 222: 581-597) from single colonies for assay. ELISAs are performed with microtitre plates coated with either 10 μg/ml of the marker protein of interest in 50 mM bicarbonate pH 9.6. Clones positive in ELISA are further characterized by PCR fingerprinting (see, e.g., PCT publication WO 92/01047) and then by sequence analysis.

Monoclonal Antibodies a) Materials:

1. Complete Media No Sera (CMNS) for washing of the myeloma and spleen cells; Hybridoma medium CM-HAT (Cell Mab (BD), 10% FBS (or HS); 5% Origen HCF (hybridoma cloning factor) containing 4 mM L-glutamine and antibiotics) to be used for plating hybridomas after the fusion.

2. Hybridoma medium CM-HT (no aminopterin) (Cell Mab (BD), 10% FBS 5% Origen HCF containing 4 mM L-glutamine and antibiotics) to be used for fusion maintenance is stored in the refrigerator at 4-6° C. The fusions are fed on days 4, 8, and 12, and subsequent passages. Inactivated and pre-filtered commercial fetal bovine serum (FBS) or horse serum (HS) are thawed and stored in the refrigerator at 4° C. and is pretested for myeloma growth from single cells prior to use.

3. The L-glutamine (200 mM, 100× solution), which is stored at −20° C., is thawed and warmed until completely in solution. The L-glutamine is dispensed into media to supplement growth. L-glutamine is added to 2 mM for myelomas and 4 mM for hybridoma media. Further, the penicillin, streptomycin, amphotericin (antibacterial-antifungal stored at −20° C.) is thawed and added to Cell Mab Media to 1%.

4. Myeloma growth media is Cell Mab Media (Cell Mab Media, Quantum Yield, from BD, which is stored in the refrigerator at 4° C. in the dark), to which is added L-glutamine to 2 mM and antibiotic/antimycotic solution to 1% and is called CMNS.

5. One bottle of PEG 1500 in Hepes (Roche, N.J.) is prepared.

6. 8-Azaguanine is stored as the dried powder supplied by SIGMA at −700° C. until needed. One vial/500 ml of media is reconstituted and the entire contents are added to 500 ml media (e.g., 2 vials/liter).

7. Myeloma Media is CM which has 10% FBS (or HS) and 8-Aza (1×) stored in the refrigerator at 4° C.

8. Clonal cell medium D (Stemcell, Vancouver) contains HAT and methyl cellulose for semi-solid direct cloning from the fusion. This comes in 90 ml bottles with a CoA and is melted at 37° C. in a waterbath in the morning of the day of the fusion. The cap is loosened and the bottle is left in a $CO_2$ incubator to sufficiently gas the medium D and bring the pH down.

9. Hybridoma supplements HT [hypoxanthine, thymidine] to be used in medium for the section of hybridomas and maintenance of hybridomas through the cloning stages, respectively.

10. Origen HCF can be obtained directly from Igen and is a cell supernatant produced from a macrophage-like cell-line. It can be thawed and aliquoted to 15 ml tubes at 5 ml per tube and stored frozen at −20° C. Positive hybridomas are fed HCF through the first subcloning and are gradually weaned (individual hybridomas can continue to be supplemented, as needed). This and other additives are typically more effective in promoting new hybridoma growth than conventional feeder layers.

b) Procedure:

To generate monoclonal antibodies, mice are immunized with 5-50 μg of antigen, either intra-peritoneally (i.p.) or by intravenous injection in the tail vein (i.v.). The antigen used can be a recombinant marker protein of interest, for example. The primary immunization takes place two months prior to the harvesting of splenocytes from the mouse, and the immunization is typically boosted by i.v. injection of 5-50 μg of antigen every two weeks. At least one week prior to the expected fusion date, a fresh vial of myeloma cells is thawed and cultured. Several flasks of different densities can be maintained so that a culture at the optimum density is ensured at the time of fusion. An optimum density can be $3\text{-}6\times10^5$ cells/ml, for example. 2-5 days before the scheduled fusion, a final immunization of approximately 5 μg of antigen in PBS is administered (either i.p. or i.v).

Myeloma cells are washed with 30 ml serum free media by centrifugation at 500 g at 4° C. for 5 minutes. Viable cell density is determined in resuspended cells using hemocytometry and vital stains. Cells resuspended in complete growth medium are stored at 37° C. during the preparation of splenocytes. Meanwhile, to test aminopterin sensitivity, $1\times10^6$ myeloma cells are transferred to a 15 ml conical tube and centrifuged at 500 g at 4° C. for 5 minutes. The resulting pellet is resuspended in 15 ml of HAT media and cells plated at 2 drops/well on a 96-well plate.

To prepare splenocytes from immunized mice, the animals are euthanised and submerged in 70% ethanol. Under sterile conditions, the spleen is surgically removed and placed in 10 ml of RPMI medium supplemented with 20% fetal calf serum in a petri dish. Cells are extricated from the spleen by infusing the organ with medium >50 times using a 21 g syringe.

Cells are harvested and washed by centrifugation (at 500 g at 4° C. for 5 minutes) with 30 ml of medium. Cells are resuspended in 10 ml of medium and the density of viable cells determined by hemocytometry using vital stains. The splenocytes are mixed with myeloma cells at a ratio of 5:1 (spleen cells: myeloma cells). Both the myeloma and spleen cells are washed twice more with 30 ml of RPMI-CMNS, and the cells are spun at 800 rpm for 12 minutes.

Supernatant is removed and cells are resuspended in 5 ml of RPMI-CMNS and are pooled to fill volume to 30 ml and spun down as before. Then, the pellet is broken up by gently tapping on the flow hood surface and resuspending in 1 ml of BMB REG1500 (prewarmed to 37° C.) dropwise with a 1 cc needle over 1 minute.

RPMI-CMNS to the PEG cells and RPMI-CMNS are added to slowly dilute out the PEG. Cells are centrifuged and diluted in 5 ml of Complete media and 95 ml of Clonacell Medium D (HAT) media (with 5 ml of HCF). The cells are plated out 10 ml per small petri plate.

Myeloma/HAT control is prepared as follows: dilute about 1000 P3X63 Ag8.653 myeloma cells into 1 ml of medium D and transfer into a single well of a 24-well plate. Plates are placed in an incubator, with two plates inside of a large petri plate, with an additional petri plate full of distilled water, for 10-18 days under 5% $CO_2$ overlay at 37° C. Clones are picked from semisolid agarose into 96-well plates containing 150-200 μl of CM-HT. Supernatants are screened 4 days later in ELISA, and positive clones are moved up to 24-well plates. Heavy growth requires changing of the media at day 8 (+/− 150 ml). The HCF can be further decreased to 0.5% (gradually −2%, then 1%, then 0.5%) in the cloning plates.

6. Liquid Chromatography and Mass Spectrometry (LC/MS)

For LC/MS analysis, proteins are reduced in 2.5 mM DTT for 1 hour at 37° C., and alkylated with ICAT™ reagent according to the procedures recommended by the manufacturer (Applied Biosystems, Framingham, Mass.). The reaction is quenched by adding excess DTT. Proteins are digested using sequencing grade modified trypsin overnight at 37° C. followed by desalting using 3 cc Oasis HLB solid phase extraction columns (Waters, Milford, Mass.) and vacuum drying. Cysteine-containing peptides are purified by avidin column (Applied Biosystems, Framingham, Mass.). The peptides are reconstituted in buffer A (0.1% formic acid in water) and separated over a C18 monomeric column (150 mm, 150 μm i.d., Grace Vydac 238EV5, 5 μm) at a flow rate of 1.5 μl/min with a trap column. Peptides are eluted from the column using a gradient, 3%-30% buffer B (0.1% formic acid in 90% acetonitrile) in 215 min, 30%-90% buffer B in 30 min. Eluted peptides are analyzed using an online QSTAR XL system (MDS/Sciex, Toronto, ON). Peptide ion peaks from the map are automatically detected with RESPECT™ (PPL Inc., UK).

The sequence-composition of peptides detected, for example, at higher levels in disease samples (or drug-resistant samples) relative to adjacent normal tissue (or drug-sensitive samples) can be resolved through tandem mass spectrometry and database analysis. For data analysis, peptide ion peaks of LC/MS maps from normal and disease samples can be aligned based on mass to charge ratio (m/z), retention time (Rt), and charge state (z). The list of aligned peptide ions is loaded into Spotfire™ (Spotfire Inc. Somerville, Mass.). Intensities can be normalized before further differential analysis between disease and normal samples. Differentially expressed ions are manually verified before LC-MS/MS-based peptide sequencing and database searching for protein/protein identification.

For intensity normalization and expression analysis, a heat map can be constructed by sorting the rows by the ratio of the mean intensity in the disease samples to the mean intensity of the normal samples. Rows are included if there is at least one MS/MS identification of an ion in the row. The display colors are determined for each row separately by assigning black to the median intensity in the row, green to the lowest intensity in the row, and red to the highest intensity.

Using a mass spectrometry procedure such as this, a comprehensive analysis of proteins differentially expressed by disease cells (or drug resistant cells, for example) compared with normal cells (or cells responsive/sensitive to a drug, for example) can be carried out.

7. mRNA Expression Analysis

Expression of marker mRNA can be quantitated by RT-PCR using TaqMan® technology. The Taqman® system couples a 5' fluorogenic nuclease assay with PCR for real-time quantitation. A probe is used to monitor the formation of the amplification product.

Total RNA can be isolated from disease model cell lines using an RNEasy Kit® (Qiagen, Valencia, Calif.) with DNase treatment (per the manufacturer's instructions). Normal human tissue RNAs can be acquired from commercial vendors (e.g., Ambion, Austin, Tex.; Stratagene, La Jolla, Calif.; BioChain Institute, Newington, N.H.), as well as RNAs from matched disease/normal tissues.

Marker transcript sequences can be identified for differentially expressed peptides by database searching using a search algorithm such as BLAST. TaqMan® assays (PCR primer/probe sets) specific for those transcripts can be obtained from Applied Biosystems (AB) as part of the Assays on Demand™ product line or by custom design through the AB Assays by Design$^{SM}$ service. If desired, the assays can be designed to span exon-exon borders so as not to amplify genomic DNA.

RT-PCR can be accomplished using AmpliTaq Gold® and MultiScribe™ reverse transcriptase in the One Step RT-PCR Master Mix reagent kit (AB) (according to the manufacturer's instructions). Probe and primer concentrations are 250 nM and 900 nM, respectively, in a 15 µl reaction. For each experiment, a master mix of the above components is made and aliquoted into each optical reaction well. Eight nanograms of total RNA is used as template. Quantitative RT-PCR can be performed using the ABI Prism® 7900HT Sequence Detection System (SDS). The following cycling parameters are used: 48° C. for 30 min. for one cycle; 95° C. for 10 min for one cycle; and 95° C. for 15 sec, 60° C. for 1 min. for 40 cycles.

SDS software can be utilized to calculate the threshold cycle ($C_T$) for each reaction, and $C_T$ values are used to quantitate the relative amount of starting template in the reaction. The $C_T$ values for each set of reactions can be averaged for all subsequent calculations Data can be analyzed to determine estimated copy number per cell. Gene expression can be quantitated relative to 18S rRNA expression and copy number estimated assuming $5\times10^6$ copies of 18S rRNA per cell. Alternatively, data can be analyzed for fold difference in expression using an endogenous control for normalization and expressed relative to a normal tissue or normal cell line reference. The choice of endogenous control can be determined empirically by testing various candidates against the cell line and tissue RNA panels and selecting the one with the least variation in expression. Relative changes in expression can be quantitated using the $2^{-\Delta\Delta C_T}$ method (Livak et al., 2001, Methods 25: 402-408; User bulletin #2: ABI Prism 7700 Sequence Detection System). Alternatively, total RNA can be quantitated using a RiboGreen RNA Quantitation Kit according to manufacturer's instructions and the percentage mRNA expression calculated using total RNA for normalization. Percentage knockdown can then be calculated relative to a no addition control.

8. Flow Cytometry (FACS) Analysis

Flow cytometry is interchangeably referred to as fluorescence-activated cell sorting (FACS). Quantitative flow cytometry can be used to compare the level of expression of a protein on disease cells to the level found on normal cells, for example.

Expression levels of a marker protein on primary tissue samples can be quantified using the Quantum Simply Cellular System (Bangs Laboratories, Fishers, Ind.) and a marker-specific antibody. Normal adjacent and disease tissues can be processed into single cell suspensions, as described above, which can be stained for various markers (e.g., the epithelial marker EpCam) and the marker-specific antibody. At least $0.5\times10^6$ cells are typically used for each analysis. Cells are washed once with Flow Staining Buffer (0.5% BSA, 0.05% NaN3 in D-PBS). To the cells, 20 µl of each marker-specific antibody are added. An additional 5 µl of anti-EpCam antibody conjugated to APC can be added when unsorted cells are used. Cells are incubated with antibodies for 30 minutes at 4° C. Cells are washed once with Flow Staining Buffer and either analyzed immediately on an LSR flow cytometry apparatus or fixed in 1% formaldehyde and stored at 4° C. until LSR analysis. Antibodies used to detect a marker can be PE-conjugated. PE-conjugated mouse IgGlk can used as an isotype control antibody. Cells are analyzed by flow cytometry and epitope copy number and the percentage of viable epithelial cells positive for marker expression can be measured. Cell numbers and viability can be determined by PI exclusion (GUAVA) for cells isolated from both normal and disease tissue. Standard curve and samples can be analyzed on a LSR I (BDBiosciences, San Jose Calif.) flow cytometer. Antibody binding capacity for each lineage population can be calculated using geometric means and linear regression.

Expression levels of a marker protein can be quantified in cell lines with QIFIKIT flow cytometric indirect immunofluorescence assay (Dako A/S) using a primary antibody to the marker. Briefly, cells are detached with versene or trypsin and washed once with complete media and then PBS. $5\times10^5$ cells/sample are incubated with saturating concentration (10 µg/ml) of primary antibody for 60 minutes at 4° C. After washes, a FITC-conjugated secondary antibody (1:50 dilution) is added for 45 minutes at 4° C. QIFIKIT standard beads are simultaneously labeled with the secondary antibody. Binding of antibodies is analyzed by flow cytometry and specific antigen density is calculated by subtracting background antibody equivalent from antibody-binding capacity based on a standard curve of log mean fluorescence intensity versus log antigen binding capacity.

Cells can also be prepared for flow cytometry analysis (as well as other types of analysis) as follows: cells are incubated with 1:100 dilution of BrdU in culturing media for 2-4 hours (BrdU Flow Kit, cat #559619 BD Biosciences). Cells are washed 3 times with D-PBS and disassociated from the flask with versene. Cell numbers and viability can be determined by PI exclusion (GUAVA). Cells are washed once with Flow Staining Buffer (0.5% BSA, 0.05% NaN$_3$ in D-PBS). Cells are incubated with 400 µl of Cytofix/Cytoperm Buffer (BrdU Flow Kit, BD Biosciences) for 15-30 minutes at 4° C. Cells are washed once with Flow Staining Buffer and resuspended in 400 µl Cytoperm Plus Buffer (BrdU Flow Kit BD Biosciences). Cells are incubated for 10 minutes at 4° C. and washed once with 1× Perm/Wash Buffer (BrdU Flow Kit, BD Biosciences). Cells are incubated for 1 hour at 37° C. protected from light in DNAse solution (BrdU Flow Kit, BD Biosciences). Cells are washed once with 1× Perm/Wash Buffer and incubated for 20 min at room temperature with anti-BrdU FITC-conjugated antibody (BrdU Flow Kit, BD Biosciences), PE-conjugated active caspase 3 (BD Biosciences cat #550821), and PE mouse IgG2B isotype control. Cells are washed once with 1× Perm/Wash Buffer and resuspended in DAPI for LSR flow cytometry analysis.

9. Immunohistochemistry (IHC)

IHC of Tissue Sections

Paraffin embedded, fixed tissue sections (e.g., from disease tissue samples such as solid tumors or other cancer tissues) can be obtained from a panel of normal tissues as well as tumor (or other disease) samples with matched normal adjacent tissues, along with replicate sections (if desired). For example, for an initial survey of marker expression, a panel of common cancer formalin-fixed paraffin-embedded (FFPE) tissue microarrays (TMAs) can be used for analysis, and such TMAs can be obtained from commercial sources (TriStar, Rockville, Md.; USBiomax, Rockville, Md.; Imgenex, San Diego, Calif.; Petagen/Abxis, Seoul, Korea). Sections can be stained with hemotoxylin and eosin and histologically examined to ensure adequate representation of cell types in each tissue section.

An identical set of tissues can be obtained from frozen sections for use in those instances where it is not possible to generate antibodies that are suitable for fixed sections. Frozen tissues do not require an antigen retrieval step.

Paraffin Fixed Tissue Sections

An exemplary protocol for hemotoxylin and eosin staining of paraffin embedded, fixed tissue sections is as follows. Sections are deparaffinized in three changes of xylene or xylene substitute for 2-5 minutes each. Sections are rinsed in two changes of absolute alcohol for 1-2 minutes each, in 95% alcohol for 1 minute, followed by 80% alcohol for 1 minute. Slides are washed in running water and stained in Gill solution 3 hemotoxylin for 3-5 minutes. Following a vigorous wash in running water for 1 minute, sections are stained in Scott's solution for 2 minutes. Sections are washed for 1 minute in running water and then counterstained in eosin solution for 2-3 minutes, depending upon the desired staining intensity. Following a brief wash in 95% alcohol, sections are dehydrated in three changes of absolute alcohol for 1 minute each and three changes of xylene or xylene substitute for 1-2 minutes each. Slides are coverslipped and stored for analysis.

Optimization of Antibody Staining

For each antibody, a positive and negative control sample can be generated using data from ICAT analysis of disease cell lines or tissues. Cells can be selected that are known to express low levels of a particular marker as determined from the ICAT data, and this cell line can be used as a reference normal control. Similarly, a disease cell line that is determined to over-express the marker can also be selected.

Antigen Retrieval

Sections are deparaffinized and rehydrated by washing 3 times for 5 minutes in xylene, two times for 5 minutes in 100% ethanol, two times for 5 minutes in 95% ethanol, and once for 5 minutes in 80% ethanol. Sections are then placed in endogenous blocking solution (methanol+2% hydrogen peroxide) and incubated for 20 minutes at room temperature. Sections are rinsed twice for 5 minutes each in deionized water and twice for 5 minutes in phosphate buffered saline (PBS), pH 7.4.

Alternatively, where necessary, sections are de-parrafinized by High Energy Antigen Retrieval as follows: sections are washed three times for 5 minutes in xylene, two times for 5 minutes in 100% ethanol, two times for 5 minutes in 95% ethanol, and once for 5 minutes in 80% ethanol. Sections are placed in a Coplin jar with dilute antigen retrieval solution (10 mM citrate acid, pH 6). The Coplin jar containing slides is placed in a vessel filled with water and microwaved on high for 2-3 minutes (700 watt oven). Following cooling for 2-3 minutes, steps 3 and 4 are repeated four times (depending on the tissue), followed by cooling for 20 minutes at room temperature. Sections are then rinsed in deionized water (two times for 5 minutes), placed in modified endogenous oxidation blocking solution (PBS+2% hydrogen peroxide), and rinsed for 5 minutes in PBS.

Alternatively, formalin fixed paraffin embedded tissues can be deparaffinized and processed for antigen retrieval using the EZ-retriever system (BioGenex, San Ramon, Calif.). EZ-antigen Retrieval common solution is used for deparaffinization and EZ-retrieval citrate-based buffer used for antigen retrieval. Samples are pre-blocked with non-serum protein block (Dako A/S, Glostrup, Denmark) for 15 min. Primary antibodies (at 2.5-5.0 µg/ml, for example) are incubated overnight at room temperature. Envision Plus system HRP (Dako A/S) is used for detection with diaminobenzidine (DAB) as substrate for horseradish peroxidase.

Blocking and Staining

Sections are blocked with PBS/1% bovine serum albumin (PBA) for 1 hour at room temperature followed by incubation in normal serum diluted in PBA (2%) for 30 minutes at room temperature to reduce non-specific binding of antibody. Incubations are performed in a sealed humidity chamber to prevent air-drying of the tissue sections. The choice of blocking serum is typically the same as the species of the biotinylated secondary antibody. Excess antibody is gently removed by shaking and sections covered with primary antibody diluted in PBA and incubated either at room temperature for 1 hour or overnight at 4° C. (care is taken that the sections do not touch during incubation). Sections are rinsed twice for 5 minutes in PBS, shaking gently. Excess PBS is removed by gently shaking. The sections are covered with diluted biotinylated secondary antibody in PBA and incubated for 30 minutes to 1 hour at room temperature in the humidity chamber. If using a monoclonal primary antibody, addition of 2% rat serum can be used to decrease the background on rat tissue sections. Following incubation, sections are rinsed twice for 5 minutes in PBS, shaking gently. Excess PBS is removed and sections incubated for 1 hour at room temperature in Vectastain ABC reagent (as per kit instructions). The lid of the humidity chamber is secured during all incubations to ensure a moist environment. Sections are rinsed twice for 5 minutes in PBS, shaking gently.

Developing and Counterstaining

Sections are incubated for 2 minutes in peroxidase substrate solution that is made up immediately prior to use as follows: 10 mg diaminobenzidine (DAB) dissolved in 10 ml of 50 mM sodium phosphate buffer, pH 7.4; 12.5 microliters 3% $CoCl_2/NiCl_2$ in deionized water; and 1.25 microliters hydrogen peroxide.

Slides are rinsed well three times for 10 minutes in deionized water and counterstained with 0.01% Light Green acidified with 0.01% acetic acid for 1-2 minutes, depending on the desired intensity of counterstain.

Slides are rinsed three times for 5 minutes with deionized water and dehydrated two times for 2 minutes in 95% ethanol; two times for 2 minutes in 100% ethanol; and two times for 2 minutes in xylene. Stained slides are mounted for visualization by microscopy.

Slides are scored manually using a microscope such as the Zeiss Axiovert 200M microscope (Carl Zeiss Microimaging, Thornwood, N.Y.). Representative images are acquired using 40× objective (400× magnification).

IHC Staining of Frozen Tissue Sections

For IHC staining of frozen tissue sections, fresh tissues are embedded in OCT in plastic mold, without trapping air bubbles surrounding the tissue. Tissues are frozen by setting the mold on top of liquid nitrogen until 70-80% of the block turns white at which point the mold is placed on dry ice. The frozen blocks are stored at −80° C. Blocks are sectioned with a cryostat with care taken to avoid warming to greater than −10° C. Initially, the block is equilibrated in the cryostat for about 5 minutes and 6-10 mm sections are cut sequentially. Sections are allowed to dry for at least 30 minutes at room temperature. Following drying, tissues are stored at 4° C. for short term and −80° C. for long term storage.

Sections are fixed by immersing in an acetone jar for 1-2 minutes at room temperature, followed by drying at room temperature. Primary antibody is added (diluted in 0.05 M Tris-saline [0.05 M Tris, 0.15 M NaCl, pH 7.4], 2.5% serum) directly to the sections by covering the section dropwise to cover the tissue entirely. Binding is carried out by incubation in a chamber for 1 hour at room temperature. Without letting the sections dry out, the secondary antibody (diluted in Tris-saline/2.5% serum) is added in a similar manner to the primary antibody and incubated as before (at least 45 minutes).

Following incubation, the sections are washed gently in Tris-saline for 3-5 minutes and then in Tris-saline/2.5% serum for another 3-5 minutes. If a biotinylated primary antibody is used, in place of the secondary antibody incubation, slides are covered with 100 µl of diluted alkaline phosphatase conjugated streptavidin, incubated for 30 minutes at room temperature and washed as above. Sections are incubated with alkaline phosphatase substrate (1 mg/ml Fast Violet; 0.2 mg/ml Napthol AS-MX phosphate in Tris-Saline pH 8.5) for 10-20 minutes until the desired positive staining is achieved at which point the reaction is stopped by washing twice with Tris-saline. Slides are counter-stained with Mayer's hematoxylin for 30 seconds and washed with tap water for 2-5 minutes. Sections are mounted with Mount coverslips and mounting media.

10. RNAi Assays in Cell Lines

RNAi Transfections

Expression of a marker can be knocked down by transfection with small interfering RNA (siRNA) to that marker. Synthetic siRNA oligonucleotides can be obtained from Dharmacon (Lafayette, Colo.) or Qiagen (Valencia, Calif.). For siRNA transfection, cells (e.g., disease cells) can be seeded into 96 well tissue culture plates at a density of 2,500 cells per well 24 hours before transfection. Culture medium is removed and 50 µl of reaction mix containing siRNA (final concentration 1 to 100 nM) and 0.4 µl of DharmaFECT4 (Dharmacon, Lafayette, Colo.) diluted in Opti-MEM is added to each well. An equal volume of complete medium follows and the cells are then incubated at 5% $CO_2$ at 37° C. for 1 to 4 days.

Alternatively, in the initial screening phase, RNAi can be performed using 100 nM (final) of Smartpools (Dharmacon, Lafayette, Colo.), pool of 4—for Silencing siRNA duplexes (Qiagen, Valencia, Calif.), or non-targeting negative control siRNA (Dharmacon or Qiagen).

In the breakout phase, each individual duplex is used at 100 nM (final). In the titration phase, individual duplex is used at 0.1-100 nM (final). Transient transfections are carried out using either Lipofectamine 2000 from Invitrogen (Carlsbad, Calif.) or GeneSilencer from Gene Therapy Systems (San Diego, Calif.) (see below). One day after transfections, total RNA is isolated using the RNeasy 96 Kit (Qiagen) according to manufacturer's instructions and expression of mRNA is quantitated using TaqMan technology. Apoptosis and cell proliferation assays can be performed daily using Apop-one homogeneous caspase-3/7 kit and Alamar Blue or CellTiter 96 AQueous One Solution Cell Proliferation Assays (see below).

RNAi Transfections—Lipofectamine 2000 and GeneSilencer

Transient RNAi transfections can be carried out using Lipofectamine 2000 (Invitrogen, Carlsbad, Calif.) or GeneSilencer (Gene Therapy Systems, San Diego, Calif.), such as on sub-confluent disease cell lines, as described elsewhere (Elbashir et al., 2001, *Nature* 411: 494-498; Caplen et al., 2001, *Proc Natl Acad Sci USA* 98: 9742-9747; Sharp, 2001, *Genes and Development* 15: 485-490). Synthetic RNA to a gene of interest or non-targeting negative control siRNA are transfected using Lipofectamine 2000 or GeneSilencer according to manufacturer's instructions. Cells are plated in 96-well plates in antibiotic-free medium. The next day, the transfection reagent and siRNA are prepared for transfections as follows.

0.1-100 nM siRNA is resuspended in 20-25 µl serum-free media in each well (with Plus for Lipofectamine 2000) and incubated at room temperature for 15 minutes. 0.1-1 µl of Lipofectamine 2000 or 1-1.5 µl of GeneSilencer is also resuspended in serum-free medium to a final volume of 20-25 µl per well. After incubation, the diluted siRNA and either the Lipofectamine 2000 or the GeneSilencer are combined and incubated for 15 minutes (Lipofectamine 2000) or 5-20 minutes (GeneSilencer) at room temperature. Media is then removed from the cells and the combined siRNA-Lipofectamine 2000 reagent or siRNA-GeneSilencer reagent is added to a final volume of 50 µl per well. After further incubation at 37° C. for 4 hours, 50 µl serum-containing medium is added back to the cells. 1-4 days after transfection, expression of mRNA can be quantitated by RT-PCR using TaqMan technology, and protein expression levels can be measured by flow cytometry. Apoptosis and proliferation assays can be performed daily using Apop-one homogeneous caspase-3/7 kit and Alamar Blue or CellTiter 96 AQueous One Solution Cell Proliferation Assays (see below).

mRNA and Protein Knockdowns

Knockdown of marker mRNA levels can be monitored by Q-PCR one day after siRNA transfection by using a TaqMan® assay (Applied Biosystems, Foster City, Calif.). RT-PCR is accomplished in a one-step reaction by using M-MLV reverse transcriptase (Promega, Madison, Wis.) and AmpliTaq Gold® (ABI) and analyzed on the ABI Prism® 7900HT Sequence Detection System (ABI). Relative gene expression can be quantitated by the $\Delta\Delta Ct$ method (User Bulletin #2, ABI) with 18S rRNA serving as the endogenous control.

Protein knockdown can be monitored by FACS four days after transfection by using an antibody to the marker. The samples can be run on a LSR flow cytometer (BD Biosciences, San Jose, Calif.) and live cells monitored by using PI exclusion (50 µg/ml PI, 2.5 units/ml RNase A, 0.1% Triton X-100 in D-PBS). The data can be analyzed using CellQuest software.

Cell Proliferation—Alamar Blue

Cell growth can be assessed four days after transfection by adding a 1:10 dilution of Alamar blue reagent (Invitrogen, Carlsbad, Calif. or Biosource, Camarillo, Calif.) and incubated for 2 hours at 37° C. Analysis can be performed on a Spectrafluor Plus (Tecan, Durham, N.C.) set at excitation wavelength of 530 nm and emission wavelength of 595 nm.

Cell Proliferation—MTS

Alternatively, cell proliferation assays can be performed using a CellTiter 96 AQueous One Solution Cell Proliferation Assay kit (Promega, Madison, Wis.). 20 µl of CellTiter 96 AQueous One Solution is added to 100 µl of culture medium. The plates are then incubated for 1-4 hours at 37° C. in a humidified 5% $CO_2$ incubator. After incubation, the change in absorbance is read at 490 nm.

Apoptosis

Apoptosis assays can be performed using the Apop-one homogeneous caspase-3/7 kit (Promega, Madison, Wis.). Briefly, the caspase-3/7 substrate is thawed to room temperature and diluted 1:100 with buffer. The diluted substrate is then added 1:1 to cells, control, or blank. The plates are then placed on a plate shaker for 30 minutes to 18 hours at 300-500 rpm. The fluorescence of each well is then measured using an excitation wavelength of 485+/−20 nm and an emission wavelength of 530+/−25 nm.

11. Antibody Assays in Cell Lines

Cytotoxicity Assays

Cytotoxicity can be measured using a Resazurin (Sigma, Mo.) dye reduction assay (McMillian et al., 2002, *Cell Biol. Toxicol.* 18:157-173). Briefly, cells are plated at 1,000-5,500 cells/well in 96 well plates, allowed to attach to the plates for 18 hours before addition of fresh media with or without antibody. After 96-144 hours of exposure to antibody, resazurin is added to cells to a final concentration of 50 μM. Cells are incubated for 2-6 hours depending on dye conversion of cell lines, and dye reduction is measured on a Fusion HT fluorescent plate reader (Packard Instruments, Meridien, Conn.) with excitation and emission wavelengths of 530 nm and 590 nm, respectively. The $IC_{50}$ value is defined here as the drug concentration that results in 50% reduction in growth or viability as compared with untreated control cultures.

Assays for Antibody-Dependent Cellular Cytotoxicity

Antibody-dependent cellular cytotoxicity (ADCC) assays can be carried out as follows. Cultured disease cells (e.g., tumor cells) are labeled with 100 μCi $^{51}Cr$ for 1 hour (Livingston et al., 1997, *Cancer Immunol. Immunother.* 43, 324-330). After being washed three times with culture medium, cells are resuspended at $10^5$/ml, and 100 μl/well are plated onto 96-well round-bottom plates. A range of antibody concentrations are applied to the wells, including an isotype control together with donor peripheral blood mononuclear cells that are plated at a 100:1 and 50:1 ratio. After an 18 hour incubation at 37° C., supernatant (30 μl/well) is harvested and transferred onto Lumaplate 96 (Packard), dried, and read in a Packard Top-Count NXT γ counter. Spontaneous release is determined by cpm of disease cells incubated with medium and maximum release by cpm of disease cells plus 1% Triton X-100 (Sigma). Specific lysis is defined as: % specific lysis= [(experimental release−spontaneous release)/(maximum release−spontaneous release)]×100. The percent ADCC is expressed as peak specific lysis postimmune subtracted by preimmune percent specific lysis. A doubling of the ADCC to >20% can typically be considered significant.

Assays for Complement Dependent Cytotoxicity

Chromium release assays to assess complement dependent cytotoxicity (CDC) can be carried out as follows (Dickler et al., 1999, *Clin. Cancer Res.* 5, 2773-2779). Cultured disease cells (e.g., tumor cells) are washed in FCS-free media two times, resuspended in 500 μl of media, and incubated with 100 μCi $^{51}Cr$ per 10 million cells for 2 hours at 37° C. The cells are then shaken every 15 min for 2 hours, washed 3 times in media to achieve a concentration of approximately 20,000 cells/well, and then plated in round-bottom plates. The plates contain either 50 μl cells plus 50 μl monoclonal antibody, 50 μl cells plus serum (pre- and post-therapy), or 50 μl cells plus mouse serum as a control. The plates are incubated in a cold room on a shaker for 45 min. Human complement of a 1:5 dilution (resuspended in 1 ml of ice-cold water and diluted with 3% human serum albumin) is added to each well at a volume of 100 μl. Control wells include those for maximum release of isotope in 10% Triton X-100 (Sigma) and for spontaneous release in the absence of complement with medium alone. The plates are incubated for 2 hours at 37° C., centrifuged for 3 min, and then 100 μl of supernatant is removed for radioactivity counting. The percentage of specific lysis is calculated as follows: % cytotoxicity=[(experimental release−spontaneous release)/(maximum release−spontaneous release)]×100. A doubling of the CDC to >20% can typically be considered significant.

Cell Proliferation Assays

To measure cell proliferation, cells can be plated, grown and treated as for the cytotoxicity assay (above) in 96 well plates. After 96-144 hours of treatment, 0.5 μCi/well $^3H$-Thymidine (PerkinElmer, 6.7 Ci/mmol) is added to cells and incubated for 4-6 hours at 37° C., 5% $CO_2$ in an incubator. To lyse cells, plates are frozen overnight at −20° C. and then cell lysates are harvested using FilterMate (Packard Instrument, Meridien, Conn.) into 96 well filter plates. Radioactivity associated with cells is measured on a TopCount (Packard) scintillation counter.

Other cell assays (e.g., proliferation assays such as Alamar blue and MTS, and apoptosis assays) can be carried out using antibodies, as described above for RNAi.

Testing of Function-Blocking Antibodies

For testing of function-blocking antibodies, sub-confluent disease cell lines are serum-starved overnight. The next day, serum-containing media is added back to the cells in the presence of 5-50 ng/ml of function-blocking antibodies. After 2 or 5 days incubation at 37° C. 5% $CO_2$, antibody binding is examined by flow cytometry, and apoptosis and proliferation are measured.

Cell Invasion

Cell invasion assays can be performed using a 96-well cell invasion assay kit (Chemicon). After the cell invasion chamber plates are adjusted to room temperature, 100 μl serum-free media is added to the interior of the inserts. 1-2 hours later, cell suspensions of $1\times10^6$ cells/ml are prepared. Media is then carefully removed from the inserts and 100 μl of prepared cells are added into the insert +/−0 to 50 ng function blocking antibodies. The cells are pre-incubated for 15 minutes at 37° C. before 150 μl of media containing 10% FBS is added to the lower chamber. The cells are then incubated for 48 hours at 37° C. After incubation, the cells from the top side of the insert are discarded and the invasion chamber plates are then placed on a new 96-well feeder tray containing 150 μl of pre-warmed cell detachment solution in the wells. The plates are incubated for 30 minutes at 37° C. and are periodically shaken. Lysis buffer/dye solution (4 μl CyQuant Dye/300 μl 4× lysis buffer) is prepared and added to each well of dissociation buffer/cells on feeder tray. The plates are incubated for 15 minutes at room temperature before 150 μl is transferred to a new 96-well plate. Fluorescence of invading cells is then read at 480 nm excitation and 520 nm emission.

Receptor Internalization

For quantification of receptor internalization, ELISA assays can be performed essentially as described by Daunt et al. (Daunt et al., 1997, *Mol. Pharmacol.* 51, 711-720). Cell lines are plated at $6\times10^5$ cells per in a 24-well tissue culture dishes that have previously been coated with 0.1 mg/ml poly-L-lysine. The next day, the cells are washed once with PBS and incubated in DMEM at 37° C. for several minutes. Agonist to the cell surface marker of interest is then added to the wells at a pre-determined concentration in prewarmed DMEM. The cells are then incubated for various times at 37° C. and reactions are stopped by removing the media and fixing the cells in 3.7% formaldehyde/TBS for 5 min at room temperature. The cells are then washed three times with TBS and nonspecific binding blocked with TBS containing 1% BSA for 45 min at room temperature. The first antibody is added at a pre-determined dilution in TBS/BSA for 1 hr at room temperature. Three washes with TBS follow, and cells are briefly reblocked for 15 min at room temperature. Incubation with goat anti-mouse conjugated alkaline phosphatase (Bio-Rad) diluted 1:1000 in TBS/BSA is carried out for 1 hr at room temperature. The cells are washed three times with TBS and a calorimetric alkaline phosphatase substrate is added. When the adequate color change is reached, 100 μl samples are taken for calorimetric readings.

12. Treatment with Antibodies

Treatment of Disease Cells with Monoclonal Antibodies.

Disease cells (e.g., cancer cells), or cells such as NIH 3T3 cells that express a marker of interest, are seeded at a density of $4\times10^4$ cells per well in 96-well microtiter plates and allowed to adhere for 2 hours. The cells are then treated with different concentrations of monoclonal antibody (Mab) specific for the marker protein of interest, or irrelevant isotype matched (e.g., anti-rHuIFN-gamma) Mab, at 0.05, 0.5 or 5.0 µg/ml. After a 72 hour incubation, the cell monolayers are stained with crystal violet dye for determination of relative percent viability (RPV) compared to control (untreated) cells. Each treatment group can have replicates. Cell growth inhibition is monitored.

In vivo Treatment with Monoclonal Antibodies.

NIH 3T3 cells transfected with either an expression plasmid that expresses the marker of interest or a neo-DHFR vector are injected into nu/nu (athymic) mice subcutaneously at a dose of $10^6$ cells in 0.1 ml of phosphate-buffered saline. On days 0, 1, 5, and every 4 days thereafter, 100 µg (0.1 ml in PBS) of a Mab specific for the marker protein of interest, or an irrelevant Mab, of the IgA2 subclass is injected intraperitoneally. Disease progression (e.g., tumor occurrence and size) can be monitored for a one month period of treatment, for example.

13. Identification of LCM

A mass spectrometry (MS)-based proteomics platform was used for the identification of secreted and shed proteins (secreted and shed proteins are collectively referred to herein as soluble proteins) and cell surface antigens that combines the discovery of candidate biomarkers from human lung tumor specimens resected from surgery and in a panel of lung cancer cell lines, followed by validation of expression levels in patient serum (such as by using ELISA). For example, proteomic analysis techniques such as MALDI-TOF/TOF LC/MS-based protein expression analysis was used to determine the expression levels of certain proteins in lung tumor tissues and/or lung cancer cell lines (tissues and cell lines may be collectively referred to herein as "samples") and in normal tissues and/or normal cell lines, such that proteins that are differentially expressed (e.g., over- or under-expressed) in lung cancer samples compared with normal samples were identified.

Certain candidate markers were identified by mass spectrometry-based methods that were differentially expressed on the cell surface of lung tumors, lung cancer cell lines, or secreted into the conditioned medium of cell lines. Certain of these candidate markers that were identified as differentially expressed by mass spectrometry, as well as certain other candidate markers, were assayed by ELISA and scored in panels of lung cancer patient sera and sera from individuals without lung cancer (individuals without lung cancer are referred to herein as "normal", "control", or "healthy" individuals). Individual markers were scored "positive" for a given cancer sample if the value exceeded a defined threshold (e.g., greater than or equal to two standard deviations above the mean value for a group of "normal" samples tested). From these candidate markers, lung cancer markers ("LCM") were identified that, particularly when used in combination, distinguished lung cancer samples from healthy control samples with various degrees of sensitivity and specificity.

Several methods and algorithms were applied to select optimum panels/combinations of LCM including sum of the logs of the ratios of the tumor concentration to the mean of the normal concentration, defining a concentration cutoff manually for each marker to optimize sensitivity and specificity, and use of Naïve Bayes to assign a probability that a sample is a tumor based on the expression level of each marker. Additionally, ROC curves may be constructed for each panel and their effectiveness may be evaluated in several ways, such as maximizing the AUC of the ROC curve as well as maximizing the sensitivity at a desired specificity or maximizing the specificity at a desired sensitivity.

To further validate the specificity of certain panels, co-morbidity studies were carried out to challenge certain panels with other lung disease samples besides lung cancer, particularly chronic obstructive pulmonary disease (COPD), asthma, bronchitis, and other benign lung diseases (FIG. 20). Prevalence of COPD/asthma is 10-25% in smokers. An initial panel of 30 bronchitis/asthma/benign lung disease samples was tested. Results indicated that these co-morbidities may reduce specificity only marginally if considered independent of false positives in 54 control samples (the specificity of the 9-member panel of Cyfra, SLPI, TIMP1, SCC, TFPI, CEACAM5, MMP2, OPN, and MDK in a 54 normal/53 lung tumor sample set was 98% on samples from smoking controls).

14. ELISA Immunoassays

Immunoassay kits, such as for performing ELISA assays, for various LCM disclosed herein are commercially available. For example, immunoassay kits can be obtained from a variety of commercial sources, as follows: SLPI, MMP2, MIF, and OPN immunoassay kits can be obtained from R&D Systems (Minneapolis, Minn.); CYFRA 21-1 and SCC immunoassay kits can be obtained from DRG-International (Mountainside, N.J.); DEFA1 immunoassay kits can be obtained from Cell Sciences (Canton, Mass.); TIMP1 immunoassay kits can be obtained from Siemens Healthcare Diagnostics (Cambridge, Mass.); CEA and GRP immunoassay kits can be obtained from IBL International (Toronto, Ontario); TFPI immunoassay kits can be obtained from American Diagnostica (Stamford, Conn.); and MDK immunoassay kits can be obtained from BioVendor (Candler, N.C.) or R&D Systems (Minneapolis, Minn.). Assays can be performed following manufacturers instructions. Plates can be read on a Spectra Max M2 Microplate Reader (Molecular Devices, Sunnyvale, Calif.) with the appropriate baseline correction for each assay.

HNP1-3 (defensin, DEFA1) is employed as a representative marker in the following exemplary ELISA protocol, which can be used for the analysis of LCM. An HNP1-3 ELISA test kit can be used that is a solid-phase enzyme-linked immunosorbent assay based on the sandwich principle. Samples and standards are incubated in microtiter wells coated with antibodies recognizing human HNP1-3. During this incubation, human HNP1-3 is captured by solid bound antibody. Unbound material present in the sample is removed by washing. Biotinylated second antibody (tracer) to human HNP 1-3 is then added to the wells. If HNP1-3 is present in the sample, the tracer antibodies will bind to the captured HNP1-3. The excess tracer is removed by washing. A streptavidin-peroxidase conjugate is then applied to the wells, which reacts specifically with the biotinylated tracer antibody bound onto the detected HNP1-3. The excess streptavidin-peroxidase conjugate is removed by washing and substrate tetramethylbenzidine (TMB) is added to the wells. Color develops proportionally to the amount of human HNP1-3 present in the sample. The enzyme reaction is stopped by the addition of citric acid and the absorption at 450 nm is measured with a spectrophotometer. A standard curve is obtained by plotting the absorptions versus the corresponding concentrations of the known standards. The concentration of human HNP1-3 in test samples, which are run concurrently with the standards, can be determined from the standard curve.

15. Scoring of LCM Levels

This example describes an exemplary method of scoring LCM levels using split-point analysis.

The term "split-point analysis" refers to a method adapted from Mor et al., *PNAS,* (2005) 102, 7677-7682. In this exemplary method, measurements for each marker are taken on all samples. A cutoff value is determined for each marker. This cutoff value may be set to, for example, maximize the accuracy of correct classifications between the groups of interest (e.g., tumor and control sample groups) or may be set to maximize the sensitivity or specificity of one group. For each marker, a score is assigned to that sample whenever the value of that marker is found to be on the diseased side of the cutoff value (e.g., the side of the cutoff corresponding to lung tumor samples). After all the measurements have been taken on one sample, the scores are summed to produce a total score for the panel of markers. All markers can be weighted equally such that a panel of 9 markers may have a maximum score of 9 (each marker having a score of either 1 or 0) and a minimum score of 0, for example. Alternatively, markers can be weighted unequally, with a higher individual score for more significant measures.

Other more sophisticated statistical modeling methods can also be applied such as logistic regression (see, e.g., Planque et al., *Clin Cancer Res* (2008), 14, 1355-1362) and decision tree modeling (see, e.g., Patz et al., *J Clin Oncol* (2007), 25, 5578-5583).

An exemplary method of applying split-point analysis to an LCM panel is described for illustrative purposes.

A patients sample can be tested to determine the patient's likelihood of having lung cancer using a panel comprising the 9 biomarkers Cyfra, CEA, SLPI, OPN, MDK, TFPI, TIMP1, MMP2, and SCC and the split and score method. The predetermined total score (or threshold) for the panel can be set at 1 (or other value).

After obtaining a test sample from the patient, the amount of each of the 9 biomarkers (Cyfra, CEA, SLPI, OPN, MDK, TFPI, TIMP1, MMP2, SCC) in the patient's test sample is quantified. For the purpose of this example, the amount of each of the 9 biomarkers in the test sample is determined to be as follows (values are expressed in ng/ml): Cyfra=0.891, CEA=4.087, SLPI=62.94, OPN 21.514, MDK=0.174, TFPI=104.503, TIMP1=398.7, MMP2=194.41, and SCC=1.35. The amount of each of these biomarkers is then compared to the corresponding predetermined cutoff (or split point). For the purpose of this example, the predetermined cutoffs for each of the biomarkers are as follows: Cyfra=1.20, CEA=5.00, SLPI=52, OPN=32, MDK=0.15, TFPI=150, TIMP1=385, MMP2=210, and SCC=2.2. For each biomarker having an amount that is higher than its corresponding predetermined cutoff (split point), a score of 1 can be assigned. For each biomarker having an amount that is less than or equal to its corresponding predetermined cutoff, a score of 0 can be assigned. Thereupon, based on said comparison, each biomarker would be assigned a score as follows: Cyfra=0, CEA=0, SLPI=1, OPN=0, MDK=1, TFPI=0, TIMP1=1, MMP2=0, and SCC=0.

The score for each of the 9 biomarkers can then be combined mathematically (e.g., by adding each of the scores of the biomarkers together) to arrive at the total score for the patient. In this particular example, the total score for the patient is 3 (the total score is calculated as follows: 0+0+1+0+1+0+1+0+0=3). The total score for the patient is compared to the predetermined total score, which is 1 in this particular example. A total score greater than the predetermined total score of 1 would indicate a positive result for the patient (i.e., in this particular example, a total score of 2 or greater would indicate that the patient has lung cancer). A total score equal to or less than 1 would indicate a negative result for the patient. In this example, because the patient's total score is greater than 1, the patient would be considered to have a positive result (and thus may be referred for further testing for an indication or suspicion of lung cancer). In contrast, had the patient's total score been 1 or 0, the patient would have been considered to have a negative result (and thus would not be referred for any further testing).

All publications and patents mentioned in the above specification are herein incorporated by reference. Various modifications and variations of the described methods and compositions of the invention will be apparent to those skilled in the art without departing from the scope and spirit of the invention. Although the invention has been described in connection with specific exemplary embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. A method for determining whether a human has lung cancer, the method comprising detecting the level of one or more protein markers selected from the group consisting of tissue factor pathway inhibitor (TFPI), matrix metalloproteinase 2 (MMP2), tissue inhibitor of metalloproteinase (TIMP1), carcinoembryonic antigen-related cell adhesion molecule 5 (CEACAM5), and Cyfra 21-1 (Cyfra) in a body fluid sample from said human, wherein said one or more protein markers that is detected includes TFPI, and correlating an elevated level of at least one of said one or more protein markers with the presence of lung cancer in said human.

2. The method of claim 1, wherein said human has been identified as having a lung lesion prior to said detecting.

3. The method of claim 2, wherein said lung lesion was observed by computed tomography (CT) screening.

4. The method of claim 1, wherein the detecting comprises detecting the protein markers by immunoassay.

5. The method of claim 4, wherein the immunoassay is ELISA.

6. The method of claim 1, wherein the detecting comprises contacting the sample with antibodies that selectively bind to each of the protein markers and detecting the binding of the antibodies to the protein markers.

7. The method of claim 1, wherein the body fluid sample is blood, serum, plasma, or bronchial lavage.

8. The method of claim 1, further comprising the step of providing a prognosis to said human.

9. The method of claim 1, wherein the method is carried out following lung cancer treatment of said human.

10. The method of claim 1, further comprising administering a lung cancer treatment to said human if said method indicates that said human has lung cancer.

11. The method of claim 1, further comprising enrolling said human in a clinical trial of a therapeutic agent.

12. The method of claim 1, wherein said elevated level is either greater than a predetermined cutoff level, or greater than or equal to a predetermined cutoff level.

13. The method of claim 1, further comprising detecting the level of at least one additional protein marker.

14. The method of claim 13, wherein said additional protein marker comprises at least one protein marker selected from the group consisting of secretory leukocyte protease inhibitor (SLPI), osteopontin (OPN), midkine (MDK), and squamous cell carcinoma antigen (SCC).

15. The method of claim 13, wherein said additional protein marker comprises any two protein markers selected from the group consisting of SLPI, OPN, MDK, and SCC.

16. The method of claim 13, wherein said additional protein marker comprises any three protein markers selected from the group consisting of SLPI, OPN, MDK, and SCC.

17. The method of claim 13, wherein said additional protein marker comprises all of SLPI, OPN, MDK, and SCC.

18. The method of claim 13, wherein said additional protein marker comprises at least one protein marker selected from the group consisting of defensin (DEFA1), CA125, gamma enolase (ENO2), and pro-gastrin-releasing peptide (GRP).

19. The method of claim 1, wherein said elevated level of at least one of said one or more protein markers is elevated levels of at least two of said protein markers.

20. The method of claim 1, wherein said elevated level of at least one of said one or more protein markers is elevated levels of at least three of said protein markers.

21. The method of claim 1, wherein said elevated level of at least one of said one or more protein markers is elevated levels of at least four of said protein markers.

22. The method of claim 1, wherein said elevated level of at least one of said one or more protein markers is elevated levels of at least five of said protein markers.

23. The method of claim 2, further comprising classifying said lung lesion as either malignant or benign.

24. The method of claim 1, further comprising performing computed tomography (CT) screening of said human if said method indicates that said human has lung cancer.

25. The method of claim 1, wherein the method is carried out following computed tomography (CT) screening of said human.

26. The method of claim 1, further comprising obtaining said sample from said human prior to said detecting.

27. The method of claim 1, wherein said body fluid sample is serum or plasma, and wherein the method further comprises separating said serum or said plasma from a blood sample from said human.

28. The method of claim 1, wherein said correlating is performed by computer software.

29. The method of claim 1, further comprising correlating the absence of said elevated level with the absence of lung cancer in said human.

30. The method of claim 29, wherein said correlating is performed by computer software.

31. The method of claim 1, wherein the method comprises analyzing said elevated level by split-point analysis or logistic regression analysis.

32. The method of claim 31, wherein said split-point analysis or said logistic regression analysis is performed by computer software.

33. The method of claim 1, wherein an elevated level of said TFPI indicates that said human has lung cancer.

34. A method for determining whether a human has lung cancer, the method comprising detecting the level of tissue factor pathway inhibitor (TFPI) in a body fluid sample from said human, and correlating an elevated level of said TFPI with the presence of lung cancer in said human.

35. A method for determining whether a human has lung cancer, the method comprising detecting the levels of tissue factor pathway inhibitor (TFPI) and one or more protein markers selected from the group consisting of matrix metalloproteinase 2 (MMP2), tissue inhibitor of metalloproteinase (TIMP1), carcinoembryonic antigen-related cell adhesion molecule 5 (CEACAM5), and Cyfra 21-1 (Cyfra) in a body fluid sample from said human, wherein said one or more protein markers that is detected includes TFPI, and correlating an elevated level of said TFPI or at least one of said one or more other protein markers with the presence of lung cancer in said human.

36. The method of claim 35, wherein elevated levels of at least two protein markers selected from the group consisting of said TFPI and said one or more other protein markers indicates that said human has lung cancer.

37. The method of claim 36, wherein elevated levels of said TFPI and at least one of said one or more other protein markers indicates that said human has lung cancer.

38. The method of claim 12, wherein said predetermined cutoff level comprises a number of standard deviations above the normal mean level of each protein marker in individuals who do not have lung cancer.

39. The method of claim 38, wherein said number of standard deviations is two standard deviations.

* * * * *

SEQUENCE LISTING

```
<160> NUMBER OF SEQ ID NOS: 65

<210> SEQ ID NO 1
<211> LENGTH: 132
<212> TYPE: PRT
<213> ORGANISM: Homo sapiens

<400> SEQUENCE: 1

Met Lys Ser Ser Gly Leu Phe Pro Phe Leu Val Leu Leu Ala Leu Gly
 1               5                  10                  15

Thr Leu Ala Pro Trp Ala Val Glu Gly Ser Gly Lys Ser Phe Lys Ala
             20                  25                  30

Gly Val Cys Pro Pro Lys Lys Ser Ala Gln Cys Leu Arg Tyr Lys Lys
         35                  40                  45

Pro Glu Cys Gln Ser Asp Trp Gln Cys Pro Gly Lys Lys Arg Cys Cys
     50                  55                  60

Pro Asp Thr Cys Gly Ile Lys Cys Leu Asp Pro Val Asp Thr Pro Asn
```

```
            65                  70                  75                  80
Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala
        130

<210> SEQ ID NO 2
<211> LENGTH: 115
<212> TYPE: PRT
<213> ORGANISM: Homo sapiens

<400> SEQUENCE: 2

Met Pro Met Phe Ile Val Asn Thr Asn Val Pro Arg Ala Ser Val Pro
 1               5                  10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala
        115

<210> SEQ ID NO 3
<211> LENGTH: 207
<212> TYPE: PRT
<213> ORGANISM: Homo sapiens

<400> SEQUENCE: 3

Met Ala Pro Phe Glu Pro Leu Ala Ser Gly Ile Leu Leu Leu Leu Trp
 1               5                  10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
```

```
            130                 135                 140
Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
            195                 200                 205

<210> SEQ ID NO 4
<211> LENGTH: 304
<212> TYPE: PRT
<213> ORGANISM: Homo sapiens

<400> SEQUENCE: 4

Met Ile Tyr Thr Met Lys Lys Val His Ala Leu Trp Ala Ser Val Cys
  1               5                  10                  15

Leu Leu Leu Asn Leu Ala Pro Ala Pro Leu Asn Ala Asp Ser Glu Glu
                20                  25                  30

Asp Glu Glu His Thr Ile Ile Thr Asp Thr Glu Leu Pro Pro Leu Lys
            35                  40                  45

Leu Met His Ser Phe Cys Ala Phe Lys Ala Asp Asp Gly Pro Cys Lys
        50                  55                  60

Ala Ile Met Lys Arg Phe Phe Phe Asn Ile Phe Thr Arg Gln Cys Glu
 65                  70                  75                  80

Glu Phe Ile Tyr Gly Gly Cys Glu Gly Asn Gln Asn Arg Phe Glu Ser
                85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
        275                 280                 285

Lys Gln Arg Val Lys Ile Ala Tyr Glu Glu Ile Phe Val Lys Asn Met
    290                 295                 300
```

<210> SEQ ID NO 5
<211> LENGTH: 434
<212> TYPE: PRT
<213> ORGANISM: Homo sapiens

<400> SEQUENCE: 5

```
Met Ser Ile Glu Lys Ile Trp Ala Arg Glu Ile Leu Asp Ser Arg Gly
  1               5                  10                  15

Asn Pro Thr Val Glu Val Asp Leu Tyr Thr Ala Lys Gly Leu Phe Arg
                 20                  25                  30

Ala Ala Val Pro Ser Gly Ala Ser Thr Gly Ile Tyr Glu Ala Leu Glu
             35                  40                  45

Leu Arg Asp Gly Asp Lys Gln Arg Tyr Leu Gly Lys Gly Val Leu Lys
         50                  55                  60

Ala Val Asp His Ile Asn Ser Thr Ile Ala Pro Ala Leu Ile Ser Ser
 65                  70                  75                  80

Gly Leu Ser Val Val Glu Gln Glu Lys Leu Asp Asn Leu Met Leu Glu
                 85                  90                  95

Leu Asp Gly Thr Glu Asn Lys Ser Lys Phe Gly Ala Asn Ala Ile Leu
                100                 105                 110

Gly Val Ser Leu Ala Val Cys Lys Ala Gly Ala Ala Glu Arg Glu Leu
            115                 120                 125

Pro Leu Tyr Arg His Ile Ala Gln Leu Ala Gly Asn Ser Asp Leu Ile
        130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Thr Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
        355                 360                 365

Val Ser His Arg Ser Gly Glu Thr Glu Asp Thr Phe Ile Ala Asp Leu
    370                 375                 380
```

```
Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu

<210> SEQ ID NO 6
<211> LENGTH: 702
<212> TYPE: PRT
<213> ORGANISM: Homo sapiens

<400> SEQUENCE: 6

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Leu Val His Asn Leu Pro Gln His Leu Phe Gly
        50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
                100                 105                 110

Ile Gln Asn Asp Thr Gly Phe Tyr Thr Leu His Val Ile Lys Ser Asp
            115                 120                 125

Leu Val Asn Glu Glu Ala Thr Gly Gln Phe Arg Val Tyr Pro Glu Leu
        130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
                180                 185                 190

Leu Ser Asn Gly Asn Arg Thr Leu Thr Leu Phe Asn Val Thr Arg Asn
            195                 200                 205

Asp Thr Ala Ser Tyr Lys Cys Glu Thr Gln Asn Pro Val Ser Ala Arg
        210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
                260                 265                 270

Val Asn Gly Thr Phe Gln Gln Ser Thr Gln Glu Leu Phe Ile Pro Asn
            275                 280                 285

Ile Thr Val Asn Asn Ser Gly Ser Tyr Thr Cys Gln Ala His Asn Ser
        290                 295                 300

Asp Thr Gly Leu Asn Arg Thr Thr Val Thr Thr Ile Thr Val Tyr Ala
305                 310                 315                 320
```

-continued

```
Glu Pro Pro Lys Pro Phe Ile Thr Ser Asn Asn Ser Asn Pro Val Glu
            325                 330                 335

Asp Glu Asp Ala Val Ala Leu Thr Cys Glu Pro Glu Ile Gln Asn Thr
        340                 345                 350

Thr Tyr Leu Trp Trp Val Asn Asn Gln Ser Leu Pro Val Ser Pro Arg
    355                 360                 365

Leu Gln Leu Ser Asn Asp Asn Arg Thr Leu Thr Leu Leu Ser Val Thr
370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
            405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
    435                 440                 445

Trp Leu Ile Asp Gly Asn Ile Gln Gln His Thr Gln Glu Leu Phe Ile
450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
            485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
    515                 520                 525

Asn Thr Thr Tyr Leu Trp Trp Val Asn Gly Gln Ser Leu Pro Val Ser
530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
            565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
    595                 600                 605

Ala Asn Leu Asn Leu Ser Cys His Ser Ala Ser Asn Pro Ser Pro Gln
610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
            645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
    675                 680                 685

Val Gly Ile Met Ile Gly Val Leu Val Gly Val Ala Leu Ile
690                 695                 700
```

<210> SEQ ID NO 7
<211> LENGTH: 660
<212> TYPE: PRT
<213> ORGANISM: Homo sapiens

<400> SEQUENCE: 7

```
Met Glu Ala Leu Met Ala Arg Gly Ala Leu Thr Gly Pro Leu Arg Ala
 1               5                  10                  15

Leu Cys Leu Leu Gly Cys Leu Leu Ser His Ala Ala Ala Pro Ser
             20                  25                  30

Pro Ile Ile Lys Phe Pro Gly Asp Val Ala Pro Lys Thr Asp Lys Glu
             35                  40                  45

Leu Ala Val Gln Tyr Leu Asn Thr Phe Tyr Gly Cys Pro Lys Glu Ser
         50                  55                  60

Cys Asn Leu Phe Val Leu Lys Asp Thr Leu Lys Lys Met Gln Lys Phe
 65                  70                  75                  80

Phe Gly Leu Pro Gln Thr Gly Asp Leu Asp Gln Asn Thr Ile Glu Thr
                 85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
            115                 120                 125

Ile Gly Tyr Thr Pro Asp Leu Asp Pro Glu Thr Val Asp Asp Ala Phe
        130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
    210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
        275                 280                 285

Gln Pro Cys Lys Phe Pro Phe Arg Phe Gln Gly Thr Ser Tyr Asp Ser
    290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
        355                 360                 365

Ser Asp Gly Lys Met Trp Cys Ala Thr Thr Ala Asn Tyr Asp Asp Asp
    370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415
```

Pro Gly Ala Leu Met Ala Pro Ile Tyr Thr Tyr Thr Lys Asn Phe Arg
            420                 425                 430

Leu Ser Gln Asp Asp Ile Lys Gly Ile Gln Glu Leu Tyr Gly Ala Ser
        435                 440                 445

Pro Asp Ile Asp Leu Gly Thr Gly Pro Thr Pro Thr Leu Gly Pro Val
    450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
                485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
        515                 520                 525

Glu Glu Lys Ala Val Phe Phe Ala Gly Asn Glu Tyr Trp Ile Tyr Ser
    530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
        595                 600                 605

Ala Trp Asn Ala Ile Pro Asp Asn Leu Asp Ala Val Val Asp Leu Gln
    610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 8
<211> LENGTH: 352
<212> TYPE: PRT
<213> ORGANISM: Homo sapiens

<400> SEQUENCE: 8

Met Arg Ser Leu Gly Ala Leu Leu Leu Leu Ser Ala Cys Leu Ala
1               5                   10                  15

Val Ser Ala Gly Pro Val Pro Thr Pro Pro Asp Asn Ile Gln Val Gln
            20                  25                  30

Glu Asn Phe Asn Ile Ser Arg Ile Tyr Gly Lys Trp Tyr Asn Leu Ala
        35                  40                  45

Ile Gly Ser Thr Cys Pro Trp Leu Lys Lys Ile Met Asp Arg Met Thr
    50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp

-continued

```
                115                 120                 125
Glu Tyr Ala Ile Phe Leu Thr Lys Lys Phe Ser Arg His His Gly Pro
    130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
            180                 185                 190

Gln Glu Pro Glu Pro Ile Leu Ile Pro Arg Val Arg Arg Ala Val Leu
        195                 200                 205

Pro Gln Glu Glu Glu Gly Ser Gly Gly Gln Leu Val Thr Glu Val
    210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
        275                 280                 285

Leu Pro Ile Val Arg Gly Pro Cys Arg Ala Phe Ile Gln Leu Trp Ala
    290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
                325                 330                 335

Cys Gly Val Pro Gly Asp Gly Asp Glu Glu Leu Leu Arg Phe Ser Asn
            340                 345                 350

<210> SEQ ID NO 9
<211> LENGTH: 400
<212> TYPE: PRT
<213> ORGANISM: Homo sapiens

<400> SEQUENCE: 9

Met Thr Ser Tyr Ser Tyr Arg Gln Ser Ser Ala Thr Ser Ser Phe Gly
1               5                   10                  15

Gly Leu Gly Gly Gly Ser Val Arg Phe Gly Pro Gly Val Ala Phe Arg
            20                  25                  30

Ala Pro Ser Ile His Gly Gly Ser Gly Gly Arg Gly Val Ser Val Ser
        35                  40                  45

Ser Ala Arg Phe Val Ser Ser Ser Ser Gly Gly Tyr Gly Gly Gly
    50                  55                  60

Tyr Gly Gly Val Leu Thr Ala Ser Asp Gly Leu Leu Ala Gly Asn Glu
65                  70                  75                  80

Lys Leu Thr Met Gln Asn Leu Asn Asp Arg Leu Ala Ser Tyr Leu Asp
                85                  90                  95

Lys Val Arg Ala Leu Glu Ala Ala Asn Gly Glu Leu Glu Val Lys Ile
            100                 105                 110

Arg Asp Trp Tyr Gln Lys Gln Gly Pro Gly Pro Ser Arg Asp Tyr Ser
        115                 120                 125

His Tyr Tyr Thr Thr Ile Gln Asp Leu Arg Asp Lys Ile Leu Gly Ala
    130                 135                 140
```

-continued

```
Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Gln Ala Leu Arg
                165                 170                 175

Met Ser Val Glu Ala Asp Ile Asn Gly Leu Arg Arg Val Leu Asp Glu
            180                 185                 190

Leu Thr Leu Ala Arg Thr Asp Leu Glu Met Gln Ile Glu Gly Leu Lys
        195                 200                 205

Glu Glu Leu Ala Tyr Leu Lys Lys Asn His Glu Glu Ile Ser Thr
    210                 215                 220

Leu Arg Gly Gln Val Gly Gly Gln Val Ser Glu Val Asp Ser Ala
225                 230                 235                 240

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
            260                 265                 270

Ser Arg Thr Glu Glu Leu Asn Arg Glu Val Ala Gly His Thr Glu Gln
        275                 280                 285

Leu Gln Met Ser Arg Ser Glu Val Thr Asp Leu Arg Arg Thr Leu Gln
    290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Gly Asp Val
            340                 345                 350

Arg Ala Asp Ser Glu Arg Gln Asn Gln Glu Tyr Gln Arg Leu Met Asp
        355                 360                 365

Ile Lys Ser Arg Leu Glu Gln Glu Ile Ala Thr Tyr Arg Ser Leu Leu
    370                 375                 380

Glu Gly Gln Glu Asp His Tyr Asn Asn Leu Ser Ala Ser Lys Val Leu
385                 390                 395                 400

<210> SEQ ID NO 10
<211> LENGTH: 390
<212> TYPE: PRT
<213> ORGANISM: Homo sapiens

<400> SEQUENCE: 10

Met Asn Ser Leu Ser Glu Ala Asn Thr Lys Phe Met Phe Asp Leu Phe
1               5                   10                  15

Gln Gln Phe Arg Lys Ser Lys Glu Asn Asn Ile Phe Tyr Ser Pro Ile
                20                  25                  30

Ser Ile Thr Ser Ala Leu Gly Met Val Leu Leu Gly Ala Lys Asp Asn
            35                  40                  45

Thr Ala Gln Gln Ile Lys Lys Val Leu His Phe Asp Gln Val Thr Glu
        50                  55                  60

Asn Thr Thr Gly Lys Ala Ala Thr Tyr His Val Asp Arg Ser Gly Asn
65                  70                  75                  80

Val His His Gln Phe Gln Lys Leu Leu Thr Glu Phe Asn Lys Ser Thr
                85                  90                  95

Asp Ala Tyr Glu Leu Lys Ile Ala Asn Lys Leu Phe Gly Glu Lys Thr
            100                 105                 110

Tyr Leu Phe Leu Gln Glu Tyr Leu Asp Ala Ile Lys Lys Phe Tyr Gln
        115                 120                 125
```

Thr Ser Val Glu Ser Val Asp Phe Ala Asn Ala Pro Glu Ser Arg
            130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
                165                 170                 175

Val Asn Ala Ile Tyr Phe Lys Gly Gln Trp Glu Lys Lys Phe Asn Lys
            180                 185                 190

Glu Asp Thr Lys Glu Glu Lys Phe Trp Pro Asn Lys Asn Thr Tyr Lys
        195                 200                 205

Ser Ile Gln Met Met Arg Gln Tyr Thr Ser Phe His Phe Ala Ser Leu
    210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
                245                 250                 255

Leu Glu Glu Lys Leu Thr Ala Glu Lys Leu Met Glu Trp Thr Ser Leu
            260                 265                 270

Gln Asn Met Arg Glu Thr Arg Val Asp Leu His Leu Pro Arg Phe Lys
        275                 280                 285

Val Glu Glu Ser Tyr Asp Leu Lys Asp Thr Leu Arg Thr Met Gly Met
    290                 295                 300

Val Asp Ile Phe Asn Gly Asp Ala Asp Leu Ser Gly Met Thr Gly Ser
305                 310                 315                 320

Arg Gly Leu Val Leu Ser Gly Val Leu His Lys Ala Phe Val Glu Val
                325                 330                 335

Thr Glu Glu Gly Ala Glu Ala Ala Ala Thr Ala Val Val Gly Phe
            340                 345                 350

Gly Ser Ser Pro Thr Ser Thr Asn Glu Glu Phe His Cys Asn His Pro
        355                 360                 365

Phe Leu Phe Phe Ile Arg Gln Asn Lys Thr Asn Ser Ile Leu Phe Tyr
    370                 375                 380

Gly Arg Phe Ser Ser Pro
385                 390

<210> SEQ ID NO 11
<211> LENGTH: 314
<212> TYPE: PRT
<213> ORGANISM: Homo sapiens

<400> SEQUENCE: 11

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp

-continued

```
                    100                 105                 110
Asp Thr Asp Asp Ser His Gln Ser Asp Glu Ser His His Ser Asp Glu
                115                 120                 125

Ser Asp Glu Leu Val Thr Asp Phe Pro Thr Asp Leu Pro Ala Thr Glu
            130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                    165                 170                 175

Pro Asp Ile Gln Tyr Pro Asp Ala Thr Asp Glu Asp Ile Thr Ser His
                180                 185                 190

Met Glu Ser Glu Glu Leu Asn Gly Ala Tyr Lys Ala Ile Pro Val Ala
            195                 200                 205

Gln Asp Leu Asn Ala Pro Ser Asp Trp Asp Ser Arg Gly Lys Asp Ser
        210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 12
<211> LENGTH: 94
<212> TYPE: PRT
<213> ORGANISM: Homo sapiens

<400> SEQUENCE: 12

Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Val Ser Leu Ala
        35                  40                  45

Trp Asp Glu Ser Leu Ala Pro Lys His Pro Gly Ser Arg Lys Asn Met
    50                  55                  60

Ala Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90

<210> SEQ ID NO 13
<211> LENGTH: 459
<212> TYPE: PRT
<213> ORGANISM: Homo sapiens

<400> SEQUENCE: 13

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
```

-continued

```
                 20                  25                  30

Val Pro Val His Pro Gln Arg Leu Pro Arg Met Gln Glu Asp Ser Pro
             35                  40                  45

Leu Gly Gly Gly Ser Ser Gly Glu Asp Asp Pro Leu Gly Glu Glu Asp
 50                  55                  60

Leu Pro Ser Glu Glu Asp Ser Pro Arg Glu Glu Asp Pro Pro Gly Glu
 65                  70                  75                  80

Glu Asp Leu Pro Gly Glu Glu Asp Leu Pro Gly Glu Glu Asp Leu Pro
                 85                  90                  95

Glu Val Lys Pro Lys Ser Glu Glu Gly Ser Leu Lys Leu Glu Asp
             100                 105                 110

Leu Pro Thr Val Glu Ala Pro Gly Asp Pro Gln Glu Pro Gln Asn Asn
             115                 120                 125

Ala His Arg Asp Lys Glu Gly Asp Asp Gln Ser His Trp Arg Tyr Gly
             130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                 165                 170                 175

Leu Arg Pro Leu Glu Leu Leu Gly Phe Gln Leu Pro Pro Leu Pro Glu
             180                 185                 190

Leu Arg Leu Arg Asn Asn Gly His Ser Val Gln Leu Thr Leu Pro Pro
             195                 200                 205

Gly Leu Glu Met Ala Leu Gly Pro Gly Arg Glu Tyr Arg Ala Leu Gln
             210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                 245                 250                 255

Thr Ala Phe Ala Arg Val Asp Glu Ala Leu Gly Arg Pro Gly Gly Leu
             260                 265                 270

Ala Val Leu Ala Ala Phe Leu Glu Glu Gly Pro Glu Glu Asn Ser Ala
             275                 280                 285

Tyr Glu Gln Leu Leu Ser Arg Leu Glu Glu Ile Ala Glu Glu Gly Ser
             290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                 325                 330                 335

Ala Gln Gly Val Ile Trp Thr Val Phe Asn Gln Thr Val Met Leu Ser
             340                 345                 350

Ala Lys Gln Leu His Thr Leu Ser Asp Thr Leu Trp Gly Pro Gly Asp
             355                 360                 365

Ser Arg Leu Gln Leu Asn Phe Arg Ala Thr Gln Pro Leu Asn Gly Arg
             370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                 405                 410                 415

Ala Leu Val Phe Gly Leu Leu Phe Ala Val Thr Ser Val Ala Phe Leu
             420                 425                 430

Val Gln Met Arg Arg Gln His Arg Arg Gly Thr Lys Gly Gly Val Ser
             435                 440                 445
```

Tyr Arg Pro Ala Glu Val Ala Glu Thr Gly Ala
    450                 455

<210> SEQ ID NO 14
<211> LENGTH: 148
<212> TYPE: PRT
<213> ORGANISM: Homo sapiens

<400> SEQUENCE: 14

Met Arg Gly Ser Glu Leu Pro Leu Val Leu Ala Leu Val Leu Cys
 1               5                  10                  15

Leu Ala Pro Arg Gly Arg Ala Val Pro Leu Pro Ala Gly Gly Thr
                20                  25                  30

Val Leu Thr Lys Met Tyr Pro Arg Gly Asn His Trp Ala Val Gly His
                35                  40                  45

Leu Met Gly Lys Lys Ser Thr Gly Glu Ser Ser Val Ser Glu Arg
50                  55                  60

Gly Ser Leu Lys Gln Gln Leu Arg Glu Tyr Ile Arg Trp Glu Glu Ala
65                  70                  75                  80

Ala Arg Asn Leu Leu Gly Leu Ile Glu Ala Lys Glu Asn Arg Asn His
                85                  90                  95

Gln Pro Pro Gln Pro Lys Ala Leu Gly Asn Gln Gln Pro Ser Trp Asp
                100                 105                 110

Ser Glu Asp Ser Ser Asn Phe Lys Asp Val Gly Ser Lys Gly Lys Val
                115                 120                 125

Gly Arg Leu Ser Ala Pro Gly Ser Gln Arg Glu Gly Arg Asn Pro Gln
                130                 135                 140

Leu Asn Gln Gln
145

<210> SEQ ID NO 15
<211> LENGTH: 430
<212> TYPE: PRT
<213> ORGANISM: Homo sapiens

<400> SEQUENCE: 15

Met Ser Phe Thr Thr Arg Ser Thr Phe Ser Thr Asn Tyr Arg Ser Leu
 1               5                  10                  15

Gly Ser Val Gln Ala Pro Ser Tyr Gly Ala Arg Pro Val Ser Ser Ala
                20                  25                  30

Ala Ser Val Tyr Ala Gly Ala Gly Gly Ser Gly Ser Arg Ile Ser Val
                35                  40                  45

Ser Arg Ser Thr Ser Phe Arg Gly Gly Met Gly Ser Gly Gly Leu Ala
50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
                100                 105                 110

Arg Glu His Leu Glu Lys Lys Gly Pro Gln Val Arg Asp Trp Ser His
                115                 120                 125

Tyr Phe Lys Ile Ile Glu Asp Leu Arg Ala Gln Ile Phe Ala Asn Thr
                130                 135                 140

Val Asp Asn Ala Arg Ile Val Leu Gln Ile Asp Asn Ala Arg Leu Ala
145                 150                 155                 160

```
Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
            180                 185                 190

Asn Ile Thr Arg Leu Gln Leu Glu Thr Glu Ile Glu Ala Leu Lys Glu
        195                 200                 205

Glu Leu Leu Phe Met Lys Lys Asn His Glu Glu Val Lys Gly Leu
    210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255

Asp Glu Leu Ala Arg Lys Asn Arg Glu Glu Leu Asp Lys Tyr Trp Ser
                260                 265                 270

Gln Gln Ile Glu Glu Ser Thr Thr Val Val Thr Thr Gln Ser Ala Glu
                275                 280                 285

Val Gly Ala Ala Glu Thr Thr Leu Thr Glu Leu Arg Arg Thr Val Gln
    290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
                340                 345                 350

Arg Ala Glu Gly Gln Arg Gln Ala Gln Glu Tyr Glu Ala Leu Leu Asn
            355                 360                 365

Ile Lys Val Lys Leu Glu Ala Glu Ile Ala Thr Tyr Arg Arg Leu Leu
        370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
                420                 425                 430

<210> SEQ ID NO 16
<211> LENGTH: 882
<212> TYPE: PRT
<213> ORGANISM: Homo sapiens

<400> SEQUENCE: 16

Met Gly Pro Trp Ser Arg Ser Leu Ser Ala Leu Leu Leu Leu Leu Gln
 1               5                  10                  15

Val Ser Ser Trp Leu Cys Gln Glu Pro Glu Pro Cys His Pro Gly Phe
                20                  25                  30

Asp Ala Glu Ser Tyr Thr Phe Thr Val Pro Arg Arg His Leu Glu Arg
            35                  40                  45

Gly Arg Val Leu Gly Arg Val Asn Phe Glu Asp Cys Thr Gly Arg Gln
        50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
```

-continued

```
                100                 105                 110
Lys Val Thr Leu Asn Thr Val Gly His His Arg Pro Pro His
            115                 120                 125

Gln Ala Ser Val Ser Gly Ile Gln Ala Glu Leu Leu Thr Phe Pro Asn
            130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
            195                 200                 205

Arg Glu Thr Gly Trp Leu Lys Val Thr Glu Pro Leu Asp Arg Glu Arg
            210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
            275                 280                 285

Ala Asp Asp Asp Val Asn Thr Tyr Asn Ala Ala Ile Ala Tyr Thr Ile
            290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
            355                 360                 365

Asn Asp Asn Pro Pro Ile Phe Asn Pro Thr Thr Tyr Lys Gly Gln Val
            370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
            435                 440                 445

Gln Tyr Ile Leu His Val Ala Val Thr Asn Val Val Pro Phe Glu Val
            450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
            515                 520                 525
```

-continued

```
Thr Ala Asn Trp Leu Glu Ile Asn Pro Asp Thr Gly Ala Ile Ser Thr
            530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Ile Leu Ser Asp Val Asn Asp Asn Ala
                580                 585                 590

Pro Ile Pro Glu Pro Arg Thr Ile Phe Phe Cys Glu Arg Asn Pro Lys
                595                 600                 605

Pro Gln Val Ile Asn Ile Ile Asp Ala Asp Leu Pro Pro Asn Thr Ser
            610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
                660                 665                 670

Gln Asn Lys Asp Gln Val Thr Thr Leu Glu Val Ser Val Cys Asp Cys
            675                 680                 685

Glu Gly Ala Ala Gly Val Cys Arg Lys Ala Gln Pro Val Glu Ala Gly
690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
                740                 745                 750

Tyr Tyr Tyr Asp Glu Glu Gly Gly Gly Glu Glu Asp Gln Asp Phe Asp
                755                 760                 765

Leu Ser Gln Leu His Arg Gly Leu Asp Ala Arg Pro Glu Val Thr Arg
770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
                820                 825                 830

Phe Asp Tyr Glu Gly Ser Gly Ser Glu Ala Ala Ser Leu Ser Ser Leu
                835                 840                 845

Asn Ser Ser Glu Ser Asp Lys Asp Gln Asp Tyr Asp Tyr Leu Asn Glu
                850                 855                 860

Trp Gly Asn Arg Phe Lys Lys Leu Ala Asp Met Tyr Gly Gly Gly Glu
865                 870                 875                 880

Asp Asp
```

<210> SEQ ID NO 17
<211> LENGTH: 220
<212> TYPE: PRT
<213> ORGANISM: Homo sapiens

<400> SEQUENCE: 17

```
Met Gly Ala Ala Ala Arg Thr Leu Arg Leu Ala Leu Gly Leu Leu Leu
1               5                   10                  15
```

```
Leu Ala Thr Leu Leu Arg Pro Ala Asp Ala Cys Ser Cys Ser Pro Val
             20                  25                  30

His Pro Gln Gln Ala Phe Cys Asn Ala Asp Val Val Ile Arg Ala Lys
         35                  40                  45

Ala Val Ser Glu Lys Glu Val Asp Ser Gly Asn Asp Ile Tyr Gly Asn
     50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                 85                  90                  95

Val Cys Gly Val Ser Leu Asp Val Gly Gly Lys Lys Glu Tyr Leu Ile
             100                 105                 110

Ala Gly Lys Ala Glu Gly Asp Gly Lys Met His Ile Thr Leu Cys Asp
         115                 120                 125

Phe Ile Val Pro Trp Asp Thr Leu Ser Thr Thr Gln Lys Lys Ser Leu
130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                 165                 170                 175

Trp Val Thr Glu Lys Asn Ile Asn Gly His Gln Ala Lys Phe Phe Ala
             180                 185                 190

Cys Ile Lys Arg Ser Asp Gly Ser Cys Ala Trp Tyr Arg Gly Ala Ala
         195                 200                 205

Pro Pro Lys Gln Glu Phe Leu Asp Ile Glu Asp Pro
         210                 215                 220

<210> SEQ ID NO 18
<211> LENGTH: 742
<212> TYPE: PRT
<213> ORGANISM: Homo sapiens

<400> SEQUENCE: 18

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
             20                  25                  30

Val Phe His Val Glu Lys Asn Gly Arg Tyr Ser Ile Ser Arg Thr Glu
         35                  40                  45

Ala Ala Asp Leu Cys Lys Ala Phe Asn Ser Thr Leu Pro Thr Met Ala
     50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                 85                  90                  95

Cys Ala Ala Asn Asn Thr Gly Val Tyr Ile Leu Thr Ser Asn Thr Ser
             100                 105                 110

Gln Tyr Asp Thr Tyr Cys Phe Asn Ala Ser Ala Pro Pro Glu Glu Asp
         115                 120                 125

Cys Thr Ser Val Thr Asp Leu Pro Asn Ala Phe Asp Gly Pro Ile Thr
     130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
```

-continued

```
                165                 170                 175
Asp Val Ser Ser Gly Ser Ser Glu Arg Ser Ser Thr Ser Gly Gly
                180                 185                 190
Tyr Ile Phe Tyr Thr Phe Ser Thr Val His Pro Ile Pro Asp Glu Asp
                195                 200                 205
Ser Pro Trp Ile Thr Asp Ser Thr Asp Arg Ile Pro Ala Thr Thr Leu
                210                 215                 220
Met Ser Thr Ser Ala Thr Ala Thr Glu Thr Ala Thr Lys Arg Gln Glu
225                 230                 235                 240
Thr Trp Asp Trp Phe Ser Trp Leu Phe Leu Pro Ser Glu Ser Lys Asn
                245                 250                 255
His Leu His Thr Thr Thr Gln Met Ala Gly Thr Ser Ser Asn Thr Ile
                260                 265                 270
Ser Ala Gly Trp Glu Pro Asn Glu Glu Asn Glu Asp Glu Arg Asp Arg
                275                 280                 285
His Leu Ser Phe Ser Gly Ser Gly Ile Asp Asp Glu Asp Phe Ile
                290                 295                 300
Ser Ser Thr Ile Ser Thr Thr Pro Arg Ala Phe Asp His Thr Lys Gln
305                 310                 315                 320
Asn Gln Asp Trp Thr Gln Trp Asn Pro Ser His Ser Asn Pro Glu Val
                325                 330                 335
Leu Leu Gln Thr Thr Thr Arg Met Thr Asp Val Asp Arg Asn Gly Thr
                340                 345                 350
Thr Ala Tyr Glu Gly Asn Trp Asn Pro Glu Ala His Pro Pro Leu Ile
                355                 360                 365
His His Glu His His Glu Glu Glu Thr Pro His Ser Thr Ser Thr
                370                 375                 380
Ile Gln Ala Thr Pro Ser Ser Thr Thr Glu Glu Thr Ala Thr Gln Lys
385                 390                 395                 400
Glu Gln Trp Phe Gly Asn Arg Trp His Glu Gly Tyr Arg Gln Thr Pro
                405                 410                 415
Arg Glu Asp Ser His Ser Thr Thr Gly Thr Ala Ala Ala Ser Ala His
                420                 425                 430
Thr Ser His Pro Met Gln Gly Arg Thr Thr Pro Ser Pro Glu Asp Ser
                435                 440                 445
Ser Trp Thr Asp Phe Phe Asn Pro Ile Ser His Pro Met Gly Arg Gly
                450                 455                 460
His Gln Ala Gly Arg Arg Met Asp Met Asp Ser Ser His Ser Thr Thr
465                 470                 475                 480
Leu Gln Pro Thr Ala Asn Pro Asn Thr Gly Leu Val Glu Asp Leu Asp
                485                 490                 495
Arg Thr Gly Pro Leu Ser Met Thr Thr Gln Gln Ser Asn Ser Gln Ser
                500                 505                 510
Phe Ser Thr Ser His Glu Gly Leu Glu Glu Asp Lys Asp His Pro Thr
                515                 520                 525
Thr Ser Thr Leu Thr Ser Ser Asn Arg Asn Asp Val Thr Gly Gly Arg
                530                 535                 540
Arg Asp Pro Asn His Ser Glu Gly Ser Thr Thr Leu Leu Glu Gly Tyr
545                 550                 555                 560
Thr Ser His Tyr Pro His Thr Lys Glu Ser Arg Thr Phe Ile Pro Val
                565                 570                 575
Thr Ser Ala Lys Thr Gly Ser Phe Gly Val Thr Ala Val Thr Val Gly
                580                 585                 590
```

```
Asp Ser Asn Ser Asn Val Asn Arg Ser Leu Ser Gly Asp Gln Asp Thr
            595                 600                 605

Phe His Pro Ser Gly Gly Ser His Thr Thr His Gly Ser Glu Ser Asp
        610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 19
<211> LENGTH: 585
<212> TYPE: PRT
<213> ORGANISM: Homo sapiens

<400> SEQUENCE: 19

Met Thr Pro Pro Arg Leu Phe Trp Val Trp Leu Leu Val Ala Gly Thr
1               5                   10                  15

Gln Gly Val Asn Asp Gly Asp Met Arg Leu Ala Asp Gly Gly Ala Thr
            20                  25                  30

Asn Gln Gly Arg Val Glu Ile Phe Tyr Arg Gly Gln Trp Gly Thr Val
        35                  40                  45

Cys Asp Asn Leu Trp Asp Leu Thr Asp Ala Ser Val Val Cys Arg Ala
    50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
                85                  90                  95

Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
        115                 120                 125

Ser Thr His Thr Leu Asp Leu Ser Arg Glu Leu Ser Glu Ala Leu Gly
    130                 135                 140

Gln Ile Phe Asp Ser Gln Arg Gly Cys Asp Leu Ser Ile Ser Val Asn
145                 150                 155                 160

Val Gln Gly Glu Asp Ala Leu Gly Phe Cys Gly His Thr Val Ile Leu
                165                 170                 175

Thr Ala Asn Leu Glu Ala Gln Ala Leu Trp Lys Glu Pro Gly Ser Asn
            180                 185                 190

Val Thr Met Ser Val Asp Ala Glu Cys Val Pro Met Val Arg Asp Leu
        195                 200                 205

Leu Arg Tyr Phe Tyr Ser Arg Arg Ile Asp Ile Thr Leu Ser Ser Val
```

```
            210                 215                 220
Lys Cys Phe His Lys Leu Ala Ser Ala Tyr Gly Ala Arg Gln Leu Gln
225                 230                 235                 240

Gly Tyr Cys Ala Ser Leu Phe Ala Ile Leu Leu Pro Gln Asp Pro Ser
                245                 250                 255

Phe Gln Met Pro Leu Asp Leu Tyr Ala Tyr Val Ala Thr Gly Asp
            260                 265                 270

Ala Leu Leu Glu Lys Leu Cys Leu Gln Phe Leu Ala Trp Asn Phe Glu
            275                 280                 285

Ala Leu Thr Gln Ala Glu Ala Trp Pro Ser Val Pro Thr Asp Leu Leu
290                 295                 300

Gln Leu Leu Pro Arg Ser Asp Leu Ala Val Pro Ser Glu Leu Ala
305                 310                 315                 320

Leu Leu Lys Ala Val Asp Thr Trp Ser Trp Gly Glu Arg Ala Ser His
                325                 330                 335

Glu Glu Val Glu Gly Leu Val Glu Lys Ile Arg Phe Pro Met Met Leu
                340                 345                 350

Pro Glu Glu Leu Phe Glu Leu Gln Phe Asn Leu Ser Leu Tyr Trp Ser
            355                 360                 365

His Glu Ala Leu Phe Gln Lys Lys Thr Leu Gln Ala Leu Glu Phe His
            370                 375                 380

Thr Val Pro Phe Gln Leu Leu Ala Arg Tyr Lys Gly Leu Asn Leu Thr
385                 390                 395                 400

Glu Asp Thr Tyr Lys Pro Arg Ile Tyr Thr Ser Pro Thr Trp Ser Ala
                405                 410                 415

Phe Val Thr Asp Ser Ser Trp Ser Ala Arg Lys Ser Gln Leu Val Tyr
                420                 425                 430

Gln Ser Arg Arg Gly Pro Leu Val Lys Tyr Ser Ser Asp Tyr Phe Gln
            435                 440                 445

Ala Pro Ser Asp Tyr Arg Tyr Tyr Pro Tyr Gln Ser Phe Gln Thr Pro
            450                 455                 460

Gln His Pro Ser Phe Leu Phe Gln Asp Lys Arg Val Ser Trp Ser Leu
465                 470                 475                 480

Val Tyr Leu Pro Thr Ile Gln Ser Cys Trp Asn Tyr Gly Phe Ser Cys
                485                 490                 495

Ser Ser Asp Glu Leu Pro Val Leu Gly Leu Thr Lys Ser Gly Gly Ser
            500                 505                 510

Asp Arg Thr Ile Ala Tyr Glu Asn Lys Ala Leu Met Leu Cys Glu Gly
            515                 520                 525

Leu Phe Val Ala Asp Val Thr Asp Phe Glu Gly Trp Lys Ala Ala Ile
            530                 535                 540

Pro Ser Ala Leu Asp Thr Asn Ser Ser Lys Ser Thr Ser Ser Phe Pro
545                 550                 555                 560

Cys Pro Ala Gly His Phe Asn Gly Phe Arg Thr Val Ile Arg Pro Phe
                565                 570                 575

Tyr Leu Thr Asn Ser Ser Gly Val Asp
            580                 585

<210> SEQ ID NO 20
<211> LENGTH: 1255
<212> TYPE: PRT
<213> ORGANISM: Homo sapiens

<400> SEQUENCE: 20
```

-continued

```
Met Glu Leu Ala Ala Leu Cys Arg Trp Gly Leu Leu Ala Leu Leu
 1               5                  10                  15

Pro Pro Gly Ala Ala Ser Thr Gln Val Cys Thr Gly Thr Asp Met Lys
             20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
 65              70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
             100                 105                 110

Ala Leu Ala Val Leu Asp Asn Gly Asp Pro Leu Asn Asn Thr Thr Pro
         115                 120                 125

Val Thr Gly Ala Ser Pro Gly Gly Leu Arg Glu Leu Gln Leu Arg Ser
 130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                 165                 170                 175

Asn Gln Leu Ala Leu Thr Leu Ile Asp Thr Asn Arg Ser Arg Ala Cys
             180                 185                 190

His Pro Cys Ser Pro Met Cys Lys Gly Ser Arg Cys Trp Gly Glu Ser
         195                 200                 205

Ser Glu Asp Cys Gln Ser Leu Thr Arg Thr Val Cys Ala Gly Gly Cys
 210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                 245                 250                 255

His Phe Asn His Ser Gly Ile Cys Glu Leu His Cys Pro Ala Leu Val
             260                 265                 270

Thr Tyr Asn Thr Asp Thr Phe Glu Ser Met Pro Asn Pro Glu Gly Arg
         275                 280                 285

Tyr Thr Phe Gly Ala Ser Cys Val Thr Ala Cys Pro Tyr Asn Tyr Leu
 290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                 325                 330                 335

Pro Cys Ala Arg Val Cys Tyr Gly Leu Gly Met Glu His Leu Arg Glu
             340                 345                 350

Val Arg Ala Val Thr Ser Ala Asn Ile Gln Glu Phe Ala Gly Cys Lys
         355                 360                 365

Lys Ile Phe Gly Ser Leu Ala Phe Leu Pro Glu Ser Phe Asp Gly Asp
 370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                 405                 410                 415

Asp Ser Leu Pro Asp Leu Ser Val Phe Gln Asn Leu Gln Val Ile Arg
```

-continued

```
                420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
            820                 825                 830
Met Ser Tyr Leu Glu Asp Val Arg Leu Val His Arg Asp Leu Ala Ala
        835                 840                 845
```

```
Arg Asn Val Leu Val Lys Ser Pro Asn His Val Lys Ile Thr Asp Phe
    850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                    885                 890                 895
Arg Arg Phe Thr His Gln Ser Asp Val Trp Ser Tyr Gly Val Thr Val
                900                 905                 910
Trp Glu Leu Met Thr Phe Gly Ala Lys Pro Tyr Asp Gly Ile Pro Ala
                915                 920                 925
Arg Glu Ile Pro Asp Leu Leu Glu Lys Gly Glu Arg Leu Pro Gln Pro
            930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
                980                 985                 990
Asp Leu Gly Pro Ala Ser Pro Leu Asp Ser Thr Phe Tyr Arg Ser Leu
            995                 1000                1005
Leu Glu Asp Asp Asp Met Gly Asp Leu Val Asp Ala Glu Glu Tyr Leu
    1010                1015                1020
Val Pro Gln Gln Gly Phe Phe Cys Pro Asp Pro Ala Pro Gly Ala Gly
1025                1030                1035                1040
Gly Met Val His His Arg His Arg Ser Ser Ser Thr Arg Ser Gly Gly
                1045                1050                1055
Gly Asp Leu Thr Leu Gly Leu Glu Pro Ser Glu Glu Glu Ala Pro Arg
                1060                1065                1070
Ser Pro Leu Ala Pro Ser Glu Gly Ala Gly Ser Asp Val Phe Asp Gly
            1075                1080                1085
Asp Leu Gly Met Gly Ala Ala Lys Gly Leu Gln Ser Leu Pro Thr His
    1090                1095                1100
Asp Pro Ser Pro Leu Gln Arg Tyr Ser Glu Asp Pro Thr Val Pro Leu
1105                1110                1115                1120
Pro Ser Glu Thr Asp Gly Tyr Val Ala Pro Leu Thr Cys Ser Pro Gln
                1125                1130                1135
Pro Glu Tyr Val Asn Gln Pro Asp Val Arg Pro Gln Pro Pro Ser Pro
                1140                1145                1150
Arg Glu Gly Pro Leu Pro Ala Ala Arg Pro Ala Gly Ala Thr Leu Glu
            1155                1160                1165
Arg Pro Lys Thr Leu Ser Pro Gly Lys Asn Gly Val Val Lys Asp Val
    1170                1175                1180
Phe Ala Phe Gly Gly Ala Val Glu Asn Pro Glu Tyr Leu Thr Pro Gln
1185                1190                1195                1200
Gly Gly Ala Ala Pro Gln Pro His Pro Pro Pro Ala Phe Ser Pro Ala
                1205                1210                1215
Phe Asp Asn Leu Tyr Tyr Trp Asp Gln Asp Pro Pro Glu Arg Gly Ala
                1220                1225                1230
Pro Pro Ser Thr Phe Lys Gly Thr Pro Thr Ala Glu Asn Pro Glu Tyr
            1235                1240                1245
Leu Gly Leu Asp Val Pro Val
    1250                1255
```

<210> SEQ ID NO 21
<211> LENGTH: 431
<212> TYPE: PRT
<213> ORGANISM: Homo sapiens

<400> SEQUENCE: 21

```
Met Arg Ala Leu Leu Ala Arg Leu Leu Leu Cys Val Leu Val Val Ser
  1               5                  10                  15

Asp Ser Lys Gly Ser Asn Glu Leu His Gln Val Pro Ser Asn Cys Asp
             20                  25                  30

Cys Leu Asn Gly Gly Thr Cys Val Ser Asn Lys Tyr Phe Ser Asn Ile
         35                  40                  45

His Trp Cys Asn Cys Pro Lys Lys Phe Gly Gly Gln His Cys Glu Ile
     50                  55                  60

Asp Lys Ser Lys Thr Cys Tyr Glu Gly Asn Gly His Phe Tyr Arg Gly
 65                  70                  75                  80

Lys Ala Ser Thr Asp Thr Met Gly Arg Pro Cys Leu Pro Trp Asn Ser
                 85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125

Arg Arg Pro Trp Cys Tyr Val Gln Val Gly Leu Lys Pro Leu Val Gln
    130                 135                 140

Glu Cys Met Val His Asp Cys Ala Asp Gly Lys Lys Pro Ser Ser Pro
145                 150                 155                 160

Pro Glu Glu Leu Lys Phe Gln Cys Gly Gln Lys Thr Leu Arg Pro Arg
                165                 170                 175

Phe Lys Ile Ile Gly Gly Glu Phe Thr Thr Ile Glu Asn Gln Pro Trp
            180                 185                 190

Phe Ala Ala Ile Tyr Arg Arg His Arg Gly Gly Ser Val Thr Tyr Val
        195                 200                 205

Cys Gly Gly Ser Leu Met Ser Pro Cys Trp Val Ile Ser Ala Thr His
    210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                245                 250                 255

Glu Asn Leu Ile Leu His Lys Asp Tyr Ser Ala Asp Thr Leu Ala His
            260                 265                 270

His Asn Asp Ile Ala Leu Leu Lys Ile Arg Ser Lys Glu Gly Arg Cys
        275                 280                 285

Ala Gln Pro Ser Arg Thr Ile Gln Thr Ile Cys Leu Pro Ser Met Tyr
    290                 295                 300

Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
                325                 330                 335

Val Lys Leu Ile Ser His Arg Glu Cys Gln Gln Pro His Tyr Tyr Gly
            340                 345                 350

Ser Glu Val Thr Thr Lys Met Leu Cys Ala Ala Asp Pro Gln Trp Lys
        355                 360                 365

Thr Asp Ser Cys Gln Gly Asp Ser Gly Gly Pro Leu Val Cys Ser Leu
    370                 375                 380
```

```
Gln Gly Arg Met Thr Leu Thr Gly Ile Val Ser Trp Arg Gly Cys
385                 390                 395                 400

Ala Leu Lys Asp Lys Pro Gly Val Tyr Thr Arg Val Ser His Phe Leu
            405                 410                 415

Pro Trp Ile Arg Ser His Thr Lys Glu Glu Asn Gly Leu Ala Leu
            420                 425                 430
```

<210> SEQ ID NO 22
<211> LENGTH: 266
<212> TYPE: PRT
<213> ORGANISM: Homo sapiens

<400> SEQUENCE: 22

```
Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
                20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
            115                 120                 125

Pro Gly Asn Tyr Cys Lys Asn Gly Ile Cys Val Ser Ser Asp Gln Asn
            130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
            195                 200                 205

Ile Cys Lys Pro Val Leu Lys Glu Gly Gln Val Cys Thr Lys His Arg
210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265
```

<210> SEQ ID NO 23
<211> LENGTH: 457
<212> TYPE: PRT
<213> ORGANISM: Homo sapiens

<400> SEQUENCE: 23

```
Met Arg Ser Ala Ala Val Leu Ala Leu Leu Leu Cys Ala Gly Gln Val
1               5                   10                  15
```

-continued

```
Thr Ala Leu Pro Val Asn Ser Pro Met Asn Lys Gly Asp Thr Glu Val
             20                  25                  30

Met Lys Cys Ile Val Glu Val Ile Ser Asp Thr Leu Ser Lys Pro Ser
         35                  40                  45

Pro Met Pro Val Ser Gln Glu Cys Phe Glu Thr Leu Arg Gly Asp Glu
     50                  55                  60

Arg Ile Leu Ser Ile Leu Arg His Gln Asn Leu Leu Lys Glu Leu Gln
 65                  70                  75                  80

Asp Leu Ala Leu Gln Gly Ala Lys Glu Arg Ala His Gln Gln Lys Lys
                 85                  90                  95

His Ser Gly Phe Glu Asp Glu Leu Ser Glu Val Leu Glu Asn Gln Ser
             100                 105                 110

Ser Gln Ala Glu Leu Lys Glu Ala Val Glu Glu Pro Ser Ser Lys Asp
         115                 120                 125

Val Met Glu Lys Arg Glu Asp Ser Lys Glu Ala Glu Lys Ser Gly Glu
     130                 135                 140

Ala Thr Asp Gly Ala Arg Pro Gln Ala Leu Pro Glu Pro Met Gln Glu
145                 150                 155                 160

Ser Lys Ala Glu Gly Asn Asn Gln Ala Pro Gly Glu Glu Glu Glu Glu
                165                 170                 175

Glu Glu Glu Ala Thr Asn Thr His Pro Pro Ala Ser Leu Pro Ser Gln
             180                 185                 190

Lys Tyr Pro Gly Pro Gln Ala Glu Gly Asp Ser Glu Gly Leu Ser Gln
         195                 200                 205

Gly Leu Val Asp Arg Glu Lys Gly Leu Ser Ala Glu Pro Gly Trp Gln
     210                 215                 220

Ala Lys Arg Glu Glu Glu Glu Glu Glu Glu Ala Glu Ala Gly
225                 230                 235                 240

Glu Glu Ala Val Pro Glu Glu Gly Pro Thr Val Val Leu Asn Pro
                245                 250                 255

His Pro Ser Leu Gly Tyr Lys Glu Ile Arg Lys Gly Glu Ser Arg Ser
             260                 265                 270

Glu Ala Leu Ala Val Asp Gly Ala Gly Lys Pro Gly Ala Glu Glu Ala
         275                 280                 285

Gln Asp Pro Glu Gly Lys Gly Glu Gln Glu His Ser Gln Gln Lys Glu
     290                 295                 300

Glu Glu Glu Glu Met Ala Val Val Pro Gln Gly Leu Phe Arg Gly Gly
305                 310                 315                 320

Lys Ser Gly Glu Leu Glu Gln Glu Glu Arg Leu Ser Lys Glu Trp
                325                 330                 335

Glu Asp Ser Lys Arg Trp Ser Lys Met Asp Gln Leu Ala Lys Glu Leu
             340                 345                 350

Thr Ala Glu Lys Arg Leu Glu Gly Gln Glu Glu Glu Asp Asn Arg
         355                 360                 365

Asp Ser Ser Met Lys Leu Ser Phe Arg Ala Arg Ala Tyr Gly Phe Arg
     370                 375                 380

Gly Pro Gly Pro Gln Leu Arg Arg Gly Trp Arg Pro Ser Arg Glu Glu
385                 390                 395                 400

Asp Ser Leu Glu Ala Gly Leu Pro Leu Gln Val Arg Gly Tyr Pro Glu
                405                 410                 415

Glu Lys Lys Glu Glu Glu Gly Ser Ala Asn Arg Arg Pro Glu Asp Gln
             420                 425                 430
```

```
Glu Leu Glu Ser Leu Ser Ala Ile Glu Ala Glu Leu Glu Lys Val Ala
            435                 440                 445

His Gln Leu Gln Ala Leu Arg Arg Gly
    450                 455

<210> SEQ ID NO 24
<211> LENGTH: 232
<212> TYPE: PRT
<213> ORGANISM: Homo sapiens

<400> SEQUENCE: 24

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 25
<211> LENGTH: 273
<212> TYPE: PRT
<213> ORGANISM: Homo sapiens

<400> SEQUENCE: 25

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60
```

```
Pro Ser His Cys Trp Ile Ser Glu Met Val Val Gln Leu Ser Asp Ser
 65                  70                  75                  80

Leu Thr Asp Leu Leu Asp Lys Phe Ser Asn Ile Ser Glu Gly Leu Ser
             85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Glu Phe Phe Arg Ile Phe
130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Asn Arg Lys Ala Lys Asn Pro Pro
        195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
                260                 265                 270

Val

<210> SEQ ID NO 26
<211> LENGTH: 491
<212> TYPE: PRT
<213> ORGANISM: Homo sapiens

<400> SEQUENCE: 26

Met Asn Pro Ala Ala Glu Ala Glu Phe Asn Ile Leu Leu Ala Thr Asp
  1               5                  10                  15

Ser Tyr Lys Val Thr His Tyr Lys Gln Tyr Pro Pro Asn Thr Ser Lys
             20                  25                  30

Val Tyr Ser Tyr Phe Glu Cys Arg Glu Lys Lys Thr Glu Asn Ser Lys
         35                  40                  45

Leu Arg Lys Val Lys Tyr Glu Glu Thr Val Phe Tyr Gly Leu Gln Tyr
 50                  55                  60

Ile Leu Asn Lys Tyr Leu Lys Gly Lys Val Val Thr Lys Glu Lys Ile
 65                  70                  75                  80

Gln Glu Ala Lys Asp Val Tyr Lys Glu His Phe Gln Asp Asp Val Phe
             85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
130                 135                 140

Thr Asn Trp Ile Glu Thr Ile Leu Val Gln Ser Trp Tyr Pro Ile Thr
145                 150                 155                 160
```

```
Val Ala Thr Asn Ser Arg Glu Gln Lys Lys Ile Leu Ala Lys Tyr Leu
            165                 170                 175

Leu Glu Thr Ser Gly Asn Leu Asp Gly Leu Glu Tyr Lys Leu His Asp
        180                 185                 190

Phe Gly Tyr Arg Gly Val Ser Ser Gln Glu Thr Ala Gly Ile Gly Ala
            195                 200                 205

Ser Ala His Leu Val Asn Phe Lys Gly Thr Asp Thr Val Ala Gly Leu
210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
            245                 250                 255

His Glu Lys Asp Ala Phe Glu His Ile Val Thr Gln Phe Ser Ser Val
            260                 265                 270

Pro Val Ser Val Val Ser Asp Ser Tyr Asp Ile Tyr Asn Ala Cys Glu
        275                 280                 285

Lys Ile Trp Gly Glu Asp Leu Arg His Leu Ile Val Ser Arg Ser Thr
        290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
            325                 330                 335

Asn Ser Lys Gly Tyr Lys Leu Leu Pro Pro Tyr Leu Arg Val Ile Gln
            340                 345                 350

Gly Asp Gly Val Asp Ile Asn Thr Leu Gln Glu Ile Val Glu Gly Met
        355                 360                 365

Lys Gln Lys Met Trp Ser Ile Glu Asn Ile Ala Phe Gly Ser Gly Gly
        370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
            405                 410                 415

Pro Val Ala Asp Pro Asn Lys Ser Lys Lys Gly Arg Leu Ser Leu
            420                 425                 430

His Arg Thr Pro Ala Gly Asn Phe Val Thr Leu Glu Glu Gly Lys Gly
            435                 440                 445

Asp Leu Glu Glu Tyr Gly Gln Asp Leu Leu His Thr Val Phe Lys Asn
        450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
            485                 490

<210> SEQ ID NO 27
<211> LENGTH: 831
<212> TYPE: PRT
<213> ORGANISM: Homo sapiens

<400> SEQUENCE: 27

Met Glu Arg Pro Trp Gly Ala Ala Asp Gly Leu Ser Arg Trp Pro His
1               5                   10                  15

Gly Leu Gly Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
        35                  40                  45
```

-continued

```
Arg Trp Ser Gly Pro Ile Gly Val Ser Trp Gly Leu Arg Ala Ala Ala
     50                  55                  60

Ala Gly Gly Ala Phe Pro Arg Gly Gly Arg Trp Arg Arg Ser Ala Pro
 65                  70                  75                  80

Gly Glu Asp Glu Glu Cys Gly Arg Val Arg Asp Phe Val Ala Lys Leu
                 85                  90                  95

Ala Asn Asn Thr His Gln His Val Phe Asp Asp Leu Arg Gly Ser Val
             100                 105                 110

Ser Leu Ser Trp Val Gly Asp Ser Thr Gly Val Ile Leu Val Leu Thr
         115                 120                 125

Thr Phe His Val Pro Leu Val Ile Met Thr Phe Gly Gln Ser Lys Leu
     130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460
```

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
            485                 490                 495

Ala Ile Ser Val Met Val Pro Asp Val Tyr Ile Ser Asp Asp Gly Gly
        500                 505                 510

Tyr Ser Trp Thr Lys Met Leu Glu Gly Pro His Tyr Tyr Thr Ile Leu
    515                 520                 525

Asp Ser Gly Gly Ile Ile Val Ala Ile Glu His Ser Ser Arg Pro Ile
530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Gly Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
        755                 760                 765

Val Thr Val Val Ala Gly Val Leu Ile Val Lys Lys Tyr Val Cys Gly
    770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
            820                 825                 830

<210> SEQ ID NO 28
<211> LENGTH: 143
<212> TYPE: PRT
<213> ORGANISM: Homo sapiens

<400> SEQUENCE: 28

Met Gln His Arg Gly Phe Leu Leu Leu Thr Leu Leu Ala Leu Leu Ala
1               5                   10                  15

-continued

```
Leu Thr Ser Ala Val Ala Lys Lys Asp Lys Val Lys Lys Gly Gly
             20                  25                  30

Pro Gly Ser Glu Cys Ala Glu Trp Ala Trp Gly Pro Cys Thr Pro Ser
         35                  40                  45

Ser Lys Asp Cys Gly Val Gly Phe Arg Glu Gly Thr Cys Gly Ala Gln
 50                  55                  60

Thr Gln Arg Ile Arg Cys Arg Val Pro Cys Asn Trp Lys Lys Glu Phe
 65                  70                  75                  80

Gly Ala Asp Cys Lys Tyr Lys Phe Glu Asn Trp Gly Ala Cys Asp Gly
                 85                  90                  95

Gly Thr Gly Thr Lys Val Arg Gln Gly Thr Leu Lys Lys Ala Arg Tyr
            100                 105                 110

Asn Ala Gln Cys Gln Glu Thr Ile Arg Val Thr Lys Pro Cys Thr Pro
            115                 120                 125

Lys Thr Lys Ala Lys Ala Lys Ala Lys Lys Gly Lys Gly Lys Asp
        130                 135                 140

<210> SEQ ID NO 29
<211> LENGTH: 291
<212> TYPE: PRT
<213> ORGANISM: Homo sapiens

<400> SEQUENCE: 29

Met Gln Arg Ala Arg Pro Thr Leu Trp Ala Ala Leu Thr Leu Leu
 1               5                  10                  15

Val Leu Leu Arg Gly Pro Pro Val Ala Arg Ala Gly Ala Ser Ser Ala
             20                  25                  30

Gly Leu Gly Pro Val Val Arg Cys Glu Pro Cys Asp Ala Arg Ala Leu
         35                  40                  45

Ala Gln Cys Ala Pro Pro Pro Ala Val Cys Ala Glu Leu Val Arg Glu
 50                  55                  60

Pro Gly Cys Gly Cys Cys Leu Thr Cys Ala Leu Ser Glu Gly Gln Pro
 65                  70                  75                  80

Cys Gly Ile Tyr Thr Glu Arg Cys Gly Ser Gly Leu Arg Cys Gln Pro
                 85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
            115                 120                 125

Pro Ala Pro Pro Ala Pro Gly Asn Ala Ser Glu Ser Glu Glu Asp Arg
        130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
    210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Lys Gln Cys Arg Pro Ser Lys Gly
```

```
                    245                 250                 255
Arg Lys Arg Gly Phe Cys Trp Cys Val Asp Lys Tyr Gly Gln Pro Leu
                260                 265                 270
Pro Gly Tyr Thr Thr Lys Gly Lys Glu Asp Val His Cys Tyr Ser Met
            275                 280                 285
Gln Ser Lys
        290

<210> SEQ ID NO 30
<211> LENGTH: 258
<212> TYPE: PRT
<213> ORGANISM: Homo sapiens

<400> SEQUENCE: 30

Met Leu Pro Leu Cys Leu Val Ala Ala Leu Leu Ala Ala Gly Pro
 1               5                  10                  15

Gly Pro Ser Leu Gly Asp Glu Ala Ile His Cys Pro Pro Cys Ser Glu
                20                  25                  30

Glu Lys Leu Ala Arg Cys Arg Pro Pro Val Gly Cys Glu Glu Leu Val
                35                  40                  45

Arg Glu Pro Gly Cys Gly Cys Cys Ala Thr Cys Ala Leu Gly Leu Gly
            50                  55                  60

Met Pro Cys Gly Val Tyr Thr Pro Arg Cys Gly Ser Gly Leu Arg Cys
65                  70                  75                  80

Tyr Pro Pro Arg Gly Val Glu Lys Pro Leu His Thr Leu Met His Gly
                    85                  90                  95

Gln Gly Val Cys Met Glu Leu Ala Glu Ile Glu Ala Ile Gln Glu Ser
                100                 105                 110

Leu Gln Pro Ser Asp Lys Asp Glu Gly Asp His Pro Asn Asn Ser Phe
            115                 120                 125

Ser Pro Cys Ser Ala His Asp Arg Arg Cys Leu Gln Lys His Phe Ala
        130                 135                 140

Lys Ile Arg Asp Arg Ser Thr Ser Gly Gly Lys Met Lys Val Asn Gly
145                 150                 155                 160

Ala Pro Arg Glu Asp Ala Arg Pro Val Pro Gln Gly Ser Cys Gln Ser
                165                 170                 175

Glu Leu His Arg Ala Leu Glu Arg Leu Ala Ala Ser Gln Ser Arg Thr
            180                 185                 190

His Glu Asp Leu Tyr Ile Ile Pro Ile Pro Asn Cys Asp Arg Asn Gly
        195                 200                 205

Asn Phe His Pro Lys Gln Cys His Pro Ala Leu Asp Gly Gln Arg Gly
    210                 215                 220

Lys Cys Trp Cys Val Asp Arg Lys Thr Gly Val Lys Leu Pro Gly Gly
225                 230                 235                 240

Leu Glu Pro Lys Gly Glu Leu Asp Cys His Gln Leu Ala Asp Ser Phe
                245                 250                 255

Arg Glu

<210> SEQ ID NO 31
<211> LENGTH: 463
<212> TYPE: PRT
<213> ORGANISM: Homo sapiens

<400> SEQUENCE: 31

Met Gly Ala Gly Pro Ser Leu Leu Leu Ala Ala Leu Leu Leu Leu Leu
 1               5                  10                  15
```

-continued

```
Ser Gly Asp Gly Ala Val Arg Cys Asp Thr Pro Ala Asn Cys Thr Tyr
            20                  25                  30
Leu Asp Leu Leu Gly Thr Trp Val Phe Gln Val Gly Ser Ser Gly Ser
            35                  40                  45
Gln Arg Asp Val Asn Cys Ser Val Met Gly Pro Gln Glu Lys Lys Val
        50                  55                  60
Val Val Tyr Leu Gln Lys Leu Asp Thr Ala Tyr Asp Asp Leu Gly Asn
65                  70                  75                  80
Ser Gly His Phe Thr Ile Ile Tyr Asn Gln Gly Phe Glu Ile Val Leu
                85                  90                  95
Asn Asp Tyr Lys Trp Phe Ala Phe Lys Tyr Lys Glu Glu Gly Ser
            100                 105                 110
Lys Val Thr Thr Tyr Cys Asn Glu Thr Met Thr Gly Trp Val His Asp
            115                 120                 125
Val Leu Gly Arg Asn Trp Ala Cys Phe Thr Gly Lys Lys Val Gly Thr
        130                 135                 140
Ala Ser Glu Asn Val Tyr Val Asn Thr Ala His Leu Lys Asn Ser Gln
145                 150                 155                 160
Glu Lys Tyr Ser Asn Arg Leu Tyr Lys Tyr Asp His Asn Phe Val Lys
                165                 170                 175
Ala Ile Asn Ala Ile Gln Lys Ser Trp Thr Ala Thr Thr Tyr Met Glu
            180                 185                 190
Tyr Glu Thr Leu Thr Leu Gly Asp Met Ile Arg Arg Ser Gly Gly His
        195                 200                 205
Ser Arg Lys Ile Pro Arg Pro Lys Pro Ala Pro Leu Thr Ala Glu Ile
210                 215                 220
Gln Gln Lys Ile Leu His Leu Pro Thr Ser Trp Asp Trp Arg Asn Val
225                 230                 235                 240
His Gly Ile Asn Phe Val Ser Pro Val Arg Asn Gln Ala Ser Cys Gly
                245                 250                 255
Ser Cys Tyr Ser Phe Ala Ser Met Gly Met Leu Glu Ala Arg Ile Arg
            260                 265                 270
Ile Leu Thr Asn Asn Ser Gln Thr Pro Ile Leu Ser Pro Gln Glu Val
        275                 280                 285
Val Ser Cys Ser Gln Tyr Ala Gln Gly Cys Glu Gly Gly Phe Pro Tyr
        290                 295                 300
Leu Ile Ala Gly Lys Tyr Ala Gln Asp Phe Gly Leu Val Glu Glu Ala
305                 310                 315                 320
Cys Phe Pro Tyr Thr Gly Thr Asp Ser Pro Cys Lys Met Lys Glu Asp
                325                 330                 335
Cys Phe Arg Tyr Tyr Ser Ser Glu Tyr His Tyr Val Gly Gly Phe Tyr
            340                 345                 350
Gly Gly Cys Asn Glu Ala Leu Met Lys Leu Glu Leu Val His His Gly
        355                 360                 365
Pro Met Ala Val Ala Phe Glu Val Tyr Asp Asp Phe Leu His Tyr Lys
    370                 375                 380
Lys Gly Ile Tyr His His Thr Gly Leu Arg Asp Pro Phe Asn Pro Phe
385                 390                 395                 400
Glu Leu Thr Asn His Ala Val Leu Leu Val Gly Tyr Gly Thr Asp Ser
                405                 410                 415
Ala Ser Gly Met Asp Tyr Trp Ile Val Lys Asn Ser Trp Gly Thr Gly
            420                 425                 430
```

-continued

Trp Gly Glu Asn Gly Tyr Phe Arg Ile Arg Arg Gly Thr Asp Glu Cys
            435                 440                 445

Ala Ile Glu Ser Ile Ala Val Ala Ala Thr Pro Ile Pro Lys Leu
    450                 455                 460

<210> SEQ ID NO 32
<211> LENGTH: 547
<212> TYPE: PRT
<213> ORGANISM: Homo sapiens

<400> SEQUENCE: 32

Met Ala Thr Met Val Pro Ser Val Leu Trp Pro Arg Ala Cys Trp Thr
  1               5                  10                  15

Leu Leu Val Cys Cys Leu Leu Thr Pro Gly Val Gln Gly Gln Glu Phe
                 20                  25                  30

Leu Leu Arg Val Glu Pro Gln Asn Pro Val Leu Ser Ala Gly Gly Ser
             35                  40                  45

Leu Phe Val Asn Cys Ser Thr Asp Cys Pro Ser Ser Glu Lys Ile Ala
 50                  55                  60

Leu Glu Thr Ser Leu Ser Lys Glu Leu Val Ala Ser Gly Met Gly Trp
 65                  70                  75                  80

Ala Ala Phe Asn Leu Ser Asn Val Thr Gly Asn Ser Arg Ile Leu Cys
                 85                  90                  95

Ser Val Tyr Cys Asn Gly Ser Gln Ile Thr Gly Ser Ser Asn Ile Thr
                100                 105                 110

Val Tyr Gly Leu Pro Glu Arg Val Glu Leu Ala Pro Leu Pro Pro Trp
            115                 120                 125

Gln Pro Val Gly Gln Asn Phe Thr Leu Arg Cys Gln Val Glu Gly Gly
        130                 135                 140

Ser Pro Arg Thr Ser Leu Thr Val Val Leu Leu Arg Trp Glu Glu Glu
145                 150                 155                 160

Leu Ser Arg Gln Pro Ala Val Glu Glu Pro Ala Glu Val Thr Ala Thr
                165                 170                 175

Val Leu Ala Ser Arg Asp Asp His Gly Ala Pro Phe Ser Cys Arg Thr
            180                 185                 190

Glu Leu Asp Met Gln Pro Gln Gly Leu Gly Leu Phe Val Asn Thr Ser
        195                 200                 205

Ala Pro Arg Gln Leu Arg Thr Phe Val Leu Pro Val Thr Pro Pro Arg
    210                 215                 220

Leu Val Ala Pro Arg Phe Leu Glu Val Glu Thr Ser Trp Pro Val Asp
225                 230                 235                 240

Cys Thr Leu Asp Gly Leu Phe Pro Ala Ser Glu Ala Gln Val Tyr Leu
                245                 250                 255

Ala Leu Gly Asp Gln Met Leu Asn Ala Thr Val Met Asn His Gly Asp
            260                 265                 270

Thr Leu Thr Ala Thr Ala Thr Ala Thr Ala Arg Ala Asp Gln Glu Gly
        275                 280                 285

Ala Arg Glu Ile Val Cys Asn Val Thr Leu Gly Gly Glu Arg Arg Glu
    290                 295                 300

Ala Arg Glu Asn Leu Thr Val Phe Ser Phe Leu Gly Pro Ile Val Asn
305                 310                 315                 320

Leu Ser Glu Pro Thr Ala His Glu Gly Ser Thr Val Thr Val Ser Cys
                325                 330                 335

Met Ala Gly Ala Arg Val Gln Val Thr Leu Asp Gly Val Pro Ala Ala
            340                 345                 350

-continued

```
Ala Pro Gly Gln Pro Ala Gln Leu Gln Leu Asn Ala Thr Glu Ser Asp
            355                 360                 365

Asp Gly Arg Ser Phe Phe Cys Ser Ala Thr Leu Glu Val Asp Gly Glu
        370                 375                 380

Phe Leu His Arg Asn Ser Ser Val Gln Leu Arg Val Leu Tyr Gly Pro
385                 390                 395                 400

Lys Ile Asp Arg Ala Thr Cys Pro Gln His Leu Lys Trp Lys Asp Lys
                405                 410                 415

Thr Arg His Val Leu Gln Cys Gln Ala Arg Gly Asn Pro Tyr Pro Glu
            420                 425                 430

Leu Arg Cys Leu Lys Glu Gly Ser Ser Arg Glu Val Pro Val Gly Ile
        435                 440                 445

Pro Phe Phe Val Asn Val Thr His Asn Gly Thr Tyr Gln Cys Gln Ala
    450                 455                 460

Ser Ser Ser Arg Gly Lys Tyr Thr Leu Val Val Val Met Asp Ile Glu
465                 470                 475                 480

Ala Gly Ser Ser His Phe Val Pro Val Phe Val Ala Val Leu Leu Thr
                485                 490                 495

Leu Gly Val Val Thr Ile Val Leu Ala Leu Met Tyr Val Phe Arg Glu
            500                 505                 510

His Gln Arg Ser Gly Ser Tyr His Val Arg Glu Glu Ser Thr Tyr Leu
        515                 520                 525

Pro Leu Thr Ser Met Gln Pro Thr Glu Ala Met Gly Glu Glu Pro Ser
    530                 535                 540

Arg Ala Glu
545

<210> SEQ ID NO 33
<211> LENGTH: 349
<212> TYPE: PRT
<213> ORGANISM: Homo sapiens

<400> SEQUENCE: 33

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys His Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
```

```
                165                 170                 175
Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
            195                 200                 205

Cys Ser Lys Thr Cys Gly Met Gly Ile Ser Thr Arg Val Thr Asn Asp
            210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
            275                 280                 285

Asp Gly Arg Cys Cys Thr Pro His Arg Thr Thr Thr Leu Pro Val Glu
            290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345

<210> SEQ ID NO 34
<211> LENGTH: 198
<212> TYPE: PRT
<213> ORGANISM: Homo sapiens

<400> SEQUENCE: 34

Met Pro Leu Gly Leu Leu Trp Leu Gly Leu Ala Leu Leu Gly Ala Leu
 1               5                  10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
            115                 120                 125

Arg Val Val Ser Thr Asn Tyr Asn Gln His Ala Met Val Phe Phe Lys
        130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190
```

Asp Gln Cys Ile Asp Gly
         195

<210> SEQ ID NO 35
<211> LENGTH: 1210
<212> TYPE: PRT
<213> ORGANISM: Homo sapiens

<400> SEQUENCE: 35

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

-continued

```
Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
    770                 775                 780
```

```
Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
        850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
        930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
                995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
                1060                1065                1070

Pro Thr Gly Ala Leu Thr Glu Asp Ser Ile Asp Asp Thr Phe Leu Pro
        1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
                1140                1145                1150

Ser Pro Ala His Trp Ala Gln Lys Gly Ser His Gln Ile Ser Leu Asp
            1155                1160                1165

Asn Pro Asp Tyr Gln Gln Asp Phe Phe Pro Lys Glu Ala Lys Pro Asn
        1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
```

<210> SEQ ID NO 36
<211> LENGTH: 368
<212> TYPE: PRT
<213> ORGANISM: Homo sapiens

<400> SEQUENCE: 36

```
Met Trp Pro Leu Trp Arg Leu Val Ser Leu Leu Ala Leu Ser Gln Ala
 1               5                  10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
 50                  55                  60

Phe Gly Cys His Cys His Leu Arg Val Val Gln Cys Ser Asp Leu Gly
 65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
    130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
    210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
    290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365
```

-continued

```
<210> SEQ ID NO 37
<211> LENGTH: 211
<212> TYPE: PRT
<213> ORGANISM: Homo sapiens

<400> SEQUENCE: 37

Met Thr Pro Trp Leu Gly Leu Ile Val Leu Leu Gly Ser Trp Ser Leu
1               5                   10                  15

Gly Asp Trp Gly Ala Glu Ala Cys Thr Cys Ser Pro Ser His Pro Gln
                20                  25                  30

Asp Ala Phe Cys Asn Ser Asp Ile Val Ile Arg Ala Lys Val Val Gly
            35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210

<210> SEQ ID NO 38
<211> LENGTH: 728
<212> TYPE: PRT
<213> ORGANISM: Homo sapiens

<400> SEQUENCE: 38

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110
```

-continued

```
Gly His Glu Phe Asp Leu Tyr Glu Asn Lys Asp Tyr Ile Arg Asn Cys
    115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
```

```
                    530                 535                 540
Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
                595                 600                 605

Lys Thr Ser Cys Ser Val Tyr Gly Trp Gly Tyr Thr Gly Leu Ile Asn
            610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
                675                 680                 685

Gly Val Ile Val Pro Gly Arg Gly Cys Ala Ile Pro Asn Arg Pro Gly
            690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 39
<211> LENGTH: 393
<212> TYPE: PRT
<213> ORGANISM: Homo sapiens

<400> SEQUENCE: 39

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
                35                  40                  45

Asp Ile Glu Gln Trp Phe Thr Glu Asp Pro Gly Pro Asp Glu Ala Pro
50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
            130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175
```

```
Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 40
<211> LENGTH: 638
<212> TYPE: PRT
<213> ORGANISM: Homo sapiens

<400> SEQUENCE: 40

Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
            20                  25                  30

Gly Gly Asp Val Ala Ser Met Tyr Thr Pro Asn Ala Gln Tyr Cys Gln
        35                  40                  45

Met Arg Cys Thr Phe His Pro Arg Cys Leu Leu Phe Ser Phe Leu Pro
    50                  55                  60

Ala Ser Ser Ile Asn Asp Met Glu Lys Arg Phe Gly Cys Phe Leu Lys
65                  70                  75                  80

Asp Ser Val Thr Gly Thr Leu Pro Lys Val His Arg Thr Gly Ala Val
                85                  90                  95

Ser Gly His Ser Leu Lys Gln Cys Gly His Gln Ile Ser Ala Cys His
            100                 105                 110

Arg Asp Ile Tyr Lys Gly Val Asp Met Arg Gly Val Asn Phe Asn Val
        115                 120                 125

Ser Lys Val Ser Ser Val Glu Glu Cys Gln Lys Arg Cys Thr Asn Asn
    130                 135                 140

Ile Arg Cys Gln Phe Phe Ser Tyr Ala Thr Gln Thr Phe His Lys Ala
145                 150                 155                 160
```

-continued

```
Glu Tyr Arg Asn Asn Cys Leu Leu Lys Tyr Ser Pro Gly Thr Pro
                165                 170                 175

Thr Ala Ile Lys Val Leu Ser Asn Val Glu Ser Gly Phe Ser Leu Lys
            180                 185                 190

Pro Cys Ala Leu Ser Glu Ile Gly Cys His Met Asn Ile Phe Gln His
        195                 200                 205

Leu Ala Phe Ser Asp Val Asp Val Ala Arg Val Leu Thr Pro Asp Ala
    210                 215                 220

Phe Val Cys Arg Thr Ile Cys Thr Tyr His Pro Asn Cys Leu Phe Phe
225                 230                 235                 240

Thr Phe Tyr Thr Asn Val Trp Lys Ile Glu Ser Gln Arg Asn Val Cys
            245                 250                 255

Leu Leu Lys Thr Ser Glu Ser Gly Thr Pro Ser Ser Thr Pro Gln
        260                 265                 270

Glu Asn Thr Ile Ser Gly Tyr Ser Leu Leu Thr Cys Lys Arg Thr Leu
    275                 280                 285

Pro Glu Pro Cys His Ser Lys Ile Tyr Pro Gly Val Asp Phe Gly Gly
        290                 295                 300

Glu Glu Leu Asn Val Thr Phe Val Lys Gly Val Asn Val Cys Gln Glu
305                 310                 315                 320

Thr Cys Thr Lys Met Ile Arg Cys Gln Phe Phe Thr Tyr Ser Leu Leu
            325                 330                 335

Pro Glu Asp Cys Lys Glu Glu Lys Cys Lys Cys Phe Leu Arg Leu Ser
        340                 345                 350

Met Asp Gly Ser Pro Thr Arg Ile Ala Tyr Gly Thr Gln Gly Ser Ser
            355                 360                 365

Gly Tyr Ser Leu Arg Leu Cys Asn Thr Gly Asp Asn Ser Val Cys Thr
        370                 375                 380

Thr Lys Thr Ser Thr Arg Ile Val Gly Gly Thr Asn Ser Ser Trp Gly
385                 390                 395                 400

Glu Trp Pro Trp Gln Val Ser Leu Gln Val Lys Leu Thr Ala Gln Arg
            405                 410                 415

His Leu Cys Gly Gly Ser Leu Ile Gly His Gln Trp Val Leu Thr Ala
        420                 425                 430

Ala His Cys Phe Asp Gly Leu Pro Leu Gln Asp Val Trp Arg Ile Tyr
    435                 440                 445

Ser Gly Ile Leu Asn Leu Ser Asp Ile Thr Lys Asp Thr Pro Phe Ser
    450                 455                 460

Gln Ile Lys Glu Ile Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
            485                 490                 495

Glu Phe Gln Lys Pro Ile Cys Leu Pro Ser Lys Gly Asp Thr Ser Thr
        500                 505                 510

Ile Tyr Thr Asn Cys Trp Val Thr Gly Trp Gly Phe Ser Lys Glu Lys
    515                 520                 525

Gly Glu Ile Gln Asn Ile Leu Gln Lys Val Asn Ile Pro Leu Val Thr
    530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Gly Lys Asp Ala Cys Lys Gly
            565                 570                 575
```

```
Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
            595                 600                 605

Gly Val Tyr Thr Lys Val Ala Glu Tyr Met Asp Trp Ile Leu Glu Lys
    610                 615                 620

Thr Gln Ser Ser Asp Gly Lys Ala Gln Met Gln Ser Pro Ala
625                 630                 635

<210> SEQ ID NO 41
<211> LENGTH: 166
<212> TYPE: PRT
<213> ORGANISM: Homo sapiens

<400> SEQUENCE: 41

Met Ala Ser Gly Val Ala Val Ser Asp Gly Val Ile Lys Val Phe Asn
1               5                   10                  15

Asp Met Lys Val Arg Lys Ser Ser Thr Pro Glu Glu Val Lys Lys Arg
                20                  25                  30

Lys Lys Ala Val Leu Phe Cys Leu Ser Glu Asp Lys Lys Asn Ile Ile
            35                  40                  45

Leu Glu Glu Gly Lys Glu Ile Leu Val Gly Asp Val Gly Gln Thr Val
    50                  55                  60

Asp Asp Pro Tyr Ala Thr Phe Val Lys Met Leu Pro Asp Lys Asp Cys
65                  70                  75                  80

Arg Tyr Ala Leu Tyr Asp Ala Thr Tyr Glu Thr Lys Glu Ser Lys Lys
                85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
        115                 120                 125

Thr Gly Ile Lys His Glu Leu Gln Ala Asn Cys Tyr Glu Glu Val Lys
    130                 135                 140

Asp Arg Cys Thr Leu Ala Glu Lys Leu Gly Gly Ser Ala Val Ile Ser
145                 150                 155                 160

Leu Glu Gly Lys Pro Leu
                165

<210> SEQ ID NO 42
<211> LENGTH: 437
<212> TYPE: PRT
<213> ORGANISM: Homo sapiens

<400> SEQUENCE: 42

Met Ala Ala Gly Thr Leu Tyr Thr Tyr Pro Glu Asn Trp Arg Ala Phe
1               5                   10                  15

Lys Ala Leu Ile Ala Ala Gln Tyr Ser Gly Ala Gln Val Arg Val Leu
                20                  25                  30

Ser Ala Pro Pro His Phe His Phe Gly Gln Thr Asn Arg Thr Pro Glu
            35                  40                  45

Phe Leu Arg Lys Phe Pro Ala Gly Lys Val Pro Ala Phe Glu Gly Asp
    50                  55                  60

Asp Gly Phe Cys Val Phe Glu Ser Asn Ala Ile Ala Tyr Tyr Val Ser
65                  70                  75                  80

Asn Glu Glu Leu Arg Gly Ser Thr Pro Glu Ala Ala Ala Gln Val Val
                85                  90                  95
```

```
Gln Trp Val Ser Phe Ala Asp Ser Asp Ile Val Pro Pro Ala Ser Thr
                100                 105                 110

Trp Val Phe Pro Thr Leu Gly Ile Met His His Asn Lys Gln Ala Thr
            115                 120                 125

Glu Asn Ala Lys Glu Val Arg Arg Ile Leu Gly Leu Leu Asp Ala
        130                 135                 140

Tyr Leu Lys Thr Arg Thr Phe Leu Val Gly Glu Arg Val Thr Leu Ala
145                 150                 155                 160

Asp Ile Thr Val Val Cys Thr Leu Leu Trp Leu Tyr Lys Gln Val Leu
                165                 170                 175

Glu Pro Ser Phe Arg Gln Ala Phe Pro Asn Thr Asn Arg Trp Phe Leu
            180                 185                 190

Thr Cys Ile Asn Gln Pro Gln Phe Arg Ala Val Leu Gly Glu Val Lys
        195                 200                 205

Leu Cys Glu Lys Met Ala Gln Phe Asp Ala Lys Lys Phe Ala Glu Thr
210                 215                 220

Gln Pro Lys Lys Asp Thr Pro Arg Lys Glu Lys Gly Ser Arg Glu Glu
225                 230                 235                 240

Lys Gln Lys Pro Gln Ala Glu Arg Lys Glu Lys Lys Ala Ala Ala
                245                 250                 255

Pro Ala Pro Glu Glu Met Asp Glu Cys Glu Gln Ala Leu Ala Ala
            260                 265                 270

Glu Pro Lys Ala Lys Asp Pro Phe Ala His Leu Pro Lys Ser Thr Phe
        275                 280                 285

Val Leu Asp Glu Phe Lys Arg Lys Tyr Ser Asn Glu Asp Thr Leu Ser
            290                 295                 300

Val Ala Leu Pro Tyr Phe Trp Glu His Phe Asp Lys Asp Gly Trp Ser
305                 310                 315                 320

Leu Trp Tyr Ser Glu Tyr Arg Phe Pro Glu Glu Leu Thr Gln Thr Phe
                325                 330                 335

Met Ser Cys Asn Leu Ile Thr Gly Met Phe Gln Arg Leu Asp Lys Leu
            340                 345                 350

Arg Lys Asn Ala Phe Ala Ser Val Ile Leu Phe Gly Thr Asn Asn Ser
        355                 360                 365

Ser Ser Ile Ser Gly Val Trp Val Phe Arg Gly Gln Glu Leu Ala Phe
370                 375                 380

Pro Leu Ser Pro Asp Trp Gln Val Asp Tyr Glu Ser Tyr Thr Trp Arg
385                 390                 395                 400

Lys Leu Asp Pro Gly Ser Glu Thr Gln Thr Leu Val Arg Glu Tyr
                405                 410                 415

Phe Ser Trp Glu Gly Ala Phe Gln His Val Gly Lys Ala Phe Asn Gln
            420                 425                 430

Gly Lys Ile Phe Lys
        435

<210> SEQ ID NO 43
<211> LENGTH: 854
<212> TYPE: PRT
<213> ORGANISM: Homo sapiens

<400> SEQUENCE: 43

Met Pro Pro Cys Ser Gly Gly Asp Gly Ser Thr Pro Gly Pro Ser
1               5                   10                  15

Leu Arg Asp Arg Asp Cys Pro Ala Gln Ser Ala Glu Tyr Pro Arg Asp
                20                  25                  30
```

```
Arg Leu Asp Pro Arg Pro Gly Ser Pro Ser Glu Ala Ser Pro Pro
         35                  40                  45

Phe Leu Arg Ser Arg Ala Pro Val Asn Trp Tyr Gln Glu Lys Ala Gln
         50                  55                  60

Val Phe Leu Trp His Leu Met Val Ser Gly Thr Thr Leu Leu Cys
 65              70                  75                  80

Leu Trp Lys Gln Pro Phe His Val Ser Ala Phe Pro Val Thr Ala Ser
                 85                  90                  95

Leu Ala Phe Arg Gln Ser Gln Gly Ala Gly Gln His Leu Tyr Lys Asp
             100                 105                 110

Leu Gln Pro Phe Ile Leu Leu Arg Leu Leu Met Pro Glu Glu Thr Gln
             115                 120                 125

Thr Gln Asp Gln Pro Met Glu Glu Glu Val Glu Thr Phe Ala Phe
         130                 135                 140

Gln Ala Glu Ile Ala Gln Leu Met Ser Leu Ile Ile Asn Thr Phe Tyr
145                 150                 155                 160

Ser Asn Lys Glu Ile Phe Leu Arg Glu Leu Ile Ser Asn Ser Ser Asp
                 165                 170                 175

Ala Leu Asp Lys Ile Arg Tyr Glu Ser Leu Thr Asp Pro Ser Lys Leu
             180                 185                 190

Asp Ser Gly Lys Glu Leu His Ile Asn Leu Ile Pro Asn Lys Gln Asp
             195                 200                 205

Arg Thr Leu Thr Ile Val Asp Thr Gly Ile Gly Met Thr Lys Ala Asp
             210                 215                 220

Leu Ile Asn Asn Leu Gly Thr Ile Ala Lys Ser Gly Thr Lys Ala Phe
225                 230                 235                 240

Met Glu Ala Leu Gln Ala Gly Ala Asp Ile Ser Met Ile Gly Gln Phe
                 245                 250                 255

Gly Val Gly Phe Tyr Ser Ala Tyr Leu Val Ala Glu Lys Val Thr Val
             260                 265                 270

Ile Thr Lys His Asn Asp Asp Glu Gln Tyr Ala Trp Glu Ser Ser Ala
             275                 280                 285

Gly Gly Ser Phe Thr Val Arg Thr Asp Thr Gly Glu Pro Met Gly Arg
             290                 295                 300

Gly Thr Lys Val Ile Leu His Leu Lys Glu Asp Gln Thr Glu Tyr Leu
305                 310                 315                 320

Glu Glu Arg Arg Ile Lys Glu Ile Val Lys Lys His Ser Gln Phe Ile
                 325                 330                 335

Gly Tyr Pro Ile Thr Leu Phe Val Glu Lys Glu Arg Asp Lys Glu Val
             340                 345                 350

Ser Asp Asp Glu Ala Glu Glu Lys Glu Asp Lys Glu Glu Glu Lys Glu
             355                 360                 365

Lys Glu Glu Lys Glu Ser Glu Asp Lys Pro Glu Ile Glu Asp Val Gly
             370                 375                 380

Ser Asp Glu Glu Glu Glu Lys Lys Asp Gly Asp Lys Lys Lys Lys
385                 390                 395                 400

Lys Ile Lys Glu Lys Tyr Ile Asp Gln Glu Glu Leu Asn Lys Thr Lys
                 405                 410                 415

Pro Ile Trp Thr Arg Asn Pro Asp Asp Ile Thr Asn Glu Glu Tyr Gly
             420                 425                 430

Glu Phe Tyr Lys Ser Leu Thr Asn Asp Trp Glu Asp His Leu Ala Val
             435                 440                 445
```

```
Lys His Phe Ser Val Glu Gly Gln Leu Glu Phe Arg Ala Leu Leu Phe
    450                 455                 460
Val Pro Arg Arg Ala Pro Phe Asp Leu Phe Glu Asn Arg Lys Lys Lys
465                 470                 475                 480
Asn Asn Ile Lys Leu Tyr Val Arg Arg Val Phe Ile Met Asp Asn Cys
                485                 490                 495
Glu Glu Leu Ile Pro Glu Tyr Leu Asn Phe Ile Arg Gly Val Val Asp
                500                 505                 510
Ser Glu Asp Leu Pro Leu Asn Ile Ser Arg Glu Met Leu Gln Gln Ser
                515                 520                 525
Lys Ile Leu Lys Val Ile Arg Lys Asn Leu Val Lys Lys Cys Leu Glu
    530                 535                 540
Leu Phe Thr Glu Leu Ala Glu Asp Lys Glu Asn Tyr Lys Lys Phe Tyr
545                 550                 555                 560
Glu Gln Phe Ser Lys Asn Ile Lys Leu Gly Ile His Glu Asp Ser Gln
                565                 570                 575
Asn Arg Lys Lys Leu Ser Glu Leu Leu Arg Tyr Tyr Thr Ser Ala Ser
                580                 585                 590
Gly Asp Glu Met Val Ser Leu Lys Asp Tyr Cys Thr Arg Met Lys Glu
                595                 600                 605
Asn Gln Lys His Ile Tyr Tyr Ile Thr Gly Glu Thr Lys Asp Gln Val
    610                 615                 620
Ala Asn Ser Ala Phe Val Glu Arg Leu Arg Lys His Gly Leu Glu Val
625                 630                 635                 640
Ile Tyr Met Ile Glu Pro Ile Asp Glu Tyr Cys Val Gln Gln Leu Lys
                645                 650                 655
Glu Phe Glu Gly Lys Thr Leu Val Ser Val Thr Lys Glu Gly Leu Glu
                660                 665                 670
Leu Pro Glu Asp Glu Glu Glu Lys Lys Lys Gln Glu Glu Lys Lys Thr
                675                 680                 685
Lys Phe Glu Asn Leu Cys Lys Ile Met Lys Asp Ile Leu Glu Lys Lys
    690                 695                 700
Val Glu Lys Val Val Val Ser Asn Arg Leu Val Thr Ser Pro Cys Cys
705                 710                 715                 720
Ile Val Thr Ser Thr Tyr Gly Trp Thr Ala Asn Met Glu Arg Ile Met
                725                 730                 735
Lys Ala Gln Ala Leu Arg Asp Asn Ser Thr Met Gly Tyr Met Ala Ala
                740                 745                 750
Lys Lys His Leu Glu Ile Asn Pro Asp His Ser Ile Ile Glu Thr Leu
    755                 760                 765
Arg Gln Lys Ala Glu Ala Asp Lys Asn Asp Lys Ser Val Lys Asp Leu
    770                 775                 780
Val Ile Leu Leu Tyr Glu Thr Ala Leu Leu Ser Ser Gly Phe Ser Leu
785                 790                 795                 800
Glu Asp Pro Gln Thr His Ala Asn Arg Ile Tyr Arg Met Ile Lys Leu
                805                 810                 815
Gly Leu Gly Ile Asp Glu Asp Asp Pro Thr Ala Asp Asp Thr Ser Ala
                820                 825                 830
Ala Val Thr Glu Glu Met Pro Pro Leu Glu Gly Asp Asp Asp Thr Ser
                835                 840                 845
Arg Met Glu Glu Val Asp
    850
```

<210> SEQ ID NO 44
<211> LENGTH: 1192
<212> TYPE: PRT
<213> ORGANISM: Homo sapiens

<400> SEQUENCE: 44

```
Met Glu Asp Leu Asp Gln Ser Pro Leu Val Ser Ser Asp Ser Pro
 1               5                  10                  15

Pro Arg Pro Gln Pro Ala Phe Lys Tyr Gln Phe Val Arg Glu Pro
                20                  25                  30

Asp Glu Glu Glu Glu Glu Glu Glu Glu Glu Asp Glu Asp Glu Asp
                35                  40                  45

Leu Glu Glu Leu Glu Val Leu Glu Arg Lys Pro Ala Ala Gly Leu Ser
 50                  55                  60

Ala Ala Pro Val Pro Thr Ala Pro Ala Ala Gly Ala Pro Leu Met Asp
 65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
                100                 105                 110

Val Ser Ser Thr Val Pro Ala Pro Ser Pro Leu Ser Ala Ala Ala Val
                115                 120                 125

Ser Pro Ser Lys Leu Pro Glu Asp Asp Glu Pro Ala Arg Pro Pro
                130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
                180                 185                 190

Pro Ala Ala Ser Glu Pro Val Ile Arg Ser Ser Ala Glu Asn Met Asp
                195                 200                 205

Leu Lys Glu Gln Pro Gly Asn Thr Ile Ser Ala Gly Gln Glu Asp Phe
                210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
                260                 265                 270

Ser Lys Glu Val Ser Glu Lys Ala Lys Thr Leu Leu Ile Asp Arg Asp
                275                 280                 285

Leu Thr Glu Phe Ser Glu Leu Glu Tyr Ser Glu Met Gly Ser Ser Phe
                290                 295                 300

Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Glu Lys Leu Val Ser
                325                 330                 335

Asn Asn Ile Leu His Asn Gln Gln Glu Leu Pro Thr Ala Leu Thr Lys
                340                 345                 350

Leu Val Lys Glu Asp Glu Val Val Ser Ser Glu Lys Ala Lys Asp Ser
                355                 360                 365

Phe Asn Glu Lys Arg Val Ala Val Glu Ala Pro Met Arg Glu Glu Tyr
                370                 375                 380
```

-continued

```
Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu
            405                 410                 415

Glu Ser Lys Val Asp Lys Lys Cys Phe Ala Asp Ser Leu Glu Gln Thr
        420                 425                 430

Asn His Glu Lys Asp Ser Glu Ser Ser Asn Asp Asp Thr Ser Phe Pro
    435                 440                 445

Ser Thr Pro Glu Gly Ile Lys Asp Arg Ser Gly Ala Tyr Ile Thr Cys
450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys Lys
            485                 490                 495

Ile Glu Glu Lys Lys Ala Gln Ile Val Thr Glu Lys Asn Thr Ser Thr
        500                 505                 510

Lys Thr Ser Asn Pro Phe Leu Val Ala Ala Gln Asp Ser Glu Thr Asp
    515                 520                 525

Tyr Val Thr Thr Asp Asn Leu Thr Lys Val Thr Glu Glu Val Val Ala
530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
            565                 570                 575

Met Asp Leu Val Gln Thr Ser Glu Val Met Gln Glu Ser Leu Tyr Pro
        580                 585                 590

Ala Ala Gln Leu Cys Pro Ser Phe Glu Glu Ser Glu Ala Thr Pro Ser
    595                 600                 605

Pro Val Leu Pro Asp Ile Val Met Glu Ala Pro Leu Asn Ser Ala Val
610                 615                 620

Pro Ser Ala Gly Ala Ser Val Ile Gln Pro Ser Ser Ser Pro Leu Glu
625                 630                 635                 640

Ala Ser Ser Val Asn Tyr Glu Ser Ile Lys His Glu Pro Glu Asn Pro
            645                 650                 655

Pro Pro Tyr Glu Glu Ala Met Ser Val Ser Leu Lys Lys Val Ser Gly
        660                 665                 670

Ile Lys Glu Glu Ile Lys Glu Pro Glu Asn Ile Asn Ala Ala Leu Gln
    675                 680                 685

Glu Thr Glu Ala Pro Tyr Ile Ser Ile Ala Cys Asp Leu Ile Lys Glu
690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
            725                 730                 735

Asp Ser Ser Pro Asp Ser Glu Pro Val Asp Leu Phe Ser Asp Asp Ser
        740                 745                 750

Ile Pro Asp Val Pro Gln Lys Gln Asp Glu Thr Val Met Leu Val Lys
    755                 760                 765

Glu Ser Leu Thr Glu Thr Ser Phe Glu Ser Met Ile Glu Tyr Glu Asn
770                 775                 780

Lys Glu Lys Leu Ser Ala Leu Pro Pro Glu Gly Gly Lys Pro Tyr Leu
785                 790                 795                 800

Glu Ser Phe Lys Leu Ser Leu Asp Asn Thr Lys Asp Thr Leu Leu Pro
```

```
                805                 810                 815
Asp Glu Val Ser Thr Leu Ser Lys Lys Glu Lys Ile Pro Leu Gln Met
            820                 825                 830
Glu Glu Leu Ser Thr Ala Val Tyr Ser Asn Asp Asp Leu Phe Ile Ser
            835                 840                 845
Lys Glu Ala Gln Ile Arg Glu Thr Glu Thr Phe Ser Asp Ser Ser Pro
            850                 855                 860
Ile Glu Ile Ile Asp Glu Phe Pro Thr Leu Ile Ser Ser Lys Thr Asp
865                 870                 875                 880
Ser Phe Ser Lys Leu Ala Arg Glu Tyr Thr Asp Leu Glu Val Ser His
                885                 890                 895
Lys Ser Glu Ile Ala Asn Ala Pro Asp Gly Ala Gly Ser Leu Pro Cys
            900                 905                 910
Thr Glu Leu Pro His Asp Leu Ser Leu Lys Asn Ile Gln Pro Lys Val
            915                 920                 925
Glu Glu Lys Ile Ser Phe Ser Asp Asp Phe Ser Lys Asn Gly Ser Ala
            930                 935                 940
Thr Ser Lys Val Leu Leu Leu Pro Pro Asp Val Ser Ala Leu Ala Thr
945                 950                 955                 960
Gln Ala Glu Ile Glu Ser Ile Val Lys Pro Lys Val Leu Val Lys Glu
                965                 970                 975
Ala Glu Lys Lys Leu Pro Ser Asp Thr Glu Lys Glu Asp Arg Ser Pro
            980                 985                 990
Ser Ala Ile Phe Ser Ala Glu Leu Ser Lys Thr Ser Val Val Asp Leu
            995                 1000                1005
Leu Tyr Trp Arg Asp Ile Lys Lys Thr Gly Val Val Phe Gly Ala Ser
            1010                1015                1020
Leu Phe Leu Leu Leu Ser Leu Thr Val Phe Ser Ile Val Ser Val Thr
1025                1030                1035                1040
Ala Tyr Ile Ala Leu Ala Leu Leu Ser Val Thr Ile Ser Phe Arg Ile
                1045                1050                1055
Tyr Lys Gly Val Ile Gln Ala Ile Gln Lys Ser Asp Glu Gly His Pro
            1060                1065                1070
Phe Arg Ala Tyr Leu Glu Ser Glu Val Ala Ile Ser Glu Glu Leu Val
            1075                1080                1085
Gln Lys Tyr Ser Asn Ser Ala Leu Gly His Val Asn Cys Thr Ile Lys
            1090                1095                1100
Glu Leu Arg Arg Leu Phe Leu Val Asp Asp Leu Val Asp Ser Leu Lys
1105                1110                1115                1120
Phe Ala Val Leu Met Trp Val Phe Thr Tyr Val Gly Ala Leu Phe Asn
                1125                1130                1135
Gly Leu Thr Leu Leu Ile Leu Ala Leu Ile Ser Leu Phe Ser Val Pro
            1140                1145                1150
Val Ile Tyr Glu Arg His Gln Ala Gln Ile Asp His Tyr Leu Gly Leu
            1155                1160                1165
Ala Asn Lys Asn Val Lys Asp Ala Met Ala Lys Ile Gln Ala Lys Ile
            1170                1175                1180
Pro Gly Leu Lys Arg Lys Ala Glu
1185                1190

<210> SEQ ID NO 45
<211> LENGTH: 364
<212> TYPE: PRT
<213> ORGANISM: Homo sapiens
```

<400> SEQUENCE: 45

```
Met Pro Tyr Gln Tyr Pro Ala Leu Thr Pro Glu Gln Lys Lys Glu Leu
1               5                   10                  15

Ser Asp Ile Ala His Arg Ile Val Ala Pro Gly Lys Gly Ile Leu Ala
            20                  25                  30

Ala Asp Glu Ser Thr Gly Ser Ile Ala Lys Arg Leu Gln Ser Ile Gly
        35                  40                  45

Thr Glu Asn Thr Glu Glu Asn Arg Arg Phe Tyr Arg Gln Leu Leu Leu
    50                  55                  60

Thr Ala Asp Asp Arg Val Asn Pro Cys Ile Gly Val Ile Leu Phe
65                  70                  75                  80

His Glu Thr Leu Tyr Gln Lys Ala Asp Asp Gly Arg Pro Phe Pro Gln
                85                  90                  95

Val Ile Lys Ser Lys Gly Gly Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Ser Glu Arg Cys Ala Gln Tyr Lys Lys Asp Gly Ala Asp
    130                 135                 140

Phe Ala Lys Trp Arg Cys Val Leu Lys Ile Gly Glu His Thr Pro Ser
145                 150                 155                 160

Ala Leu Ala Ile Met Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
            180                 185                 190

Pro Asp Gly Asp His Asp Leu Lys Arg Cys Gln Tyr Val Thr Glu Lys
        195                 200                 205

Val Leu Ala Ala Val Tyr Lys Ala Leu Ser Asp His His Ile Tyr Leu
    210                 215                 220

Glu Gly Thr Leu Leu Lys Pro Asn Met Val Thr Pro Gly His Ala Cys
225                 230                 235                 240

Thr Gln Lys Phe Ser His Glu Glu Ile Ala Met Ala Thr Val Thr Ala
                245                 250                 255

Leu Arg Arg Thr Val Pro Pro Ala Val Thr Gly Ile Thr Phe Leu Ser
            260                 265                 270

Gly Gly Gln Ser Glu Glu Glu Ala Ser Ile Asn Leu Asn Ala Ile Asn
        275                 280                 285

Lys Cys Pro Leu Leu Lys Pro Trp Ala Leu Thr Phe Ser Tyr Gly Arg
    290                 295                 300

Ala Leu Gln Ala Ser Ala Leu Lys Ala Trp Gly Gly Lys Lys Glu Asn
305                 310                 315                 320

Leu Lys Ala Ala Gln Glu Glu Tyr Val Lys Arg Ala Leu Ala Asn Ser
                325                 330                 335

Leu Ala Cys Gln Gly Lys Tyr Thr Pro Ser Gly Gln Ala Gly Ala Ala
            340                 345                 350

Ala Ser Glu Ser Leu Phe Val Ser Asn His Ala Tyr
        355                 360
```

<210> SEQ ID NO 46
<211> LENGTH: 1203
<212> TYPE: PRT
<213> ORGANISM: Homo sapiens

<400> SEQUENCE: 46

-continued

```
Met Ala Ala Cys Gly Arg Val Arg Arg Met Phe Arg Leu Ser Ala Ala
 1               5                  10                 15

Leu His Leu Leu Leu Leu Phe Ala Ala Gly Ala Glu Lys Leu Pro Gly
            20                  25                  30

Gln Gly Val His Ser Gln Gly Gln Gly Pro Gly Ala Asn Phe Val Ser
         35                  40                  45

Phe Val Gly Gln Ala Gly Gly Gly Pro Ala Gly Gln Gln Leu Pro
     50                  55                  60

Gln Leu Pro Gln Ser Ser Gln Leu Gln Gln Gln Gln Gln Gln Gln Gln
 65                  70                  75                  80

Gln Gln Gln Gln Pro Gln Pro Pro Gln Pro Pro Phe Pro Ala Gly Gly
                85                  90                  95

Pro Pro Ala Arg Arg Gly Gly Ala Ala Gly Gly Gly Trp Lys Leu
             100                 105                 110

Ala Glu Glu Glu Ser Cys Arg Glu Asp Val Thr Arg Val Cys Pro Lys
            115                 120                 125

His Thr Trp Ser Asn Asn Leu Ala Val Leu Glu Cys Leu Gln Asp Val
    130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Glu Cys Ala Asp
            180                 185                 190

Glu Pro Val Gly Lys Gly Tyr Met Val Ser Cys Leu Val Asp His Arg
            195                 200                 205

Gly Asn Ile Thr Glu Tyr Gln Cys His Gln Tyr Ile Thr Lys Met Thr
    210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
            260                 265                 270

Gly Leu Val Lys Glu Ala Glu Arg Glu Pro Lys Ile Gln Val Ser
            275                 280                 285

Glu Leu Cys Lys Lys Ala Ile Leu Arg Val Ala Glu Leu Ser Ser Asp
    290                 295                 300

Asp Phe His Leu Asp Arg His Leu Tyr Phe Ala Cys Arg Asp Asp Arg
305                 310                 315                 320

Glu Arg Phe Cys Glu Asn Thr Gln Ala Gly Glu Gly Arg Val Tyr Lys
            325                 330                 335

Cys Leu Phe Asn His Lys Phe Glu Glu Ser Met Ser Glu Lys Cys Arg
            340                 345                 350

Glu Ala Leu Thr Thr Arg Gln Lys Leu Ile Ala Gln Asp Tyr Lys Val
        355                 360                 365

Ser Tyr Ser Leu Ala Lys Ser Cys Lys Ser Asp Leu Lys Lys Tyr Arg
    370                 375                 380

Cys Asn Val Glu Asn Leu Pro Arg Ser Arg Ala Arg Leu Ser Tyr
385                 390                 395                 400

Leu Leu Met Cys Leu Glu Ser Ala Val His Arg Gly Arg Gln Val Ser
            405                 410                 415
```

```
Ser Glu Cys Gln Gly Glu Met Leu Asp Tyr Arg Arg Met Leu Met Glu
            420                 425                 430

Asp Phe Ser Leu Ser Pro Glu Ile Ile Leu Ser Cys Arg Gly Glu Ile
            435                 440                 445

Glu His His Cys Ser Gly Leu His Arg Lys Gly Arg Thr Leu His Cys
            450                 455                 460

Leu Met Lys Val Val Arg Gly Glu Lys Gly Asn Leu Gly Met Asn Cys
465                 470                 475                 480

Gln Gln Ala Leu Gln Thr Leu Ile Gln Glu Thr Asp Pro Gly Ala Asp
            485                 490                 495

Tyr Arg Ile Asp Arg Ala Leu Asn Glu Ala Cys Glu Ser Val Ile Gln
            500                 505                 510

Thr Ala Cys Lys His Ile Arg Ser Gly Asp Pro Met Ile Leu Ser Cys
            515                 520                 525

Leu Met Glu His Leu Tyr Thr Glu Lys Met Val Glu Asp Cys Glu His
            530                 535                 540

Arg Leu Leu Glu Leu Gln Tyr Phe Ile Ser Arg Asp Trp Lys Leu Asp
545                 550                 555                 560

Pro Val Leu Tyr Arg Lys Cys Gln Gly Asp Ala Ser Arg Leu Cys His
            565                 570                 575

Thr His Gly Trp Asn Glu Thr Ser Glu Phe Met Pro Gln Gly Ala Val
            580                 585                 590

Phe Ser Cys Leu Tyr Arg His Ala Tyr Arg Thr Glu Glu Gln Gly Arg
            595                 600                 605

Arg Leu Ser Arg Glu Cys Arg Ala Glu Val Gln Arg Ile Leu His Gln
            610                 615                 620

Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
            645                 650                 655

Leu Glu Cys Leu Gln Asp His Leu Asp Asp Leu Val Val Glu Cys Arg
            660                 665                 670

Asp Ile Val Gly Asn Leu Thr Glu Leu Glu Ser Glu Asp Ile Gln Ile
            675                 680                 685

Glu Ala Leu Leu Met Arg Ala Cys Glu Pro Ile Ile Gln Asn Phe Cys
            690                 695                 700

His Asp Val Ala Asp Asn Gln Ile Asp Ser Gly Asp Leu Met Glu Cys
705                 710                 715                 720

Leu Ile Gln Asn Lys His Gln Lys Asp Met Asn Glu Lys Cys Ala Ile
            725                 730                 735

Gly Val Thr His Phe Gln Leu Val Gln Met Lys Asp Phe Arg Phe Ser
            740                 745                 750

Tyr Lys Phe Lys Met Ala Cys Lys Glu Asp Val Leu Lys Leu Cys Pro
            755                 760                 765

Asn Ile Lys Lys Lys Val Asp Val Val Ile Cys Leu Ser Thr Thr Val
770                 775                 780

Arg Asn Asp Thr Leu Gln Glu Ala Lys Glu His Arg Val Ser Leu Lys
785                 790                 795                 800

Cys Arg Arg Gln Leu Arg Val Glu Glu Leu Glu Met Thr Glu Asp Ile
            805                 810                 815

Arg Leu Glu Pro Asp Leu Tyr Glu Ala Cys Lys Ser Asp Ile Lys Asn
            820                 825                 830

Phe Cys Ser Ala Val Gln Tyr Gly Asn Ala Gln Ile Ile Glu Cys Leu
```

```
                835                 840                 845
Lys Glu Asn Lys Lys Gln Leu Ser Thr Arg Cys His Gln Lys Val Phe
850                 855                 860

Lys Leu Gln Glu Thr Glu Met Met Asp Pro Glu Leu Asp Tyr Thr Leu
865                 870                 875                 880

Met Arg Val Cys Lys Gln Met Ile Lys Arg Phe Cys Pro Glu Ala Asp
                885                 890                 895

Ser Lys Thr Met Leu Gln Cys Leu Lys Gln Asn Lys Asn Ser Glu Leu
            900                 905                 910

Met Asp Pro Lys Cys Lys Gln Met Ile Thr Lys Arg Gln Ile Thr Gln
        915                 920                 925

Asn Thr Asp Tyr Arg Leu Asn Pro Met Leu Arg Lys Ala Cys Lys Ala
    930                 935                 940

Asp Ile Pro Lys Phe Cys His Gly Ile Leu Thr Lys Ala Lys Asp Asp
945                 950                 955                 960

Ser Glu Leu Glu Gly Gln Val Ile Ser Cys Leu Lys Leu Arg Tyr Ala
                965                 970                 975

Asp Gln Arg Leu Ser Ser Asp Cys Glu Asp Gln Ile Arg Ile Ile Ile
            980                 985                 990

Gln Glu Ser Ala Leu Asp Tyr Arg Leu Asp Pro Gln Leu Gln Leu His
        995                 1000                1005

Cys Ser Asp Glu Ile Ser Ser Leu Cys Ala Glu Glu Ala Ala Ala Gln
    1010                1015                1020

Glu Gln Thr Gly Gln Val Glu Glu Cys Leu Lys Val Asn Leu Leu Lys
1025                1030                1035                1040

Ile Lys Thr Glu Leu Cys Lys Lys Glu Val Leu Asn Met Leu Lys Glu
                1045                1050                1055

Ser Lys Ala Asp Ile Phe Val Asp Pro Val Leu His Thr Ala Cys Ala
            1060                1065                1070

Leu Asp Ile Lys His His Cys Ala Ala Ile Thr Pro Gly Arg Gly Arg
        1075                1080                1085

Gln Met Ser Cys Leu Met Glu Ala Leu Glu Asp Lys Arg Val Arg Leu
    1090                1095                1100

Gln Pro Glu Cys Lys Lys Arg Leu Asn Asp Arg Ile Glu Met Trp Ser
1105                1110                1115                1120

Tyr Ala Ala Lys Val Ala Pro Ala Asp Gly Phe Ser Asp Leu Ala Met
                1125                1130                1135

Gln Val Met Thr Ser Pro Ser Lys Asn Tyr Ile Leu Ser Val Ile Ser
            1140                1145                1150

Gly Ser Ile Cys Ile Leu Phe Leu Ile Gly Leu Met Cys Gly Arg Ile
        1155                1160                1165

Thr Lys Arg Val Thr Arg Glu Leu Lys Asp Arg Leu Gln Tyr Arg Ser
    1170                1175                1180

Glu Thr Met Ala Tyr Lys Gly Leu Val Trp Ser Gln Asp Val Thr Gly
1185                1190                1195                1200

Ser Pro Ala

<210> SEQ ID NO 47
<211> LENGTH: 1070
<212> TYPE: PRT
<213> ORGANISM: Homo sapiens

<400> SEQUENCE: 47

Met Gly Ala Ala Arg Gly Ser Pro Ala Arg Pro Arg Arg Leu Pro Leu
```

-continued

```
  1               5                  10                 15
Leu Ser Val Leu Leu Pro Leu Leu Gly Gly Thr Gln Thr Ala Ile
              20                 25                 30

Val Phe Ile Lys Gln Pro Ser Ser Gln Asp Ala Leu Gln Gly Arg Arg
              35                 40                 45

Ala Leu Leu Arg Cys Glu Val Glu Ala Pro Gly Pro Val His Val Tyr
50                 55                 60

Trp Leu Leu Asp Gly Ala Pro Val Gln Asp Thr Glu Arg Arg Phe Ala
65                 70                 75                 80

Gln Gly Ser Ser Leu Ser Phe Ala Ala Val Asp Arg Leu Gln Asp Ser
              85                 90                 95

Gly Thr Phe Gln Cys Val Ala Arg Asp Asp Val Thr Gly Glu Glu Ala
              100                105                110

Arg Ser Ala Asn Ala Ser Phe Asn Ile Lys Trp Ile Glu Ala Gly Pro
              115                120                125

Val Val Leu Lys His Pro Ala Ser Glu Ala Glu Ile Gln Pro Gln Thr
              130                135                140

Gln Val Thr Leu Arg Cys His Ile Asp Gly His Pro Arg Pro Thr Tyr
145                150                155                160

Gln Trp Phe Arg Asp Gly Thr Pro Leu Ser Asp Gly Gln Ser Asn His
              165                170                175

Thr Val Ser Ser Lys Glu Arg Asn Leu Thr Leu Arg Pro Ala Gly Pro
              180                185                190

Glu His Ser Gly Leu Tyr Ser Cys Cys Ala His Ser Ala Phe Gly Gln
              195                200                205

Ala Cys Ser Ser Gln Asn Phe Thr Leu Ser Ile Ala Asp Glu Ser Phe
210                215                220

Ala Arg Val Val Leu Ala Pro Gln Asp Val Val Ala Arg Tyr Glu
225                230                235                240

Glu Ala Met Phe His Cys Gln Phe Ser Ala Gln Pro Pro Pro Ser Leu
              245                250                255

Gln Trp Leu Phe Glu Asp Glu Thr Pro Ile Thr Asn Arg Ser Arg Pro
              260                265                270

Pro His Leu Arg Arg Ala Thr Val Phe Ala Asn Gly Ser Leu Leu Leu
              275                280                285

Thr Gln Val Arg Pro Arg Asn Ala Gly Ile Tyr Arg Cys Ile Gly Gln
              290                295                300

Gly Gln Arg Gly Pro Pro Ile Ile Leu Glu Ala Thr Leu His Leu Ala
305                310                315                320

Glu Ile Glu Asp Met Pro Leu Phe Glu Pro Arg Val Phe Thr Ala Gly
              325                330                335

Ser Glu Glu Arg Val Thr Cys Leu Pro Pro Lys Gly Leu Pro Glu Pro
              340                345                350

Ser Val Trp Trp Glu His Ala Gly Val Arg Leu Pro Thr His Gly Arg
              355                360                365

Val Tyr Gln Lys Gly His Glu Leu Val Leu Ala Asn Ile Ala Glu Ser
              370                375                380

Asp Ala Gly Val Tyr Thr Cys His Ala Ala Asn Leu Ala Gly Gln Arg
385                390                395                400

Arg Gln Asp Val Asn Ile Thr Val Ala Thr Val Pro Ser Trp Leu Lys
              405                410                415

Lys Pro Gln Asp Ser Gln Leu Glu Glu Gly Lys Pro Gly Tyr Leu Asp
              420                425                430
```

-continued

```
Cys Leu Thr Gln Ala Thr Pro Lys Pro Thr Val Val Trp Tyr Arg Asn
            435                 440                 445

Gln Met Leu Ile Ser Glu Asp Ser Arg Phe Glu Val Phe Lys Asn Gly
        450                 455                 460

Thr Leu Arg Ile Asn Ser Val Glu Val Tyr Asp Gly Thr Trp Tyr Arg
465                 470                 475                 480

Cys Met Ser Ser Thr Pro Ala Gly Ser Ile Glu Ala Gln Ala Arg Val
                485                 490                 495

Gln Val Leu Glu Lys Leu Lys Phe Thr Pro Pro Gln Pro Gln Gln
            500                 505                 510

Cys Met Glu Phe Asp Lys Glu Ala Thr Val Pro Cys Ser Ala Thr Gly
        515                 520                 525

Arg Glu Lys Pro Thr Ile Lys Trp Glu Arg Ala Asp Gly Ser Ser Leu
    530                 535                 540

Pro Glu Trp Val Thr Asp Asn Ala Gly Thr Leu His Phe Ala Arg Val
545                 550                 555                 560

Thr Arg Asp Asp Ala Gly Asn Tyr Thr Cys Ile Ala Ser Asn Gly Pro
                565                 570                 575

Gln Gly Gln Ile Arg Ala His Val Gln Leu Thr Val Ala Val Phe Ile
            580                 585                 590

Thr Phe Lys Val Glu Pro Glu Arg Thr Thr Val Tyr Gln Gly His Thr
        595                 600                 605

Ala Leu Leu Gln Cys Glu Ala Gln Gly Asp Pro Lys Pro Leu Ile Gln
    610                 615                 620

Trp Lys Gly Lys Asp Arg Ile Leu Asp Pro Thr Lys Leu Gly Pro Arg
625                 630                 635                 640

Met His Ile Phe Gln Asn Gly Ser Leu Val Ile His Asp Val Ala Pro
                645                 650                 655

Glu Asp Ser Gly Arg Tyr Thr Cys Ile Ala Gly Asn Ser Cys Asn Ile
            660                 665                 670

Lys His Thr Glu Ala Pro Leu Tyr Val Val Asp Lys Pro Val Pro Glu
        675                 680                 685

Glu Ser Glu Gly Pro Gly Ser Pro Pro Tyr Lys Met Ile Gln Thr
    690                 695                 700

Ile Gly Leu Ser Val Gly Ala Ala Val Ala Tyr Ile Ile Ala Val Leu
705                 710                 715                 720

Gly Leu Met Phe Tyr Cys Lys Lys Arg Cys Lys Ala Lys Arg Leu Gln
                725                 730                 735

Lys Gln Pro Glu Gly Glu Glu Pro Glu Met Glu Cys Leu Asn Gly Gly
            740                 745                 750

Pro Leu Gln Asn Gly Gln Pro Ser Ala Glu Ile Gln Glu Glu Val Ala
        755                 760                 765

Leu Thr Ser Leu Gly Ser Gly Pro Ala Ala Thr Asn Lys Arg His Ser
    770                 775                 780

Thr Ser Asp Lys Met His Phe Pro Arg Ser Ser Leu Gln Pro Ile Thr
785                 790                 795                 800

Thr Leu Gly Lys Ser Glu Phe Gly Glu Val Phe Leu Ala Lys Ala Gln
                805                 810                 815

Gly Leu Glu Glu Gly Val Ala Glu Thr Leu Val Leu Val Lys Ser Leu
            820                 825                 830

Gln Ser Lys Asp Glu Gln Gln Gln Leu Asp Phe Arg Arg Glu Leu Glu
        835                 840                 845
```

```
Met Phe Gly Lys Leu Asn His Ala Asn Val Val Arg Leu Leu Gly Leu
    850                 855                 860

Cys Arg Glu Ala Glu Pro His Tyr Met Val Leu Glu Tyr Val Asp Leu
865                 870                 875                 880

Gly Asp Leu Lys Gln Phe Leu Arg Ile Ser Lys Ser Lys Asp Glu Lys
                885                 890                 895

Leu Lys Ser Gln Pro Leu Ser Thr Lys Gln Lys Val Ala Leu Cys Thr
            900                 905                 910

Gln Val Ala Leu Gly Met Glu His Leu Ser Asn Asn Arg Phe Val His
        915                 920                 925

Lys Asp Leu Ala Ala Arg Asn Cys Leu Val Ser Ala Gln Arg Gln Val
930                 935                 940

Lys Val Ser Ala Leu Gly Leu Ser Lys Asp Val Tyr Asn Ser Glu Tyr
945                 950                 955                 960

Tyr His Phe Arg Gln Ala Trp Val Pro Leu Arg Trp Met Ser Pro Glu
                965                 970                 975

Ala Ile Leu Glu Gly Asp Phe Ser Thr Lys Ser Asp Val Trp Ala Phe
            980                 985                 990

Gly Val Leu Met Trp Glu Val Phe Thr His Gly Glu Met Pro His Gly
        995                 1000                1005

Gly Gln Ala Asp Asp Glu Val Leu Ala Asp Leu Gln Ala Gly Lys Ala
    1010                1015                1020

Arg Leu Pro Gln Pro Glu Gly Cys Pro Ser Lys Leu Tyr Arg Leu Met
1025                1030                1035                1040

Gln Arg Cys Trp Ala Leu Ser Pro Lys Asp Arg Pro Ser Phe Ser Glu
                1045                1050                1055

Ile Ala Ser Ala Leu Gly Asp Ser Thr Val Asp Ser Lys Pro
            1060                1065                1070

<210> SEQ ID NO 48
<211> LENGTH: 493
<212> TYPE: PRT
<213> ORGANISM: Homo sapiens

<400> SEQUENCE: 48

Met Leu Lys Ala Leu Phe Leu Thr Met Leu Thr Leu Ala Leu Val Lys
1               5                   10                  15

Ser Gln Asp Thr Glu Glu Thr Ile Thr Tyr Thr Gln Cys Thr Asp Gly
            20                  25                  30

Tyr Glu Trp Asp Pro Val Arg Gln Gln Cys Lys Asp Ile Asp Glu Cys
        35                  40                  45

Asp Ile Val Pro Asp Ala Cys Lys Gly Gly Met Lys Cys Val Asn His
50                  55                  60

Tyr Gly Gly Tyr Leu Cys Leu Pro Lys Thr Ala Gln Ile Ile Val Asn
65                  70                  75                  80

Asn Glu Gln Pro Gln Gln Thr Gln Pro Ala Glu Gly Thr Ser Gly
            85                  90                  95

Ala Thr Thr Gly Val Val Ala Ala Ser Ser Met Ala Thr Ser Gly Val
            100                 105                 110

Leu Pro Gly Gly Gly Phe Val Ala Ser Ala Ala Val Ala Gly Pro
        115                 120                 125

Glu Met Gln Thr Gly Arg Asn Asn Phe Val Ile Arg Arg Asn Pro Ala
    130                 135                 140

Asp Pro Gln Arg Ile Pro Ser Asn Pro Ser His Arg Ile Gln Cys Ala
145                 150                 155                 160
```

```
Ala Gly Tyr Glu Gln Ser Glu His Asn Val Cys Gln Asp Ile Asp Glu
                165                 170                 175
Cys Thr Ala Gly Thr His Asn Cys Arg Ala Asp Gln Val Cys Ile Asn
            180                 185                 190
Leu Arg Gly Ser Phe Ala Cys Gln Cys Pro Pro Gly Tyr Gln Lys Arg
        195                 200                 205
Gly Glu Gln Cys Val Asp Ile Asp Glu Cys Thr Ile Pro Pro Tyr Cys
    210                 215                 220
His Gln Arg Cys Val Asn Thr Pro Gly Ser Phe Tyr Cys Gln Cys Ser
225                 230                 235                 240
Pro Gly Phe Gln Leu Ala Ala Asn Asn Tyr Thr Cys Val Asp Ile Asn
                245                 250                 255
Glu Cys Asp Ala Ser Asn Gln Cys Ala Gln Gln Cys Tyr Asn Ile Leu
            260                 265                 270
Gly Ser Phe Ile Cys Gln Cys Asn Gln Gly Tyr Glu Leu Ser Ser Asp
        275                 280                 285
Arg Leu Asn Cys Glu Asp Ile Asp Glu Cys Arg Thr Ser Ser Tyr Leu
    290                 295                 300
Cys Gln Tyr Gln Cys Val Asn Glu Pro Gly Lys Phe Ser Cys Met Cys
305                 310                 315                 320
Pro Gln Gly Tyr Gln Val Val Arg Ser Arg Thr Cys Gln Asp Ile Asn
                325                 330                 335
Glu Cys Glu Thr Thr Asn Glu Cys Arg Glu Asp Glu Met Cys Trp Asn
            340                 345                 350
Tyr His Gly Gly Phe Arg Cys Tyr Pro Arg Asn Pro Cys Gln Asp Pro
        355                 360                 365
Tyr Ile Leu Thr Pro Glu Asn Arg Cys Val Cys Pro Val Ser Asn Ala
    370                 375                 380
Met Cys Arg Glu Leu Pro Gln Ser Ile Val Tyr Lys Tyr Met Ser Ile
385                 390                 395                 400
Arg Ser Asp Arg Ser Val Pro Ser Asp Ile Phe Gln Ile Gln Ala Thr
                405                 410                 415
Thr Ile Tyr Ala Asn Thr Ile Asn Thr Phe Arg Ile Lys Ser Gly Asn
            420                 425                 430
Glu Asn Gly Glu Phe Tyr Leu Arg Gln Thr Ser Pro Val Ser Ala Met
        435                 440                 445
Leu Val Leu Val Lys Ser Leu Ser Gly Pro Arg Glu His Ile Val Asp
    450                 455                 460
Leu Glu Met Leu Thr Val Ser Ser Ile Gly Thr Phe Arg Thr Ser Ser
465                 470                 475                 480
Val Leu Arg Leu Thr Ile Ile Val Gly Pro Phe Ser Phe
                485                 490

<210> SEQ ID NO 49
<211> LENGTH: 661
<212> TYPE: PRT
<213> ORGANISM: Homo sapiens

<400> SEQUENCE: 49

Met Glu Leu Gln Pro Pro Glu Ala Ser Ile Ala Val Val Ser Ile Pro
  1               5                  10                  15
Arg Gln Leu Pro Gly Ser His Ser Glu Ala Gly Val Gln Gly Leu Ser
                20                  25                  30
Ala Gly Asp Asp Ser Glu Leu Gly Ser His Cys Val Ala Gln Thr Gly
```

-continued

```
                35                  40                  45
Leu Glu Leu Ala Ser Gly Asp Pro Leu Pro Ser Ala Ser Gln Asn
 50                  55                  60

Ala Glu Met Ile Glu Thr Gly Ser Asp Cys Val Thr Gln Ala Gly Leu
 65                  70                  75                  80

Gln Leu Leu Ala Ser Ser Asp Pro Pro Ala Leu Ala Ser Lys Asn Ala
                 85                  90                  95

Glu Val Thr Glu Thr Gly Phe His His Val Ser Gln Ala Asp Ile Glu
                100                 105                 110

Phe Leu Thr Ser Ile Asp Pro Thr Ala Ser Ala Ser Gly Ser Ala Gly
                115                 120                 125

Ile Thr Gly Thr Met Ser Gln Asp Thr Glu Val Asp Met Lys Glu Val
130                 135                 140

Glu Leu Asn Glu Leu Glu Pro Glu Lys Gln Pro Met Asn Ala Ala Ser
145                 150                 155                 160

Gly Ala Ala Met Ser Leu Ala Gly Ala Glu Lys Asn Gly Leu Val Lys
                165                 170                 175

Ile Lys Val Ala Glu Asp Glu Ala Glu Ala Ala Ala Ala Lys Phe
                180                 185                 190

Thr Gly Leu Ser Lys Glu Glu Leu Leu Lys Val Ala Gly Ser Pro Gly
                195                 200                 205

Trp Val Arg Thr Arg Trp Ala Leu Leu Leu Phe Trp Leu Gly Trp
210                 215                 220

Leu Gly Met Leu Ala Gly Ala Val Val Ile Ile Val Arg Ala Pro Arg
225                 230                 235                 240

Cys Arg Glu Leu Pro Ala Gln Lys Trp Trp His Thr Gly Ala Leu Tyr
                245                 250                 255

Arg Ile Gly Asp Leu Gln Ala Phe Gln Gly His Gly Ala Gly Asn Leu
                260                 265                 270

Ala Gly Leu Lys Gly Arg Leu Asp Tyr Leu Ser Ser Leu Lys Val Lys
                275                 280                 285

Gly Leu Val Leu Gly Pro Ile His Lys Asn Gln Lys Asp Asp Val Ala
                290                 295                 300

Gln Thr Asp Leu Leu Gln Ile Asp Pro Asn Phe Gly Ser Lys Glu Asp
305                 310                 315                 320

Phe Asp Ser Leu Leu Gln Ser Ala Lys Lys Ser Ile Arg Val Ile
                325                 330                 335

Leu Asp Leu Thr Pro Asn Tyr Arg Gly Glu Asn Ser Trp Phe Ser Thr
                340                 345                 350

Gln Val Asp Thr Val Ala Thr Lys Val Lys Asp Ala Leu Glu Phe Trp
                355                 360                 365

Leu Gln Ala Gly Val Asp Gly Phe Gln Val Arg Asp Ile Glu Asn Leu
                370                 375                 380

Lys Asp Ala Ser Ser Phe Leu Ala Glu Trp Gln Asn Ile Thr Lys Gly
385                 390                 395                 400

Phe Ser Glu Asp Arg Leu Leu Ile Ala Gly Thr Asn Ser Ser Asp Leu
                405                 410                 415

Gln Gln Ile Leu Ser Leu Leu Glu Ser Asn Lys Asp Leu Leu Leu Thr
                420                 425                 430

Ser Ser Tyr Leu Ser Asp Ser Gly Ser Thr Gly Glu His Thr Lys Ser
                435                 440                 445

Leu Val Thr Gln Tyr Leu Asn Ala Thr Gly Asn Arg Trp Cys Ser Trp
450                 455                 460
```

```
Ser Leu Ser Gln Ala Arg Leu Leu Thr Ser Phe Leu Pro Ala Gln Leu
465                 470                 475                 480

Leu Arg Leu Tyr Gln Leu Met Leu Phe Thr Leu Pro Gly Thr Pro Val
            485                 490                 495

Phe Ser Tyr Gly Asp Glu Ile Gly Leu Asp Ala Ala Leu Pro Gly
            500                 505                 510

Gln Pro Met Glu Ala Pro Val Met Leu Trp Asp Glu Ser Ser Phe Pro
            515                 520                 525

Asp Ile Pro Gly Ala Val Ser Ala Asn Met Thr Val Lys Gly Gln Ser
            530                 535                 540

Glu Asp Pro Gly Ser Leu Leu Ser Leu Phe Arg Arg Leu Ser Asp Gln
545                 550                 555                 560

Arg Ser Lys Glu Arg Ser Leu Leu His Gly Asp Phe His Ala Phe Ser
                565                 570                 575

Ala Gly Pro Gly Leu Phe Ser Tyr Ile Arg His Trp Asp Gln Asn Glu
            580                 585                 590

Arg Phe Leu Val Val Leu Asn Phe Gly Asp Val Gly Leu Ser Ala Gly
            595                 600                 605

Leu Gln Ala Ser Asp Leu Pro Ala Ser Ala Ser Leu Pro Ala Lys Ala
            610                 615                 620

Asp Leu Leu Ser Thr Gln Pro Gly Arg Glu Gly Ser Pro Leu
625                 630                 635                 640

Glu Leu Glu Arg Leu Lys Leu Glu Pro His Glu Gly Leu Leu Leu Arg
                645                 650                 655

Phe Pro Tyr Ala Ala
            660

<210> SEQ ID NO 50
<211> LENGTH: 677
<212> TYPE: PRT
<213> ORGANISM: Homo sapiens

<400> SEQUENCE: 50

Met Gln Pro Thr Leu Leu Leu Ser Leu Leu Gly Ala Val Gly Leu Ala
1               5                   10                  15

Ala Val Asn Ser Met Pro Val Asp Asn Arg Asn His Asn Glu Gly Met
            20                  25                  30

Val Thr Arg Cys Ile Ile Glu Val Leu Ser Asn Ala Leu Ser Lys Ser
            35                  40                  45

Ser Ala Pro Pro Ile Thr Pro Glu Cys Arg Gln Val Leu Lys Thr Ser
50                  55                  60

Arg Lys Asp Val Lys Asp Lys Glu Thr Thr Glu Asn Glu Asn Thr Lys
65                  70                  75                  80

Phe Glu Val Arg Leu Leu Arg Asp Pro Ala Asp Ala Ser Glu Ala His
                85                  90                  95

Glu Ser Ser Ser Arg Gly Glu Ala Gly Ala Pro Gly Glu Glu Asp Ile
            100                 105                 110

Gln Gly Pro Thr Lys Ala Asp Thr Glu Lys Trp Ala Glu Gly Gly Gly
            115                 120                 125

His Ser Arg Glu Arg Ala Asp Glu Pro Gln Trp Ser Leu Tyr Pro Ser
            130                 135                 140

Asp Ser Gln Val Ser Glu Glu Val Lys Thr Arg His Ser Glu Lys Ser
145                 150                 155                 160

Gln Arg Glu Asp Glu Glu Glu Glu Glu Gly Glu Asn Tyr Gln Lys Gly
```

```
                165                 170                 175
Glu Arg Gly Glu Asp Ser Ser Glu Glu Lys His Leu Glu Glu Pro Gly
            180                 185                 190
Glu Thr Gln Asn Ala Phe Leu Asn Glu Arg Lys Gln Ala Ser Ala Ile
        195                 200                 205
Lys Lys Glu Glu Leu Val Ala Arg Ser Glu Thr His Ala Ala Gly His
    210                 215                 220
Ser Gln Glu Lys Thr His Ser Arg Glu Lys Ser Ser Gln Glu Ser Gly
225                 230                 235                 240
Glu Glu Ala Gly Ser Gln Glu Asn His Pro Gln Glu Ser Lys Gly Gln
                245                 250                 255
Pro Arg Ser Gln Glu Glu Ser Glu Glu Gly Glu Glu Asp Ala Thr Ser
            260                 265                 270
Glu Val Asp Lys Arg Arg Thr Arg Pro Arg His His His Gly Arg Ser
        275                 280                 285
Arg Pro Asp Arg Ser Ser Gln Gly Gly Ser Leu Pro Ser Glu Glu Lys
    290                 295                 300
Gly His Pro Gln Glu Glu Ser Glu Glu Ser Asn Val Ser Met Ala Ser
305                 310                 315                 320
Leu Gly Glu Lys Arg Asp His His Ser Thr His Tyr Arg Ala Ser Glu
                325                 330                 335
Glu Glu Pro Glu Tyr Gly Glu Glu Ile Lys Gly Tyr Pro Gly Val Gln
            340                 345                 350
Ala Pro Glu Asp Leu Glu Trp Glu Arg Tyr Arg Gly Arg Gly Ser Glu
        355                 360                 365
Glu Tyr Arg Ala Pro Arg Pro Gln Ser Glu Glu Ser Trp Asp Glu Glu
    370                 375                 380
Asp Lys Arg Asn Tyr Pro Ser Leu Glu Leu Asp Lys Met Ala His Gly
385                 390                 395                 400
Tyr Gly Glu Glu Ser Glu Glu Arg Gly Leu Glu Pro Gly Lys Gly
                405                 410                 415
Arg His His Arg Gly Arg Gly Glu Pro Arg Ala Tyr Phe Met Ser
            420                 425                 430
Asp Thr Arg Glu Glu Lys Arg Phe Leu Gly Glu Gly His His Arg Val
        435                 440                 445
Gln Glu Asn Gln Met Asp Lys Ala Arg Arg His Pro Gln Gly Ala Trp
    450                 455                 460
Lys Glu Leu Asp Arg Asn Tyr Leu Asn Tyr Gly Glu Glu Gly Ala Pro
465                 470                 475                 480
Gly Lys Trp Gln Gln Gln Gly Asp Leu Gln Asp Thr Lys Glu Asn Arg
                485                 490                 495
Glu Glu Ala Arg Phe Gln Asp Lys Gln Tyr Ser Ser His His Thr Ala
            500                 505                 510
Glu Lys Arg Lys Arg Leu Gly Glu Leu Phe Asn Pro Tyr Tyr Asp Pro
        515                 520                 525
Leu Gln Trp Lys Ser Ser His Phe Glu Arg Arg Asp Asn Met Asn Asp
    530                 535                 540
Asn Phe Leu Glu Gly Glu Glu Asn Glu Leu Thr Leu Asn Glu Lys
545                 550                 555                 560
Asn Phe Phe Pro Glu Tyr Asn Tyr Asp Trp Trp Glu Lys Lys Pro Phe
                565                 570                 575
Ser Glu Asp Val Asn Trp Gly Tyr Glu Lys Arg Asn Leu Ala Arg Val
            580                 585                 590
```

```
Pro Lys Leu Asp Leu Lys Arg Gln Tyr Asp Arg Val Ala Gln Leu Asp
        595                 600                 605

Gln Leu Leu His Tyr Arg Lys Lys Ser Ala Glu Phe Pro Asp Phe Tyr
        610                 615                 620

Asp Ser Glu Glu Pro Val Ser Thr His Gln Glu Ala Glu Asn Glu Lys
625                 630                 635                 640

Asp Arg Ala Asp Gln Thr Val Leu Thr Glu Asp Glu Lys Lys Glu Leu
                645                 650                 655

Glu Asn Leu Ala Ala Met Asp Leu Glu Leu Gln Lys Ile Ala Glu Lys
            660                 665                 670

Phe Ser Gln Arg Gly
        675

<210> SEQ ID NO 51
<211> LENGTH: 526
<212> TYPE: PRT
<213> ORGANISM: Homo sapiens

<400> SEQUENCE: 51

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
```

```
                275                 280                 285
Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
            500                 505                 510

Leu Thr Ala Thr Glu Ile Ile Tyr Ser Glu Val Lys Lys Gln
        515                 520                 525

<210> SEQ ID NO 52
<211> LENGTH: 583
<212> TYPE: PRT
<213> ORGANISM: Homo sapiens

<400> SEQUENCE: 52

Met Glu Ser Lys Gly Ala Ser Ser Cys Arg Leu Leu Phe Cys Leu Leu
1               5                   10                  15

Ile Ser Ala Thr Val Phe Arg Pro Gly Leu Gly Trp Tyr Thr Val Asn
            20                  25                  30

Ser Ala Tyr Gly Asp Thr Ile Ile Ile Pro Cys Arg Leu Asp Val Pro
        35                  40                  45

Gln Asn Leu Met Phe Gly Lys Trp Lys Tyr Glu Lys Pro Asp Gly Ser
    50                  55                  60

Pro Val Phe Ile Ala Phe Arg Ser Ser Thr Lys Lys Ser Val Gln Tyr
65                  70                  75                  80

Asp Asp Val Pro Glu Tyr Lys Asp Arg Leu Asn Leu Ser Glu Asn Tyr
                85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
        115                 120                 125
```

```
Lys Val Phe Lys Gln Pro Ser Lys Pro Glu Ile Val Ser Lys Ala Leu
130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Phe Lys Lys Glu Met
                180                 185                 190

Asp Pro Val Thr Gln Leu Tyr Thr Met Thr Ser Thr Leu Glu Tyr Lys
                195                 200                 205

Thr Thr Lys Ala Asp Ile Gln Met Pro Phe Thr Cys Ser Val Thr Tyr
210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Lys Cys Leu Gly
                260                 265                 270

Asn Gly Asn Pro Pro Pro Glu Glu Phe Leu Phe Tyr Leu Pro Gly Gln
                275                 280                 285

Pro Glu Gly Ile Arg Ser Ser Asn Thr Tyr Thr Leu Thr Asp Val Arg
                290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
                340                 345                 350

Ser Cys Thr Ile Ser Ala Ser Arg Asn Ala Thr Val Val Trp Met Lys
                355                 360                 365

Asp Asn Ile Arg Leu Arg Ser Ser Pro Ser Phe Ser Ser Leu His Tyr
370                 375                 380

Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
                405                 410                 415

Gln Ile Lys Met Thr Lys Lys Thr Asp Pro Ser Gly Leu Ser Lys Thr
                420                 425                 430

Ile Ile Cys His Val Glu Gly Phe Pro Lys Pro Ala Ile Gln Trp Thr
                435                 440                 445

Ile Thr Gly Ser Gly Ser Val Ile Asn Gln Thr Glu Glu Ser Pro Tyr
                450                 455                 460

Ile Asn Gly Arg Tyr Tyr Ser Lys Ile Ile Ser Pro Glu Glu Asn
465                 470                 475                 480

Val Thr Leu Thr Cys Thr Ala Glu Asn Gln Leu Glu Arg Thr Val Asn
                485                 490                 495

Ser Leu Asn Val Ser Ala Ile Ser Ile Pro Glu His Asp Glu Ala Asp
                500                 505                 510

Glu Ile Ser Asp Glu Asn Arg Glu Lys Val Asn Asp Gln Ala Lys Leu
                515                 520                 525

Ile Val Gly Ile Val Gly Leu Leu Leu Ala Ala Leu Val Ala Gly
                530                 535                 540

Val Val Tyr Trp Leu Tyr Met Lys Lys Ser Lys Thr Ala Ser Lys His
```

```
                545                 550                 555                 560
Val Asn Lys Asp Leu Gly Asn Met Glu Glu Asn Lys Lys Leu Glu Glu
                565                 570                 575

Asn Asn His Lys Thr Glu Ala
            580

<210> SEQ ID NO 53
<211> LENGTH: 205
<212> TYPE: PRT
<213> ORGANISM: Homo sapiens

<400> SEQUENCE: 53

Met Thr Glu Arg Arg Val Pro Phe Ser Leu Arg Gly Pro Ser Trp
  1               5                  10                  15

Asp Pro Phe Arg Asp Trp Tyr Pro His Ser Arg Leu Phe Asp Gln Ala
                 20                  25                  30

Phe Gly Leu Pro Arg Leu Pro Glu Glu Trp Ser Gln Trp Leu Gly Gly
                 35                  40                  45

Ser Ser Trp Pro Gly Tyr Val Arg Pro Leu Pro Pro Ala Ala Ile Glu
 50                  55                  60

Ser Pro Ala Val Ala Ala Pro Ala Tyr Ser Arg Ala Leu Ser Arg Gln
65                  70                  75                  80

Leu Ser Ser Gly Val Ser Glu Ile Arg His Thr Ala Asp Arg Trp Arg
                 85                  90                  95

Val Ser Leu Asp Val Asn His Phe Ala Pro Asp Glu Leu Thr Val Lys
                100                 105                 110

Thr Lys Asp Gly Val Val Glu Ile Thr Gly Lys His Glu Glu Arg Gln
                115                 120                 125

Asp Glu His Gly Tyr Ile Ser Arg Cys Phe Thr Arg Lys Tyr Thr Leu
            130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
            195                 200                 205

<210> SEQ ID NO 54
<211> LENGTH: 135
<212> TYPE: PRT
<213> ORGANISM: Homo sapiens

<400> SEQUENCE: 54

Met Ala Cys Gly Leu Val Ala Ser Asn Leu Asn Leu Lys Pro Gly Glu
  1               5                  10                  15

Cys Leu Arg Val Arg Gly Glu Val Ala Pro Asp Ala Lys Ser Phe Val
                 20                  25                  30

Leu Asn Leu Gly Lys Asp Ser Asn Asn Leu Cys Leu His Phe Asn Pro
                 35                  40                  45

Arg Phe Asn Ala His Gly Asp Ala Asn Thr Ile Val Cys Asn Ser Lys
             50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
```

-continued

```
                  85                  90                  95
Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
            115                 120                 125

Ile Lys Cys Val Ala Phe Asp
            130             135

<210> SEQ ID NO 55
<211> LENGTH: 534
<212> TYPE: PRT
<213> ORGANISM: Homo sapiens

<400> SEQUENCE: 55

Met Leu Arg Arg Arg Gly Ser Pro Gly Met Gly Val His Val Gly Ala
  1               5                  10                  15

Ala Leu Gly Ala Leu Trp Phe Cys Leu Thr Gly Ala Leu Glu Val Gln
             20                  25                  30

Val Pro Glu Asp Pro Val Val Ala Leu Val Gly Thr Asp Ala Thr Leu
             35                  40                  45

Cys Cys Ser Phe Ser Pro Glu Pro Gly Phe Ser Leu Ala Gln Leu Asn
         50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
            115                 120                 125

Phe Gly Ser Ala Ala Val Ser Leu Gln Val Ala Ala Pro Tyr Ser Lys
            130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
            195                 200                 205

Arg Val Val Leu Gly Ala Asn Gly Thr Tyr Ser Cys Leu Val Arg Asn
            210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
            275                 280                 285

Asp Thr Lys Gln Leu Val His Ser Phe Thr Glu Gly Arg Asp Gln Gly
            290                 295                 300

Ser Ala Tyr Ala Asn Arg Thr Ala Leu Phe Pro Asp Leu Leu Ala Gln
305                 310                 315                 320
```

```
Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
                340                 345                 350

Ser Leu Gln Val Ala Ala Pro Tyr Ser Lys Pro Ser Met Thr Leu Glu
                355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
                420                 425                 430

Asn Gly Thr Tyr Ser Cys Leu Val Arg Asn Pro Val Leu Gln Gln Asp
                435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
                500                 505                 510

Ser Lys Thr Ala Leu Gln Pro Leu Lys His Ser Asp Ser Lys Glu Asp
                515                 520                 525

Asp Gly Gln Glu Ile Ala
    530

<210> SEQ ID NO 56
<211> LENGTH: 22152
<212> TYPE: PRT
<213> ORGANISM: Homo sapiens
<220> FEATURE:
<221> NAME/KEY: VARIANT
<222> LOCATION: (1)...(22152)
<223> OTHER INFORMATION: Xaa = Any Amino Acid

<400> SEQUENCE: 56

Met Leu Lys Pro Ser Gly Leu Pro Gly Ser Ser Pro Thr Arg Ser
  1               5                  10                  15

Leu Met Thr Gly Ser Arg Ser Thr Lys Ala Thr Pro Glu Met Asp Ser
                20                  25                  30

Gly Leu Thr Gly Ala Thr Leu Ser Pro Lys Thr Ser Thr Gly Ala Ile
                35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
                100                 105                 110

Pro Ser Arg Asn Tyr Pro Ala Thr Ser Met Val Ser Gly Leu Ser Ser
                115                 120                 125

Pro Arg Thr Arg Thr Ser Ser Thr Glu Gly Asn Phe Thr Lys Glu Ala
```

-continued

```
            130                 135                 140
Ser Thr Tyr Thr Leu Thr Val Glu Thr Thr Ser Gly Pro Val Thr Glu
145                 150                 155                 160

Lys Tyr Thr Val Pro Thr Glu Thr Ser Thr Thr Glu Gly Asp Ser Thr
                165                 170                 175

Glu Thr Pro Trp Asp Thr Arg Tyr Ile Pro Val Lys Ile Thr Ser Pro
            180                 185                 190

Met Lys Thr Phe Ala Asp Ser Thr Ala Ser Lys Glu Asn Ala Pro Val
                195                 200                 205

Ser Met Thr Pro Ala Glu Thr Thr Val Thr Asp Ser His Thr Pro Gly
210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
                260                 265                 270

Ala Gly His Ser Arg Ile Ser Thr Ser Ala Pro Leu Ser Ser Ser Ala
                275                 280                 285

Ser Val Leu Asp Asn Lys Ile Ser Glu Thr Ser Ile Phe Ser Gly Gln
290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
                340                 345                 350

Pro Ser Ile Ser Thr Lys Gln Thr Ala Glu Thr Ile Leu Thr Phe His
                355                 360                 365

Ala Phe Ala Glu Thr Met Asp Ile Pro Ser Thr His Ile Ala Lys Thr
            370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Thr Ser Gly Lys Glu Thr Glu Gly Thr
                420                 425                 430

Leu Asn Thr Ser Met Thr Pro Leu Glu Thr Ser Ala Pro Gly Glu Glu
            435                 440                 445

Ser Glu Met Thr Ala Thr Leu Val Pro Thr Leu Gly Phe Thr Thr Leu
450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
                500                 505                 510

Thr Ser Lys Ala Ser Ser Trp Thr Ser Glu Ser Thr Ala Gln Gln Phe
            515                 520                 525

Ser Glu Pro Gln His Thr Gln Trp Val Glu Thr Ser Pro Ser Met Lys
            530                 535                 540

Thr Glu Arg Pro Pro Ala Ser Thr Ser Val Ala Ala Pro Ile Thr Thr
545                 550                 555                 560
```

-continued

```
Ser Val Pro Ser Val Val Ser Gly Phe Thr Thr Leu Lys Thr Ser Ser
            565                 570                 575
Thr Lys Gly Ile Trp Leu Glu Glu Thr Ser Ala Asp Thr Leu Ile Gly
            580                 585                 590
Glu Ser Thr Ala Gly Pro Thr Thr His Gln Phe Ala Val Pro Thr Gly
            595                 600                 605
Ile Ser Met Thr Gly Gly Ser Ser Thr Arg Gly Ser Gln Gly Thr Thr
            610                 615                 620
His Leu Leu Thr Arg Ala Thr Ala Ser Ser Glu Thr Ser Ala Asp Leu
625                 630                 635                 640
Thr Leu Ala Thr Asn Gly Val Pro Val Ser Val Ser Pro Ala Val Ser
            645                 650                 655
Lys Thr Ala Ala Gly Ser Ser Pro Pro Gly Gly Thr Lys Pro Ser Tyr
            660                 665                 670
Thr Met Val Ser Ser Val Ile Pro Glu Thr Ser Ser Leu Gln Ser Ser
            675                 680                 685
Ala Phe Arg Glu Gly Thr Ser Leu Gly Leu Thr Pro Leu Asn Thr Arg
            690                 695                 700
His Pro Phe Ser Ser Pro Glu Pro Asp Ser Ala Gly His Thr Lys Ile
705                 710                 715                 720
Ser Thr Ser Ile Pro Leu Leu Ser Ser Ala Ser Val Leu Glu Asp Lys
            725                 730                 735
Val Ser Ala Thr Ser Thr Phe Ser His His Lys Ala Thr Ser Ser Ile
            740                 745                 750
Thr Thr Gly Thr Pro Glu Ile Ser Thr Lys Thr Lys Pro Ser Ser Ala
            755                 760                 765
Val Leu Ser Ser Met Thr Leu Ser Asn Ala Ala Thr Ser Pro Glu Arg
            770                 775                 780
Val Arg Asn Ala Thr Ser Pro Leu Thr His Pro Ser Pro Ser Gly Glu
785                 790                 795                 800
Glu Thr Ala Gly Ser Val Leu Thr Leu Ser Thr Ser Ala Glu Thr Thr
            805                 810                 815
Asp Ser Pro Asn Ile His Pro Thr Gly Thr Leu Thr Ser Glu Ser Ser
            820                 825                 830
Glu Ser Pro Ser Thr Leu Ser Leu Pro Ser Val Ser Gly Val Lys Thr
            835                 840                 845
Thr Phe Ser Ser Ser Thr Pro Ser Thr His Leu Phe Thr Ser Gly Glu
            850                 855                 860
Glu Thr Glu Glu Thr Ser Asn Pro Ser Val Ser Gln Pro Glu Thr Ser
865                 870                 875                 880
Val Ser Arg Val Arg Thr Thr Leu Ala Ser Thr Ser Val Pro Thr Pro
            885                 890                 895
Val Phe Pro Thr Met Asp Thr Trp Pro Thr Arg Ser Ala Gln Phe Ser
            900                 905                 910
Ser Ser His Leu Val Ser Glu Leu Arg Ala Thr Ser Ser Thr Ser Val
            915                 920                 925
Thr Asn Ser Thr Gly Ser Ala Leu Pro Lys Ile Ser His Leu Thr Gly
            930                 935                 940
Thr Ala Thr Met Ser Gln Thr Asn Arg Asp Thr Phe Asn Asp Ser Ala
945                 950                 955                 960
Ala Pro Gln Ser Thr Thr Trp Pro Glu Thr Ser Pro Arg Phe Lys Thr
            965                 970                 975
```

-continued

```
Gly Leu Pro Ser Ala Thr Thr Thr Val Ser Thr Ser Ala Thr Ser Leu
            980                 985                 990

Ser Ala Thr Val Met Val Ser Lys Phe Thr Ser Pro Ala Thr Ser Ser
            995                 1000                1005

Met Glu Ala Thr Ser Ile Arg Glu Pro Ser Thr Thr Ile Leu Thr Thr
            1010                1015                1020

Glu Thr Thr Asn Gly Pro Gly Ser Met Ala Val Ala Ser Thr Asn Ile
1025                1030                1035                1040

Pro Ile Gly Lys Gly Tyr Ile Thr Glu Gly Arg Leu Asp Thr Ser His
                1045                1050                1055

Leu Pro Ile Gly Thr Thr Ala Ser Ser Glu Thr Ser Met Asp Phe Thr
                1060                1065                1070

Met Ala Lys Glu Ser Val Ser Met Ser Val Ser Pro Ser Gln Ser Met
            1075                1080                1085

Asp Ala Ala Gly Ser Ser Thr Pro Gly Arg Thr Ser Gln Phe Val Asp
            1090                1095                1100

Thr Phe Ser Asp Asp Val Tyr His Leu Thr Ser Arg Glu Ile Thr Ile
1105                1110                1115                1120

Pro Arg Asp Gly Thr Ser Ser Ala Leu Thr Pro Gln Met Thr Ala Thr
                1125                1130                1135

His Pro Pro Ser Pro Asp Pro Gly Ser Ala Arg Ser Thr Trp Leu Gly
                1140                1145                1150

Ile Leu Ser Ser Ser Pro Ser Ser Pro Thr Pro Lys Val Thr Met Ser
            1155                1160                1165

Ser Thr Phe Ser Thr Gln Arg Val Thr Thr Ser Met Ile Met Asp Thr
            1170                1175                1180

Val Glu Thr Ser Arg Trp Asn Met Pro Asn Leu Pro Ser Thr Thr Ser
1185                1190                1195                1200

Leu Thr Pro Ser Asn Ile Pro Thr Ser Gly Ala Ile Gly Lys Ser Thr
                1205                1210                1215

Leu Val Pro Leu Asp Thr Pro Ser Pro Ala Thr Ser Leu Glu Ala Ser
                1220                1225                1230

Glu Gly Gly Leu Pro Thr Leu Ser Thr Tyr Pro Glu Ser Thr Asn Thr
            1235                1240                1245

Pro Ser Ile His Leu Gly Ala His Ala Ser Ser Glu Ser Pro Ser Thr
            1250                1255                1260

Ile Lys Leu Thr Met Ala Ser Val Val Lys Pro Gly Ser Tyr Thr Pro
1265                1270                1275                1280

Leu Thr Phe Pro Ser Ile Glu Thr His Ile His Val Ser Thr Ala Arg
                1285                1290                1295

Met Ala Tyr Ser Ser Gly Ser Ser Pro Glu Met Thr Ala Pro Gly Glu
            1300                1305                1310

Thr Asn Thr Gly Ser Thr Trp Asp Pro Thr Thr Tyr Ile Thr Thr Thr
            1315                1320                1325

Asp Pro Lys Asp Thr Ser Ser Ala Gln Val Ser Thr Pro His Ser Val
            1330                1335                1340

Arg Thr Leu Arg Thr Glu Asn His Pro Lys Thr Glu Ser Ala Thr
1345                1350                1355                1360

Pro Ala Ala Tyr Ser Gly Ser Pro Lys Ile Ser Ser Pro Asn Leu
                1365                1370                1375

Thr Ser Pro Ala Thr Lys Ala Trp Thr Ile Thr Asp Thr Thr Glu His
            1380                1385                1390

Ser Thr Gln Leu His Tyr Thr Lys Leu Ala Glu Lys Ser Ser Gly Phe
```

-continued

```
          1395                1400                1405
Glu Thr Gln Ser Ala Pro Gly Pro Val Ser Val Ile Pro Thr Ser
    1410                1415                1420
Pro Thr Ile Gly Ser Ser Thr Leu Glu Leu Thr Ser Asp Val Pro Gly
1425                1430                1435                1440
Glu Pro Leu Val Leu Ala Pro Ser Glu Gln Thr Thr Ile Thr Leu Pro
            1445                1450                1455
Met Ala Thr Trp Leu Ser Thr Ser Leu Thr Glu Glu Met Ala Ser Thr
            1460                1465                1470
Asp Leu Asp Ile Ser Ser Pro Ser Ser Pro Met Ser Thr Phe Ala Ile
        1475                1480                1485
Phe Pro Pro Met Ser Thr Pro Ser His Glu Leu Ser Lys Ser Glu Ala
        1490                1495                1500
Asp Thr Ser Ala Ile Arg Asn Thr Asp Ser Thr Thr Leu Asp Gln His
1505                1510                1515                1520
Leu Gly Ile Arg Ser Leu Gly Arg Thr Gly Asp Leu Thr Thr Val Pro
            1525                1530                1535
Ile Thr Pro Leu Thr Thr Thr Trp Thr Ser Val Ile Glu His Ser Thr
            1540                1545                1550
Gln Ala Gln Asp Thr Leu Ser Ala Thr Met Ser Pro Thr His Val Thr
            1555                1560                1565
Gln Ser Leu Lys Asp Gln Thr Ser Ile Pro Ala Ser Ala Ser Pro Ser
        1570                1575                1580
His Leu Thr Glu Val Tyr Pro Glu Leu Gly Thr Gln Gly Arg Ser Ser
1585                1590                1595                1600
Ser Glu Ala Thr Thr Phe Trp Lys Pro Ser Thr Asp Thr Leu Ser Arg
            1605                1610                1615
Glu Ile Glu Thr Gly Pro Thr Asn Ile Gln Ser Thr Pro Pro Met Asp
            1620                1625                1630
Asn Thr Thr Thr Gly Ser Ser Ser Ser Gly Val Thr Leu Gly Ile Ala
            1635                1640                1645
His Leu Pro Ile Gly Thr Ser Ser Pro Ala Glu Thr Ser Thr Asn Met
        1650                1655                1660
Ala Leu Glu Arg Arg Ser Ser Thr Ala Thr Val Ser Met Ala Gly Thr
1665                1670                1675                1680
Met Gly Leu Leu Val Thr Ser Ala Pro Gly Arg Ser Ile Ser Gln Ser
            1685                1690                1695
Leu Gly Arg Val Ser Ser Val Leu Ser Glu Ser Thr Thr Glu Gly Val
            1700                1705                1710
Thr Asp Ser Ser Lys Gly Ser Ser Pro Arg Leu Asn Thr Gln Gly Asn
        1715                1720                1725
Thr Ala Leu Ser Ser Ser Leu Glu Pro Ser Tyr Ala Glu Gly Ser Gln
        1730                1735                1740
Met Ser Thr Ser Ile Pro Leu Thr Ser Ser Pro Thr Thr Pro Asp Val
1745                1750                1755                1760
Glu Phe Ile Gly Gly Ser Thr Phe Trp Thr Lys Glu Val Thr Thr Val
            1765                1770                1775
Met Thr Ser Asp Ile Ser Lys Ser Ser Ala Arg Thr Glu Ser Ser Ser
            1780                1785                1790
Ala Thr Leu Met Ser Thr Ala Leu Gly Ser Thr Glu Asn Thr Gly Lys
        1795                1800                1805
Glu Lys Leu Arg Thr Ala Ser Met Asp Leu Pro Ser Pro Thr Pro Ser
    1810                1815                1820
```

-continued

```
Met Glu Val Thr Pro Trp Ile Ser Leu Thr Leu Ser Asn Ala Pro Asn
1825                1830                1835                1840

Thr Thr Asp Ser Leu Asp Leu Ser His Gly Val His Thr Ser Ser Ala
            1845                1850                1855

Gly Thr Leu Ala Thr Asp Arg Ser Leu Asn Thr Gly Val Thr Arg Ala
            1860                1865                1870

Ser Arg Leu Glu Asn Gly Ser Asp Thr Ser Ser Lys Ser Leu Ser Met
        1875                1880                1885

Gly Asn Ser Thr His Thr Ser Met Thr Asp Glu Lys Ser Glu Val
        1890                1895                1900

Ser Ser Ser Ile His Pro Arg Pro Glu Thr Ser Ala Pro Gly Ala Glu
1905                1910                1915                1920

Thr Thr Leu Thr Ser Thr Pro Gly Asn Arg Ala Ile Ser Leu Thr Leu
            1925                1930                1935

Pro Phe Ser Ser Ile Pro Val Glu Glu Val Ile Ser Thr Gly Ile Thr
            1940                1945                1950

Ser Gly Pro Asp Ile Asn Ser Ala Pro Met Thr His Ser Pro Ile Thr
        1955                1960                1965

Pro Pro Thr Ile Val Trp Thr Ser Thr Gly Thr Ile Glu Gln Ser Thr
1970                1975                1980

Gln Pro Leu His Ala Val Ser Ser Glu Lys Val Ser Val Gln Thr Gln
1985                1990                1995                2000

Ser Thr Pro Tyr Val Asn Ser Val Ala Val Ser Ala Ser Pro Thr His
            2005                2010                2015

Glu Asn Ser Val Ser Ser Gly Ser Ser Thr Ser Ser Pro Tyr Ser Ser
        2020                2025                2030

Ala Ser Leu Glu Ser Leu Asp Ser Thr Ile Ser Arg Arg Asn Ala Ile
        2035                2040                2045

Thr Ser Trp Leu Trp Asp Leu Thr Thr Ser Leu Pro Thr Thr Thr Trp
        2050                2055                2060

Pro Ser Thr Ser Leu Ser Glu Ala Leu Ser Ser Gly His Ser Gly Val
2065                2070                2075                2080

Ser Asn Pro Ser Ser Thr Thr Thr Glu Phe Pro Leu Phe Ser Ala Ala
            2085                2090                2095

Ser Thr Ser Ala Ala Lys Gln Arg Asn Pro Glu Thr Glu Thr His Gly
        2100                2105                2110

Pro Gln Asn Thr Ala Ala Ser Thr Leu Asn Thr Asp Ala Ser Ser Val
        2115                2120                2125

Thr Gly Leu Ser Glu Thr Pro Val Gly Ala Ser Ile Ser Ser Glu Val
        2130                2135                2140

Pro Leu Pro Met Ala Ile Thr Ser Arg Ser Asp Val Ser Gly Leu Thr
2145                2150                2155                2160

Ser Glu Ser Thr Ala Asn Pro Ser Leu Gly Thr Ala Ser Ser Ala Gly
            2165                2170                2175

Thr Lys Leu Thr Arg Thr Ile Ser Leu Pro Thr Ser Glu Ser Leu Val
            2180                2185                2190

Ser Phe Arg Met Asn Lys Asp Pro Trp Thr Val Ser Ile Pro Leu Gly
        2195                2200                2205

Ser His Pro Thr Thr Asn Thr Glu Thr Ser Ile Pro Val Asn Ser Ala
        2210                2215                2220

Gly Pro Pro Gly Leu Ser Thr Val Ala Ser Asp Val Ile Asp Thr Pro
2225                2230                2235                2240
```

-continued

```
Ser Asp Gly Ala Glu Ser Ile Pro Thr Val Ser Phe Ser Pro Ser Pro
            2245                2250                2255

Asp Thr Glu Val Thr Thr Ile Ser His Phe Pro Glu Lys Thr Thr His
        2260                2265                2270

Ser Phe Arg Thr Ile Ser Ser Leu Thr His Glu Leu Thr Ser Arg Val
    2275                2280                2285

Thr Pro Ile Pro Gly Asp Trp Met Ser Ser Ala Met Ser Thr Lys Pro
2290                2295                2300

Thr Gly Ala Ser Pro Ser Ile Thr Leu Gly Glu Arg Arg Thr Ile Thr
2305                2310                2315                2320

Ser Ala Ala Pro Thr Thr Ser Pro Ile Val Leu Thr Ala Ser Phe Thr
                2325                2330                2335

Glu Thr Ser Thr Val Ser Leu Asp Asn Glu Thr Thr Val Lys Thr Ser
            2340                2345                2350

Asp Ile Leu Asp Ala Arg Lys Thr Asn Glu Leu Pro Ser Asp Ser Ser
        2355                2360                2365

Ser Ser Ser Asp Leu Ile Asn Thr Ser Ile Ala Ser Ser Thr Met Asp
    2370                2375                2380

Val Thr Lys Thr Ala Ser Ile Ser Pro Thr Ser Ile Ser Gly Met Thr
2385                2390                2395                2400

Ala Ser Ser Ser Pro Ser Leu Phe Ser Ser Asp Arg Pro Gln Val Pro
                2405                2410                2415

Thr Ser Thr Thr Glu Thr Asn Thr Ala Thr Ser Pro Ser Val Ser Ser
            2420                2425                2430

Asn Thr Tyr Ser Leu Asp Gly Gly Ser Asn Val Gly Gly Thr Pro Ser
        2435                2440                2445

Thr Leu Pro Pro Phe Thr Ile Thr His Pro Val Glu Thr Ser Ser Ala
    2450                2455                2460

Leu Leu Ala Trp Ser Arg Pro Val Arg Thr Phe Ser Thr Met Val Ser
2465                2470                2475                2480

Thr Asp Thr Ala Ser Gly Glu Asn Pro Thr Ser Ser Asn Ser Val Val
                2485                2490                2495

Thr Ser Val Pro Ala Pro Gly Thr Trp Ala Ser Val Gly Ser Thr Thr
            2500                2505                2510

Asp Leu Pro Ala Met Gly Phe Leu Lys Thr Ser Pro Ala Gly Glu Ala
        2515                2520                2525

His Ser Leu Leu Ala Ser Thr Ile Glu Pro Ala Thr Ala Phe Thr Pro
    2530                2535                2540

His Leu Ser Ala Ala Val Val Thr Gly Ser Ser Ala Thr Ser Glu Ala
2545                2550                2555                2560

Ser Leu Leu Thr Thr Ser Glu Ser Lys Ala Ile His Ser Ser Pro Gln
                2565                2570                2575

Thr Pro Thr Thr Pro Thr Ser Gly Ala Asn Trp Glu Thr Ser Ala Thr
            2580                2585                2590

Pro Glu Ser Leu Leu Val Val Thr Glu Thr Ser Asp Thr Thr Leu Thr
        2595                2600                2605

Ser Lys Ile Leu Val Thr Asp Thr Ile Leu Phe Ser Thr Val Ser Thr
    2610                2615                2620

Pro Pro Ser Lys Phe Pro Ser Thr Gly Thr Leu Ser Gly Ala Ser Phe
2625                2630                2635                2640

Pro Thr Leu Leu Pro Asp Thr Pro Ala Ile Pro Leu Thr Ala Thr Glu
                2645                2650                2655

Pro Thr Ser Ser Leu Ala Thr Ser Phe Asp Ser Thr Pro Leu Val Thr
```

-continued

```
                2660                2665                2670
Ile Ala Ser Asp Ser Leu Gly Thr Val Pro Glu Thr Thr Leu Thr Met
            2675                2680                2685
Ser Glu Thr Ser Asn Gly Asp Ala Leu Val Leu Lys Thr Val Ser Asn
        2690                2695                2700
Pro Asp Arg Ser Ile Pro Gly Ile Thr Ile Gln Gly Val Thr Glu Ser
2705                2710                2715                2720
Pro Leu His Pro Ser Ser Thr Ser Pro Ser Lys Ile Val Ala Pro Arg
            2725                2730                2735
Asn Thr Thr Tyr Glu Gly Ser Ile Thr Val Ala Leu Ser Thr Leu Pro
        2740                2745                2750
Ala Gly Thr Thr Gly Ser Leu Val Phe Ser Gln Ser Ser Glu Asn Ser
        2755                2760                2765
Glu Thr Thr Ala Leu Val Asp Ser Ser Ala Gly Leu Glu Arg Ala Ser
        2770                2775                2780
Val Met Pro Leu Thr Thr Gly Ser Gln Gly Met Ala Ser Ser Gly Gly
2785                2790                2795                2800
Ile Arg Ser Gly Ser Thr His Ser Thr Gly Thr Lys Thr Phe Ser Ser
            2805                2810                2815
Leu Pro Leu Thr Met Asn Pro Gly Glu Val Thr Ala Met Ser Glu Ile
            2820                2825                2830
Thr Thr Asn Arg Leu Thr Ala Thr Gln Ser Thr Ala Pro Lys Gly Ile
            2835                2840                2845
Pro Val Lys Pro Thr Ser Ala Glu Ser Gly Leu Leu Thr Pro Val Ser
            2850                2855                2860
Ala Ser Ser Ser Pro Ser Lys Ala Phe Ala Ser Leu Thr Thr Ala Pro
2865                2870                2875                2880
Pro Ser Thr Trp Gly Ile Pro Gln Ser Thr Leu Thr Phe Glu Phe Ser
                2885                2890                2895
Glu Val Pro Ser Leu Asp Thr Lys Ser Ala Ser Leu Pro Thr Pro Gly
            2900                2905                2910
Gln Ser Leu Asn Thr Ile Pro Asp Ser Asp Ala Ser Thr Ala Ser Ser
            2915                2920                2925
Ser Leu Ser Lys Ser Pro Glu Lys Asn Pro Arg Ala Arg Met Met Thr
        2930                2935                2940
Ser Thr Lys Ala Ile Ser Ala Ser Ser Phe Gln Ser Thr Gly Phe Thr
2945                2950                2955                2960
Glu Thr Pro Glu Gly Ser Ala Ser Pro Ser Met Ala Gly His Glu Pro
                2965                2970                2975
Arg Val Pro Thr Ser Gly Thr Gly Asp Pro Arg Tyr Ala Ser Glu Ser
                2980                2985                2990
Met Ser Tyr Pro Asp Pro Ser Lys Ala Ser Ser Ala Met Thr Ser Thr
            2995                3000                3005
Ser Leu Ala Ser Lys Leu Thr Thr Leu Phe Ser Thr Gly Gln Ala Ala
        3010                3015                3020
Arg Ser Gly Ser Ser Ser Pro Ile Ser Leu Ser Thr Glu Lys Glu
3025                3030                3035                3040
Thr Ser Phe Leu Ser Pro Thr Ala Ser Thr Ser Arg Lys Thr Ser Leu
                3045                3050                3055
Phe Leu Gly Pro Ser Met Ala Arg Gln Pro Asn Ile Leu Val His Leu
            3060                3065                3070
Gln Thr Ser Ala Leu Thr Leu Ser Pro Thr Ser Thr Leu Asn Met Ser
            3075                3080                3085
```

```
Gln Glu Glu Pro Pro Glu Leu Thr Ser Ser Gln Thr Ile Ala Glu Glu
        3090                3095                3100
Glu Gly Thr Thr Ala Glu Thr Gln Thr Leu Thr Phe Thr Pro Ser Glu
3105                3110                3115                3120
Thr Pro Thr Ser Leu Leu Pro Val Ser Ser Pro Thr Glu Pro Thr Ala
                3125                3130                3135
Arg Arg Lys Ser Ser Pro Glu Trp Ala Ser Ser Ile Ser Val Pro
            3140                3145                3150
Ala Lys Thr Ser Leu Val Glu Thr Thr Asp Gly Thr Leu Val Thr Thr
            3155                3160                3165
Ile Lys Met Ser Ser Gln Ala Ala Gln Gly Asn Ser Thr Trp Pro Ala
        3170                3175                3180
Pro Ala Glu Glu Thr Gly Thr Ser Pro Ala Gly Thr Ser Pro Gly Ser
3185                3190                3195                3200
Pro Glu Val Ser Thr Thr Leu Lys Ile Met Ser Ser Lys Glu Pro Ser
                3205                3210                3215
Ile Ser Pro Glu Ile Arg Ser Thr Val Arg Asn Ser Pro Trp Lys Thr
            3220                3225                3230
Pro Glu Thr Thr Val Pro Met Glu Thr Thr Val Glu Pro Val Thr Leu
        3235                3240                3245
Gln Ser Thr Ala Leu Gly Ser Gly Ser Thr Ser Ile Ser His Leu Pro
        3250                3255                3260
Thr Gly Thr Thr Ser Pro Thr Lys Ser Pro Thr Glu Asn Met Leu Ala
3265                3270                3275                3280
Thr Glu Arg Val Ser Leu Ser Pro Ser Pro Glu Ala Trp Thr Asn
            3285                3290                3295
Leu Tyr Ser Gly Thr Pro Gly Gly Thr Arg Gln Ser Leu Ala Thr Met
            3300                3305                3310
Ser Ser Val Ser Leu Glu Ser Pro Thr Ala Arg Ser Ile Thr Gly Thr
            3315                3320                3325
Gly Gln Gln Ser Ser Pro Glu Leu Val Ser Lys Thr Thr Gly Met Glu
        3330                3335                3340
Phe Ser Met Trp His Gly Ser Thr Gly Gly Thr Thr Gly Asp Thr His
3345                3350                3355                3360
Val Ser Leu Ser Thr Ser Ser Asn Ile Leu Glu Asp Pro Val Thr Ser
                3365                3370                3375
Pro Asn Ser Val Ser Ser Leu Thr Asp Lys Ser Lys His Lys Thr Glu
            3380                3385                3390
Thr Trp Val Ser Thr Thr Ala Ile Pro Ser Thr Val Leu Asn Asn Lys
            3395                3400                3405
Ile Met Ala Ala Glu Gln Gln Thr Ser Arg Ser Val Asp Glu Ala Tyr
        3410                3415                3420
Ser Ser Thr Ser Ser Trp Ser Asp Gln Thr Ser Gly Ser Asp Ile Thr
3425                3430                3435                3440
Leu Gly Ala Ser Pro Asp Val Thr Asn Thr Leu Tyr Ile Thr Ser Thr
                3445                3450                3455
Ala Gln Thr Thr Ser Leu Val Ser Leu Pro Ser Gly Asp Gln Gly Ile
            3460                3465                3470
Thr Ser Leu Thr Asn Pro Ser Gly Gly Lys Thr Ser Ser Ala Ser Ser
            3475                3480                3485
Val Thr Ser Pro Ser Ile Gly Leu Glu Thr Leu Arg Ala Asn Val Ser
        3490                3495                3500
```

-continued

```
Ala Val Lys Ser Asp Ile Ala Pro Thr Ala Gly His Leu Ser Gln Thr
3505                3510                3515                3520

Ser Ser Pro Ala Glu Val Ser Ile Leu Asp Val Thr Thr Ala Pro Thr
                3525                3530                3535

Pro Gly Ile Ser Thr Thr Ile Thr Thr Met Gly Thr Asn Ser Ile Ser
            3540                3545                3550

Thr Thr Thr Pro Asn Pro Glu Val Gly Met Ser Thr Met Asp Ser Thr
        3555                3560                3565

Pro Ala Thr Glu Arg Arg Thr Thr Ser Thr Glu His Pro Ser Thr Trp
    3570                3575                3580

Ser Ser Thr Ala Ala Ser Asp Ser Trp Thr Val Thr Asp Met Thr Ser
3585                3590                3595                3600

Asn Leu Lys Val Ala Arg Ser Pro Gly Thr Ile Ser Thr Met His Thr
                3605                3610                3615

Thr Ser Phe Leu Ala Ser Ser Thr Glu Leu Asp Ser Met Ser Thr Pro
            3620                3625                3630

His Gly Arg Ile Thr Val Ile Gly Thr Ser Leu Val Thr Pro Ser Ser
        3635                3640                3645

Asp Ala Ser Ala Val Lys Thr Glu Thr Ser Thr Ser Glu Arg Thr Leu
    3650                3655                3660

Ser Pro Ser Asp Thr Thr Ala Ser Thr Pro Ile Ser Thr Phe Ser Arg
3665                3670                3675                3680

Val Gln Arg Met Ser Ile Ser Val Pro Asp Ile Leu Ser Thr Ser Trp
                3685                3690                3695

Thr Pro Ser Ser Thr Glu Ala Glu Asp Val Pro Val Ser Met Val Ser
            3700                3705                3710

Thr Asp His Ala Ser Thr Lys Thr Asp Pro Asn Thr Pro Leu Ser Thr
        3715                3720                3725

Phe Leu Phe Asp Ser Leu Ser Thr Leu Asp Trp Asp Thr Gly Arg Ser
    3730                3735                3740

Leu Ser Ser Ala Thr Ala Thr Thr Ser Ala Pro Gln Gly Ala Thr Thr
3745                3750                3755                3760

Pro Gln Glu Leu Thr Leu Glu Thr Met Ile Ser Pro Ala Thr Ser Gln
                3765                3770                3775

Leu Pro Phe Ser Ile Gly His Ile Thr Ser Ala Val Thr Pro Ala Ala
            3780                3785                3790

Met Ala Arg Ser Ser Gly Val Thr Phe Ser Arg Pro Asp Pro Thr Ser
        3795                3800                3805

Lys Lys Ala Glu Gln Thr Ser Thr Gln Leu Pro Thr Thr Thr Ser Ala
    3810                3815                3820

His Pro Gly Gln Val Pro Arg Ser Ala Ala Thr Thr Leu Asp Val Ile
3825                3830                3835                3840

Pro His Thr Ala Lys Thr Pro Asp Ala Thr Phe Gln Arg Gln Gly Gln
                3845                3850                3855

Thr Ala Leu Thr Thr Glu Ala Arg Ala Thr Ser Asp Ser Trp Asn Glu
            3860                3865                3870

Lys Glu Lys Ser Thr Pro Ser Ala Pro Trp Ile Thr Glu Met Met Asn
        3875                3880                3885

Ser Val Ser Glu Asp Thr Ile Lys Glu Val Thr Ser Ser Ser Ser Val
    3890                3895                3900

Leu Lys Asp Pro Glu Tyr Ala Gly His Lys Leu Gly Ile Trp Asp Asp
3905                3910                3915                3920

Phe Ile Pro Lys Phe Gly Lys Ala Ala His Met Arg Glu Leu Pro Leu
```

| | | 3925 | | | | 3930 | | | | 3935 | |
|---|---|---|---|---|---|---|---|---|---|---|---|

Leu Ser Pro Pro Gln Asp Lys Glu Ala Ile His Pro Ser Thr Asn Thr
            3940                   3945              3950

Val Glu Thr Thr Gly Trp Val Thr Ser Ser Glu His Ala Ser His Ser
            3955                   3960              3965

Thr Ile Pro Ala His Ser Ala Ser Ser Lys Leu Thr Ser Pro Val Val
            3970                   3975              3980

Thr Thr Ser Thr Arg Glu Gln Ala Ile Val Ser Met Ser Thr Thr Thr
3985                  3990                   3995              4000

Trp Pro Glu Ser Thr Arg Ala Arg Thr Glu Pro Asn Ser Phe Leu Thr
            4005                   4010              4015

Ile Glu Leu Arg Asp Val Ser Pro Tyr Met Asp Thr Ser Ser Thr Thr
            4020                   4025              4030

Gln Thr Ser Ile Ile Ser Ser Pro Gly Ser Thr Ala Ile Thr Lys Gly
            4035                   4040              4045

Pro Arg Thr Glu Ile Thr Ser Ser Lys Arg Ile Ser Ser Ser Phe Leu
            4050                   4055              4060

Ala Gln Ser Met Arg Ser Ser Asp Ser Pro Ser Glu Ala Ile Thr Arg
4065                  4070                   4075              4080

Leu Ser Asn Phe Pro Ala Met Thr Glu Ser Gly Gly Met Ile Leu Ala
            4085                   4090              4095

Met Gln Thr Ser Pro Pro Gly Ala Thr Ser Leu Ser Ala Pro Thr Leu
            4100                   4105              4110

Asp Thr Ser Ala Thr Ala Ser Trp Thr Gly Thr Pro Leu Ala Thr Thr
            4115                   4120              4125

Gln Arg Phe Thr Tyr Ser Glu Lys Thr Thr Leu Phe Ser Lys Gly Pro
            4130                   4135              4140

Glu Asp Thr Ser Gln Pro Ser Pro Ser Val Glu Glu Thr Ser Ser
4145                  4150                   4155              4160

Ser Ser Ser Leu Val Pro Ile His Ala Thr Thr Ser Pro Ser Asn Ile
            4165                   4170              4175

Leu Leu Thr Ser Gln Gly His Ser Pro Ser Ser Thr Pro Pro Val Thr
            4180                   4185              4190

Ser Val Phe Leu Ser Glu Thr Ser Gly Leu Gly Lys Thr Thr Asp Met
            4195                   4200              4205

Ser Arg Ile Ser Leu Glu Pro Gly Thr Ser Leu Pro Pro Asn Leu Ser
            4210                   4215              4220

Ser Thr Ala Gly Glu Ala Leu Ser Thr Tyr Glu Ala Ser Arg Asp Thr
4225                  4230                   4235              4240

Lys Ala Ile His His Ser Ala Asp Thr Ala Val Thr Asn Met Glu Ala
            4245                   4250              4255

Thr Ser Ser Glu Tyr Ser Pro Ile Pro Gly His Thr Lys Pro Ser Lys
            4260                   4265              4270

Ala Thr Ser Pro Leu Val Thr Ser His Ile Met Gly Asp Ile Thr Ser
            4275                   4280              4285

Ser Thr Ser Val Phe Gly Ser Ser Glu Thr Thr Glu Ile Glu Thr Val
            4290                   4295              4300

Ser Ser Val Asn Gln Gly Leu Gln Glu Arg Ser Thr Ser Gln Val Ala
4305                  4310                   4315              4320

Ser Ser Ala Thr Glu Thr Ser Thr Val Ile Thr His Val Ser Ser Gly
            4325                   4330              4335

Asp Ala Thr Thr His Val Thr Lys Thr Gln Ala Thr Phe Ser Ser Gly
            4340                   4345              4350

```
Thr Ser Ile Ser Ser Pro His Gln Phe Ile Thr Ser Thr Asn Thr Phe
        4355                4360                4365

Thr Asp Val Ser Thr Asn Pro Ser Thr Ser Leu Ile Met Thr Glu Ser
        4370                4375                4380

Ser Gly Val Thr Ile Thr Thr Gln Thr Gly Pro Thr Gly Ala Ala Thr
4385                4390                4395                4400

Gln Gly Pro Tyr Leu Leu Asp Thr Ser Thr Met Pro Tyr Leu Thr Glu
            4405                4410                4415

Thr Pro Leu Ala Val Thr Pro Asp Phe Met Gln Ser Glu Lys Thr Thr
            4420                4425                4430

Leu Ile Ser Lys Gly Pro Lys Asp Val Thr Trp Thr Ser Pro Pro Ser
            4435                4440                4445

Val Ala Glu Thr Ser Tyr Pro Ser Ser Leu Thr Pro Phe Leu Val Thr
            4450                4455                4460

Thr Ile Pro Pro Ala Thr Ser Thr Leu Gln Gly Gln His Thr Ser Ser
4465                4470                4475                4480

Pro Val Ser Ala Thr Ser Val Leu Thr Ser Gly Leu Val Lys Thr Thr
                4485                4490                4495

Asp Met Leu Asn Thr Ser Met Glu Pro Val Thr Asn Ser Pro Gln Asn
            4500                4505                4510

Leu Asn Asn Pro Ser Asn Glu Ile Leu Ala Thr Leu Ala Ala Thr Thr
            4515                4520                4525

Asp Ile Glu Thr Ile His Pro Ser Ile Asn Lys Ala Val Thr Asn Met
            4530                4535                4540

Gly Thr Ala Ser Ser Ala His Val Leu His Ser Thr Leu Pro Val Ser
4545                4550                4555                4560

Ser Glu Pro Ser Thr Ala Thr Ser Pro Met Val Pro Ala Ser Ser Met
                4565                4570                4575

Gly Asp Ala Leu Ala Ser Ile Ser Ile Pro Gly Ser Glu Thr Thr Asp
            4580                4585                4590

Ile Glu Gly Glu Pro Thr Ser Ser Leu Thr Ala Gly Arg Lys Glu Asn
            4595                4600                4605

Ser Thr Leu Gln Glu Met Asn Ser Thr Thr Glu Ser Asn Ile Ile Leu
    4610                4615                4620

Ser Asn Val Ser Val Gly Ala Ile Thr Glu Ala Thr Lys Met Glu Val
4625                4630                4635                4640

Pro Ser Phe Asp Ala Thr Phe Ile Pro Thr Pro Ala Gln Ser Thr Lys
            4645                4650                4655

Phe Pro Asp Ile Phe Ser Val Ala Ser Ser Arg Leu Ser Asn Ser Pro
            4660                4665                4670

Pro Met Thr Ile Ser Thr His Met Thr Thr Thr Gln Thr Gly Ser Ser
            4675                4680                4685

Gly Ala Thr Ser Lys Ile Pro Leu Ala Leu Asp Thr Ser Thr Leu Glu
            4690                4695                4700

Thr Ser Ala Gly Thr Pro Ser Val Val Thr Glu Gly Phe Ala His Ser
4705                4710                4715                4720

Lys Ile Thr Thr Ala Met Asn Asn Asp Val Lys Asp Val Ser Gln Thr
                4725                4730                4735

Asn Pro Pro Phe Gln Asp Glu Ala Ser Ser Pro Ser Ser Gln Ala Pro
            4740                4745                4750

Val Leu Val Thr Thr Leu Pro Ser Ser Val Ala Phe Thr Pro Gln Trp
            4755                4760                4765
```

```
His Ser Thr Ser Ser Pro Val Ser Met Ser Ser Val Leu Thr Ser Ser
    4770            4775            4780

Leu Val Lys Thr Ala Gly Lys Val Asp Thr Ser Leu Glu Thr Val Thr
4785            4790            4795            4800

Ser Ser Pro Gln Ser Met Ser Asn Thr Leu Asp Asp Ile Ser Val Thr
        4805            4810            4815

Ser Ala Ala Thr Thr Asp Ile Glu Thr Thr His Pro Ser Ile Asn Thr
        4820            4825            4830

Val Val Thr Asn Val Gly Thr Thr Gly Ser Ala Phe Glu Ser His Ser
        4835            4840            4845

Thr Val Ser Ala Tyr Pro Glu Pro Ser Lys Val Thr Ser Pro Asn Val
    4850            4855            4860

Thr Thr Ser Thr Met Glu Asp Thr Thr Ile Ser Arg Ser Ile Pro Lys
4865            4870            4875            4880

Ser Ser Lys Thr Thr Arg Thr Glu Thr Glu Thr Thr Ser Ser Leu Thr
            4885            4890            4895

Pro Lys Leu Arg Glu Thr Ser Ile Ser Gln Glu Ile Thr Ser Ser Thr
            4900            4905            4910

Glu Thr Ser Thr Val Pro Tyr Lys Glu Leu Thr Gly Ala Thr Thr Glu
    4915            4920            4925

Val Ser Arg Thr Asp Val Thr Ser Ser Ser Thr Ser Phe Pro Gly
    4930            4935            4940

Pro Asp Gln Ser Thr Val Ser Leu Asp Ile Ser Thr Glu Thr Asn Thr
4945            4950            4955            4960

Arg Leu Ser Thr Ser Pro Ile Met Thr Glu Ser Ala Glu Ile Thr Ile
            4965            4970            4975

Thr Thr Gln Thr Gly Pro His Gly Ala Thr Ser Gln Asp Thr Phe Thr
        4980            4985            4990

Met Asp Pro Ser Asn Thr Thr Pro Gln Ala Gly Ile His Ser Ala Met
            4995            5000            5005

Thr His Gly Phe Ser Gln Leu Asp Val Thr Thr Leu Met Ser Arg Ile
    5010            5015            5020

Pro Gln Asp Val Ser Trp Thr Ser Pro Pro Ser Val Asp Lys Thr Ser
5025            5030            5035            5040

Ser Pro Ser Ser Phe Leu Ser Ser Pro Ala Met Thr Thr Pro Ser Leu
            5045            5050            5055

Ile Ser Ser Thr Leu Pro Glu Asp Lys Leu Ser Ser Pro Met Thr Ser
            5060            5065            5070

Leu Leu Thr Ser Gly Leu Val Lys Ile Thr Asp Ile Leu Arg Thr Arg
    5075            5080            5085

Leu Glu Pro Val Thr Ser Ser Leu Pro Asn Phe Ser Ser Thr Ser Asp
    5090            5095            5100

Lys Ile Leu Ala Thr Ser Lys Asp Ser Lys Asp Thr Lys Glu Ile Phe
5105            5110            5115            5120

Pro Ser Ile Asn Thr Glu Glu Thr Asn Val Lys Ala Asn Asn Ser Gly
            5125            5130            5135

His Glu Ser His Ser Pro Ala Leu Ala Asp Ser Glu Thr Pro Lys Ala
            5140            5145            5150

Thr Thr Gln Met Val Ile Thr Thr Val Gly Asp Pro Ala Pro Ser
        5155            5160            5165

Thr Ser Met Pro Val His Gly Ser Ser Glu Thr Thr Asn Ile Lys Arg
    5170            5175            5180

Glu Pro Thr Tyr Phe Leu Thr Pro Arg Leu Arg Glu Thr Ser Thr Ser
```

-continued

```
        5185                5190                5195                5200
Gln Glu Ser Ser Phe Pro Thr Asp Thr Ser Phe Leu Leu Ser Lys Val
            5205                5210                5215
Pro Thr Gly Thr Ile Thr Glu Val Ser Ser Thr Gly Val Asn Ser Ser
            5220                5225                5230
Ser Lys Ile Ser Thr Pro Asp His Asp Lys Ser Thr Val Pro Pro Asp
            5235                5240                5245
Thr Phe Thr Gly Glu Ile Pro Arg Val Phe Thr Ser Ser Ile Lys Thr
            5250                5255                5260
Lys Ser Ala Glu Met Thr Ile Thr Thr Gln Ala Ser Pro Pro Glu Ser
5265                5270                5275                5280
Ala Ser His Ser Thr Leu Pro Leu Asp Thr Ser Thr Thr Leu Ser Gln
            5285                5290                5295
Gly Gly Thr His Ser Thr Val Thr Gln Gly Phe Pro Tyr Ser Glu Val
            5300                5305                5310
Thr Thr Leu Met Gly Met Gly Pro Gly Asn Val Ser Trp Met Thr Thr
            5315                5320                5325
Pro Pro Val Glu Glu Thr Ser Ser Val Ser Ser Leu Met Ser Ser Pro
            5330                5335                5340
Ala Met Thr Ser Pro Ser Pro Val Ser Ser Thr Ser Pro Gln Ser Ile
5345                5350                5355                5360
Pro Ser Ser Pro Leu Pro Val Thr Ala Leu Pro Thr Ser Val Leu Val
            5365                5370                5375
Thr Thr Thr Asp Val Leu Gly Thr Ser Pro Glu Ser Val Thr Ser
            5380                5385                5390
Ser Pro Pro Asn Leu Ser Ser Ile Thr His Glu Arg Pro Ala Thr Tyr
            5395                5400                5405
Lys Asp Thr Ala His Thr Glu Ala Ala Met His His Ser Thr Asn Thr
            5410                5415                5420
Ala Val Thr Asn Val Gly Thr Ser Gly Ser Gly His Lys Ser Gln Ser
5425                5430                5435                5440
Ser Val Leu Ala Asp Ser Glu Thr Ser Lys Ala Thr Pro Leu Met Ser
            5445                5450                5455
Thr Thr Ser Thr Leu Gly Asp Thr Ser Val Ser Thr Ser Thr Pro Asn
            5460                5465                5470
Ile Ser Gln Thr Asn Gln Ile Gln Thr Glu Pro Thr Ala Ser Leu Ser
            5475                5480                5485
Pro Arg Leu Arg Glu Ser Ser Thr Ser Glu Lys Thr Ser Ser Thr Thr
            5490                5495                5500
Glu Thr Asn Thr Ala Phe Ser Tyr Val Pro Thr Gly Ala Ile Thr Gln
5505                5510                5515                5520
Ala Ser Arg Thr Glu Ile Ser Ser Ser Arg Thr Ser Ile Ser Asp Leu
            5525                5530                5535
Asp Arg Pro Thr Ile Ala Pro Asp Ile Ser Thr Gly Met Ile Thr Arg
            5540                5545                5550
Leu Phe Thr Ser Pro Ile Met Thr Lys Ser Ala Glu Met Thr Val Thr
            5555                5560                5565
Thr Gln Thr Thr Thr Pro Gly Ala Thr Ser Gln Gly Ile Leu Pro Trp
            5570                5575                5580
Asp Thr Ser Thr Thr Leu Phe Gln Gly Gly Thr His Ser Thr Val Ser
5585                5590                5595                5600
Gln Gly Phe Pro His Ser Glu Ile Thr Thr Leu Arg Ser Arg Thr Pro
            5605                5610                5615
```

```
Gly Asp Val Ser Trp Met Thr Thr Pro Pro Val Glu Glu Thr Ser Ser
            5620                5625                5630

Gly Phe Ser Leu Met Ser Pro Ser Met Thr Ser Pro Ser Pro Val Ser
            5635                5640                5645

Ser Thr Ser Pro Glu Ser Ile Pro Ser Ser Pro Leu Pro Val Thr Ala
            5650                5655                5660

Leu Leu Thr Ser Val Leu Val Thr Thr Thr Asn Val Leu Gly Thr Thr
5665                5670                5675                5680

Ser Pro Glu Thr Val Thr Ser Ser Pro Pro Asn Leu Ser Ser Pro Thr
            5685                5690                5695

Gln Glu Arg Leu Thr Thr Tyr Lys Asp Thr Ala His Thr Glu Ala Met
            5700                5705                5710

His Ala Ser Met His Thr Asn Thr Ala Val Ala Asn Val Gly Thr Ser
            5715                5720                5725

Ile Ser Gly His Glu Ser Gln Ser Ser Val Pro Ala Asp Ser His Thr
            5730                5735                5740

Ser Lys Ala Thr Ser Pro Met Gly Ile Thr Phe Ala Met Gly Asp Thr
5745                5750                5755                5760

Ser Val Ser Thr Ser Thr Pro Ala Phe Phe Glu Thr Arg Ile Gln Thr
            5765                5770                5775

Glu Ser Thr Ser Ser Leu Ile Pro Gly Leu Arg Asp Thr Arg Thr Ser
            5780                5785                5790

Glu Glu Ile Asn Thr Val Thr Glu Thr Ser Thr Val Leu Ser Glu Val
            5795                5800                5805

Pro Thr Thr Thr Thr Thr Glu Val Ser Arg Thr Glu Val Ile Thr Ser
            5810                5815                5820

Ser Arg Thr Thr Ile Ser Gly Pro Asp His Ser Lys Met Ser Pro Tyr
5825                5830                5835                5840

Ile Ser Thr Glu Thr Ile Thr Arg Leu Ser Thr Phe Pro Phe Val Thr
            5845                5850                5855

Gly Ser Thr Glu Met Ala Ile Thr Asn Gln Thr Gly Pro Ile Gly Thr
            5860                5865                5870

Ile Ser Gln Ala Thr Leu Thr Leu Asp Thr Ser Ser Thr Ala Ser Trp
            5875                5880                5885

Glu Gly Thr His Ser Pro Val Thr Gln Arg Phe Pro His Ser Glu Glu
            5890                5895                5900

Thr Thr Thr Met Ser Arg Ser Thr Lys Gly Val Ser Trp Gln Ser Pro
5905                5910                5915                5920

Pro Ser Val Glu Glu Thr Ser Pro Ser Pro Val Pro Leu Pro
            5925                5930                5935

Ala Ile Thr Ser His Ser Ser Leu Tyr Ser Ala Val Ser Gly Ser Ser
            5940                5945                5950

Pro Thr Ser Ala Leu Pro Val Thr Ser Leu Leu Thr Ser Gly Arg Arg
            5955                5960                5965

Lys Thr Ile Asp Met Leu Asp Thr His Ser Glu Leu Val Thr Ser Ser
5970                5975                5980

Leu Pro Ser Ala Ser Ser Phe Ser Gly Glu Ile Leu Thr Ser Glu Ala
5985                5990                5995                6000

Ser Thr Asn Thr Glu Thr Ile His Phe Ser Glu Asn Thr Ala Glu Thr
            6005                6010                6015

Asn Met Gly Thr Thr Asn Ser Met His Lys Leu His Ser Ser Val Ser
            6020                6025                6030
```

-continued

```
Ile His Ser Gln Pro Ser Gly His Thr Pro Pro Lys Val Thr Gly Ser
        6035                6040                6045
Met Met Glu Asp Ala Ile Val Ser Thr Ser Thr Pro Gly Ser Pro Glu
6050                6055                6060
Thr Lys Asn Val Asp Arg Asp Ser Thr Ser Pro Leu Thr Pro Glu Leu
6065                6070                6075                6080
Lys Glu Asp Ser Thr Ala Leu Val Met Asn Ser Thr Thr Glu Ser Asn
                6085                6090                6095
Thr Val Phe Ser Ser Val Ser Leu Asp Ala Ala Thr Glu Val Ser Arg
            6100                6105                6110
Ala Glu Val Thr Tyr Tyr Asp Pro Thr Phe Met Pro Ala Ser Ala Gln
        6115                6120                6125
Ser Thr Lys Ser Pro Asp Ile Ser Pro Glu Ala Ser Ser Ser His Ser
    6130                6135                6140
Asn Ser Pro Pro Leu Thr Ile Ser Thr His Lys Thr Ile Ala Thr Gln
6145                6150                6155                6160
Thr Gly Pro Ser Gly Val Thr Ser Leu Gly Gln Leu Thr Leu Asp Thr
                6165                6170                6175
Ser Thr Ile Ala Thr Ser Ala Gly Thr Pro Ser Ala Arg Thr Gln Asp
            6180                6185                6190
Phe Val Asp Ser Glu Thr Thr Ser Val Met Asn Asn Asp Leu Asn Asp
        6195                6200                6205
Val Leu Lys Thr Ser Pro Phe Ser Ala Glu Glu Ala Asn Ser Leu Ser
    6210                6215                6220
Ser Gln Ala Pro Leu Leu Val Thr Thr Ser Pro Ser Pro Val Thr Ser
6225                6230                6235                6240
Thr Leu Gln Glu His Ser Thr Ser Ser Leu Val Ser Val Thr Ser Val
                6245                6250                6255
Pro Thr Pro Thr Leu Ala Lys Ile Thr Asp Met Asp Thr Asn Leu Glu
            6260                6265                6270
Pro Val Thr Arg Ser Pro Gln Asn Leu Arg Asn Thr Leu Ala Thr Ser
        6275                6280                6285
Glu Ala Thr Thr Asp Thr His Thr Met His Pro Ser Ile Asn Thr Ala
    6290                6295                6300
Met Ala Asn Val Gly Thr Thr Ser Ser Pro Asn Glu Phe Tyr Phe Thr
6305                6310                6315                6320
Val Ser Pro Asp Ser Asp Pro Tyr Lys Ala Thr Ser Ala Val Val Ile
                6325                6330                6335
Thr Ser Thr Ser Gly Asp Ser Ile Val Ser Thr Ser Met Pro Arg Ser
            6340                6345                6350
Ser Ala Met Lys Lys Ile Glu Ser Glu Thr Thr Phe Ser Leu Ile Phe
        6355                6360                6365
Arg Leu Arg Glu Thr Ser Thr Ser Gln Lys Ile Gly Ser Ser Ser Asp
    6370                6375                6380
Thr Ser Thr Val Phe Asp Lys Ala Phe Thr Ala Ala Thr Thr Glu Val
6385                6390                6395                6400
Ser Arg Thr Glu Leu Thr Ser Ser Ser Arg Thr Ser Ile Gln Gly Thr
                6405                6410                6415
Glu Lys Pro Thr Met Ser Pro Asp Thr Ser Thr Arg Ser Val Thr Met
            6420                6425                6430
Leu Ser Thr Phe Ala Gly Leu Thr Lys Ser Glu Glu Arg Thr Ile Ala
        6435                6440                6445
Thr Gln Thr Gly Pro His Arg Ala Thr Ser Gln Gly Thr Leu Thr Trp
```

```
                     6450                6455                6460

Asp Thr Ser Ile Thr Thr Ser Gln Ala Gly Thr His Ser Ala Met Thr
6465                6470                6475                6480

His Gly Phe Ser Gln Leu Asp Leu Ser Thr Leu Thr Ser Arg Val Pro
                    6485                6490                6495

Glu Tyr Ile Ser Gly Thr Ser Pro Ser Val Glu Lys Thr Ser Ser
                6500            6505                6510

Ser Ser Ser Leu Leu Ser Leu Pro Ala Ile Thr Ser Pro Ser Pro Val
            6515                6520            6525

Pro Thr Thr Leu Pro Glu Ser Arg Pro Ser Ser Pro Val His Leu Thr
    6530                6535                6540

Ser Leu Pro Thr Ser Gly Leu Val Lys Thr Thr Asp Met Leu Ala Ser
6545                6550                6555                6560

Val Ala Ser Leu Pro Pro Asn Leu Gly Ser Thr Ser His Lys Ile Pro
                6565                6570            6575

Thr Thr Ser Glu Asp Ile Lys Asp Thr Glu Lys Met Tyr Pro Ser Thr
            6580                6585                6590

Asn Ile Ala Val Thr Asn Val Gly Thr Thr Thr Ser Glu Lys Glu Ser
                6595            6600                6605

Tyr Ser Ser Val Pro Ala Tyr Ser Glu Pro Pro Lys Val Thr Ser Pro
            6610            6615                6620

Met Val Thr Ser Phe Asn Ile Arg Asp Thr Ile Val Ser Thr Ser Met
6625                6630                6635                6640

Pro Gly Ser Ser Glu Ile Thr Arg Ile Glu Met Glu Ser Thr Phe Ser
                6645                6650                6655

Val Ala His Gly Leu Lys Gly Thr Ser Thr Ser Gln Asp Pro Ile Val
                6660            6665                6670

Ser Thr Glu Lys Ser Ala Val Leu His Lys Leu Thr Thr Gly Ala Thr
        6675            6680            6685

Glu Thr Ser Arg Thr Glu Val Ala Ser Ser Arg Arg Thr Ser Ile Pro
    6690                6695                6700

Gly Pro Asp His Ser Thr Glu Ser Pro Asp Ile Ser Thr Glu Val Ile
6705                6710                6715                6720

Pro Ser Leu Pro Ile Ser Leu Gly Ile Thr Glu Ser Ser Asn Met Thr
                6725                6730                6735

Ile Ile Thr Arg Thr Gly Pro Pro Leu Gly Ser Thr Ser Gln Gly Thr
                6740            6745                6750

Phe Thr Leu Asp Thr Pro Thr Thr Ser Ser Arg Ala Gly Thr His Ser
            6755                6760                6765

Met Ala Thr Gln Glu Phe Pro His Ser Glu Met Thr Thr Val Met Asn
    6770                6775                6780

Lys Asp Pro Glu Ile Leu Ser Trp Thr Ile Pro Pro Ser Ile Glu Lys
6785                6790                6795                6800

Thr Ser Phe Ser Ser Ser Leu Met Pro Ser Pro Ala Met Thr Ser Pro
                6805                6810                6815

Pro Val Ser Ser Thr Leu Pro Lys Thr Ile His Thr Thr Pro Ser Pro
                6820            6825                6830

Met Thr Ser Leu Leu Thr Pro Ser Leu Val Met Thr Thr Asp Thr Leu
            6835                6840            6845

Gly Thr Ser Pro Glu Pro Thr Thr Ser Ser Pro Pro Asn Leu Ser Ser
    6850                6855                6860

Thr Ser His Val Ile Leu Thr Asp Glu Asp Thr Thr Ala Ile Glu
6865                6870                6875                6880
```

```
Ala Met His Pro Ser Thr Ser Thr Ala Ala Thr Asn Val Glu Thr Thr
                6885                6890                6895

Cys Ser Gly His Gly Ser Gln Ser Ser Val Leu Thr Asp Ser Glu Lys
                6900                6905                6910

Thr Lys Ala Thr Ala Pro Met Asp Thr Thr Ser Thr Met Gly His Thr
                6915                6920                6925

Thr Val Ser Thr Ser Met Ser Val Ser Ser Glu Thr Lys Ile Lys
                6930                6935                6940

Arg Glu Ser Thr Tyr Ser Leu Thr Pro Gly Leu Arg Glu Thr Ser Ile
6945                6950                6955                6960

Ser Gln Asn Ala Ser Phe Ser Thr Asp Thr Ser Ile Val Leu Ser Glu
                6965                6970                6975

Val Pro Thr Gly Thr Thr Ala Glu Val Ser Arg Thr Glu Val Thr Ser
                6980                6985                6990

Ser Gly Arg Thr Ser Ile Pro Gly Pro Ser Gln Ser Thr Val Leu Pro
                6995                7000                7005

Glu Ile Ser Thr Arg Thr Met Thr Arg Leu Phe Ala Ser Pro Thr Met
                7010                7015                7020

Thr Glu Ser Ala Glu Met Thr Ile Pro Thr Gln Thr Gly Pro Ser Gly
7025                7030                7035                7040

Ser Thr Ser Gln Asp Thr Leu Thr Leu Asp Thr Ser Thr Thr Lys Ser
                7045                7050                7055

Gln Ala Lys Thr His Ser Thr Leu Thr Gln Arg Phe Pro His Ser Glu
                7060                7065                7070

Met Thr Thr Leu Met Ser Arg Gly Pro Gly Asp Met Ser Trp Gln Ser
                7075                7080                7085

Ser Pro Ser Leu Glu Asn Pro Ser Ser Leu Pro Ser Leu Leu Ser Leu
                7090                7095                7100

Pro Ala Thr Thr Ser Pro Pro Ile Ser Ser Thr Leu Pro Val Thr
7105                7110                7115                7120

Ile Ser Ser Ser Pro Leu Pro Val Thr Ser Leu Leu Thr Ser Ser Pro
                7125                7130                7135

Val Thr Thr Thr Asp Met Leu His Thr Ser Pro Glu Leu Val Thr Ser
                7140                7145                7150

Ser Pro Pro Lys Leu Ser His Thr Ser Asp Glu Arg Leu Thr Thr Gly
                7155                7160                7165

Lys Asp Thr Thr Asn Thr Glu Ala Val His Pro Ser Thr Asn Thr Ala
7170                7175                7180

Ala Ser Asn Val Glu Ile Pro Ser Phe Gly His Glu Ser Pro Ser Ser
7185                7190                7195                7200

Ala Leu Ala Asp Ser Glu Thr Ser Lys Ala Thr Ser Pro Met Phe Ile
                7205                7210                7215

Thr Ser Thr Gln Glu Asp Thr Ser Val Ala Ile Ser Thr Pro His Phe
                7220                7225                7230

Leu Glu Thr Ser Arg Ile Gln Lys Gly Ser Ile Ser Ser Leu Ser Pro
                7235                7240                7245

Lys Leu Arg Glu Thr Gly Ser Ser Val Glu Thr Ser Ser Ala Ile Glu
                7250                7255                7260

Thr Ser Ala Val Leu Ser Glu Val Ser Ile Gly Ala Thr Thr Glu Ile
7265                7270                7275                7280

Ser Arg Thr Glu Val Thr Ser Ser Arg Thr Ser Ile Ser Gly Ser
                7285                7290                7295
```

```
Ala Glu Ser Thr Met Leu Pro Glu Ile Ser Thr Thr Arg Lys Ile Ile
            7300                7305                7310

Lys Phe Pro Thr Ser Pro Ile Leu Ala Glu Ser Ser Glu Met Thr Ile
            7315                7320            7325

Lys Thr Gln Thr Ser Pro Pro Gly Ser Thr Ser Glu Ser Thr Phe Thr
            7330                7335                7340

Leu Asp Thr Ser Thr Thr Pro Ser Leu Val Ile Thr His Ser Thr Met
7345                7350                7355                7360

Thr Gln Arg Leu Pro His Ser Glu Ile Thr Thr Leu Val Ser Arg Gly
            7365                7370                7375

Ala Gly Asp Val Pro Arg Pro Ser Ser Leu Pro Val Glu Glu Thr Ser
            7380                7385                7390

Pro Pro Ser Ser Gln Leu Ser Leu Ser Ala Met Ile Ser Pro Ser Pro
            7395                7400            7405

Val Ser Ser Thr Leu Pro Ala Ser Ser His Ser Ser Ser Ala Ser Val
            7410                7415                7420

Thr Ser Pro Leu Thr Pro Gly Gln Val Lys Thr Thr Glu Val Leu Asp
7425                7430                7435                7440

Ala Ser Ala Glu Pro Glu Thr Ser Ser Pro Pro Ser Leu Ser Ser Thr
            7445                7450                7455

Ser Val Glu Ile Leu Ala Thr Ser Glu Val Thr Thr Asp Thr Glu Lys
            7460                7465            7470

Ile His Pro Phe Pro Asn Thr Ala Val Thr Lys Val Gly Thr Ser Ser
            7475                7480                7485

Ser Gly His Glu Ser Pro Ser Ser Val Leu Pro Asp Ser Glu Thr Thr
            7490                7495            7500

Lys Ala Thr Ser Ala Met Gly Thr Ile Ser Ile Met Gly Asp Thr Ser
7505                7510                7515                7520

Val Ser Thr Leu Thr Pro Ala Leu Ser Asn Thr Arg Lys Ile Gln Ser
            7525                7530                7535

Glu Pro Ala Ser Ser Leu Thr Thr Arg Leu Arg Glu Thr Ser Thr Ser
            7540                7545            7550

Glu Glu Thr Ser Leu Ala Thr Glu Ala Asn Thr Val Leu Ser Lys Val
            7555                7560            7565

Ser Thr Gly Ala Thr Thr Glu Val Ser Arg Thr Glu Ala Ile Ser Phe
            7570                7575            7580

Ser Arg Thr Ser Met Ser Gly Pro Glu Gln Ser Thr Met Ser Gln Asp
7585                7590                7595                7600

Ile Ser Ile Gly Thr Ile Pro Arg Ile Ser Ala Ser Ser Val Leu Thr
            7605                7610            7615

Glu Ser Ala Lys Met Thr Ile Thr Gln Thr Gly Pro Ser Glu Ser
            7620                7625            7630

Thr Leu Glu Ser Thr Leu Asn Leu Asn Thr Ala Thr Thr Pro Ser Trp
            7635                7640            7645

Val Glu Thr His Ser Ile Val Ile Gln Gly Phe Pro His Pro Glu Met
            7650                7655            7660

Thr Thr Ser Met Gly Arg Gly Pro Gly Val Ser Trp Pro Ser Pro
7665                7670                7675                7680

Pro Phe Val Lys Glu Thr Ser Pro Ser Ser Pro Leu Ser Leu Pro
            7685                7690            7695

Ala Val Thr Ser Pro His Pro Val Ser Thr Thr Phe Leu Ala His Ile
            7700                7705            7710

Pro Pro Ser Pro Leu Pro Val Thr Ser Leu Leu Thr Ser Gly Pro Ala
```

```
                    7715                7720                7725
Thr Thr Thr Asp Ile Leu Gly Thr Ser Thr Glu Pro Gly Thr Ser Ser
                7730                7735                7740
Ser Ser Ser Leu Ser Thr Thr Ser His Glu Arg Leu Thr Thr Tyr Lys
7745                7750                7755                7760
Asp Thr Ala His Thr Glu Ala Val His Pro Ser Thr Asn Thr Gly Gly
                    7765                7770                7775
Thr Asn Val Ala Thr Thr Ser Ser Gly Tyr Lys Ser Gln Ser Ser Val
                7780                7785                7790
Leu Ala Asp Ser Ser Pro Met Cys Thr Thr Ser Thr Met Gly Asp Thr
                7795                7800                7805
Ser Val Leu Thr Ser Thr Pro Ala Phe Leu Glu Thr Arg Arg Ile Gln
                7810                7815                7820
Thr Glu Leu Ala Ser Ser Leu Thr Pro Gly Leu Arg Glu Ser Ser Gly
7825                7830                7835                7840
Ser Glu Gly Thr Ser Ser Gly Thr Lys Met Ser Thr Val Leu Ser Lys
                    7845                7850                7855
Val Pro Thr Gly Ala Thr Thr Glu Ile Ser Lys Glu Asp Val Thr Ser
                7860                7865                7870
Ile Pro Gly Pro Ala Gln Ser Thr Ile Ser Pro Asp Ile Ser Thr Arg
                7875                7880                7885
Thr Val Ser Trp Phe Ser Thr Ser Pro Val Met Thr Glu Ser Ala Glu
                7890                7895                7900
Ile Thr Met Asn Thr His Thr Ser Pro Leu Gly Ala Thr Thr Gln Gly
7905                7910                7915                7920
Thr Ser Thr Leu Ala Thr Ser Ser Thr Thr Ser Leu Thr Met Thr His
                    7925                7930                7935
Ser Thr Ile Ser Gln Gly Phe Ser His Ser Gln Met Ser Thr Leu Met
                7940                7945                7950
Arg Arg Gly Pro Glu Asp Val Ser Trp Met Ser Pro Leu Leu Glu
                7955                7960                7965
Lys Thr Arg Pro Ser Phe Ser Leu Met Ser Ser Pro Ala Thr Thr Ser
                7970                7975                7980
Pro Ser Pro Val Ser Ser Thr Leu Pro Glu Ser Ile Ser Ser Ser Pro
7985                7990                7995                8000
Leu Pro Val Thr Ser Leu Leu Thr Ser Gly Leu Ala Lys Thr Thr Asp
                    8005                8010                8015
Met Leu His Lys Ser Ser Glu Pro Val Thr Asn Ser Pro Ala Asn Leu
                8020                8025                8030
Ser Ser Thr Ser Val Glu Ile Leu Ala Thr Ser Glu Val Thr Thr Asp
                8035                8040                8045
Thr Glu Lys Thr His Pro Ser Ser Asn Arg Thr Val Thr Asp Val Gly
                8050                8055                8060
Thr Ser Ser Ser Gly His Glu Ser Thr Ser Phe Val Leu Ala Asp Ser
8065                8070                8075                8080
Gln Thr Ser Lys Val Thr Ser Pro Met Val Ile Thr Ser Thr Met Glu
                    8085                8090                8095
Asp Thr Ser Val Ser Thr Ser Thr Pro Gly Phe Phe Glu Thr Ser Arg
                8100                8105                8110
Ile Gln Thr Glu Pro Thr Ser Ser Leu Thr Leu Gly Leu Arg Lys Thr
                8115                8120                8125
Ser Ser Ser Glu Gly Thr Ser Leu Ala Thr Glu Met Ser Thr Val Leu
                8130                8135                8140
```

```
Ser Gly Val Pro Thr Gly Ala Thr Ala Glu Val Ser Arg Thr Glu Val
8145                8150                8155                8160

Thr Ser Ser Ser Arg Thr Ser Ile Ser Gly Phe Ala Gln Leu Thr Val
                8165                8170                8175

Ser Pro Glu Thr Ser Glu Thr Ile Thr Arg Leu Pro Thr Ser Ser
            8180                8185                8190

Ile Met Thr Glu Ser Ala Glu Met Met Ile Lys Thr Gln Thr Asp Pro
            8195                8200                8205

Pro Gly Ser Thr Pro Glu Ser Thr His Thr Val Asp Ile Ser Thr Thr
        8210                8215                8220

Pro Asn Trp Val Glu Thr His Ser Thr Val Thr Gln Arg Phe Ser His
8225                8230                8235                8240

Ser Glu Met Thr Thr Leu Val Ser Arg Ser Pro Gly Asp Met Leu Trp
                8245                8250                8255

Pro Ser Gln Ser Ser Val Glu Glu Thr Ser Ser Ala Ser Ser Leu Leu
            8260                8265                8270

Ser Leu Pro Ala Thr Thr Ser Pro Ser Pro Val Ser Ser Thr Leu Val
            8275                8280                8285

Glu Asp Phe Pro Ser Ala Ser Leu Pro Val Thr Ser Leu Leu Thr Pro
    8290                8295                8300

Gly Leu Val Ile Thr Thr Asp Arg Met Gly Ile Ser Arg Glu Pro Gly
8305                8310                8315                8320

Thr Ser Ser Thr Ser Asn Leu Ser Ser Thr Ser His Glu Arg Leu Thr
                8325                8330                8335

Thr Leu Glu Asp Thr Val Asp Thr Glu Asp Met Gln Pro Ser Thr His
            8340                8345                8350

Thr Ala Val Thr Asn Val Arg Thr Ser Ile Ser Gly His Glu Ser Gln
            8355                8360                8365

Ser Ser Val Leu Ser Asp Ser Glu Thr Pro Lys Ala Thr Ser Pro Met
    8370                8375                8380

Gly Thr Thr Tyr Thr Met Gly Glu Thr Ser Val Ser Ile Ser Thr Ser
8385                8390                8395                8400

Asp Phe Phe Glu Thr Ser Arg Ile Gln Ile Glu Pro Thr Ser Ser Leu
            8405                8410                8415

Thr Ser Gly Leu Arg Glu Thr Ser Ser Ser Glu Arg Ile Ser Ser Ala
            8420                8425                8430

Thr Glu Gly Ser Thr Val Leu Ser Glu Val Pro Ser Gly Ala Thr Thr
            8435                8440                8445

Glu Val Ser Arg Thr Glu Val Ile Ser Ser Arg Gly Thr Ser Met Ser
    8450                8455                8460

Gly Pro Asp Gln Phe Thr Ile Ser Pro Asp Ile Ser Thr Glu Ala Ile
8465                8470                8475                8480

Thr Arg Leu Ser Thr Ser Pro Ile Met Thr Glu Ser Ala Glu Ser Ala
            8485                8490                8495

Ile Thr Ile Glu Thr Gly Ser Pro Gly Ala Thr Ser Glu Gly Thr Leu
        8500                8505                8510

Thr Leu Asp Thr Ser Thr Thr Thr Phe Trp Ser Gly Thr His Ser Thr
        8515                8520                8525

Ala Ser Pro Gly Phe Ser His Ser Glu Met Thr Thr Leu Met Ser Arg
            8530                8535                8540

Thr Pro Gly Asp Val Pro Trp Pro Ser Leu Pro Ser Val Glu Glu Ala
8545                8550                8555                8560
```

```
Ser Ser Val Ser Ser Ser Leu Ser Ser Pro Ala Met Thr Ser Thr Ser
            8565                8570                8575

Phe Phe Ser Ala Leu Pro Glu Ser Ile Ser Ser Pro His Pro Val
        8580                8585                8590

Thr Ala Leu Leu Thr Leu Gly Pro Val Lys Thr Thr Asp Met Leu Arg
            8595                8600                8605

Thr Ser Ser Glu Pro Glu Thr Ser Ser Pro Pro Asn Leu Ser Ser Thr
            8610                8615                8620

Ser Ala Glu Ile Leu Ala Thr Ser Glu Val Thr Lys Asp Arg Glu Lys
8625                8630                8635                8640

Ile His Pro Ser Ser Asn Thr Pro Val Val Asn Val Gly Thr Val Ile
            8645                8650                8655

Tyr Lys His Leu Ser Pro Ser Ser Val Leu Ala Asp Leu Val Thr Thr
            8660                8665                8670

Lys Pro Thr Ser Pro Met Ala Thr Thr Ser Thr Leu Gly Asn Thr Ser
            8675                8680                8685

Val Ser Thr Ser Thr Pro Ala Phe Pro Glu Thr Met Met Thr Gln Pro
            8690                8695                8700

Thr Ser Ser Leu Thr Ser Gly Leu Arg Glu Ile Ser Thr Ser Gln Glu
8705                8710                8715                8720

Thr Ser Ser Ala Thr Glu Arg Ser Ala Ser Leu Ser Gly Met Pro Thr
            8725                8730                8735

Gly Ala Thr Thr Lys Val Ser Arg Thr Glu Ala Leu Ser Leu Gly Arg
            8740                8745                8750

Thr Ser Thr Pro Gly Pro Ala Gln Ser Thr Ile Ser Pro Glu Ile Ser
            8755                8760                8765

Thr Glu Thr Ile Thr Arg Ile Ser Thr Pro Leu Thr Thr Thr Gly Ser
            8770                8775                8780

Ala Glu Met Thr Ile Thr Pro Lys Thr Gly His Ser Gly Ala Ser Ser
8785                8790                8795                8800

Gln Gly Thr Phe Thr Leu Asp Thr Ser Ser Arg Ala Ser Trp Pro Gly
            8805                8810                8815

Thr His Ser Ala Ala Thr His Arg Ser Pro His Ser Gly Met Thr Thr
            8820                8825                8830

Pro Met Ser Arg Gly Pro Glu Asp Val Ser Trp Pro Ser Arg Pro Ser
            8835                8840                8845

Val Glu Lys Thr Ser Pro Pro Ser Ser Leu Val Ser Leu Ser Ala Val
            8850                8855                8860

Thr Ser Pro Ser Pro Leu Tyr Ser Thr Pro Ser Glu Ser Ser His Ser
8865                8870                8875                8880

Ser Pro Leu Arg Val Thr Ser Leu Phe Thr Pro Val Met Met Lys Thr
            8885                8890                8895

Thr Asp Met Leu Asp Thr Ser Leu Glu Pro Val Thr Thr Ser Pro Pro
            8900                8905                8910

Ser Met Asn Ile Thr Ser Asp Glu Ser Leu Ala Thr Ser Lys Ala Thr
            8915                8920                8925

Met Glu Thr Glu Ala Ile Gln Leu Ser Glu Asn Thr Ala Val Thr Gln
            8930                8935                8940

Met Gly Thr Ile Ser Ala Arg Gln Glu Phe Tyr Ser Ser Tyr Pro Gly
8945                8950                8955                8960

Leu Pro Glu Pro Ser Lys Val Thr Ser Pro Val Val Thr Ser Ser Thr
            8965                8970                8975

Ile Lys Asp Ile Val Ser Thr Thr Ile Pro Ala Ser Ser Glu Ile Thr
```

-continued

```
            8980                8985                8990
Arg Ile Glu Met Glu Ser Thr Ser Thr Leu Thr Pro Thr Pro Arg Glu
        8995                9000                9005
Thr Ser Thr Ser Gln Glu Ile His Ser Ala Thr Lys Pro Ser Thr Val
    9010                9015                9020
Pro Tyr Lys Ala Leu Thr Ser Ala Thr Ile Glu Asp Ser Met Thr Gln
9025                9030                9035                9040
Val Met Ser Ser Ser Arg Gly Pro Ser Pro Asp Gln Ser Thr Met Ser
                9045                9050                9055
Gln Asp Ile Ser Ser Glu Val Ile Thr Arg Leu Ser Thr Ser Pro Ile
            9060                9065                9070
Lys Ala Glu Ser Thr Glu Met Thr Ile Thr Thr Gln Thr Gly Ser Pro
        9075                9080                9085
Gly Ala Thr Ser Arg Gly Thr Leu Thr Leu Asp Thr Ser Thr Thr Phe
    9090                9095                9100
Met Ser Gly Thr His Ser Thr Ala Ser Gln Gly Phe Ser His Ser Gln
9105                9110                9115                9120
Met Thr Ala Leu Met Ser Arg Thr Pro Gly Asp Val Pro Trp Leu Ser
                9125                9130                9135
His Pro Ser Val Glu Glu Ala Ser Ser Ala Ser Phe Ser Leu Ser Ser
            9140                9145                9150
Pro Val Met Thr Ser Ser Ser Pro Val Ser Ser Thr Leu Pro Asp Ser
        9155                9160                9165
Ile His Ser Ser Ser Leu Pro Val Thr Ser Leu Leu Thr Ser Gly Leu
    9170                9175                9180
Val Lys Thr Thr Glu Leu Leu Gly Thr Ser Ser Glu Pro Glu Thr Ser
9185                9190                9195                9200
Ser Pro Pro Asn Leu Ser Ser Thr Ser Ala Glu Ile Leu Ala Thr Thr
                9205                9210                9215
Glu Val Thr Thr Asp Thr Glu Lys Leu Glu Met Thr Asn Val Val Thr
            9220                9225                9230
Ser Gly Tyr Thr His Glu Ser Pro Ser Ser Val Leu Ala Asp Ser Val
        9235                9240                9245
Thr Thr Lys Ala Thr Ser Ser Met Gly Ile Thr Tyr Pro Thr Gly Asp
    9250                9255                9260
Thr Asn Val Leu Thr Ser Thr Pro Ala Phe Ser Asp Thr Ser Arg Ile
9265                9270                9275                9280
Gln Thr Lys Ser Lys Leu Ser Leu Thr Pro Gly Leu Met Glu Thr Ser
                9285                9290                9295
Ile Ser Glu Glu Thr Ser Ser Ala Thr Glu Lys Ser Thr Val Leu Ser
            9300                9305                9310
Ser Val Pro Thr Gly Ala Thr Thr Glu Val Ser Arg Thr Glu Ala Ile
        9315                9320                9325
Ser Ser Ser Arg Thr Ser Ile Pro Gly Pro Ala Gln Ser Thr Met Ser
    9330                9335                9340
Ser Asp Thr Ser Met Glu Thr Ile Thr Arg Ile Ser Thr Pro Leu Thr
9345                9350                9355                9360
Arg Lys Glu Ser Thr Asp Met Ala Ile Thr Pro Lys Thr Gly Pro Ser
                9365                9370                9375
Gly Ala Thr Ser Gln Gly Thr Phe Thr Leu Asp Ser Ser Ser Thr Ala
            9380                9385                9390
Ser Trp Pro Gly Thr His Ser Ala Thr Thr Gln Arg Phe Pro Gln Ser
        9395                9400                9405
```

```
Val Val Thr Thr Pro Met Ser Arg Gly Pro Glu Asp Val Ser Trp Pro
    9410            9415            9420

Ser Pro Leu Ser Val Glu Lys Asn Ser Pro Ser Ser Leu Val Ser
9425            9430            9435            9440

Ser Ser Ser Val Thr Ser Pro Ser Pro Leu Tyr Ser Thr Pro Ser Gly
            9445            9450            9455

Ser Ser His Ser Ser Pro Val Pro Val Thr Ser Leu Phe Thr Ser Ile
            9460            9465            9470

Met Met Lys Ala Thr Asp Met Leu Asp Ala Ser Leu Glu Pro Glu Thr
            9475            9480            9485

Thr Ser Ala Pro Asn Met Asn Ile Thr Ser Asp Glu Ser Leu Ala Thr
            9490            9495            9500

Ser Lys Ala Thr Thr Glu Thr Glu Ala Ile His Val Phe Glu Asn Thr
9505            9510            9515            9520

Ala Ala Ser His Val Glu Thr Thr Ser Ala Thr Glu Glu Leu Tyr Ser
            9525            9530            9535

Ser Ser Pro Gly Phe Ser Glu Pro Thr Lys Val Ile Ser Pro Val Val
            9540            9545            9550

Thr Ser Ser Ser Ile Arg Asp Asn Met Val Ser Thr Thr Met Pro Gly
            9555            9560            9565

Ser Ser Gly Ile Thr Arg Ile Glu Ile Glu Ser Met Ser Ser Leu Thr
            9570            9575            9580

Pro Gly Leu Arg Glu Thr Arg Thr Ser Gln Asp Ile Thr Ser Ser Thr
9585            9590            9595            9600

Glu Thr Ser Thr Val Leu Tyr Lys Met Ser Ser Gly Ala Thr Pro Glu
            9605            9610            9615

Val Ser Arg Thr Glu Val Met Pro Ser Ser Arg Thr Ser Ile Pro Gly
            9620            9625            9630

Pro Ala Gln Ser Thr Met Ser Leu Asp Ile Ser Asp Glu Val Val Thr
            9635            9640            9645

Arg Leu Ser Thr Ser Pro Ile Met Thr Glu Ser Ala Glu Ile Thr Ile
            9650            9655            9660

Thr Thr Gln Thr Gly Tyr Ser Leu Ala Thr Ser Gln Val Thr Leu Pro
9665            9670            9675            9680

Leu Gly Thr Ser Met Thr Phe Leu Ser Gly Thr His Ser Thr Met Ser
            9685            9690            9695

Gln Gly Leu Ser His Ser Glu Met Thr Asn Leu Met Ser Arg Gly Pro
            9700            9705            9710

Glu Ser Leu Ser Trp Thr Ser Pro Arg Phe Val Glu Thr Thr Arg Ser
            9715            9720            9725

Ser Ser Ser Leu Thr Ser Leu Pro Leu Thr Thr Ser Leu Ser Pro Val
            9730            9735            9740

Ser Ser Thr Leu Leu Asp Ser Pro Ser Ser Pro Leu Pro Val Thr
9745            9750            9755            9760

Ser Leu Ile Leu Pro Gly Leu Val Lys Thr Thr Glu Val Leu Asp Thr
            9765            9770            9775

Ser Ser Glu Pro Lys Thr Ser Ser Pro Asn Leu Ser Ser Thr Ser
            9780            9785            9790

Val Glu Ile Pro Ala Thr Ser Glu Ile Met Thr Asp Thr Glu Lys Ile
            9795            9800            9805

His Pro Ser Ser Asn Thr Ala Val Ala Lys Val Arg Thr Ser Ser Ser
            9810            9815            9820
```

-continued

```
Val His Glu Ser His Ser Ser Val Leu Ala Asp Ser Glu Thr Thr Ile
9825                9830                9835                9840

Thr Ile Pro Ser Met Gly Ile Thr Ser Ala Val Asp Asp Thr Thr Val
                9845                9850                9855

Phe Thr Ser Asn Pro Ala Phe Ser Glu Thr Arg Arg Ile Pro Thr Glu
                9860                9865                9870

Pro Thr Phe Ser Leu Thr Pro Gly Phe Arg Glu Thr Ser Thr Ser Glu
                9875                9880                9885

Glu Thr Thr Ser Ile Thr Glu Thr Ser Ala Val Leu Tyr Gly Val Pro
9890                9895                9900

Thr Ser Ala Thr Thr Glu Val Ser Met Thr Glu Ile Met Ser Ser Asn
9905                9910                9915                9920

Arg Thr His Ile Pro Asp Ser Asp Gln Ser Thr Met Ser Pro Asp Ile
                9925                9930                9935

Ile Thr Glu Val Ile Thr Arg Leu Ser Ser Ser Met Met Ser Glu
                9940                9945                9950

Ser Thr Gln Met Thr Ile Thr Thr Gln Lys Ser Ser Pro Gly Ala Thr
                9955                9960                9965

Ala Gln Ser Thr Leu Thr Leu Ala Thr Thr Ala Pro Leu Ala Arg
                9970                9975                9980

Thr His Ser Thr Val Pro Pro Arg Phe Leu His Ser Glu Met Thr Thr
9985                9990                9995                10000

Leu Met Ser Arg Ser Pro Glu Asn Pro Ser Trp Lys Ser Ser Pro Phe
                10005               10010               10015

Val Glu Lys Thr Ser Ser Ser Ser Leu Leu Ser Leu Pro Val Thr
                10020               10025               10030

Thr Ser Pro Ser Val Ser Ser Thr Leu Pro Gln Ser Ile Pro Ser Ser
                10035               10040               10045

Ser Phe Ser Val Thr Ser Leu Leu Thr Pro Gly Met Val Lys Thr Thr
                10050               10055               10060

Asp Thr Ser Thr Glu Pro Gly Thr Ser Leu Ser Pro Asn Leu Ser Gly
10065               10070               10075               10080

Thr Ser Val Glu Ile Leu Ala Ala Ser Glu Val Thr Thr Asp Thr Glu
                10085               10090               10095

Lys Ile His Pro Ser Ser Ser Met Ala Val Thr Asn Val Gly Thr Thr
                10100               10105               10110

Ser Ser Gly His Glu Leu Tyr Ser Ser Val Ser Ile His Ser Glu Pro
                10115               10120               10125

Ser Lys Ala Thr Tyr Pro Val Gly Thr Pro Ser Ser Met Ala Glu Thr
                10130               10135               10140

Ser Ile Ser Thr Ser Met Pro Ala Asn Phe Glu Thr Thr Gly Phe Glu
10145               10150               10155               10160

Ala Glu Pro Phe Ser His Leu Thr Ser Gly Phe Arg Lys Thr Asn Met
                10165               10170               10175

Ser Leu Asp Thr Ser Ser Val Thr Pro Thr Asn Thr Pro Ser Ser Pro
                10180               10185               10190

Gly Ser Thr His Leu Leu Gln Ser Ser Lys Thr Asp Phe Thr Ser Ser
                10195               10200               10205

Ala Lys Thr Ser Ser Pro Asp Trp Pro Pro Ala Ser Gln Tyr Thr Glu
                10210               10215               10220

Ile Pro Val Asp Ile Ile Thr Pro Phe Asn Ala Ser Pro Ser Ile Thr
10225               10230               10235               10240

Glu Ser Thr Gly Ile Thr Ser Phe Pro Glu Ser Arg Phe Thr Met Ser
```

-continued

```
            10245           10250           10255
Val Thr Glu Ser Thr His His Leu Ser Thr Asp Leu Leu Pro Ser Ala
        10260           10265           10270
Glu Thr Ile Ser Thr Gly Thr Val Met Pro Ser Leu Ser Glu Ala Met
        10275           10280           10285
Thr Ser Phe Ala Thr Thr Gly Val Pro Arg Ala Ile Ser Gly Ser Gly
        10290           10295           10300
Ser Pro Phe Ser Arg Thr Glu Ser Gly Pro Gly Asp Ala Thr Leu Ser
10305           10310           10315           10320
Thr Ile Ala Glu Ser Leu Pro Ser Ser Thr Pro Val Pro Phe Ser Ser
            10325           10330           10335
Ser Thr Phe Thr Thr Thr Asp Ser Ser Thr Ile Pro Ala Leu His Glu
            10340           10345           10350
Ile Thr Ser Ser Ser Ala Thr Pro Tyr Arg Val Asp Thr Ser Leu Gly
            10355           10360           10365
Thr Glu Ser Ser Thr Thr Glu Gly Arg Leu Val Met Val Ser Thr Leu
            10370           10375           10380
Asp Thr Ser Ser Gln Pro Gly Arg Thr Ser Ser Thr Pro Ile Leu Asp
10385           10390           10395           10400
Thr Arg Met Thr Glu Ser Val Glu Leu Gly Thr Val Thr Ser Ala Tyr
            10405           10410           10415
Gln Val Pro Ser Leu Ser Thr Arg Leu Thr Arg Thr Asp Gly Ile Met
            10420           10425           10430
Glu His Ile Thr Lys Ile Pro Asn Glu Ala Ala His Arg Gly Thr Ile
            10435           10440           10445
Arg Pro Val Lys Gly Pro Gln Thr Ser Thr Ser Pro Ala Ser Pro Lys
    10450           10455           10460
Gly Leu His Thr Gly Gly Thr Lys Arg Met Glu Thr Thr Thr Thr Ala
10465           10470           10475           10480
Leu Lys Thr Thr Thr Thr Ala Leu Lys Thr Thr Ser Arg Ala Thr Leu
            10485           10490           10495
Thr Thr Ser Val Tyr Thr Pro Thr Leu Gly Thr Leu Thr Pro Leu Asn
            10500           10505           10510
Ala Ser Arg Gln Met Ala Ser Thr Ile Leu Thr Glu Met Met Ile Thr
            10515           10520           10525
Thr Pro Tyr Val Phe Pro Asp Val Pro Glu Thr Thr Ser Ser Leu Ala
            10530           10535           10540
Thr Ser Leu Gly Ala Glu Thr Ser Thr Ala Leu Pro Arg Thr Thr Pro
10545           10550           10555           10560
Ser Val Leu Asn Arg Glu Ser Glu Thr Thr Ala Ser Leu Val Ser Arg
            10565           10570           10575
Ser Gly Ala Glu Arg Ser Pro Val Ile Gln Thr Leu Asp Val Ser Ser
            10580           10585           10590
Ser Glu Pro Asp Thr Thr Ala Ser Trp Val Ile His Pro Ala Glu Thr
            10595           10600           10605
Ile Pro Thr Val Ser Lys Thr Thr Pro Asn Phe Phe His Ser Glu Leu
            10610           10615           10620
Asp Thr Val Ser Ser Thr Ala Thr Ser His Gly Ala Asp Val Ser Ser
10625           10630           10635           10640
Ala Ile Pro Thr Asn Ile Ser Pro Ser Glu Leu Asp Ala Leu Thr Pro
            10645           10650           10655
Leu Val Thr Ile Ser Gly Thr Asp Thr Ser Thr Thr Phe Pro Thr Leu
            10660           10665           10670
```

-continued

```
Thr Lys Ser Pro His Glu Thr Glu Thr Arg Thr Thr Trp Leu Thr His
        10675               10680               10685

Pro Ala Glu Thr Ser Ser Thr Ile Pro Arg Thr Ile Pro Asn Phe Ser
        10690               10695               10700

His His Glu Ser Asp Ala Thr Pro Ser Ile Ala Thr Ser Pro Gly Ala
10705               10710               10715               10720

Glu Thr Ser Ser Ala Ile Pro Ile Met Thr Val Ser Pro Gly Ala Glu
            10725               10730               10735

Asp Leu Val Thr Ser Gln Val Thr Ser Ser Gly Thr Asp Arg Asn Met
                10740               10745               10750

Thr Ile Pro Thr Leu Thr Leu Ser Pro Gly Glu Pro Lys Thr Ile Ala
        10755               10760               10765

Ser Leu Val Thr His Pro Glu Ala Gln Thr Ser Ser Ala Ile Pro Thr
    10770               10775               10780

Ser Thr Ile Ser Pro Ala Val Ser Arg Leu Val Thr Ser Met Val Thr
10785               10790               10795               10800

Ser Leu Ala Ala Lys Thr Ser Thr Thr Asn Arg Ala Leu Thr Asn Ser
            10805               10810               10815

Pro Gly Glu Pro Ala Thr Thr Val Ser Leu Val Thr His Pro Ala Gln
                10820               10825               10830

Thr Ser Pro Thr Val Pro Trp Thr Thr Ser Ile Phe Phe His Ser Lys
        10835               10840               10845

Ser Asp Thr Thr Pro Ser Met Thr Thr Ser His Gly Ala Glu Ser Ser
    10850               10855               10860

Ser Ala Val Pro Thr Pro Thr Val Ser Thr Glu Val Pro Gly Val Val
10865               10870               10875               10880

Thr Pro Leu Val Thr Ser Ser Arg Ala Val Ile Ser Thr Thr Ile Pro
            10885               10890               10895

Ile Leu Thr Leu Ser Pro Gly Glu Pro Glu Thr Thr Pro Ser Met Ala
                10900               10905               10910

Thr Ser His Gly Glu Glu Ala Ser Ser Ala Ile Pro Thr Pro Thr Val
        10915               10920               10925

Ser Pro Gly Val Pro Gly Val Val Thr Ser Leu Val Thr Ser Ser Arg
    10930               10935               10940

Ala Val Thr Ser Thr Thr Ile Pro Ile Leu Thr Phe Ser Leu Gly Glu
10945               10950               10955               10960

Pro Glu Thr Thr Pro Ser Met Ala Thr Ser His Gly Thr Glu Ala Gly
            10965               10970               10975

Ser Ala Val Pro Thr Val Leu Pro Glu Val Pro Gly Met Val Thr Ser
                10980               10985               10990

Leu Val Ala Ser Ser Arg Ala Val Thr Ser Thr Thr Leu Pro Thr Leu
        10995               11000               11005

Thr Leu Ser Pro Gly Glu Pro Glu Thr Thr Pro Ser Met Ala Thr Ser
    11010               11015               11020

His Gly Ala Glu Ala Ser Ser Thr Val Pro Thr Val Ser Pro Glu Val
11025               11030               11035               11040

Pro Gly Val Val Thr Ser Leu Val Thr Ser Ser Ser Gly Val Asn Ser
            11045               11050               11055

Thr Ser Ile Pro Thr Leu Ile Leu Ser Pro Gly Glu Leu Glu Thr Thr
                11060               11065               11070

Pro Ser Met Ala Thr Ser His Gly Ala Glu Ala Ser Ser Ala Val Pro
        11075               11080               11085
```

```
Thr Pro Thr Val Ser Pro Gly Val Ser Gly Val Val Thr Pro Leu Val
    11090              11095              11100

Thr Ser Ser Arg Ala Val Thr Ser Thr Thr Ile Pro Ile Leu Thr Leu
11105              11110              11115              11120

Ser Ser Ser Glu Pro Glu Thr Pro Ser Met Ala Thr Ser His Gly
        11125              11130              11135

Val Glu Ala Ser Ser Ala Val Leu Thr Val Ser Pro Glu Val Pro Gly
        11140              11145              11150

Met Val Thr Ser Leu Val Thr Ser Ser Arg Ala Val Thr Ser Thr Thr
        11155              11160              11165

Ile Pro Thr Leu Thr Ile Ser Ser Asp Glu Pro Glu Thr Thr Thr Ser
        11170              11175              11180

Leu Val Thr His Ser Glu Ala Lys Met Ile Ser Ala Ile Pro Thr Leu
11185              11190              11195              11200

Ala Val Ser Pro Thr Val Gln Gly Leu Val Thr Ser Leu Val Thr Ser
        11205              11210              11215

Ser Gly Ser Glu Thr Ser Ala Phe Ser Asn Leu Thr Val Ala Ser Ser
        11220              11225              11230

Gln Pro Glu Thr Ile Asp Ser Trp Val Ala His Pro Gly Thr Glu Ala
        11235              11240              11245

Ser Ser Val Val Pro Thr Leu Thr Val Ser Thr Gly Glu Pro Phe Thr
        11250              11255              11260

Asn Ile Ser Leu Val Thr His Pro Ala Glu Ser Ser Ser Thr Leu Pro
11265              11270              11275              11280

Arg Thr Thr Ser Arg Phe Ser His Ser Glu Leu Asp Thr Met Pro Ser
        11285              11290              11295

Thr Val Thr Ser Pro Glu Ala Glu Ser Ser Ser Ala Ile Ser Thr Thr
        11300              11305              11310

Ile Ser Pro Gly Ile Pro Gly Val Leu Thr Ser Leu Val Thr Ser Ser
        11315              11320              11325

Gly Arg Asp Ile Ser Ala Thr Phe Pro Thr Val Pro Glu Ser Pro His
        11330              11335              11340

Glu Ser Glu Ala Thr Ala Ser Trp Val Thr His Pro Ala Val Thr Ser
11345              11350              11355              11360

Thr Thr Val Pro Arg Thr Thr Pro Asn Tyr Ser His Ser Glu Pro Asp
        11365              11370              11375

Thr Thr Pro Ser Ile Ala Thr Ser Pro Gly Ala Glu Ala Thr Ser Asp
        11380              11385              11390

Phe Pro Thr Ile Thr Val Ser Pro Asp Val Pro Asp Met Val Thr Ser
        11395              11400              11405

Gln Val Thr Ser Ser Gly Thr Asp Thr Ser Ile Thr Ile Pro Thr Leu
        11410              11415              11420

Thr Leu Ser Ser Gly Glu Pro Glu Thr Thr Thr Ser Phe Ile Thr Tyr
11425              11430              11435              11440

Ser Glu Thr His Thr Ser Ser Ala Ile Pro Thr Leu Pro Val Ser Pro
        11445              11450              11455

Gly Ala Ser Lys Met Leu Thr Ser Leu Val Ile Ser Ser Gly Thr Asp
        11460              11465              11470

Ser Thr Thr Thr Phe Pro Thr Leu Thr Glu Pro Tyr Glu Pro Glu
        11475              11480              11485

Thr Thr Ala Ile Gln Leu Ile His Pro Ala Glu Thr Asn Thr Met Val
        11490              11495              11500

Pro Lys Thr Thr Pro Lys Phe Ser His Ser Lys Ser Asp Thr Thr Leu
```

-continued

```
        11505               11510               11515               11520

Pro Val Ala Ile Thr Ser Gly Pro Glu Ala Ser Ser Ala Val Ser
                11525               11530               11535

Thr Thr Thr Ile Ser Pro Asp Met Ser Asp Leu Val Thr Ser Leu Val
        11540               11545               11550

Pro Ser Ser Gly Thr Asp Thr Ser Thr Thr Phe Pro Thr Leu Ser Glu
        11555               11560               11565

Thr Pro Tyr Glu Pro Glu Thr Thr Val Thr Trp Leu Thr His Pro Ala
        11570               11575               11580

Glu Thr Ser Thr Thr Val Ser Gly Thr Ile Pro Asn Phe Ser His Arg
11585               11590               11595               11600

Gly Ser Asp Thr Ala Pro Ser Met Val Thr Ser Pro Gly Val Asp Thr
                11605               11610               11615

Arg Ser Gly Val Pro Thr Thr Ile Pro Pro Ser Ile Pro Gly Val
                11620               11625               11630

Val Thr Ser Gln Val Thr Ser Ser Ala Thr Asp Thr Ser Thr Ala Ile
                11635               11640               11645

Pro Thr Leu Thr Pro Ser Pro Gly Glu Pro Glu Thr Thr Ala Ser Ser
        11650               11655               11660

Ala Thr His Pro Gly Thr Gln Thr Gly Phe Thr Val Pro Ile Arg Thr
11665               11670               11675               11680

Val Pro Ser Ser Glu Pro Asp Thr Met Ala Ser Trp Val Thr His Pro
                11685               11690               11695

Pro Gln Thr Ser Thr Pro Val Ser Arg Thr Thr Ser Ser Phe Ser His
                11700               11705               11710

Ser Ser Pro Asp Ala Thr Pro Val Met Ala Thr Ser Pro Arg Thr Glu
                11715               11720               11725

Ala Ser Ser Ala Val Leu Thr Thr Ile Ser Pro Gly Ala Pro Glu Met
        11730               11735               11740

Val Thr Ser Gln Ile Thr Ser Ser Gly Ala Ala Thr Ser Thr Thr Val
11745               11750               11755               11760

Pro Thr Leu Thr His Ser Pro Gly Met Pro Glu Thr Thr Ala Leu Leu
                11765               11770               11775

Ser Thr His Pro Arg Thr Gly Thr Ser Lys Thr Phe Pro Ala Ser Thr
                11780               11785               11790

Val Phe Pro Gln Val Ser Glu Thr Thr Ala Ser Leu Thr Ile Arg Pro
        11795               11800               11805

Gly Ala Glu Thr Ser Thr Ala Leu Pro Thr Gln Thr Thr Ser Ser Leu
        11810               11815               11820

Phe Thr Leu Leu Val Thr Gly Thr Ser Arg Val Asp Leu Ser Pro Thr
11825               11830               11835               11840

Ala Ser Pro Gly Val Ser Ala Lys Thr Ala Pro Leu Ser Thr His Pro
                11845               11850               11855

Gly Thr Glu Thr Ser Thr Met Ile Pro Thr Ser Thr Leu Ser Leu Gly
        11860               11865               11870

Leu Leu Glu Thr Thr Gly Leu Leu Ala Thr Ser Ser Ser Ala Glu Thr
        11875               11880               11885

Ser Thr Ser Thr Leu Thr Leu Thr Val Ser Pro Ala Val Ser Gly Leu
        11890               11895               11900

Ser Ser Ala Ser Ile Thr Thr Asp Lys Pro Gln Thr Val Thr Ser Trp
11905               11910               11915               11920

Asn Thr Glu Thr Ser Pro Ser Val Thr Ser Val Gly Pro Pro Glu Phe
                11925               11930               11935
```

```
Ser Arg Thr Val Thr Gly Thr Thr Met Thr Leu Ile Pro Ser Glu Met
        11940                11945                11950

Pro Thr Pro Pro Lys Thr Ser His Gly Glu Gly Val Ser Pro Thr Thr
        11955                11960                11965

Ile Leu Arg Thr Thr Met Val Glu Ala Thr Asn Leu Ala Thr Thr Gly
        11970                11975                11980

Ser Ser Pro Thr Val Ala Lys Thr Thr Thr Thr Phe Asn Thr Leu Ala
11985                11990                11995                12000

Gly Ser Leu Phe Thr Pro Leu Thr Thr Pro Gly Met Ser Thr Leu Ala
                12005                12010                12015

Ser Glu Ser Val Thr Ser Arg Thr Ser Tyr Asn His Arg Ser Trp Ile
        12020                12025                12030

Ser Thr Thr Ser Ser Tyr Asn Arg Arg Tyr Trp Thr Pro Ala Thr Ser
        12035                12040                12045

Thr Pro Val Thr Ser Thr Phe Ser Pro Gly Ile Ser Thr Ser Ser Ile
        12050                12055                12060

Pro Ser Ser Thr Ala Ala Thr Val Pro Phe Met Val Pro Phe Thr Leu
12065                12070                12075                12080

Asn Phe Thr Ile Thr Asn Leu Gln Tyr Glu Glu Asp Met Arg His Pro
                12085                12090                12095

Gly Ser Arg Lys Phe Asn Ala Thr Glu Arg Glu Leu Gln Gly Leu Leu
                12100                12105                12110

Lys Pro Leu Phe Arg Asn Ser Ser Leu Glu Tyr Leu Tyr Ser Gly Cys
                12115                12120                12125

Arg Leu Ala Ser Leu Arg Pro Glu Lys Asp Ser Ser Ala Met Ala Val
        12130                12135                12140

Asp Ala Ile Cys Thr His Arg Pro Asp Pro Glu Asp Leu Gly Leu Asp
12145                12150                12155                12160

Arg Glu Arg Leu Tyr Trp Glu Leu Ser Asn Leu Thr Asn Gly Ile Gln
                12165                12170                12175

Glu Leu Gly Pro Tyr Thr Leu Asp Arg Asn Ser Leu Tyr Val Asn Gly
                12180                12185                12190

Phe Thr His Arg Ser Ser Met Pro Thr Thr Ser Thr Pro Gly Thr Ser
        12195                12200                12205

Thr Val Asp Val Gly Thr Ser Gly Thr Pro Ser Ser Pro Ser Pro
        12210                12215                12220

Thr Ala Ala Gly Pro Leu Leu Met Pro Phe Thr Leu Asn Phe Thr Ile
12225                12230                12235                12240

Thr Asn Leu Gln Tyr Glu Glu Asp Met Arg Arg Thr Gly Ser Arg Lys
                12245                12250                12255

Phe Asn Thr Met Glu Ser Val Leu Gln Gly Leu Leu Lys Pro Leu Phe
                12260                12265                12270

Lys Asn Thr Ser Val Gly Pro Leu Tyr Ser Gly Cys Arg Leu Thr Leu
                12275                12280                12285

Leu Arg Pro Glu Lys Asp Gly Ala Ala Thr Gly Val Asp Ala Ile Cys
        12290                12295                12300

Thr His Arg Leu Asp Pro Lys Ser Pro Gly Leu Asn Arg Glu Gln Leu
12305                12310                12315                12320

Tyr Trp Glu Leu Ser Lys Leu Thr Asn Asp Ile Glu Glu Leu Gly Pro
                12325                12330                12335

Tyr Thr Leu Asp Arg Asn Ser Leu Tyr Val Asn Gly Phe Thr His Gln
                12340                12345                12350
```

```
Ser Ser Val Ser Thr Thr Ser Thr Pro Gly Thr Ser Thr Val Asp Leu
        12355               12360               12365

Arg Thr Ser Gly Thr Pro Ser Ser Leu Ser Ser Pro Thr Ile Met Ala
        12370               12375               12380

Ala Gly Pro Leu Leu Val Pro Phe Thr Leu Asn Phe Thr Ile Thr Asn
12385               12390               12395               12400

Leu Gln Tyr Gly Glu Asp Met Gly His Pro Gly Ser Arg Lys Phe Asn
            12405               12410               12415

Thr Thr Glu Arg Val Leu Gln Gly Leu Leu Gly Pro Ile Phe Lys Asn
            12420               12425               12430

Thr Ser Val Gly Pro Leu Tyr Ser Gly Cys Arg Leu Thr Ser Leu Arg
            12435               12440               12445

Ser Glu Lys Asp Gly Ala Ala Thr Gly Val Asp Ala Ile Cys Ile His
        12450               12455               12460

His Leu Asp Pro Lys Ser Pro Gly Leu Asn Arg Glu Arg Leu Tyr Trp
12465               12470               12475               12480

Glu Leu Ser Gln Leu Thr Asn Gly Ile Lys Glu Leu Gly Pro Tyr Thr
            12485               12490               12495

Leu Asp Arg Asn Ser Leu Tyr Val Asn Gly Phe Thr His Arg Thr Ser
        12500               12505               12510

Val Pro Thr Thr Ser Thr Pro Gly Thr Ser Thr Val Asp Leu Gly Thr
        12515               12520               12525

Ser Gly Thr Pro Phe Ser Leu Pro Ser Pro Ala Thr Ala Gly Pro Leu
        12530               12535               12540

Leu Val Leu Phe Thr Leu Asn Phe Thr Ile Thr Asn Leu Lys Tyr Glu
12545               12550               12555               12560

Glu Asp Met His Arg Pro Gly Ser Arg Lys Phe Asn Thr Thr Glu Arg
            12565               12570               12575

Val Leu Gln Thr Leu Leu Gly Pro Met Phe Lys Asn Thr Ser Val Gly
            12580               12585               12590

Leu Leu Tyr Ser Gly Cys Arg Leu Thr Leu Leu Arg Ser Glu Lys Asp
        12595               12600               12605

Gly Ala Ala Thr Gly Val Asp Ala Ile Cys Thr His Arg Leu Asp Pro
        12610               12615               12620

Lys Ser Pro Gly Leu Asp Arg Glu Gln Leu Tyr Trp Glu Leu Ser Gln
12625               12630               12635               12640

Leu Thr Asn Gly Ile Lys Glu Leu Gly Pro Tyr Thr Leu Asp Arg Asn
            12645               12650               12655

Ser Leu Tyr Val Asn Gly Phe Thr His Trp Ile Pro Val Pro Thr Ser
            12660               12665               12670

Ser Thr Pro Gly Thr Ser Thr Val Asp Leu Gly Ser Gly Thr Pro Ser
            12675               12680               12685

Ser Leu Pro Ser Pro Thr Ala Ala Gly Pro Leu Leu Val Pro Phe Thr
        12690               12695               12700

Leu Asn Phe Thr Ile Thr Asn Leu Gln Tyr Glu Glu Asp Met His His
12705               12710               12715               12720

Pro Gly Ser Arg Lys Phe Asn Thr Thr Glu Arg Val Leu Gln Gly Leu
            12725               12730               12735

Leu Gly Pro Met Phe Lys Asn Thr Ser Val Gly Leu Leu Tyr Ser Gly
            12740               12745               12750

Cys Arg Leu Thr Leu Leu Arg Ser Glu Lys Asp Gly Ala Ala Thr Gly
        12755               12760               12765

Val Asp Ala Ile Cys Thr His Arg Leu Asp Pro Lys Ser Pro Gly Val
```

```
            12770               12775               12780

Asp Arg Glu Gln Leu Tyr Trp Glu Leu Ser Gln Leu Thr Asn Gly Ile
12785               12790               12795               12800

Lys Glu Leu Gly Pro Tyr Thr Leu Asp Arg Asn Ser Leu Tyr Val Asn
                12805               12810               12815

Gly Phe Thr His Gln Thr Ser Ala Pro Asn Thr Ser Thr Pro Gly Thr
            12820               12825               12830

Ser Thr Val Asp Leu Gly Thr Ser Gly Thr Pro Ser Ser Leu Pro Ser
                12835               12840               12845

Pro Thr Ser Ala Gly Pro Leu Leu Val Pro Phe Thr Leu Asn Phe Thr
            12850               12855               12860

Ile Thr Asn Leu Gln Tyr Glu Glu Asp Met Arg His Pro Gly Ser Arg
12865               12870               12875               12880

Lys Phe Asn Thr Thr Glu Arg Val Leu Gln Gly Leu Leu Lys Pro Leu
                12885               12890               12895

Phe Lys Ser Thr Ser Val Gly Pro Leu Tyr Ser Gly Cys Arg Leu Thr
            12900               12905               12910

Leu Leu Arg Ser Glu Lys Asp Gly Ala Ala Thr Gly Val Asp Ala Ile
                12915               12920               12925

Cys Thr His Arg Leu Asp Pro Lys Ser Pro Gly Val Asp Arg Glu Gln
            12930               12935               12940

Leu Tyr Trp Glu Leu Ser Gln Leu Thr Asn Gly Ile Lys Glu Leu Gly
12945               12950               12955               12960

Pro Tyr Thr Leu Asp Arg Asn Ser Leu Tyr Val Asn Gly Phe Thr His
                12965               12970               12975

Gln Thr Ser Ala Pro Asn Thr Ser Thr Pro Gly Thr Ser Thr Val Asp
            12980               12985               12990

Leu Gly Thr Ser Gly Thr Pro Ser Ser Leu Pro Ser Pro Thr Ser Ala
                12995               13000               13005

Gly Pro Leu Leu Val Pro Phe Thr Leu Asn Phe Thr Ile Thr Asn Leu
            13010               13015               13020

Gln Tyr Glu Glu Asp Met His His Pro Gly Ser Arg Lys Phe Asn Thr
13025               13030               13035               13040

Thr Glu Arg Val Leu Gln Gly Leu Leu Gly Pro Met Phe Lys Asn Thr
                13045               13050               13055

Ser Val Gly Leu Leu Tyr Ser Gly Cys Arg Leu Thr Leu Leu Arg Pro
            13060               13065               13070

Glu Lys Asn Gly Ala Ala Thr Gly Met Asp Ala Ile Cys Ser His Arg
                13075               13080               13085

Leu Asp Pro Lys Ser Pro Gly Leu Asn Arg Glu Gln Leu Tyr Trp Glu
            13090               13095               13100

Leu Ser Gln Leu Thr His Gly Ile Lys Glu Leu Gly Pro Tyr Thr Leu
13105               13110               13115               13120

Asp Arg Asn Ser Leu Tyr Val Asn Gly Phe Thr His Arg Ser Ser Val
                13125               13130               13135

Ala Pro Thr Ser Thr Pro Gly Thr Ser Thr Val Asp Leu Gly Thr Ser
            13140               13145               13150

Gly Thr Pro Ser Ser Leu Pro Ser Pro Thr Thr Ala Val Pro Leu Leu
                13155               13160               13165

Val Pro Phe Thr Leu Asn Phe Thr Ile Thr Asn Leu Gln Tyr Gly Glu
            13170               13175               13180

Asp Met Arg His Pro Gly Ser Arg Lys Phe Asn Thr Thr Glu Arg Val
13185               13190               13195               13200
```

```
Leu Gln Gly Leu Leu Gly Pro Leu Phe Lys Asn Ser Ser Val Gly Pro
        13205               13210               13215

Leu Tyr Ser Gly Cys Arg Leu Ile Ser Leu Arg Ser Glu Lys Asp Gly
        13220               13225           13230

Ala Ala Thr Gly Val Asp Ala Ile Cys Thr His His Leu Asn Pro Gln
        13235               13240               13245

Ser Pro Gly Leu Asp Arg Glu Gln Leu Tyr Trp Gln Leu Ser Gln Met
        13250               13255           13260

Thr Asn Gly Ile Lys Glu Leu Gly Pro Tyr Thr Leu Asp Arg Asn Ser
13265               13270               13275               13280

Leu Tyr Val Asn Gly Phe Thr His Arg Ser Ser Gly Leu Thr Thr Ser
            13285           13290               13295

Thr Pro Trp Thr Ser Thr Val Asp Leu Gly Thr Ser Gly Thr Pro Ser
        13300               13305               13310

Pro Val Pro Ser Pro Thr Thr Ala Gly Pro Leu Leu Val Pro Phe Thr
            13315           13320               13325

Leu Asn Phe Thr Ile Thr Asn Leu Gln Tyr Glu Glu Asp Met His Arg
        13330               13335           13340

Pro Gly Ser Arg Lys Phe Asn Thr Thr Glu Arg Val Leu Gln Gly Leu
13345               13350               13355               13360

Leu Ser Pro Ile Phe Lys Asn Ser Ser Val Gly Pro Leu Tyr Ser Gly
            13365           13370               13375

Cys Arg Leu Thr Ser Leu Arg Pro Glu Lys Asp Gly Ala Ala Thr Gly
            13380           13385               13390

Met Asp Ala Val Cys Leu Tyr His Pro Asn Pro Lys Arg Pro Gly Leu
        13395               13400               13405

Asp Arg Glu Gln Leu Tyr Trp Glu Leu Ser Gln Leu Thr His Asn Ile
        13410               13415           13420

Thr Glu Leu Gly Pro Tyr Ser Leu Asp Arg Asp Ser Leu Tyr Val Asn
13425               13430               13435               13440

Gly Phe Thr His Gln Asn Ser Val Pro Thr Thr Ser Thr Pro Gly Thr
            13445               13450           13455

Ser Thr Val Tyr Trp Ala Thr Thr Gly Thr Pro Ser Ser Phe Pro Gly
        13460               13465               13470

His Thr Glu Pro Gly Pro Leu Leu Ile Pro Phe Thr Phe Asn Phe Thr
        13475               13480           13485

Ile Thr Asn Leu His Tyr Glu Glu Asn Met Gln His Pro Gly Ser Arg
        13490               13495           13500

Lys Phe Asn Thr Thr Glu Arg Val Leu Gln Gly Leu Leu Lys Pro Leu
13505               13510               13515               13520

Phe Lys Asn Thr Ser Val Gly Pro Leu Tyr Ser Gly Cys Arg Leu Thr
            13525           13530               13535

Ser Leu Arg Pro Glu Lys Asp Gly Ala Ala Thr Gly Met Asp Ala Val
            13540           13545               13550

Cys Leu Tyr His Pro Asn Pro Lys Arg Pro Gly Leu Asp Arg Glu Gln
        13555               13560               13565

Leu Tyr Trp Glu Leu Ser Gln Leu Thr His Asn Ile Thr Glu Leu Gly
        13570               13575           13580

Pro Tyr Ser Leu Asp Arg Asp Ser Leu Tyr Val Asn Gly Phe Thr His
13585               13590               13595               13600

Gln Asn Ser Val Pro Thr Thr Ser Thr Pro Gly Thr Ser Thr Val Tyr
            13605               13610               13615
```

```
Trp Ala Thr Thr Gly Thr Pro Ser Ser Phe Pro Gly His Thr Glu Pro
            13620               13625               13630
Gly Pro Leu Leu Ile Pro Phe Thr Phe Asn Phe Thr Ile Thr Asn Leu
        13635               13640               13645
His Tyr Glu Glu Asn Met Gln His Pro Gly Ser Arg Lys Phe Asn Thr
    13650               13655               13660
Thr Glu Arg Val Leu Gln Gly Leu Leu Lys Pro Leu Phe Lys Asn Thr
13665               13670               13675               13680
Ser Val Gly Pro Leu Tyr Ser Gly Cys Arg Leu Thr Leu Leu Arg Pro
            13685               13690               13695
Glu Lys His Glu Ala Ala Thr Gly Val Asp Thr Ile Cys Thr His Arg
        13700               13705               13710
Val Asp Pro Ile Gly Pro Gly Leu Asp Arg Glu Arg Leu Tyr Trp Glu
    13715               13720               13725
Leu Ser Gln Leu Thr Asn Ser Ile Thr Glu Leu Gly Pro Tyr Thr Leu
    13730               13735               13740
Asp Arg Asp Ser Leu Tyr Val Asn Gly Phe Asn Pro Arg Ser Ser Val
13745               13750               13755               13760
Pro Thr Thr Ser Thr Pro Gly Thr Ser Thr Val His Leu Ala Thr Ser
            13765               13770               13775
Gly Thr Pro Ser Ser Leu Pro Gly His Thr Ala Pro Val Pro Leu Leu
        13780               13785               13790
Ile Pro Phe Thr Leu Asn Phe Thr Ile Thr Asn Leu His Tyr Glu Glu
    13795               13800               13805
Asn Met Gln His Pro Gly Ser Arg Lys Phe Asn Thr Thr Glu Arg Val
    13810               13815               13820
Leu Gln Gly Leu Leu Lys Pro Leu Phe Lys Asn Thr Ser Val Gly Pro
13825               13830               13835               13840
Leu Tyr Ser Gly Cys Arg Leu Thr Leu Leu Arg Pro Glu Lys His Glu
            13845               13850               13855
Ala Ala Thr Gly Val Asp Thr Ile Cys Thr His Arg Val Asp Pro Ile
        13860               13865               13870
Gly Pro Gly Leu Xaa Xaa Glu Xaa Leu Tyr Trp Glu Leu Ser Xaa Leu
    13875               13880               13885
Thr Xaa Xaa Ile Xaa Glu Leu Gly Pro Tyr Thr Leu Asp Arg Xaa Ser
    13890               13895               13900
Leu Tyr Val Asn Gly Phe Thr His Xaa Xaa Ser Xaa Pro Thr Thr Ser
13905               13910               13915               13920
Thr Pro Gly Thr Ser Thr Val Xaa Xaa Gly Thr Ser Gly Thr Pro Ser
            13925               13930               13935
Ser Xaa Pro Xaa Xaa Thr Ser Ala Gly Pro Leu Leu Val Pro Phe Thr
        13940               13945               13950
Leu Asn Phe Thr Ile Thr Asn Leu Gln Tyr Glu Glu Asp Met His His
    13955               13960               13965
Pro Gly Ser Arg Lys Phe Asn Thr Thr Glu Arg Val Leu Gln Gly Leu
    13970               13975               13980
Leu Gly Pro Met Phe Lys Asn Thr Ser Val Gly Leu Leu Tyr Ser Gly
13985               13990               13995               14000
Cys Arg Leu Thr Leu Leu Arg Pro Glu Lys Asn Gly Ala Ala Thr Gly
            14005               14010               14015
Met Asp Ala Ile Cys Ser His Arg Leu Asp Pro Lys Ser Pro Gly Leu
        14020               14025               14030
Asp Arg Glu Gln Leu Tyr Trp Glu Leu Ser Gln Leu Thr His Gly Ile
```

-continued

Lys Glu Leu Gly Pro Tyr Thr Leu Asp Arg Asn Ser Leu Tyr Val Asn
14035            14040            14045
                 14050            14055            14060

Gly Phe Thr His Arg Ser Ser Val Ala Pro Thr Ser Thr Pro Gly Thr
14065            14070            14075            14080

Ser Thr Val Asp Leu Gly Thr Ser Gly Thr Pro Ser Ser Leu Pro Ser
                 14085            14090            14095

Pro Thr Thr Ala Val Pro Leu Leu Val Pro Phe Thr Leu Asn Phe Thr
            14100            14105            14110

Ile Thr Asn Leu Gln Tyr Gly Glu Asp Met Arg His Pro Gly Ser Arg
            14115            14120            14125

Lys Phe Asn Thr Thr Glu Arg Val Leu Gln Gly Leu Leu Gly Pro Leu
14130            14135            14140

Phe Lys Asn Ser Ser Val Gly Pro Leu Tyr Ser Gly Cys Arg Leu Ile
14145            14150            14155            14160

Ser Leu Arg Ser Glu Lys Asp Gly Ala Ala Thr Gly Val Asp Ala Ile
            14165            14170            14175

Cys Thr His His Leu Asn Pro Gln Ser Pro Gly Leu Asp Arg Glu Gln
            14180            14185            14190

Leu Tyr Trp Gln Leu Ser Gln Met Thr Asn Gly Ile Lys Glu Leu Gly
            14195            14200            14205

Pro Tyr Thr Leu Asp Arg Asn Ser Leu Tyr Val Asn Gly Phe Thr His
            14210            14215            14220

Arg Ser Ser Gly Leu Thr Thr Ser Thr Pro Trp Thr Ser Thr Val Asp
14225            14230            14235            14240

Leu Gly Thr Ser Gly Thr Pro Ser Pro Val Pro Ser Pro Thr Thr Ala
            14245            14250            14255

Gly Pro Leu Leu Val Pro Phe Thr Leu Asn Phe Thr Ile Thr Asn Leu
            14260            14265            14270

Gln Tyr Glu Glu Asp Met His Arg Pro Gly Ser Arg Lys Phe Asn Ala
            14275            14280            14285

Thr Glu Arg Val Leu Gln Gly Leu Leu Ser Pro Ile Phe Lys Asn Ser
            14290            14295            14300

Ser Val Gly Pro Leu Tyr Ser Gly Cys Arg Leu Thr Ser Leu Arg Pro
14305            14310            14315            14320

Glu Lys Asp Gly Ala Ala Thr Gly Met Asp Ala Val Cys Leu Tyr His
            14325            14330            14335

Pro Asn Pro Lys Arg Pro Gly Leu Asp Arg Glu Gln Leu Tyr Trp Glu
            14340            14345            14350

Leu Ser Gln Leu Thr His Asn Ile Thr Glu Leu Gly Pro Tyr Ser Leu
            14355            14360            14365

Asp Arg Asp Ser Leu Tyr Val Asn Gly Phe Thr His Gln Ser Ser Met
            14370            14375            14380

Thr Thr Thr Arg Thr Pro Asp Thr Ser Thr Met His Leu Ala Thr Ser
14385            14390            14395            14400

Arg Thr Pro Ala Ser Leu Ser Gly Pro Thr Thr Ala Ser Pro Leu Leu
            14405            14410            14415

Val Leu Phe Thr Ile Asn Cys Thr Ile Thr Asn Leu Gln Tyr Glu Glu
            14420            14425            14430

Asp Met Arg Arg Thr Gly Ser Arg Lys Phe Asn Thr Met Glu Ser Val
            14435            14440            14445

Leu Gln Gly Leu Leu Lys Pro Leu Phe Lys Asn Thr Ser Val Gly Pro
            14450            14455            14460

```
Leu Tyr Ser Gly Cys Arg Leu Thr Leu Leu Arg Pro Lys Lys Asp Gly
14465               14470               14475               14480

Ala Ala Thr Gly Val Asp Ala Ile Cys Thr His Arg Leu Asp Pro Lys
                14485               14490               14495

Ser Pro Gly Leu Asn Arg Glu Gln Leu Tyr Trp Glu Leu Ser Lys Leu
            14500               14505               14510

Thr Asn Asp Ile Glu Glu Leu Gly Pro Tyr Thr Leu Asp Arg Asn Ser
            14515               14520               14525

Leu Tyr Val Asn Gly Phe Thr His Gln Ser Ser Val Ser Thr Thr Ser
            14530               14535               14540

Thr Pro Gly Thr Ser Thr Val Asp Leu Arg Thr Ser Gly Thr Pro Ser
14545               14550               14555               14560

Ser Leu Ser Ser Pro Thr Ile Met Xaa Xaa Xaa Pro Leu Leu Xaa Pro
                14565               14570               14575

Phe Thr Xaa Asn Xaa Thr Ile Thr Asn Leu Xaa Xaa Xaa Xaa Xaa Met
            14580               14585               14590

Xaa Xaa Pro Gly Ser Arg Lys Phe Asn Thr Thr Glu Arg Val Leu Gln
            14595               14600               14605

Gly Leu Leu Arg Pro Leu Phe Lys Asn Thr Ser Val Ser Ser Leu Tyr
            14610               14615               14620

Ser Gly Cys Arg Leu Thr Leu Leu Arg Pro Glu Lys Asp Gly Ala Ala
14625               14630               14635               14640

Thr Arg Val Asp Ala Ala Cys Thr Tyr Arg Pro Asp Pro Lys Ser Pro
                14645               14650               14655

Gly Leu Asp Arg Glu Gln Leu Tyr Trp Glu Leu Ser Gln Leu Thr His
            14660               14665               14670

Ser Ile Thr Glu Leu Gly Pro Tyr Thr Leu Asp Arg Val Ser Leu Tyr
            14675               14680               14685

Val Asn Gly Phe Asn Pro Arg Ser Ser Val Pro Thr Thr Ser Thr Pro
            14690               14695               14700

Gly Thr Ser Thr Val His Leu Ala Thr Ser Gly Thr Pro Ser Ser Leu
14705               14710               14715               14720

Pro Gly His Thr Xaa Xaa Xaa Pro Leu Leu Xaa Pro Phe Thr Xaa Asn
                14725               14730               14735

Xaa Thr Ile Thr Asn Leu Xaa Xaa Xaa Xaa Xaa Met Xaa Xaa Pro Gly
            14740               14745               14750

Ser Arg Lys Phe Asn Thr Thr Glu Arg Val Leu Gln Gly Leu Leu Lys
            14755               14760               14765

Pro Leu Phe Arg Asn Ser Ser Leu Glu Tyr Leu Tyr Ser Gly Cys Arg
            14770               14775               14780

Leu Ala Ser Leu Arg Pro Glu Lys Asp Ser Ser Ala Met Ala Val Asp
14785               14790               14795               14800

Ala Ile Cys Thr His Arg Pro Asp Pro Glu Asp Leu Gly Leu Asp Arg
                14805               14810               14815

Glu Arg Leu Tyr Trp Glu Leu Ser Asn Leu Thr Asn Gly Ile Gln Glu
            14820               14825               14830

Leu Gly Pro Tyr Thr Leu Asp Arg Asn Ser Leu Tyr Val Asn Gly Phe
            14835               14840               14845

Thr His Arg Ser Ser Gly Leu Thr Ser Thr Pro Trp Thr Ser Thr
            14850               14855               14860

Val Asp Leu Gly Thr Ser Gly Thr Pro Ser Pro Val Pro Ser Pro Thr
14865               14870               14875               14880
```

-continued

Thr Ala Gly Pro Leu Leu Val Pro Phe Thr Leu Asn Phe Thr Ile Thr
            14885                14890                14895

Asn Leu Gln Tyr Glu Glu Asp Met His Arg Pro Gly Ser Arg Arg Phe
            14900                14905                14910

Asn Thr Thr Glu Arg Val Leu Gln Gly Leu Leu Thr Pro Leu Phe Lys
            14915                14920                14925

Asn Thr Ser Val Gly Pro Leu Tyr Ser Gly Cys Arg Leu Thr Leu Leu
            14930                14935                14940

Arg Pro Glu Lys Gln Glu Ala Ala Thr Gly Val Asp Thr Ile Cys Thr
14945                14950                14955                14960

His Arg Val Asp Pro Ile Gly Pro Gly Leu Asp Arg Glu Arg Leu Tyr
            14965                14970                14975

Trp Glu Leu Ser Gln Leu Thr Asn Ser Ile Thr Glu Leu Gly Pro Tyr
            14980                14985                14990

Thr Leu Asp Arg Asp Ser Leu Tyr Val Asn Gly Phe Asn Pro Trp Ser
            14995                15000                15005

Ser Val Pro Thr Thr Ser Thr Pro Gly Thr Ser Thr Val His Leu Ala
            15010                15015                15020

Thr Ser Gly Thr Pro Ser Ser Leu Pro Gly His Thr Ala Pro Val Pro
15025                15030                15035                15040

Leu Leu Ile Pro Phe Thr Leu Asn Phe Thr Ile Thr Asp Leu His Tyr
            15045                15050                15055

Glu Glu Asn Met Gln His Pro Gly Ser Arg Lys Phe Asn Thr Thr Glu
            15060                15065                15070

Arg Val Leu Gln Gly Leu Leu Lys Pro Leu Phe Lys Ser Thr Ser Val
            15075                15080                15085

Gly Pro Leu Tyr Ser Gly Cys Arg Leu Thr Leu Leu Arg Pro Glu Lys
            15090                15095                15100

His Gly Ala Ala Thr Gly Val Asp Ala Ile Cys Thr Leu Arg Leu Asp
15105                15110                15115                15120

Pro Thr Gly Pro Gly Leu Asp Arg Glu Arg Leu Tyr Trp Glu Leu Ser
            15125                15130                15135

Gln Leu Thr Asn Ser Val Thr Glu Leu Gly Pro Tyr Thr Leu Asp Arg
            15140                15145                15150

Asp Ser Leu Tyr Val Asn Gly Phe Thr His Arg Ser Ser Val Pro Thr
            15155                15160                15165

Thr Ser Ile Pro Gly Thr Ser Ala Val His Leu Glu Thr Ser Gly Thr
            15170                15175                15180

Pro Ala Ser Leu Pro Gly His Thr Ala Pro Gly Pro Leu Leu Val Pro
15185                15190                15195                15200

Phe Thr Leu Asn Phe Thr Ile Thr Asn Leu Gln Tyr Glu Glu Asp Met
            15205                15210                15215

Arg His Pro Gly Ser Arg Lys Phe Ser Thr Thr Glu Arg Val Leu Gln
            15220                15225                15230

Gly Leu Leu Lys Pro Leu Phe Lys Asn Thr Ser Val Ser Ser Leu Tyr
            15235                15240                15245

Ser Gly Cys Arg Leu Thr Leu Leu Arg Pro Glu Lys Asp Gly Ala Ala
            15250                15255                15260

Thr Arg Val Asp Ala Val Cys Thr His Arg Pro Asp Pro Lys Ser Pro
15265                15270                15275                15280

Gly Leu Asp Arg Glu Arg Leu Tyr Trp Lys Leu Ser Gln Leu Thr His
            15285                15290                15295

Gly Ile Thr Glu Leu Gly Pro Tyr Thr Leu Asp Arg His Ser Leu Tyr

-continued

```
                15300              15305              15310
Val Asn Gly Phe Thr His Gln Ser Ser Met Thr Thr Arg Thr Pro
            15315              15320              15325
Asp Thr Ser Thr Met His Leu Ala Thr Ser Arg Thr Pro Ala Ser Leu
            15330              15335              15340
Ser Gly Pro Thr Thr Ala Ser Pro Leu Leu Val Leu Phe Thr Ile Asn
15345              15350              15355              15360
Phe Thr Ile Thr Asn Leu Arg Tyr Glu Glu Asn Met His His Pro Gly
            15365              15370              15375
Ser Arg Lys Phe Asn Thr Thr Glu Arg Val Leu Gln Gly Leu Leu Arg
            15380              15385              15390
Pro Val Phe Lys Asn Thr Ser Val Gly Pro Leu Tyr Ser Gly Cys Arg
            15395              15400              15405
Leu Thr Thr Leu Arg Pro Lys Lys Asp Gly Ala Ala Thr Lys Val Asp
            15410              15415              15420
Ala Ile Cys Thr Tyr Arg Pro Asp Pro Lys Ser Pro Gly Leu Asp Arg
15425              15430              15435              15440
Glu Gln Leu Tyr Trp Glu Leu Ser Gln Leu Thr His Ser Ile Thr Glu
            15445              15450              15455
Leu Gly Pro Tyr Thr Gln Asp Arg Asp Ser Leu Tyr Val Asn Gly Phe
            15460              15465              15470
Thr His Arg Ser Ser Val Pro Thr Thr Ser Ile Pro Gly Thr Ser Ala
            15475              15480              15485
Val His Leu Glu Thr Ser Gly Thr Pro Ala Ser Leu Pro Gly His Thr
            15490              15495              15500
Ala Pro Gly Pro Leu Leu Val Pro Phe Thr Leu Asn Phe Thr Ile Thr
15505              15510              15515              15520
Asn Leu Gln Tyr Glu Glu Asp Met Arg His Pro Gly Ser Arg Lys Phe
            15525              15530              15535
Asn Thr Thr Glu Arg Val Leu Gln Gly Leu Leu Lys Pro Leu Phe Lys
            15540              15545              15550
Ser Thr Ser Val Gly Pro Leu Tyr Ser Gly Cys Arg Leu Thr Leu Leu
            15555              15560              15565
Arg Pro Glu Lys Arg Gly Ala Ala Thr Gly Val Asp Thr Ile Cys Thr
            15570              15575              15580
His Arg Leu Asp Pro Leu Asn Pro Gly Leu Asp Arg Glu Gln Leu Tyr
15585              15590              15595              15600
Trp Glu Leu Ser Lys Leu Thr Arg Gly Ile Ile Glu Leu Gly Pro Tyr
            15605              15610              15615
Leu Leu Asp Arg Gly Ser Leu Tyr Val Asn Gly Phe Thr His Arg Thr
            15620              15625              15630
Ser Val Pro Thr Thr Ser Thr Pro Gly Thr Ser Thr Val Asp Leu Gly
            15635              15640              15645
Thr Ser Gly Thr Pro Phe Ser Leu Pro Ser Pro Ala Xaa Xaa Xaa Pro
            15650              15655              15660
Leu Leu Xaa Pro Phe Thr Xaa Asn Xaa Thr Ile Thr Asn Leu Xaa Xaa
15665              15670              15675              15680
Xaa Xaa Xaa Met Xaa Xaa Pro Gly Ser Arg Lys Phe Asn Thr Thr Glu
            15685              15690              15695
Arg Val Leu Gln Thr Leu Leu Gly Pro Met Phe Lys Asn Thr Ser Val
            15700              15705              15710
Gly Leu Leu Tyr Ser Gly Cys Arg Leu Thr Leu Leu Arg Ser Glu Lys
            15715              15720              15725
```

-continued

Asp Gly Ala Ala Thr Gly Val Asp Ala Ile Cys Thr His Arg Leu Asp
    15730               15735               15740

Pro Lys Ser Pro Gly Val Asp Arg Glu Gln Leu Tyr Trp Glu Leu Ser
15745               15750               15755               15760

Gln Leu Thr Asn Gly Ile Lys Glu Leu Gly Pro Tyr Thr Leu Asp Arg
            15765               15770               15775

Asn Ser Leu Tyr Val Asn Gly Phe Thr His Trp Ile Pro Val Pro Thr
        15780               15785               15790

Ser Ser Thr Pro Gly Thr Ser Thr Val Asp Leu Gly Ser Gly Thr Pro
            15795               15800               15805

Ser Ser Leu Pro Ser Pro Thr Thr Ala Gly Pro Leu Leu Val Pro Phe
        15810               15815               15820

Thr Leu Asn Phe Thr Ile Thr Asn Leu Lys Tyr Glu Glu Asp Met His
15825               15830               15835               15840

Cys Pro Gly Ser Arg Lys Phe Asn Thr Thr Glu Arg Val Leu Gln Ser
            15845               15850               15855

Leu Leu Gly Pro Met Phe Lys Asn Thr Ser Val Gly Pro Leu Tyr Ser
        15860               15865               15870

Gly Cys Arg Leu Thr Leu Leu Arg Ser Glu Lys Asp Gly Ala Ala Thr
            15875               15880               15885

Gly Val Asp Ala Ile Cys Thr His Arg Leu Asp Pro Lys Ser Pro Gly
    15890               15895               15900

Val Asp Arg Glu Gln Leu Tyr Trp Glu Leu Ser Gln Leu Thr Asn Gly
15905               15910               15915               15920

Ile Lys Glu Leu Gly Pro Tyr Thr Leu Asp Arg Asn Ser Leu Tyr Val
            15925               15930               15935

Asn Gly Phe Thr His Gln Thr Ser Ala Pro Asn Thr Ser Thr Pro Gly
        15940               15945               15950

Thr Ser Thr Val Asp Leu Gly Thr Ser Gly Thr Pro Ser Ser Leu Pro
            15955               15960               15965

Ser Pro Thr Xaa Xaa Xaa Pro Leu Leu Xaa Pro Phe Thr Xaa Asn Xaa
    15970               15975               15980

Thr Ile Thr Asn Leu Xaa Xaa Xaa Xaa Xaa Met Xaa Xaa Pro Gly Ser
15985               15990               15995               16000

Arg Lys Phe Asn Thr Thr Glu Xaa Val Leu Gln Gly Leu Leu Xaa Pro
            16005               16010               16015

Xaa Phe Lys Asn Xaa Ser Val Gly Xaa Leu Tyr Ser Gly Cys Arg Leu
        16020               16025               16030

Thr Xaa Leu Arg Xaa Glu Lys Xaa Gly Ala Ala Thr Gly Xaa Asp Ala
            16035               16040               16045

Ile Cys Xaa His Xaa Xaa Xaa Pro Lys Xaa Pro Gly Leu Xaa Xaa Glu
    16050               16055               16060

Xaa Leu Tyr Trp Glu Leu Ser Xaa Leu Thr Xaa Xaa Ile Xaa Glu Leu
16065               16070               16075               16080

Gly Pro Tyr Thr Leu Asp Arg Xaa Ser Leu Tyr Val Asn Gly Phe Thr
            16085               16090               16095

His Trp Ile Pro Val Pro Thr Ser Ser Thr Pro Gly Thr Ser Thr Val
        16100               16105               16110

Asp Leu Gly Ser Gly Thr Pro Ser Ser Leu Pro Ser Pro Thr Thr Ala
            16115               16120               16125

Gly Pro Leu Leu Val Pro Phe Thr Leu Asn Phe Thr Ile Thr Asn Leu
    16130               16135               16140

-continued

```
Lys Tyr Glu Glu Asp Met His Cys Pro Gly Ser Arg Lys Phe Asn Thr
16145               16150               16155               16160

Thr Glu Arg Val Leu Gln Ser Leu Leu Gly Pro Met Phe Lys Asn Thr
            16165               16170               16175

Ser Val Gly Pro Leu Tyr Ser Gly Cys Arg Leu Thr Ser Leu Arg Ser
    16180               16185               16190

Glu Lys Asp Gly Ala Ala Thr Gly Val Asp Ala Ile Cys Thr His Arg
        16195               16200               16205

Val Asp Pro Lys Ser Pro Gly Val Asp Arg Glu Gln Leu Tyr Trp Glu
    16210               16215               16220

Leu Ser Gln Leu Thr Asn Gly Ile Lys Glu Leu Gly Pro Tyr Thr Leu
16225               16230               16235               16240

Asp Arg Asn Ser Leu Tyr Val Asn Gly Phe Thr His Gln Thr Ser Ala
            16245               16250               16255

Pro Asn Thr Ser Thr Pro Gly Thr Ser Thr Val Xaa Xaa Gly Thr Ser
            16260               16265               16270

Gly Thr Pro Ser Ser Xaa Pro Xaa Xaa Thr Ser Ala Gly Pro Leu Leu
        16275               16280               16285

Val Pro Phe Thr Leu Asn Phe Thr Ile Thr Asn Leu Gln Tyr Glu Glu
    16290               16295               16300

Asp Met His His Pro Gly Ser Arg Lys Phe Asn Thr Thr Glu Arg Val
16305               16310               16315               16320

Leu Gln Gly Leu Leu Gly Pro Met Phe Lys Asn Thr Ser Val Gly Leu
            16325               16330               16335

Leu Tyr Ser Gly Cys Arg Leu Thr Leu Leu Arg Pro Glu Lys Asn Gly
            16340               16345               16350

Ala Thr Thr Gly Met Asp Ala Ile Cys Thr His Arg Leu Asp Pro Lys
        16355               16360               16365

Ser Pro Gly Leu Xaa Xaa Glu Xaa Leu Tyr Trp Glu Leu Ser Xaa Leu
        16370               16375               16380

Thr Xaa Xaa Ile Xaa Glu Leu Gly Pro Tyr Thr Leu Asp Arg Xaa Ser
16385               16390               16395               16400

Leu Tyr Val Asn Gly Phe Thr His Xaa Xaa Ser Xaa Pro Thr Thr Ser
            16405               16410               16415

Thr Pro Gly Thr Ser Thr Val Xaa Xaa Gly Thr Ser Gly Thr Pro Ser
        16420               16425               16430

Ser Xaa Pro Xaa Xaa Thr Xaa Xaa Xaa Pro Leu Leu Xaa Pro Phe Thr
    16435               16440               16445

Xaa Asn Xaa Thr Ile Thr Asn Leu Xaa Xaa Xaa Xaa Xaa Met Xaa Xaa
16450               16455               16460

Pro Gly Ser Arg Lys Phe Asn Thr Thr Glu Arg Val Leu Gln Gly Leu
16465               16470               16475               16480

Leu Lys Pro Leu Phe Arg Asn Ser Ser Leu Glu Tyr Leu Tyr Ser Gly
            16485               16490               16495

Cys Arg Leu Ala Ser Leu Arg Pro Glu Lys Asp Ser Ser Ala Met Ala
            16500               16505               16510

Val Asp Ala Ile Cys Thr His Arg Pro Asp Pro Glu Asp Leu Gly Leu
        16515               16520               16525

Asp Arg Glu Arg Leu Tyr Trp Glu Leu Ser Asn Leu Thr Asn Gly Ile
        16530               16535               16540

Gln Glu Leu Gly Pro Tyr Thr Leu Asp Arg Asn Ser Leu Tyr Val Asn
16545               16550               16555               16560

Gly Phe Thr His Arg Ser Ser Met Pro Thr Thr Ser Thr Pro Gly Thr
```

-continued

```
            16565               16570               16575
Ser Thr Val Asp Val Gly Thr Ser Gly Thr Pro Ser Ser Pro Ser
            16580               16585               16590
Pro Thr Thr Ala Gly Pro Leu Leu Ile Pro Phe Thr Leu Asn Phe Thr
            16595               16600               16605
Ile Thr Asn Leu Gln Tyr Gly Glu Asp Met Gly His Pro Gly Ser Arg
            16610               16615               16620
Lys Phe Asn Thr Thr Glu Arg Val Leu Gln Gly Leu Leu Gly Pro Ile
16625               16630               16635               16640
Phe Lys Asn Thr Ser Val Gly Pro Leu Tyr Ser Gly Cys Arg Leu Thr
            16645               16650               16655
Ser Leu Arg Ser Glu Lys Asp Gly Ala Ala Thr Gly Val Asp Ala Ile
            16660               16665               16670
Cys Ile His His Leu Asp Pro Lys Ser Pro Gly Leu Asn Arg Glu Arg
            16675               16680               16685
Leu Tyr Trp Glu Leu Ser Gln Leu Thr Asn Gly Ile Lys Glu Leu Gly
            16690               16695               16700
Pro Tyr Thr Leu Asp Arg Asn Ser Leu Tyr Val Asn Gly Phe Thr His
16705               16710               16715               16720
Arg Thr Ser Val Pro Thr Thr Ser Thr Pro Gly Thr Ser Thr Val Asp
            16725               16730               16735
Leu Gly Thr Ser Gly Thr Pro Phe Ser Leu Pro Ser Pro Ala Thr Ala
            16740               16745               16750
Gly Pro Leu Leu Val Leu Phe Thr Leu Asn Phe Thr Ile Thr Asn Leu
            16755               16760               16765
Lys Tyr Glu Glu Asp Met His Arg Pro Gly Ser Arg Lys Phe Asn Thr
            16770               16775               16780
Thr Glu Arg Val Leu Gln Thr Leu Leu Gly Pro Met Phe Lys Asn Thr
16785               16790               16795               16800
Ser Val Gly Leu Leu Tyr Ser Gly Cys Arg Leu Thr Leu Leu Arg Ser
            16805               16810               16815
Glu Lys Asp Gly Ala Ala Thr Gly Val Asp Ala Ile Cys Thr His Arg
            16820               16825               16830
Leu Asp Pro Lys Ser Pro Gly Leu Xaa Xaa Glu Xaa Leu Tyr Trp Glu
            16835               16840               16845
Leu Ser Xaa Leu Thr Xaa Xaa Ile Xaa Glu Leu Gly Pro Tyr Thr Leu
            16850               16855               16860
Asp Arg Xaa Ser Leu Tyr Val Asn Gly Phe Thr His Xaa Xaa Ser Xaa
16865               16870               16875               16880
Pro Thr Thr Ser Thr Pro Gly Thr Ser Thr Val Xaa Xaa Gly Thr Ser
            16885               16890               16895
Gly Thr Pro Ser Ser Xaa Pro Xaa Xaa Thr Xaa Xaa Xaa Pro Leu Leu
            16900               16905               16910
Xaa Pro Phe Thr Xaa Asn Xaa Thr Ile Thr Asn Leu Xaa Xaa Xaa Xaa
            16915               16920               16925
Xaa Met Xaa Xaa Pro Gly Ser Arg Lys Phe Asn Thr Thr Glu Arg Val
            16930               16935               16940
Leu Gln Gly Leu Leu Arg Pro Val Phe Lys Asn Thr Ser Val Gly Pro
16945               16950               16955               16960
Leu Tyr Ser Gly Cys Arg Leu Thr Leu Leu Arg Pro Lys Lys Asp Gly
            16965               16970               16975
Ala Ala Thr Lys Val Asp Ala Ile Cys Thr Tyr Arg Pro Asp Pro Lys
            16980               16985               16990
```

-continued

```
Ser Pro Gly Leu Asp Arg Glu Gln Leu Tyr Trp Glu Leu Ser Gln Leu
         16995                17000               17005

Thr His Ser Ile Thr Glu Leu Gly Pro Tyr Thr Gln Asp Arg Asp Ser
    17010                17015               17020

Leu Tyr Val Asn Gly Phe Thr His Arg Ser Ser Val Pro Thr Thr Ser
17025               17030               17035               17040

Ile Pro Gly Thr Ser Ala Val His Leu Glu Thr Gly Thr Pro Ser
             17045               17050               17055

Ser Phe Pro Gly His Thr Glu Pro Gly Pro Leu Leu Ile Pro Phe Thr
         17060               17065               17070

Phe Asn Phe Thr Ile Thr Asn Leu Arg Tyr Glu Glu Asn Met Gln His
    17075               17080               17085

Pro Gly Ser Arg Lys Phe Asn Thr Thr Glu Arg Val Leu Gln Gly Leu
         17090               17095               17100

Leu Thr Pro Leu Phe Lys Asn Thr Ser Val Gly Pro Leu Tyr Ser Gly
17105               17110               17115               17120

Cys Arg Leu Thr Leu Leu Arg Pro Glu Lys Gln Glu Ala Ala Thr Gly
             17125               17130               17135

Val Asp Thr Ile Cys Thr His Arg Val Asp Pro Ile Gly Pro Gly Leu
         17140               17145               17150

Asp Arg Glu Arg Leu Tyr Trp Glu Leu Ser Gln Leu Thr Asn Ser Ile
         17155               17160               17165

Thr Glu Leu Gly Pro Tyr Thr Leu Asp Arg Asp Ser Leu Tyr Val Asp
         17170               17175               17180

Gly Phe Asn Pro Trp Ser Ser Val Pro Thr Thr Ser Thr Pro Gly Thr
17185               17190               17195               17200

Ser Thr Val His Leu Ala Thr Ser Gly Thr Pro Ser Pro Leu Pro Gly
             17205               17210               17215

His Thr Ala Pro Val Pro Leu Leu Ile Pro Phe Thr Leu Asn Phe Thr
         17220               17225               17230

Ile Thr Asp Leu His Tyr Glu Glu Asn Met Gln His Pro Gly Ser Arg
             17235               17240               17245

Lys Phe Asn Thr Thr Glu Arg Val Leu Gln Gly Leu Leu Lys Pro Leu
17250               17255               17260

Phe Lys Ser Thr Ser Val Gly Pro Leu Tyr Ser Gly Cys Arg Leu Thr
17265               17270               17275               17280

Leu Leu Arg Pro Glu Lys His Gly Ala Ala Thr Gly Val Asp Ala Ile
             17285               17290               17295

Cys Thr Leu Arg Leu Asp Pro Thr Gly Pro Gly Leu Asp Arg Glu Arg
             17300               17305               17310

Leu Tyr Trp Glu Leu Ser Gln Leu Thr Asn Ser Ile Thr Glu Leu Gly
         17315               17320               17325

Pro Tyr Thr Leu Asp Arg Asp Ser Leu Tyr Val Asn Gly Phe Asn Pro
         17330               17335               17340

Trp Ser Ser Val Pro Thr Thr Ser Thr Pro Gly Thr Ser Thr Val His
17345               17350               17355               17360

Leu Ala Thr Ser Gly Thr Pro Ser Ser Leu Pro Gly His Thr Thr Ala
             17365               17370               17375

Gly Pro Leu Leu Val Pro Phe Thr Leu Asn Phe Thr Ile Thr Asn Leu
         17380               17385               17390

Lys Tyr Glu Glu Asp Met His Cys Pro Gly Ser Arg Lys Phe Asn Thr
         17395               17400               17405
```

-continued

Thr Glu Arg Val Leu Gln Ser Leu His Gly Pro Met Phe Lys Asn Thr
    17410               17415               17420

Ser Val Gly Pro Leu Tyr Ser Gly Cys Arg Leu Thr Leu Leu Arg Ser
17425               17430               17435               17440

Glu Lys Asp Gly Ala Ala Thr Gly Val Asp Ala Ile Cys Thr His Arg
                17445               17450               17455

Leu Asp Pro Lys Ser Pro Gly Leu Xaa Xaa Glu Xaa Leu Tyr Trp Glu
            17460               17465               17470

Leu Ser Xaa Leu Thr Xaa Xaa Ile Xaa Glu Leu Gly Pro Tyr Thr Leu
        17475               17480               17485

Asp Arg Xaa Ser Leu Tyr Val Asn Gly Phe Thr His Xaa Xaa Ser Xaa
    17490               17495               17500

Pro Thr Thr Ser Thr Pro Gly Thr Ser Thr Val Xaa Xaa Gly Thr Ser
17505               17510               17515               17520

Gly Thr Pro Ser Ser Xaa Pro Xaa Xaa Thr Xaa Xaa Xaa Pro Leu Leu
        17525               17530               17535

Xaa Pro Phe Thr Xaa Asn Xaa Thr Ile Thr Asn Leu Xaa Xaa Xaa Xaa
            17540               17545               17550

Xaa Met Xaa Xaa Pro Gly Ser Arg Lys Phe Asn Thr Thr Glu Xaa Val
    17555               17560               17565

Leu Gln Gly Leu Leu Xaa Pro Xaa Phe Lys Asn Xaa Ser Val Gly Xaa
    17570               17575               17580

Leu Tyr Ser Gly Cys Arg Leu Thr Xaa Leu Arg Xaa Glu Lys Xaa Gly
17585               17590               17595               17600

Ala Ala Thr Gly Xaa Asp Ala Ile Cys Xaa His Xaa Xaa Xaa Pro Lys
                17605               17610               17615

Xaa Pro Gly Leu Xaa Xaa Glu Xaa Leu Tyr Trp Glu Leu Ser Xaa Leu
    17620               17625               17630

Thr Asn Ser Ile Thr Glu Leu Gly Pro Tyr Thr Leu Asp Arg Asp Ser
        17635               17640               17645

Leu Tyr Val Asn Gly Phe Thr His Arg Ser Ser Met Pro Thr Thr Ser
    17650               17655               17660

Ile Pro Gly Thr Ser Ala Val His Leu Glu Thr Ser Gly Thr Pro Ala
17665               17670               17675               17680

Ser Leu Pro Gly His Thr Ala Pro Gly Pro Leu Leu Val Pro Phe Thr
            17685               17690               17695

Leu Asn Phe Thr Ile Thr Asn Leu Gln Tyr Glu Glu Asp Met Arg His
        17700               17705               17710

Pro Gly Ser Arg Lys Phe Asn Thr Thr Glu Arg Val Leu Gln Gly Leu
            17715               17720               17725

Leu Lys Pro Leu Phe Lys Ser Thr Ser Val Gly Pro Leu Tyr Ser Gly
    17730               17735               17740

Cys Arg Leu Thr Leu Leu Arg Pro Glu Lys Arg Gly Ala Ala Thr Gly
17745               17750               17755               17760

Val Asp Thr Ile Cys Thr His Arg Leu Asp Pro Leu Asn Pro Gly Leu
        17765               17770               17775

Xaa Xaa Glu Xaa Leu Tyr Trp Glu Leu Ser Xaa Leu Thr Xaa Xaa Ile
        17780               17785               17790

Xaa Glu Leu Gly Pro Tyr Thr Leu Asp Arg Xaa Ser Leu Tyr Val Asn
    17795               17800               17805

Gly Phe Thr His Xaa Xaa Ser Xaa Pro Thr Thr Ser Thr Pro Gly Thr
    17810               17815               17820

Ser Thr Val Xaa Xaa Gly Thr Ser Gly Thr Pro Ser Ser Xaa Pro Xaa

-continued

```
        17825               17830               17835               17840
Xaa Thr Xaa Xaa Xaa Pro Leu Leu Xaa Pro Phe Thr Xaa Asn Xaa Thr
                    17845               17850               17855
Ile Thr Asn Leu Xaa Xaa Xaa Xaa Met Xaa Xaa Pro Gly Ser Arg
        17860               17865               17870
Lys Phe Asn Thr Thr Glu Xaa Val Leu Gln Gly Leu Leu Xaa Pro Xaa
                    17875               17880               17885
Phe Lys Asn Xaa Ser Val Gly Xaa Leu Tyr Ser G

```
Thr Xaa Xaa Ile Xaa Glu Leu Gly Pro Tyr Thr Leu Asp Arg Xaa Ser
        18260               18265               18270

Leu Tyr Val Asn Gly Phe Thr His Gln Asn Ser Val Pro Thr Thr Ser
    18275               18280               18285

Thr Pro Gly Thr Ser Thr Val Tyr Trp Ala Thr Thr Gly Thr Pro Ser
    18290               18295               18300

Ser Phe Pro Gly His Thr Glu Pro Gly Pro Leu Leu Ile Pro Phe Thr
18305               18310               18315               18320

Phe Asn Phe Thr Ile Thr Asn Leu His Tyr Glu Glu Asn Met Gln His
            18325               18330               18335

Pro Gly Ser Arg Lys Phe Asn Thr Thr Glu Arg Val Leu Gln Gly Leu
        18340               18345               18350

Leu Thr Pro Leu Phe Lys Asn Thr Ser Val Gly Pro Leu Tyr Ser Gly
        18355               18360               18365

Cys Arg Leu Thr Leu Leu Arg Pro Glu Lys Gln Glu Ala Ala Thr Gly
    18370               18375               18380

Val Asp Thr Ile Cys Thr His Arg Val Asp Pro Ile Gly Pro Gly Leu
18385               18390               18395               18400

Xaa Xaa Glu Xaa Leu Tyr Trp Glu Leu Ser Xaa Leu Thr Xaa Xaa Ile
            18405               18410               18415

Xaa Glu Leu Gly Pro Tyr Thr Leu Asp Arg Xaa Ser Leu Tyr Val Asn
        18420               18425               18430

Gly Phe Thr His Xaa Xaa Ser Xaa Pro Thr Thr Ser Thr Pro Gly Thr
        18435               18440               18445

Ser Thr Val Xaa Xaa Gly Thr Ser Gly Thr Pro Ser Ser Xaa Pro Xaa
    18450               18455               18460

Xaa Thr Xaa Xaa Xaa Pro Leu Leu Xaa Pro Phe Thr Xaa Asn Xaa Thr
18465               18470               18475               18480

Ile Thr Asn Leu Xaa Xaa Xaa Xaa Xaa Met Xaa Xaa Pro Gly Ser Arg
        18485               18490               18495

Lys Phe Asn Thr Thr Glu Xaa Val Leu Gln Gly Leu Leu Xaa Pro Xaa
        18500               18505               18510

Phe Lys Asn Xaa Ser Val Gly Xaa Leu Tyr Ser Gly Cys Arg Leu Thr
    18515               18520               18525

Xaa Leu Arg Xaa Glu Lys Xaa Gly Ala Ala Thr Gly Xaa Asp Ala Ile
    18530               18535               18540

Cys Xaa His Xaa Xaa Xaa Pro Lys Xaa Pro Gly Leu Xaa Xaa Glu Xaa
18545               18550               18555               18560

Leu Tyr Trp Glu Leu Ser Xaa Leu Thr Xaa Xaa Ile Xaa Glu Leu Gly
            18565               18570               18575

Pro Tyr Thr Leu Asp Arg Xaa Ser Leu Tyr Val Asn Gly Phe Thr His
    18580               18585               18590

Arg Ser Ser Val Pro Thr Thr Ser Ser Pro Gly Thr Ser Thr Val His
    18595               18600               18605

Leu Ala Thr Ser Gly Thr Pro Ser Ser Leu Pro Gly His Thr Ala Pro
    18610               18615               18620

Val Pro Leu Leu Ile Pro Phe Thr Leu Asn Phe Thr Ile Thr Asn Leu
18625               18630               18635               18640

His Tyr Glu Glu Asn Met Gln His Pro Gly Ser Arg Lys Phe Asn Thr
            18645               18650               18655

Thr Glu Arg Val Leu Gln Gly Leu Leu Lys Pro Leu Phe Lys Ser Thr
        18660               18665               18670
```

-continued

```
Ser Val Gly Pro Leu Tyr Ser Gly Cys Arg Leu Thr Leu Leu Arg Pro
        18675               18680               18685

Glu Lys His Gly Ala Ala Thr Gly Val Asp Ala Ile Cys Thr Leu Arg
        18690               18695               18700

Leu Asp Pro Thr Gly Pro Gly Leu Xaa Xaa Glu Xaa Leu Tyr Trp Glu
18705               18710               18715               18720

Leu Ser Xaa Leu Thr Xaa Xaa Ile Xaa Glu Leu Gly Pro Tyr Thr Leu
        18725               18730               18735

Asp Arg Xaa Ser Leu Tyr Val Asn Gly Phe Thr His Xaa Xaa Ser Xaa
        18740               18745               18750

Pro Thr Thr Ser Thr Pro Gly Thr Ser Thr Val Xaa Xaa Gly Thr Ser
        18755               18760               18765

Gly Thr Pro Ser Ser Xaa Pro Xaa Xaa Thr Xaa Xaa Xaa Pro Leu Leu
        18770               18775               18780

Xaa Pro Phe Thr Xaa Asn Xaa Thr Ile Thr Asn Leu Xaa Xaa Xaa Xaa
18785               18790               18795               18800

Xaa Met Xaa Xaa Pro Gly Ser Arg Lys Phe Asn Thr Thr Glu Xaa Val
        18805               18810               18815

Leu Gln Gly Leu Leu Xaa Pro Xaa Phe Lys Asn Xaa Ser Val Gly Xaa
        18820               18825               18830

Leu Tyr Ser Gly Cys Arg Leu Thr Xaa Leu Arg Xaa Glu Lys Xaa Gly
        18835               18840               18845

Ala Ala Thr Gly Xaa Asp Ala Ile Cys Xaa His Xaa Xaa Xaa Pro Lys
        18850               18855               18860

Xaa Pro Gly Leu Xaa Xaa Glu Xaa Leu Tyr Trp Glu Leu Ser Xaa Leu
18865               18870               18875               18880

Thr Xaa Xaa Ile Xaa Glu Leu Gly Pro Tyr Thr Leu Asp Arg Xaa Ser
        18885               18890               18895

Leu Tyr Val Asn Gly Phe Thr His Arg Thr Ser Val Pro Thr Thr Ser
        18900               18905               18910

Thr Pro Gly Thr Ser Thr Val His Leu Ala Thr Ser Gly Thr Pro Ser
        18915               18920               18925

Ser Leu Pro Gly His Thr Ala Pro Val Pro Leu Leu Ile Pro Phe Thr
        18930               18935               18940

Leu Asn Phe Thr Ile Thr Asn Leu Gln Tyr Glu Glu Asp Met His Arg
18945               18950               18955               18960

Pro Gly Ser Arg Lys Phe Asn Thr Thr Glu Arg Val Leu Gln Gly Leu
        18965               18970               18975

Leu Ser Pro Ile Phe Lys Asn Ser Ser Val Gly Pro Leu Tyr Ser Gly
        18980               18985               18990

Cys Arg Leu Thr Ser Leu Arg Pro Glu Lys Asp Gly Ala Ala Thr Gly
        18995               19000               19005

Met Asp Ala Val Cys Leu Tyr His Pro Asn Pro Lys Arg Pro Gly Leu
        19010               19015               19020

Asp Arg Glu Gln Leu Tyr Cys Glu Leu Ser Gln Leu Thr His Asn Ile
        19025               19030               19035               19040

Thr Glu Leu Gly Pro Tyr Ser Leu Asp Arg Asp Ser Leu Tyr Val Asn
                19045               19050               19055

Gly Phe Thr His Gln Asn Ser Val Pro Thr Thr Ser Thr Pro Gly Thr
        19060               19065               19070

Ser Thr Val Tyr Trp Ala Thr Thr Gly Thr Pro Ser Ser Phe Pro Gly
        19075               19080               19085

His Thr Xaa Xaa Xaa Pro Leu Leu Xaa Pro Phe Thr Xaa Asn Xaa Thr
```

-continued

```
                19090               19095               19100
Ile Thr Asn Leu Xaa Xaa Xaa Xaa Met Xaa Xaa Pro Gly Ser Arg
        19105               19110               19115               19120

Lys Phe Asn Thr Thr Glu Xaa Val Leu Gln Gly Leu Leu Xaa Pro Xaa
                19125               19130               19135

Phe Lys Asn Xaa Ser Val Gly Xaa Leu Tyr Ser Gly Cys Arg Leu Thr
        19140               19145               19150

Xaa Leu Arg Xaa Glu Lys Xaa Gly Ala Ala Thr Gly Xaa Asp Ala Ile
        19155               19160               19165

Cys Xaa His Xaa Xaa Xaa Pro Lys Xaa Pro Gly Leu Xaa Xaa Glu Xaa
        19170               19175               19180

Leu Tyr Trp Glu Leu Ser Xaa Leu Thr Xaa Xaa Ile Xaa Glu Leu Gly
19185               19190               19195               19200

Pro Tyr Thr Leu Asp Arg Xaa Ser Leu Tyr Val Asn Gly Phe Thr His
                19205               19210               19215

Trp Ser Ser Gly Leu Thr Thr Ser Thr Pro Trp Thr Ser Thr Val Asp
                19220               19225               19230

Leu Gly Thr Ser Gly Thr Pro Ser Pro Val Pro Ser Pro Thr Thr Ala
        19235               19240               19245

Gly Pro Leu Leu Val Pro Phe Thr Leu Asn Phe Thr Ile Thr Asn Leu
        19250               19255               19260

Gln Tyr Glu Glu Asp Met His Arg Pro Gly Ser Arg Lys Phe Asn Ala
19265               19270               19275               19280

Thr Glu Arg Val Leu Gln Gly Leu Leu Ser Pro Ile Phe Lys Asn Thr
                19285               19290               19295

Ser Val Gly Pro Leu Tyr Ser Gly Cys Arg Leu Thr Leu Leu Arg Pro
        19300               19305               19310

Glu Lys Gln Glu Ala Ala Thr Gly Val Asp Thr Ile Cys Thr His Arg
        19315               19320               19325

Val Asp Pro Ile Gly Pro Gly Leu Xaa Xaa Glu Xaa Leu Tyr Trp Glu
        19330               19335               19340

Leu Ser Xaa Leu Thr Xaa Xaa Ile Xaa Glu Leu Gly Pro Tyr Thr Leu
19345               19350               19355               19360

Asp Arg Xaa Ser Leu Tyr Val Asn Gly Phe Thr His Xaa Xaa Ser Xaa
                19365               19370               19375

Pro Thr Thr Ser Thr Pro Gly Thr Ser Thr Val Xaa Xaa Gly Thr Ser
        19380               19385               19390

Gly Thr Pro Ser Ser Xaa Pro Xaa Xaa Thr Xaa Xaa Xaa Pro Leu Leu
        19395               19400               19405

Xaa Pro Phe Thr Xaa Asn Xaa Thr Ile Thr Asn Leu Xaa Xaa Xaa Xaa
        19410               19415               19420

Xaa Met Xaa Xaa Pro Gly Ser Arg Lys Phe Asn Thr Thr Glu Xaa Val
19425               19430               19435               19440

Leu Gln Gly Leu Leu Xaa Pro Xaa Phe Lys Asn Xaa Ser Val Gly Xaa
                19445               19450               19455

Leu Tyr Ser Gly Cys Arg Leu Thr Xaa Leu Arg Xaa Glu Lys Xaa Gly
        19460               19465               19470

Ala Ala Thr Gly Xaa Asp Ala Ile Cys Xaa His Xaa Xaa Xaa Pro Lys
        19475               19480               19485

Xaa Pro Gly Leu Xaa Xaa Glu Xaa Leu Tyr Trp Glu Leu Ser Xaa Leu
        19490               19495               19500

Thr Xaa Xaa Ile Xaa Glu Leu Gly Pro Tyr Thr Leu Asp Arg Xaa Ser
19505               19510               19515               19520
```

```
Leu Tyr Val Asn Gly Phe Thr His Arg Ser Phe Gly Leu Thr Thr Ser
            19525               19530               19535

Thr Pro Trp Thr Ser Thr Val Asp Leu Gly Thr Ser Gly Thr Pro Ser
            19540               19545               19550

Pro Val Pro Ser Pro Thr Thr Ala Gly Pro Leu Leu Val Pro Phe Thr
            19555               19560               19565

Leu Asn Phe Thr Ile Thr Asn Leu Gln Tyr Glu Glu Asp Met His Arg
    19570               19575               19580

Pro Gly Ser Arg Lys Phe Asn Thr Thr Glu Arg Val Leu Gln Gly Leu
19585               19590               19595               19600

Leu Thr Pro Leu Phe Arg Asn Thr Ser Val Ser Ser Leu Tyr Ser Gly
            19605               19610               19615

Cys Arg Leu Thr Leu Leu Arg Pro Glu Lys Asp Gly Ala Ala Thr Arg
            19620               19625               19630

Val Asp Ala Val Cys Thr His Arg Pro Asp Pro Lys Ser Pro Gly Leu
            19635               19640               19645

Xaa Xaa Glu Xaa Leu Tyr Trp Glu Leu Ser Xaa Leu Thr Xaa Xaa Ile
            19650               19655               19660

Xaa Glu Leu Gly Pro Tyr Thr Leu Asp Arg Xaa Ser Leu Tyr Val Asn
19665               19670               19675               19680

Gly Phe Thr His Xaa Xaa Ser Xaa Pro Thr Thr Ser Thr Pro Gly Thr
            19685               19690               19695

Ser Thr Val Xaa Xaa Gly Thr Ser Gly Thr Pro Ser Ser Xaa Pro Xaa
            19700               19705               19710

Xaa Thr Xaa Xaa Xaa Pro Leu Leu Xaa Pro Phe Thr Xaa Asn Xaa Thr
            19715               19720               19725

Ile Thr Asn Leu Xaa Xaa Xaa Xaa Xaa Met Xaa Xaa Pro Gly Ser Arg
            19730               19735               19740

Lys Phe Asn Thr Thr Glu Xaa Val Leu Gln Gly Leu Leu Xaa Pro Xaa
19745               19750               19755               19760

Phe Lys Asn Xaa Ser Val Gly Xaa Leu Tyr Ser Gly Cys Arg Leu Thr
            19765               19770               19775

Xaa Leu Arg Xaa Glu Lys Xaa Gly Ala Ala Thr Gly Xaa Asp Ala Ile
            19780               19785               19790

Cys Xaa His Xaa Xaa Xaa Pro Lys Xaa Pro Gly Leu Xaa Xaa Glu Xaa
            19795               19800               19805

Leu Tyr Trp Glu Leu Ser Xaa Leu Thr Xaa Xaa Ile Xaa Glu Leu Gly
            19810               19815               19820

Pro Tyr Thr Leu Asp Arg Xaa Ser Leu Tyr Val Asn Gly Phe Thr His
19825               19830               19835               19840

Trp Ile Pro Val Pro Thr Ser Ser Thr Pro Gly Thr Ser Thr Val Asp
            19845               19850               19855

Leu Gly Ser Gly Thr Pro Ser Ser Leu Pro Ser Pro Thr Thr Ala Gly
            19860               19865               19870

Pro Leu Leu Val Pro Phe Thr Leu Asn Phe Thr Ile Thr Asn Leu Gln
            19875               19880               19885

Tyr Gly Glu Asp Met Gly His Pro Gly Ser Arg Lys Phe Asn Thr Thr
            19890               19895               19900

Glu Arg Val Leu Gln Gly Leu Leu Gly Pro Ile Phe Lys Asn Thr Ser
19905               19910               19915               19920

Val Gly Pro Leu Tyr Ser Gly Cys Arg Leu Thr Ser Leu Arg Ser Glu
            19925               19930               19935
```

-continued

```
Lys Asp Gly Ala Ala Thr Gly Val Asp Ala Ile Cys Ile His His Leu
                19940               19945               19950

Asp Pro Lys Ser Pro Gly Leu Xaa Xaa Glu Xaa Leu Tyr Trp Glu Leu
        19955               19960               19965

Ser Xaa Leu Thr Xaa Xaa Ile Xaa Glu Leu Gly Pro Tyr Thr Leu Asp
    19970               19975               19980

Arg Xaa Ser Leu Tyr Val Asn Gly Phe Thr His Xaa Xaa Ser Xaa Pro
19985               19990               19995               20000

Thr Thr Ser Thr Pro Gly Thr Ser Thr Val Xaa Xaa Gly Thr Ser Gly
            20005               20010               20015

Thr Pro Ser Ser Xaa Pro Xaa Xaa Thr Xaa Xaa Xaa Pro Leu Leu Xaa
            20020               20025               20030

Pro Phe Thr Xaa Asn Xaa Thr Ile Thr Asn Leu Xaa Xaa Xaa Xaa Xaa
            20035               20040               20045

Met Xaa Xaa Pro Gly Ser Arg Lys Phe Asn Thr Thr Glu Xaa Val Leu
    20050               20055               20060

Gln Gly Leu Leu Xaa Pro Xaa Phe Lys Asn Xaa Ser Val Gly Xaa Leu
20065               20070               20075               20080

Tyr Ser Gly Cys Arg Leu Thr Xaa Leu Arg Xaa Glu Lys Xaa Gly Ala
            20085               20090               20095

Ala Thr Gly Xaa Asp Ala Ile Cys Xaa His Xaa Xaa Xaa Pro Lys Xaa
            20100               20105               20110

Pro Gly Leu Xaa Xaa Glu Xaa Leu Tyr Trp Glu Leu Ser Xaa Leu Thr
            20115               20120               20125

Xaa Xaa Ile Xaa Glu Leu Gly Pro Tyr Thr Leu Asp Arg Xaa Ser Leu
    20130               20135               20140

Tyr Val Asn Gly Phe Thr His Gln Thr Phe Ala Pro Asn Thr Ser Thr
20145               20150               20155               20160

Pro Gly Thr Ser Thr Val Asp Leu Gly Thr Ser Gly Thr Pro Ser Ser
            20165               20170               20175

Leu Pro Ser Pro Thr Ser Ala Gly Pro Leu Leu Val Pro Phe Thr Leu
            20180               20185               20190

Asn Phe Thr Ile Thr Asn Leu Gln Tyr Glu Glu Asp Met His His Pro
            20195               20200               20205

Gly Ser Arg Lys Phe Asn Thr Thr Glu Arg Val Leu Gln Gly Leu Leu
    20210               20215               20220

Gly Pro Met Phe Lys Asn Thr Ser Val Gly Leu Leu Tyr Ser Gly Cys
20225               20230               20235               20240

Arg Leu Thr Leu Leu Arg Pro Glu Lys Asn Gly Ala Ala Thr Arg Val
            20245               20250               20255

Asp Ala Val Cys Thr His Arg Pro Asp Pro Lys Ser Pro Gly Leu Xaa
            20260               20265               20270

Xaa Glu Xaa Leu Tyr Trp Glu Leu Ser Xaa Leu Thr Xaa Xaa Ile Xaa
    20275               20280               20285

Glu Leu Gly Pro Tyr Thr Leu Asp Arg Xaa Ser Leu Tyr Val Asn Gly
    20290               20295               20300

Phe Thr His Xaa Xaa Ser Xaa Pro Thr Thr Ser Thr Pro Gly Thr Ser
20305               20310               20315               20320

Thr Val Xaa Xaa Gly Thr Ser Gly Thr Pro Ser Ser Xaa Pro Xaa Xaa
            20325               20330               20335

Thr Ala Pro Val Pro Leu Leu Ile Pro Phe Thr Leu Asn Phe Thr Ile
            20340               20345               20350

Thr Asn Leu His Tyr Glu Glu Asn Met Gln His Pro Gly Ser Arg Lys
```

-continued

```
            20355               20360               20365
Phe Asn Thr Thr Glu Arg Val Leu Gln Gly Leu Leu Lys Pro Leu Phe
        20370               20375               20380
Lys Ser Thr Ser Val Gly Pro Leu Tyr Ser Gly Cys Arg Leu Thr Leu
20385               20390               20395               20400
Leu Arg Pro Glu Lys His Gly Ala Ala Thr Gly Val Asp Ala Ile Cys
                20405               20410               20415
Thr Leu Arg Leu Asp Pro Thr Gly Pro Gly Leu Asp Arg Glu Arg Leu
            20420               20425               20430
Tyr Trp Glu Leu Ser Gln Leu Thr Asn Ser Val Thr Glu Leu Gly Pro
            20435               20440               20445
Tyr Thr Leu Asp Arg Asp Ser Leu Tyr Val Asn Gly Phe Thr Gln Arg
            20450               20455               20460
Ser Ser Val Pro Thr Thr Ser Ile Pro Gly Thr Ser Ala Val His Leu
20465               20470               20475               20480
Glu Thr Ser Gly Thr Pro Ala Ser Leu Pro Gly His Thr Ala Pro Gly
                20485               20490               20495
Pro Leu Leu Val Pro Phe Thr Leu Asn Phe Thr Ile Thr Asn Leu Gln
            20500               20505               20510
Tyr Glu Val Asp Met Arg His Pro Gly Ser Arg Lys Phe Asn Thr Thr
            20515               20520               20525
Glu Arg Val Leu Gln Gly Leu Leu Lys Pro Leu Phe Lys Ser Thr Ser
            20530               20535               20540
Val Gly Pro Leu Tyr Ser Gly Cys Arg Leu Thr Leu Leu Arg Pro Glu
20545               20550               20555               20560
Lys Arg Gly Ala Ala Thr Gly Val Asp Thr Ile Cys Thr His Arg Leu
                20565               20570               20575
Asp Pro Leu Asn Pro Gly Leu Asp Arg Glu Gln Leu Tyr Trp Glu Leu
            20580               20585               20590
Ser Lys Leu Thr Arg Gly Ile Ile Glu Leu Gly Pro Tyr Leu Leu Asp
            20595               20600               20605
Arg Gly Ser Leu Tyr Val Asn Gly Phe Thr His Arg Asn Phe Val Pro
            20610               20615               20620
Ile Thr Ser Thr Pro Gly Thr Ser Thr Val His Leu Gly Thr Ser Glu
20625               20630               20635               20640
Thr Pro Ser Ser Leu Pro Arg Pro Ile Val Pro Gly Pro Leu Leu Val
                20645               20650               20655
Pro Phe Thr Leu Asn Phe Thr Ile Thr Asn Leu Gln Tyr Glu Glu Ala
            20660               20665               20670
Met Arg His Pro Gly Ser Arg Lys Phe Asn Thr Thr Glu Arg Val Leu
            20675               20680               20685
Gln Gly Leu Leu Arg Pro Leu Phe Lys Asn Thr Ser Ile Gly Pro Leu
            20690               20695               20700
Tyr Ser Ser Cys Arg Leu Thr Leu Leu Arg Pro Glu Lys Asp Lys Ala
20705               20710               20715               20720
Ala Thr Arg Val Asp Ala Ile Cys Thr His His Pro Asp Pro Gln Ser
                20725               20730               20735
Pro Gly Leu Asn Arg Glu Gln Leu Tyr Trp Glu Leu Ser Gln Leu Thr
            20740               20745               20750
His Gly Ile Thr Glu Leu Gly Pro Tyr Thr Leu Asp Arg Asp Ser Leu
            20755               20760               20765
Tyr Val Asp Gly Phe Thr His Trp Ser Pro Ile Pro Thr Thr Ser Thr
            20770               20775               20780
```

```
Pro Gly Thr Ser Ile Val Asn Leu Gly Thr Ser Gly Ile Pro Pro Ser
20785               20790               20795               20800

Leu Pro Glu Thr Thr Xaa Xaa Xaa Pro Leu Leu Xaa Pro Phe Thr Xaa
        20805               20810               20815

Asn Xaa Thr Ile Thr Asn Leu Xaa Xaa Xaa Xaa Met Xaa Xaa Pro
    20820               20825               20830

Gly Ser Arg Lys Phe Asn Thr Thr Glu Arg Val Leu Gln Gly Leu Leu
        20835               20840               20845

Lys Pro Leu Phe Lys Ser Thr Ser Val Gly Pro Leu Tyr Ser Gly Cys
    20850               20855               20860

Arg Leu Thr Leu Leu Arg Pro Glu Lys Asp Gly Val Ala Thr Arg Val
20865               20870               20875               20880

Asp Ala Ile Cys Thr His Arg Pro Asp Pro Lys Ile Pro Gly Leu Asp
            20885               20890               20895

Arg Gln Gln Leu Tyr Trp Glu Leu Ser Gln Leu Thr His Ser Ile Thr
        20900               20905               20910

Glu Leu Gly Pro Tyr Thr Leu Asp Arg Asp Ser Leu Tyr Val Asn Gly
        20915               20920               20925

Phe Thr Gln Arg Ser Ser Val Pro Thr Thr Ser Thr Pro Gly Thr Phe
    20930               20935               20940

Thr Val Gln Pro Glu Thr Ser Glu Thr Pro Ser Ser Leu Pro Gly Pro
20945               20950               20955               20960

Thr Ala Thr Gly Pro Val Leu Leu Pro Phe Thr Leu Asn Phe Thr Ile
            20965               20970               20975

Thr Asn Leu Gln Tyr Glu Glu Asp Met His Arg Pro Gly Ser Arg Lys
        20980               20985               20990

Phe Asn Thr Thr Glu Arg Val Leu Gln Gly Leu Leu Met Pro Leu Phe
    20995               21000               21005

Lys Asn Thr Ser Val Ser Ser Leu Tyr Ser Gly Cys Arg Leu Thr Leu
    21010               21015               21020

Leu Arg Pro Glu Lys Asp Gly Ala Ala Thr Arg Val Asp Ala Val Cys
21025               21030               21035               21040

Thr His Arg Pro Asp Pro Lys Ser Pro Gly Leu Asp Arg Glu Arg Leu
            21045               21050               21055

Tyr Trp Lys Leu Ser Gln Leu Thr His Gly Ile Thr Glu Leu Gly Pro
        21060               21065               21070

Tyr Thr Leu Asp Arg His Ser Leu Tyr Val Asn Gly Phe Thr His Gln
    21075               21080               21085

Ser Ser Met Thr Thr Thr Arg Thr Pro Asp Thr Ser Thr Met His Leu
    21090               21095               21100

Ala Thr Ser Arg Thr Pro Ala Ser Leu Ser Gly Pro Thr Thr Ala Ser
21105               21110               21115               21120

Pro Leu Leu Val Leu Phe Thr Ile Asn Phe Thr Ile Thr Asn Leu Arg
            21125               21130               21135

Tyr Glu Glu Asn Met His His Pro Gly Ser Arg Lys Phe Asn Thr Thr
        21140               21145               21150

Glu Arg Val Leu Gln Gly Leu Leu Arg Pro Val Phe Lys Asn Thr Ser
        21155               21160               21165

Val Gly Pro Leu Tyr Ser Gly Cys Arg Leu Thr Leu Leu Arg Pro Lys
    21170               21175               21180

Lys Asp Gly Ala Ala Thr Lys Val Asp Ala Ile Cys Thr Tyr Arg Pro
    21185               21190               21195               21200
```

-continued

```
Asp Pro Lys Ser Pro Gly Leu Asp Arg Glu Gln Leu Tyr Trp Glu Leu
            21205               21210               21215

Ser Gln Leu Thr His Ser Ile Thr Glu Leu Gly Pro Tyr Thr Leu Asp
        21220               21225               21230

Arg Asp Ser Leu Tyr Val Asn Gly Phe Thr Gln Arg Ser Ser Val Pro
        21235               21240               21245

Thr Thr Ser Ile Pro Gly Thr Pro Thr Val Asp Leu Gly Thr Ser Gly
    21250               21255               21260

Thr Pro Val Ser Lys Pro Gly Pro Ser Ala Ala Ser Pro Leu Leu Val
21265               21270               21275               21280

Leu Phe Thr Leu Asn Phe Thr Ile Thr Asn Leu Arg Tyr Glu Glu Asn
            21285               21290               21295

Met Gln His Pro Gly Ser Arg Lys Phe Asn Thr Thr Glu Arg Val Leu
        21300               21305               21310

Gln Gly Leu Leu Arg Ser Leu Phe Lys Ser Thr Ser Val Gly Pro Leu
        21315               21320               21325

Tyr Ser Gly Cys Arg Leu Thr Leu Leu Arg Pro Glu Lys Asp Gly Thr
    21330               21335               21340

Ala Thr Gly Val Asp Ala Ile Cys Thr His His Pro Asp Pro Lys Ser
21345               21350               21355               21360

Pro Arg Leu Asp Arg Glu Gln Leu Tyr Trp Glu Leu Ser Gln Leu Thr
            21365               21370               21375

His Asn Ile Thr Glu Leu Gly His Tyr Ala Leu Asp Asn Asp Ser Leu
        21380               21385               21390

Phe Val Asn Gly Phe Thr His Arg Ser Ser Val Ser Thr Thr Ser Thr
        21395               21400               21405

Pro Gly Thr Pro Thr Val Tyr Leu Gly Ala Ser Lys Thr Pro Ala Ser
    21410               21415               21420

Ile Phe Gly Pro Ser Ala Ala Ser His Leu Leu Ile Leu Phe Thr Leu
21425               21430               21435               21440

Asn Phe Thr Ile Thr Asn Leu Arg Tyr Glu Glu Asn Met Trp Pro Gly
            21445               21450               21455

Ser Arg Lys Phe Asn Thr Thr Glu Arg Val Leu Gln Gly Leu Leu Arg
        21460               21465               21470

Pro Leu Phe Lys Asn Thr Ser Val Gly Pro Leu Tyr Ser Gly Ser Arg
        21475               21480               21485

Leu Thr Leu Leu Arg Pro Glu Lys Asp Gly Glu Ala Thr Gly Val Asp
    21490               21495               21500

Ala Ile Cys Thr His Arg Pro Asp Pro Thr Gly Pro Gly Leu Asp Arg
21505               21510               21515               21520

Glu Gln Leu Tyr Leu Glu Leu Ser Gln Leu Thr His Ser Ile Thr Glu
            21525               21530               21535

Leu Gly Pro Tyr Thr Leu Asp Arg Asp Ser Leu Tyr Val Asn Gly Phe
        21540               21545               21550

Thr His Arg Ser Ser Val Pro Thr Thr Ser Thr Gly Val Val Ser Glu
        21555               21560               21565

Glu Pro Phe Thr Leu Asn Phe Thr Ile Asn Asn Leu Arg Tyr Met Ala
    21570               21575               21580

Asp Met Gly Gln Pro Gly Ser Leu Lys Phe Asn Ile Thr Asp Asn Val
21585               21590               21595               21600

Met Lys His Leu Leu Ser Pro Leu Phe Gln Arg Ser Ser Leu Gly Ala
            21605               21610               21615

Arg Tyr Thr Gly Cys Arg Val Ile Ala Leu Arg Ser Val Lys Asn Gly
```

-continued

```
                   21620                21625                21630
Ala Glu Thr Arg Val Asp Leu Leu Cys Thr Tyr Leu Gln Pro Leu Ser
           21635                21640                21645
Gly Pro Gly Leu Pro Ile Lys Gln Val Phe His Glu Leu Ser Gln Gln
       21650                21655                21660
Thr His Gly Ile Thr Arg Leu Gly Pro Tyr Ser Leu Asp Lys Asp Ser
21665                21670                21675                21680
Leu Tyr Leu Asn Gly Tyr Asn Glu Pro Gly Leu Asp Glu Pro Pro Thr
               21685                21690                21695
Thr Pro Lys Pro Ala Thr Thr Phe Leu Pro Pro Leu Ser Glu Ala Thr
           21700                21705                21710
Thr Ala Met Gly Tyr His Leu Lys Thr Leu Thr Leu Asn Phe Thr Ile
       21715                21720                21725
Ser Asn Leu Gln Tyr Ser Pro Asp Met Gly Lys Gly Ser Ala Thr Phe
   21730                21735                21740
Asn Ser Thr Glu Gly Val Leu Gln His Leu Leu Arg Pro Leu Phe Gln
21745                21750                21755                21760
Lys Ser Ser Met Gly Pro Phe Tyr Leu Gly Cys Gln Leu Ile Ser Leu
               21765                21770                21775
Arg Pro Glu Lys Asp Gly Ala Ala Thr Gly Val Asp Thr Thr Cys Thr
           21780                21785                21790
Tyr His Pro Asp Pro Val Gly Pro Gly Leu Asp Ile Gln Gln Leu Tyr
       21795                21800                21805
Trp Glu Leu Ser Gln Leu Thr His Gly Val Thr Gln Leu Gly Phe Tyr
   21810                21815                21820
Val Leu Asp Arg Asp Ser Leu Phe Ile Asn Gly Tyr Ala Pro Gln Asn
21825                21830                21835                21840
Leu Ser Ile Arg Gly Glu Tyr Gln Ile Asn Phe His Ile Val Asn Trp
               21845                21850                21855
Asn Leu Ser Asn Pro Asp Pro Thr Ser Ser Glu Tyr Ile Thr Leu Leu
           21860                21865                21870
Arg Asp Ile Gln Asp Lys Val Thr Thr Leu Tyr Lys Gly Ser Gln Leu
       21875                21880                21885
His Asp Thr Phe Arg Phe Cys Leu Val Thr Asn Leu Thr Met Asp Ser
   21890                21895                21900
Val Leu Val Thr Val Lys Ala Leu Phe Ser Ser Asn Leu Asp Pro Ser
21905                21910                21915                21920
Leu Val Glu Gln Val Phe Leu Asp Lys Thr Leu Asn Ala Ser Phe His
               21925                21930                21935
Trp Leu Gly Ser Thr Tyr Gln Leu Val Asp Ile His Val Thr Glu Met
           21940                21945                21950
Glu Ser Ser Val Tyr Gln Pro Thr Ser Ser Ser Thr Gln His Phe
       21955                21960                21965
Tyr Leu Asn Phe Thr Ile Thr Asn Leu Pro Tyr Ser Gln Asp Lys Ala
   21970                21975                21980
Gln Pro Gly Thr Thr Asn Tyr Gln Arg Asn Lys Arg Asn Ile Glu Asp
21985                21990                21995                22000
Ala Leu Asn Gln Leu Phe Arg Asn Ser Ser Ile Lys Ser Tyr Phe Ser
               22005                22010                22015
Asp Cys Gln Val Ser Thr Phe Arg Ser Val Pro Asn Arg His His Thr
           22020                22025                22030
Gly Val Asp Ser Leu Cys Asn Phe Ser Pro Leu Ala Arg Arg Val Asp
       22035                22040                22045
```

-continued

```
Arg Val Ala Ile Tyr Glu Glu Phe Leu Arg Met Thr Arg Asn Gly Thr
    22050               22055               22060

Gln Leu Gln Asn Phe Thr Leu Asp Arg Ser Ser Val Leu Val Asp Gly
22065               22070               22075               22080

Tyr Ser Pro Asn Arg Asn Glu Pro Leu Thr Gly Asn Ser Asp Leu Pro
        22085               22090               22095

Phe Trp Ala Val Ile Leu Ile Gly Leu Ala Gly Leu Leu Gly Leu Ile
            22100               22105               22110

Thr Cys Leu Ile Cys Gly Val Leu Val Thr Arg Arg Arg Lys Lys
        22115               22120               22125

Glu Gly Glu Tyr Asn Val Gln Gln Gln Cys Pro Gly Tyr Tyr Gln Ser
    22130               22135               22140

His Leu Asp Leu Glu Asp Leu Gln
22145               22150

<210> SEQ ID NO 57
<211> LENGTH: 858
<212> TYPE: PRT
<213> ORGANISM: Homo sapiens

<400> SEQUENCE: 57

Met Leu Gln Thr Lys Asp Leu Ile Trp Thr Leu Phe Phe Leu Gly Thr
 1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
```

-continued

```
                260                 265                 270
Thr Ile Lys Lys Val Asp Lys Asn Asp Glu Ala Glu Tyr Ile Cys Ile
            275                 280                 285

Ala Glu Asn Lys Ala Gly Glu Gln Asp Ala Thr Ile His Leu Lys Val
290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Ala Ser Trp Thr Arg Pro Glu Lys Gln Glu Thr Leu Asp Gly His
            355                 360                 365

Met Val Val Arg Ser His Ala Arg Val Ser Ser Leu Thr Leu Lys Ser
            370                 375                 380

Ile Gln Tyr Thr Asp Ala Gly Glu Tyr Ile Cys Thr Ala Ser Asn Thr
385                 390                 395                 400

Ile Gly Gln Asp Ser Gln Ser Met Tyr Leu Glu Val Gln Tyr Ala Pro
                405                 410                 415

Lys Leu Gln Gly Pro Val Ala Val Tyr Thr Trp Glu Gly Asn Gln Val
            420                 425                 430

Asn Ile Thr Cys Glu Val Phe Ala Tyr Pro Ser Ala Thr Ile Ser Trp
            435                 440                 445

Phe Arg Asp Gly Gln Leu Leu Pro Ser Ser Asn Tyr Ser Asn Ile Lys
            450                 455                 460

Ile Tyr Asn Thr Pro Ser Ala Ser Tyr Leu Glu Val Thr Pro Asp Ser
465                 470                 475                 480

Glu Asn Asp Phe Gly Asn Tyr Asn Cys Thr Ala Val Asn Arg Ile Gly
                485                 490                 495

Gln Glu Ser Leu Glu Phe Ile Leu Val Gln Ala Asp Thr Pro Ser Ser
            500                 505                 510

Pro Ser Ile Asp Gln Val Glu Pro Tyr Ser Ser Thr Ala Gln Val Gln
            515                 520                 525

Phe Asp Glu Pro Glu Ala Thr Gly Gly Val Pro Ile Leu Lys Tyr Lys
530                 535                 540

Ala Glu Trp Arg Ala Val Gly Glu Glu Val Trp His Ser Lys Trp Tyr
545                 550                 555                 560

Asp Ala Lys Glu Ala Ser Met Glu Gly Ile Val Thr Ile Val Gly Leu
                565                 570                 575

Lys Pro Glu Thr Thr Tyr Ala Val Arg Leu Ala Ala Leu Asn Gly Lys
            580                 585                 590

Gly Leu Gly Glu Ile Ser Ala Ala Ser Glu Phe Lys Thr Gln Pro Val
            595                 600                 605

Gln Gly Glu Pro Ser Ala Pro Lys Leu Glu Gly Gln Met Gly Glu Asp
            610                 615                 620

Gly Asn Ser Ile Lys Val Asn Leu Ile Lys Gln Asp Asp Gly Gly Ser
625                 630                 635                 640

Pro Ile Arg His Tyr Leu Val Arg Tyr Arg Ala Leu Ser Ser Glu Trp
                645                 650                 655

Lys Pro Glu Ile Arg Leu Pro Ser Gly Ser Asp His Val Met Leu Lys
            660                 665                 670

Ser Leu Asp Trp Asn Ala Glu Tyr Glu Val Tyr Val Val Ala Glu Asn
            675                 680                 685
```

-continued

```
Gln Gln Gly Lys Ser Lys Ala Ala His Phe Val Phe Arg Thr Ser Ala
    690             695                 700

Gln Pro Thr Ala Ile Pro Ala Asn Gly Ser Pro Thr Ser Gly Leu Ser
705             710                 715                 720

Thr Gly Ala Ile Val Gly Ile Leu Ile Val Ile Phe Val Leu Leu Leu
                725                 730                 735

Val Val Val Asp Ile Thr Cys Tyr Phe Leu Asn Lys Cys Gly Leu Phe
            740                 745                 750

Met Cys Ile Ala Val Asn Leu Cys Gly Lys Ala Gly Pro Gly Ala Lys
        755                 760                 765

Gly Lys Asp Met Glu Glu Gly Lys Ala Ala Phe Ser Lys Asp Glu Ser
    770                 775                 780

Lys Glu Pro Ile Val Glu Val Arg Thr Glu Glu Arg Thr Pro Asn
785                 790                 795                 800

His Asp Gly Gly Lys His Thr Glu Pro Asn Glu Thr Thr Pro Leu Thr
                805                 810                 815

Glu Pro Glu Lys Gly Pro Val Glu Ala Lys Pro Glu Cys Gln Glu Thr
            820                 825                 830

Glu Thr Lys Pro Ala Pro Ala Glu Val Lys Thr Val Pro Asn Asp Ala
        835                 840                 845

Thr Gln Thr Lys Glu Asn Glu Ser Lys Ala
    850                 855

<210> SEQ ID NO 58
<211> LENGTH: 224
<212> TYPE: PRT
<213> ORGANISM: Homo sapiens

<400> SEQUENCE: 58

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
```

195                 200                 205
Lys Tyr Glu Val Gln Gly Glu Val Phe Thr Lys Pro Gln Leu Trp Pro
    210                 215                 220

<210> SEQ ID NO 59
<211> LENGTH: 418
<212> TYPE: PRT
<213> ORGANISM: Homo sapiens

<400> SEQUENCE: 59

Met Pro Ser Ser Val Ser Trp Gly Ile Leu Leu Leu Ala Gly Leu Cys
 1               5                  10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

```
Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 60
<211> LENGTH: 531
<212> TYPE: PRT
<213> ORGANISM: Homo sapiens

<400> SEQUENCE: 60

Met Ser Lys Pro His Ser Glu Ala Gly Thr Ala Phe Ile Gln Thr Gln
  1               5                  10                  15

Gln Leu His Ala Ala Met Ala Asp Thr Phe Leu Glu His Met Cys Arg
             20                  25                  30

Leu Asp Ile Asp Ser Pro Pro Ile Thr Ala Arg Asn Thr Gly Ile Ile
         35                  40                  45

Cys Thr Ile Gly Pro Ala Ser Arg Ser Val Glu Thr Leu Lys Glu Met
     50                  55                  60

Ile Lys Ser Gly Met Asn Val Ala Arg Leu Asn Phe Ser His Gly Thr
 65                  70                  75                  80

His Glu Tyr His Ala Glu Thr Ile Lys Asn Val Arg Thr Ala Thr Glu
                 85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300
```

```
Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
    370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
                405                 410                 415

Val Glu Ala Ser Phe Lys Cys Cys Ser Gly Ala Ile Ile Val Leu Thr
                420                 425                 430

Lys Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
        450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
        515                 520                 525

Pro Val Pro
    530

<210> SEQ ID NO 61
<211> LENGTH: 1257
<212> TYPE: PRT
<213> ORGANISM: Homo sapiens

<400> SEQUENCE: 61

Met Lys Ala Ala Asp Glu Pro Ala Tyr Leu Thr Val Gly Thr Asp Val
1               5                   10                  15

Ser Ala Lys Tyr Arg Gly Ala Phe Cys Glu Ala Lys Ile Lys Thr Val
                20                  25                  30

Lys Arg Leu Val Lys Val Lys Val Leu Leu Lys Gln Asp Asn Thr Thr
            35                  40                  45

Gln Leu Val Gln Asp Asp Gln Val Lys Gly Pro Leu Arg Val Gly Ala
        50                  55                  60

Ile Val Glu Thr Arg Thr Ser Asp Gly Ser Phe Gln Glu Ala Ile Ile
65                  70                  75                  80

Ser Lys Leu Thr Asp Ala Ser Trp Tyr Thr Val Val Phe Asp Asp Gly
                85                  90                  95

Asp Glu Arg Thr Leu Arg Arg Thr Ser Leu Cys Leu Lys Gly Glu Arg
                100                 105                 110

His Phe Ala Glu Ser Glu Thr Leu Asp Gln Leu Pro Leu Thr Asn Pro
            115                 120                 125

Glu His Phe Gly Thr Pro Val Ile Ala Lys Lys Thr Asn Arg Gly Arg
        130                 135                 140
```

-continued

```
Arg Ser Ser Leu Pro Val Thr Glu Asp Glu Lys Glu Glu Ser Ser
145                 150                 155                 160

Glu Glu Glu Asp Glu Asp Lys Arg Arg Leu Asn Asp Glu Leu Leu Gly
                165                 170                 175

Lys Val Val Ser Val Val Ser Ala Thr Glu Arg Thr Glu Trp Tyr Pro
            180                 185                 190

Ala Leu Val Ile Ser Pro Ser Cys Asn Asp Asp Ile Thr Val Lys Lys
                195                 200                 205

Asp Gln Cys Leu Val Arg Ser Phe Ile Asp Ser Lys Phe Tyr Ser Ile
210                 215                 220

Ala Arg Lys Asp Ile Lys Glu Val Asp Ile Leu Asn Leu Pro Glu Ser
225                 230                 235                 240

Glu Leu Ser Thr Lys Pro Gly Leu Gln Lys Ala Ser Ile Phe Leu Lys
                245                 250                 255

Thr Arg Val Val Pro Asp Asn Trp Lys Met Asp Ile Ser Glu Ile Leu
                260                 265                 270

Glu Ser Ser Ser Asp Asp Glu Asp Gly Pro Ala Glu Glu Asn Asp
                275                 280                 285

Glu Glu Lys Glu Lys Glu Ala Lys Lys Thr Glu Glu Val Pro Glu
290                 295                 300

Glu Glu Leu Asp Pro Glu Glu Arg Asp Asn Phe Leu Gln Gln Leu Tyr
305                 310                 315                 320

Lys Phe Met Glu Asp Arg Gly Thr Pro Ile Asn Lys Pro Pro Val Leu
                325                 330                 335

Gly Tyr Lys Asp Leu Asn Leu Phe Lys Leu Phe Arg Leu Val Tyr His
                340                 345                 350

Gln Gly Gly Cys Asp Asn Ile Asp Ser Gly Ala Val Trp Lys Gln Ile
                355                 360                 365

Tyr Met Asp Leu Gly Ile Pro Ile Leu Asn Ser Ala Ala Ser Tyr Asn
        370                 375                 380

Val Lys Thr Ala Tyr Arg Lys Tyr Leu Tyr Gly Phe Glu Glu Tyr Cys
385                 390                 395                 400

Arg Ser Ala Asn Ile Gln Phe Arg Thr Val His His Glu Pro Lys
                405                 410                 415

Val Lys Glu Glu Lys Lys Asp Leu Glu Glu Ser Met Glu Glu Ala Leu
            420                 425                 430

Lys Leu Asp Gln Glu Met Pro Leu Thr Glu Val Lys Ser Glu Pro Glu
                435                 440                 445

Glu Asn Ile Asp Ser Asn Ser Glu Ser Glu Arg Glu Glu Ile Glu Leu
        450                 455                 460

Lys Ser Pro Arg Gly Arg Arg Ile Ala Arg Asp Val Asn Ser Ile
465                 470                 475                 480

Lys Lys Glu Ile Glu Glu Glu Lys Thr Glu Asp Lys Leu Lys Asp Asn
                485                 490                 495

Asp Thr Glu Asn Lys Asp Val Asp Asp Tyr Glu Thr Ala Glu Lys
            500                 505                 510

Lys Glu Asn Glu Leu Leu Gly Arg Lys Asn Thr Pro Lys Gln Lys
        515                 520                 525

Glu Lys Lys Ile Lys Lys Gln Glu Asp Ser Asp Lys Asp Ser Asp Glu
            530                 535                 540

Glu Glu Glu Lys Ser Gln Glu Arg Glu Glu Thr Glu Ser Lys Cys Asp
545                 550                 555                 560
```

-continued

Ser Glu Gly Glu Glu Asp Glu Asp Met Glu Pro Cys Leu Thr Gly
                565                 570                 575

Thr Lys Val Lys Val Lys Tyr Gly Arg Gly Lys Thr Gln Lys Ile Tyr
            580                 585                 590

Glu Ala Ser Ile Lys Ser Thr Glu Ile Asp Asp Gly Glu Val Leu Tyr
            595                 600                 605

Leu Val His Tyr Tyr Gly Trp Asn Val Arg Tyr Asp Glu Trp Val Lys
        610                 615                 620

Ala Asp Arg Ile Ile Trp Pro Leu Asp Lys Gly Gly Pro Lys Lys Lys
625                 630                 635                 640

Gln Lys Lys Lys Ala Lys Asn Lys Glu Asp Ser Glu Lys Asp Glu Lys
                645                 650                 655

Arg Asp Glu Glu Arg Gln Lys Ser Lys Arg Gly Arg Pro Pro Leu Lys
            660                 665                 670

Ser Thr Leu Ser Ser Asn Met Pro Tyr Gly Leu Ser Lys Thr Ala Asn
        675                 680                 685

Ser Glu Gly Lys Ser Asp Ser Cys Ser Ser Asp Ser Glu Thr Glu Asp
    690                 695                 700

Ala Leu Glu Lys Asn Leu Ile Asn Glu Glu Leu Ser Leu Lys Asp Glu
705                 710                 715                 720

Leu Glu Lys Asn Glu Asn Leu Asn Asp Asp Lys Leu Asp Glu Glu Asn
                725                 730                 735

Pro Lys Ile Ser Ala His Ile Leu Lys Glu Asn Asp Arg Thr Gln Met
            740                 745                 750

Gln Pro Leu Glu Thr Leu Lys Leu Glu Val Gly Glu Asn Glu Gln Ile
        755                 760                 765

Val Gln Ile Phe Gly Asn Lys Met Glu Lys Thr Glu Val Lys Lys
    770                 775                 780

Glu Ala Glu Lys Ser Pro Lys Gly Lys Gly Arg Arg Ser Lys Thr Lys
785                 790                 795                 800

Asp Leu Ser Leu Glu Ile Ile Lys Ile Ser Ser Phe Gly Gln Asn Glu
                805                 810                 815

Ala Gly Ser Glu Pro His Ile Glu Ala His Ser Leu Glu Leu Ser Ser
            820                 825                 830

Leu Asp Asn Lys Asn Phe Ser Ser Ala Thr Glu Asp Glu Ile Asp Gln
        835                 840                 845

Cys Val Lys Glu Lys Lys Leu Lys Arg Lys Ile Leu Gly Gln Ser Ser
850                 855                 860

Pro Glu Lys Lys Ile Arg Ile Glu Asn Gly Met Glu Met Thr Asn Thr
865                 870                 875                 880

Val Ser Gln Glu Arg Thr Ser Asp Cys Ile Gly Ser Glu Gly Met Lys
                885                 890                 895

Asn Leu Asn Phe Glu Gln His Phe Glu Arg Glu Asn Glu Gly Met Pro
            900                 905                 910

Ser Leu Ile Ala Glu Ser Asn Gln Cys Ile Gln Gln Leu Thr Ser Glu
        915                 920                 925

Arg Phe Asp Ser Pro Ala Glu Glu Thr Val Asn Ile Pro Leu Lys Glu
    930                 935                 940

Asp Glu Asp Ala Met Pro Leu Ile Gly Pro Glu Thr Leu Val Cys His
945                 950                 955                 960

Glu Val Asp Leu Asp Asp Leu Asp Glu Lys Asp Lys Thr Ser Ile Glu
                965                 970                 975

Asp Val Ala Val Glu Ser Ser Glu Ser Asn Ser Leu Val Ser Ile Pro

-continued

```
                980                 985                 990
Pro Ala Leu Pro Pro Val Val Gln His Asn Phe Ser Val Ala Ser Pro
    995                1000                1005

Leu Thr Leu Ser Gln Asp Glu Ser Arg Ser Val Lys Ser Glu Ser Asp
   1010                1015                1020

Ile Thr Ile Glu Val Asp Ser Ile Ala Glu Glu Ser Gln Glu Gly Leu
1025                1030                1035                1040

Cys Glu Arg Glu Ser Ala Asn Gly Phe Glu Thr Asn Val Ala Ser Gly
                1045                1050                1055

Thr Cys Ser Ile Ile Val Gln Gly Arg Glu Ser Arg Glu Lys Gly Gln
            1060                1065                1070

Lys Arg Pro Ser Asp Gly Asn Ser Gly Leu Met Ala Lys Lys Gln Lys
        1075                1080                1085

Arg Thr Pro Lys Arg Thr Ser Ala Ala Lys Asn Glu Lys Asn Gly
    1090                1095                1100

Thr Gly Gln Ser Ser Asp Ser Glu Asp Leu Pro Val Leu Asp Asn Ser
1105                1110                1115                1120

Ser Lys Cys Thr Pro Val Lys His Leu Asn Val Ser Lys Pro Gln Lys
                1125                1130                1135

Leu Ala Arg Ser Pro Ala Arg Ile Ser Pro His Ile Lys Asp Gly Glu
            1140                1145                1150

Lys Asp Lys His Arg Glu Lys His Pro Asn Ser Ser Pro Arg Thr Tyr
        1155                1160                1165

Lys Trp Ser Phe Gln Leu Asn Glu Leu Asp Asn Met Asn Ser Thr Glu
    1170                1175                1180

Arg Ile Ser Phe Leu Gln Glu Lys Leu Gln Glu Ile Arg Lys Tyr Tyr
1185                1190                1195                1200

Met Ser Leu Lys Ser Glu Val Ala Thr Ile Asp Arg Arg Arg Lys Arg
                1205                1210                1215

Leu Lys Lys Lys Asp Arg Glu Val Ser His Ala Gly Ala Ser Met Ser
            1220                1225                1230

Ser Ala Ser Ser Asp Thr Gly Met Ser Pro Ser Ser Ser Pro Pro
        1235                1240                1245

Gln Asn Val Leu Ala Val Glu Cys Arg
    1250                1255

<210> SEQ ID NO 62
<211> LENGTH: 282
<212> TYPE: PRT
<213> ORGANISM: Homo sapiens

<400> SEQUENCE: 62

Met Gln Arg Leu Arg Trp Leu Arg Asp Trp Lys Ser Ser Gly Arg Gly
1               5                  10                  15

Leu Thr Ala Ala Lys Glu Pro Gly Ala Arg Ser Ser Pro Leu Gln Ala
            20                  25                  30

Met Arg Ile Leu Gln Leu Ile Leu Leu Ala Leu Ala Thr Gly Leu Val
        35                  40                  45

Gly Gly Glu Thr Arg Ile Ile Lys Gly Phe Glu Cys Lys Pro His Ser
    50                  55                  60

Gln Pro Trp Gln Ala Ala Leu Phe Glu Lys Thr Arg Leu Leu Cys Gly
65                  70                  75                  80

Ala Thr Leu Ile Ala Pro Arg Trp Leu Leu Thr Ala Ala His Cys Leu
                85                  90                  95
```

-continued

```
Lys Pro Arg Tyr Ile Val His Leu Gly Gln His Asn Leu Gln Lys Glu
                100                 105                 110

Glu Gly Cys Glu Gln Thr Arg Thr Ala Thr Glu Ser Phe Pro His Pro
            115                 120                 125

Gly Phe Asn Asn Ser Leu Pro Asn Lys Asp His Arg Asn Asp Ile Met
        130                 135                 140

Leu Val Lys Met Ala Ser Pro Val Ser Ile Thr Trp Ala Val Arg Pro
145                 150                 155                 160

Leu Thr Leu Ser Ser Arg Cys Val Thr Ala Gly Thr Ser Cys Leu Ile
                165                 170                 175

Ser Gly Trp Gly Ser Thr Ser Ser Pro Gln Leu Arg Leu Pro His Thr
            180                 185                 190

Leu Arg Cys Ala Asn Ile Thr Ile Ile Glu His Gln Lys Cys Glu Asn
        195                 200                 205

Ala Tyr Pro Gly Asn Ile Thr Asp Thr Met Val Cys Ala Ser Val Gln
        210                 215                 220

Glu Gly Gly Lys Asp Ser Cys Gln Gly Asp Ser Gly Gly Pro Leu Val
225                 230                 235                 240

Cys Asn Gln Ser Leu Gln Gly Ile Ile Ser Trp Gly Gln Asp Pro Cys
                245                 250                 255

Ala Ile Thr Arg Lys Pro Gly Val Tyr Thr Lys Val Cys Lys Tyr Val
            260                 265                 270

Asp Trp Ile Gln Glu Thr Met Lys Asn Asn
        275                 280

<210> SEQ ID NO 63
<211> LENGTH: 277
<212> TYPE: PRT
<213> ORGANISM: Homo sapiens

<400> SEQUENCE: 63

Met Trp Pro Leu Ala Leu Val Ile Ala Ser Leu Thr Leu Ala Leu Ser
1               5                   10                  15

Gly Gly Val Ser Gln Glu Ser Ser Lys Val Leu Asn Thr Asn Gly Thr
            20                  25                  30

Ser Gly Phe Leu Pro Gly Gly Tyr Thr Cys Phe Pro His Ser Gln Pro
        35                  40                  45

Trp Gln Ala Ala Leu Leu Val Gln Gly Arg Leu Leu Cys Gly Gly Val
    50                  55                  60

Leu Val His Pro Lys Trp Val Leu Thr Ala Ala His Cys Leu Lys Glu
65                  70                  75                  80

Gly Leu Lys Val Tyr Leu Gly Lys His Ala Leu Gly Arg Val Glu Ala
                85                  90                  95

Gly Glu Gln Val Arg Glu Val Val His Ser Ile Pro His Pro Glu Tyr
            100                 105                 110

Arg Arg Ser Pro Thr His Leu Asn His Asp His Asp Ile Met Leu Leu
        115                 120                 125

Glu Leu Gln Ser Pro Val Gln Leu Thr Gly Tyr Ile Gln Thr Leu Pro
        130                 135                 140

Leu Ser His Asn Asn Arg Leu Thr Pro Gly Thr Thr Cys Arg Val Ser
145                 150                 155                 160

Gly Trp Gly Thr Thr Thr Ser Pro Gln Val Asn Tyr Pro Lys Thr Leu
                165                 170                 175

Gln Cys Ala Asn Ile Gln Leu Arg Ser Asp Glu Glu Cys Arg Gln Val
            180                 185                 190
```

```
Tyr Pro Gly Lys Ile Thr Asp Asn Met Leu Cys Ala Gly Thr Lys Glu
            195                 200                 205

Gly Gly Lys Asp Ser Cys Glu Gly Asp Ser Gly Gly Pro Leu Val Cys
        210                 215                 220

Asn Arg Thr Leu Tyr Gly Ile Val Ser Trp Gly Asp Phe Pro Cys Gly
225                 230                 235                 240

Gln Pro Asp Arg Pro Gly Val Tyr Thr Arg Val Ser Arg Tyr Val Leu
                245                 250                 255

Trp Ile Arg Glu Thr Ile Arg Lys Tyr Glu Thr Gln Gln Lys Trp
            260                 265                 270

Leu Lys Gly Pro Gln
        275

<210> SEQ ID NO 64
<211> LENGTH: 122
<212> TYPE: PRT
<213> ORGANISM: Homo sapiens

<400> SEQUENCE: 64

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120

<210> SEQ ID NO 65
<211> LENGTH: 99
<212> TYPE: PRT
<213> ORGANISM: Homo sapiens

<400> SEQUENCE: 65

Met Gln Pro Arg Val Leu Leu Val Val Ala Leu Leu Ala Leu Leu Ala
1               5                   10                  15

Ser Ala Arg Ala Ser Glu Ala Glu Asp Ala Ser Leu Leu Ser Phe Met
            20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Gln Ala Arg Gly Trp Val Thr
    50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala
```